(12) United States Patent
Alcaraz et al.

(10) Patent No.: US 7,951,954 B2
(45) Date of Patent: May 31, 2011

(54) BEZOTHIAZOL DERIVATIVES AS BETA2 ADRENORECEPTOR AGONISTS

(75) Inventors: Lilian Alcaraz, Loughborough (GB); Andrew Lister, Loughborough (GB); Garry Pairaudeau, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 221 days.

(21) Appl. No.: 12/282,634

(22) PCT Filed: Mar. 12, 2007

(86) PCT No.: PCT/SE2007/000233
§ 371 (c)(1), (2), (4) Date: Sep. 11, 2008

(87) PCT Pub. No.: WO2007/106016
PCT Pub. Date: Sep. 20, 2007

(65) Prior Publication Data
US 2009/0062259 A1     Mar. 5, 2009

Related U.S. Application Data

(60) Provisional application No. 60/782,733, filed on Mar. 14, 2006, provisional application No. 60/862,651, filed on Oct. 24, 2006.

(51) Int. Cl.
C07D 277/68   (2006.01)
C07D 417/06   (2006.01)
A61K 31/5355  (2006.01)
A61K 31/4523  (2006.01)
A61K 31/428   (2006.01)

(52) U.S. Cl. ............... 548/169; 546/187; 546/270.1; 544/135

(58) Field of Classification Search .............. None
See application file for complete search history.

(56) References Cited

U.S. PATENT DOCUMENTS

| | | | |
|---|---|---|---|
| 2,653,977 | A | 9/1953 | Craig et al. |
| 3,775,477 | A | 11/1973 | Diana |
| 4,460,581 | A | 7/1984 | Schromm et al. |
| 5,648,370 | A | 7/1997 | Bonnert et al. |
| 6,686,353 | B1 | 2/2004 | Shiota et al. |
| 7,700,782 | B2 | 4/2010 | Connolly et al. |
| 7,709,511 | B2 | 5/2010 | Bonnert et al. |
| 2002/0055651 | A1 | 5/2002 | Moran et al. |
| 2003/0229058 | A1 | 12/2003 | Moran et al. |
| 2006/0106075 | A1 | 5/2006 | Cuenoud et al. |
| 2008/0207698 | A1 | 8/2008 | Connolly et al. |
| 2008/0242649 | A1 | 10/2008 | Cadogan et al. |
| 2008/0249145 | A1 | 10/2008 | Whittock et al. |
| 2008/0300275 | A1 | 12/2008 | Bonnert et al. |
| 2009/0029958 | A1 | 1/2009 | Alcaraz et al. |
| 2009/0062259 | A1 | 3/2009 | Alcaraz et al. |
| 2009/0203753 | A1 | 8/2009 | Bailey et al. |
| 2009/0221653 | A1 | 9/2009 | Bailey et al. |
| 2010/0022491 | A1 | 1/2010 | Connolly et al. |
| 2010/0210688 | A1 | 8/2010 | Bonnert et al. |
| 2010/0249200 | A1 | 9/2010 | Connolly et al. |

FOREIGN PATENT DOCUMENTS

| | | |
|---|---|---|
| EP | 0162576 | 11/1985 |
| EP | 0174811 | 3/1986 |
| EP | 0175525 | 3/1986 |
| EP | 0220878 | 5/1987 |
| EP | 0303466 | 2/1989 |
| EP | 0422889 | 4/1991 |
| JP | 2005-187357 | 7/2005 |
| SE | 7415945 | 6/1975 |
| WO | WO 92/08708 | 5/1992 |
| WO | WO 93/23385 | 11/1993 |
| WO | WO 93/24473 | 12/1993 |
| WO | WO 97/10227 | 3/1997 |
| WO | WO 97/23470 | 7/1997 |
| WO | WO 97/44329 | 11/1997 |
| WO | WO 98/38180 | 9/1998 |
| WO | WO 98/45294 | 10/1998 |
| WO | WO 99/36095 | 7/1999 |
| WO | WO 99/64035 | 12/1999 |
| WO | WO 00/75114 | 12/2000 |
| WO | WO 01/11933 | 2/2001 |
| WO | WO 01/12167 | 2/2001 |
| WO | WO 01/12191 | 2/2001 |
| WO | WO 01/12192 | 2/2001 |
| WO | WO 01/42193 | 6/2001 |
| WO | WO 02/06255 | 1/2002 |

(Continued)

OTHER PUBLICATIONS

Austin et al. "QSAR and the Rational Design of Long-Acting Dual $D_2$-Receptor/$\beta_2$-Adrenoceptor Agonists" J. Med. Chem. 2003 46:3210-3220.

(Continued)

*Primary Examiner* — Kamal A Saeed
*Assistant Examiner* — Nyeemah Grazier
(74) *Attorney, Agent, or Firm* — Fish & Richardson P.C.

(57) ABSTRACT

The present invention relates to compounds according to formula (I), a process for preparing them, the intermediate compounds of the process and the use of the compounds in the manufacture of a medicament for use in treating diseases such as ARDS, pulmonary emphysema, bronchitis, bronchiectasis, COPD, asthma and rhinitis. The compounds are beta adrenoreceptor agonists.

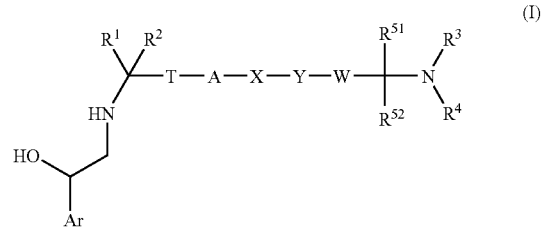

13 Claims, No Drawings

FOREIGN PATENT DOCUMENTS

| WO | WO 02/076933 | 10/2002 |
|---|---|---|
| WO | WO 03/024439 | 3/2003 |
| WO | WO 2004/016578 | 2/2004 |
| WO | WO 2004/016601 | 2/2004 |
| WO | WO 2004/039766 | 5/2004 |
| WO | WO 2004/071388 | 8/2004 |
| WO | WO 2004/074276 | 9/2004 |
| WO | WO 2004/089892 | 10/2004 |
| WO | WO 2005/030678 | 4/2005 |
| WO | WO 2005/040103 | 5/2005 |
| WO | WO 2005/044787 | 5/2005 |
| WO | WO 2005/070872 | 8/2005 |
| WO | WO 2005/074924 | 8/2005 |
| WO | WO 2005/092841 | 10/2005 |
| WO | WO 2005/092861 | 10/2005 |
| WO | WO 2005/092870 | 10/2005 |
| WO | WO 2005/110990 | 11/2005 |
| WO | WO 2005/111002 | 11/2005 |
| WO | WO 2005/111004 | 11/2005 |
| WO | WO 2005/121065 | 12/2005 |
| WO | WO 2006/014704 | 2/2006 |
| WO | WO 2006/023457 | 3/2006 |
| WO | WO 2006/023460 | 3/2006 |
| WO | WO 2006/031556 | 3/2006 |
| WO | WO 2006/056471 | 6/2006 |
| WO | WO 2006/074897 | 7/2006 |
| WO | WO 2006/128675 | 12/2006 |
| WO | WO 2007/010356 | 1/2007 |
| WO | WO 2007/018461 | 2/2007 |
| WO | WO 2007/027133 | 3/2007 |
| WO | WO 2007/027134 | 3/2007 |
| WO | WO 2007/102771 | 9/2007 |
| WO | WO 2007/106016 | 9/2007 |
| WO | WO 2008/041914 | 4/2008 |
| WO | WO 2008/075025 | 6/2008 |
| WO | WO 2008/075026 | 6/2008 |
| WO | WO 2008/096111 | 8/2008 |
| WO | WO 2008/096112 | 8/2008 |
| WO | WO 2008/096119 | 8/2008 |
| WO | WO 2008/096121 | 8/2008 |
| WO | WO 2008/104776 | 9/2008 |
| WO | WO 2008/104790 | 9/2008 |
| WO | WO 2009/037503 | 3/2009 |

OTHER PUBLICATIONS

Berge et al. "Pharmaceutical Salts" J Pharmaceutical Sciences. 1977 66(1) 1-19.

Bonnert et al. "Dual $D_2$-Receptor and $\beta_2$-Adrenoceptor Agonists for the Treatment of Airway Diseases. 1. Discovery and Biological Evaluation of Some 7-(2-Aminoethyl)-4-hydroxybenzothiazol-2(3*H*)-one Analogues" J. Med Chem. 1998 (41) 4915-4917.

Davies et al. "Indacaterol. Asthma therapy Treatment of COPD $\beta_2$-Adrenoceptor Agonist" Drugs of the Future. 2005 30(12) 1219-1224.

Dougall et al. "Dual dopamine $D_2$ receptor and $\beta_2$-adrenoceptor agonists for the treatment of chronic obstructive pulmonary disease: the pre-clinical rationale" Respir Med (Suppl A). 2003 (97) S3-S7 (Abstract).

Fernandez et al. "Alkaline Hydrolysis of 1,2,3-Trisubstituted Cyclic Amidinium Salts. Kinetic Study of N 4 N' Acyl Migration in Alkaline Solution in an Ethylenediamine Derivative" J.C.S. Perkin II. 1978 545-550.

Fernandez et al. "N 4 N' Intramolecular Acyl Transfer in Acid Media for Alkylenediamine Derivatives" J.C.S. Perkin II. 1978 550-553.

Horig et al. "From bench to clinic and back: Perspective on the 1st IQPC Translational Research conference" Journal of Translational Medicine. 2004 2(44) 1-8.

Johnson "Beta$_2$-adrenoceptors: mechanisms of action of beta$_2$-agonists" Paediatric Respiratory Reviews. 2001 (2) 57-62.

Norman, "Which of three structures is AZD-3199? WO-2008104790, WO-2008096112 and WO-2008096119" Expert Opin. Ther. Patents. 2009 19(7) 1-7.

Schäfer et al. "Failure is an option: learning from unsuccessful proof-of-concept trials" Drug Discovery Today. 2008 13(21/22) 913-916.

Weinstock et al. "Synthesis and Evaluation of Non-Catechol D-1 and D-2 Dopamine Receptor Agonists: Benzimidazol-2-one, Benzoxazol-2-one, and the Highly Potent Benzothiazol-2-one 7 Ethylamines" J Med Chem. 1987 (30) 1166-1176.

Wermuth et al., Handbook of Pharmaceutical salts: properties, selection and use, (2002) pp. 1-7: published by Wiley-VCH Verlag, ISBN: 10-3-906390-26-8.

Wright et al. "The Rearrangement of *N*-(Methylaminoalkyl)anilides" J Org Chem. 1961 26(6) 2120-2123.

USPTO Non-Final Office Action in U.S. Appl. No. 11/959,679, mailed Feb. 25, 2009, 12 pages.

Fish & Richardson P.C., Amendment in Reply to Action of Feb. 25, 2009 in U.S. Appl. No. 11/959,679, filed Jul. 15, 2009, 6 pages.

USPTO Notice of Allowance in U.S. Appl. No. 11/959,679, mailed Nov. 9, 2009, 9 pages.

Fish & Richardson P.C., Response to Notice of Allowance mailed Nov. 9, 2009 in U.S. Appl. No. 11/959,679, filed Feb. 9, 2009, 2 pages.

USPTO Notice of Allowance in U.S. Appl. No. 12/063,322, mailed Feb. 26, 2010, 12 pages.

Fish & Richardson P.C., Response to Notice of Allowance mailed Feb. 26, 2010 in U.S. Appl. No. 12/063,322, filed Mar. 5, 2010, 2 pages.

USPTO Non-Final Office Action in U.S. Appl. No. 12/069,180, mailed Feb. 3, 2010, 19 pages.

Fish & Richardson P.C., Amendment in Replay to Action of Feb. 3, 2010 in U.S. Appl. No. 12/069,180, filed Aug. 6, 2010, 8 pages.

USPTO Non-Final Office Action in U.S. Appl. No. 12/069,180, mailed Oct. 15, 2010, 19 pages.

USPTO Notice of Allowance in U.S. Appl. No. 12/065,160, mailed Jun. 15, 2010, 9 pages.

Fish and Richardson P.C., RCE/IDS in response to Notice of Allowance mailed Jun. 15, 2010 in U.S. Appl. No. 12/065,160, filed Sep. 15, 2010, 9 pages.

Swedish Search Report for Application No. PCT/SE2006/000927, dated Oct. 27, 2006, 8 pages.

European Search Report for Application No. PCT/GB2007/004861, dated Mar. 28, 2008, 4 pages.

BEZOTHIAZOL DERIVATIVES AS BETA2 ADRENORECEPTOR AGONISTS

CROSS-REFERENCE TO RELATED APPLICATIONS

This application is a national phase application under 35 U.S.C. §371 of PCT International Application No. PCT/SE2007/000233, filed Mar. 12, 2007, which claims the benefit of U.S. Provisional Application No. 60/782,733, filed Mar. 14, 2006, and U.S. Provisional Application No. 60/862,651, filed Oct. 24, 2006. Each of these prior applications is incorporated herein by reference in its entirety.

The present invention relates to diamine derivatives, processes for their preparation, pharmaceutical compositions containing them and their use in therapy.

Adrenoceptors are a group of G-protein coupled receptors divided into two major sub-families, α and β. These sub-families are further divided into sub-types of which the β sub-family has at least 3 members: β1, β2 and β3. β2 adrenoceptors (henceforth referred to as β2 receptors) are mainly expressed on smooth muscle cells.

Agonism of the β2 receptor on airway smooth muscle produces relaxation and therefore bronchodilatation. Through this mechanism, β2 agonists act as functional antagonists to all bronchoconstrictor substances such as the naturally-occurring histamine and acetylcholine as well as the experimental substances methacholine and carbachol. β2 agonists are widely used to treat airways diseases including asthma and chronic obstructive pulmonary disease (COPD), and this has been extensively reviewed in the literature and incorporated into national guidelines for the treatment of these diseases (British Guideline on the Management of Asthma, NICE guideline No. 12 on the Management of COPD).

β2 agonists are classed either as short-acting or long-acting. Short-acting β2 agonists (SABAs) such as salbutamol have a duration of action of 2-4 hours. They are suitable for rescue medication during a period of acute bronchoconstriction but are not suitable for continuous medication because the beneficial effect of these drugs wears off during the night. Long-acting β2 agonists (LABAs) currently have a duration of action of about 12 hours and are administered twice daily to provide continuous bronchodilatation. They are particularly effective when administered in combination with inhaled corticosteroids. This benefit is not seen when inhaled corticosteroids are combined with SABAs (Kips and Pauwels, *Am. J. Respir. Crit. Care Med.*, 2001, 164, 923-932). LABAs are recommended as add-on therapy to patients already receiving inhaled corticosteroids for asthma to reduce nocturnal awakening and reduce the incidence of exacerbations of the disease.

Corticosteroids and LABAs are conveniently co-administered in a single inhaler to improve patient compliance.

There are shortcomings to existing LABAs and there is a need for a new drug in this class. Salmeterol, a commonly used LABA, has a narrow safety margin and side effects related to systemic agonism of β2 receptors (such as tremor, hypokalaemia, tachycardia and hypertension) are common. Salmeterol also has a long onset of action which precludes its use as both a rescue and a maintenance therapy. All current LABAs are administered twice daily and there is a medical need for once daily treatments to improve treatment and patient compliance. Such once daily compounds, co-administered with corticosteroids, will become the mainstay of asthma treatment (Barnes, *Nature Reviews*, 2004, 3, 831-844). The advantages of once-daily bronchodilator treatment in COPD has been demonstrated with tiotropium, a non-selective muscarinic antagonist (Koumis and Samuel, *Clin. Ther.* 2005, 27(4), 377-92). There is, however, a need for a once-daily LABA for the treatment of COPD to avoid the side effects of anti-muscarinics such as tiotropium.

Benzothiazolone derivatives having dual β2 receptor and dopamine (D2) receptor agonist properties are known from WO 92/08708, WO 93/23385 and WO 97/10227.

In accordance with the present invention, there is therefore provided a compound of formula (I):

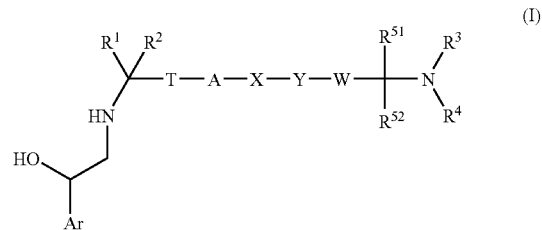

wherein: Ar is

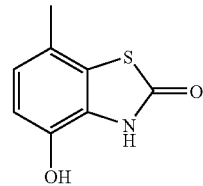

$R^1$ and $R^2$ are, independently, hydrogen or $C_{1-6}$ alkyl;
T is a bond, $CR^{33}R^{34}$, $CR^{35}R^{36}CR^{37}R^{38}$ or $CR^{39}R^{40}CR^{41}R^{42}CR^{43}R^{44}$;
W is a bond, $CR^{45}R^{46}$ or $CR^{47}R^{48}CR^{49}R^{50}$;
A is a bond, optionally substituted aryl or optionally substituted heteroaryl;
X is a bond;
Y a bond, optionally substituted aryl or optionally substituted heteroaryl;
but A and Y not both a bond;
$R^3$ and $R^4$ are, independently, hydrogen, $C_{1-6}$ alkyl (optionally substituted by hydroxy, $C_{1-6}$ alkoxy, $NR^{63}R^{64}$, optionally substituted aryl, optionally substituted phenoxy or optionally substituted heteroaryl), heterocyclyl (optionally substituted by hydroxy, $C_{1-6}$ alkyl, $C_{1-6}$ alkoxy, $NR^{65}R^{66}$, optionally substituted aryl, optionally substituted phenoxy or optionally substituted heteroaryl) or $C_{3-6}$ cycloalkyl (optionally substituted by hydroxy, $C_{1-6}$ alkyl, $C_{1-6}$ alkoxy, $NR^{67}R^{68}$, optionally substituted aryl, optionally substituted phenoxy or optionally substituted heteroaryl);
or $R^3$ and $R^4$ join to form a 4- or 12-membered monocyclic or bicyclic ring optionally substituted by hydroxy, $NR^{69}R^{70}$, $C_{1-6}$ alkyl (optionally substituted by $NR^{55}R^{56}$), $C_{1-6}$ alkoxy (optionally substituted by $NR^{57}R^{58}$), optionally substituted phenyl or optionally substituted phenoxy; said ring being optionally fused to an optionally substituted aryl or optionally substituted heteroaryl group;
all the foregoing phenyl, aryl and heteroaryl groups are, independently, optionally substituted by halogen, $CF_3$, $OCF_3$, cyano, $CO_2H$, OH, nitro, $C_{1-6}$ alkyl (optionally substituted by $NR^{59}R^{60}$), $C_{3-6}$ cycloalkyl (optionally substituted by $NR^{71}R^{72}$), $C_{1-6}$ alkoxy (optionally substituted by $NR^{61}R^{62}$), C(O)(C$_{1-6}$ alkyl), C(O)$_2$(C$_{1-6}$ alkyl), S(O)$_r$R$^{25}$, NR$^{26}$S(O)$_2$R$^{27}$, S(O)$_2$NR$^{28}$R$^{29}$, NHC(O)R$^{30}$, C(O)NR$^{31}$R$^{32}$ or NR$^{53}$R$^{54}$;

r is 0, 1 or 2;

R$^{26}$, R$^{28}$, R$^{29}$, R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$, R$^{42}$, R$^{43}$, R$^{44}$, R$^{45}$, R$^{46}$, R$^{47}$, R$^{48}$, R$^{49}$, R$^{50}$, R$^{51}$, R$^{52}$, R$^{53}$, R$^{54}$, R$^{55}$, R$^{56}$, R$^{57}$, R$^{58}$, R$^{59}$, R$^{60}$, R$^{61}$, R$^{62}$, R$^{63}$, R$^{64}$, R$^{65}$, R$^{66}$, R$^{67}$, R$^{68}$, R$^{69}$, R$^{70}$, R$^{71}$ or R$^{72}$ are, independently, hydrogen or C$_{1-6}$ alkyl;

R$^{25}$ and R$^{27}$ are, independently C$_{1-6}$ alkyl;

or a pharmaceutically acceptable salt thereof.

The compounds of the invention are selective β2 receptor agonists and possess properties that make them more suitable for once-a-day administration. In particular, the compounds of the invention are at least 5-fold (for example at least 10-fold) more potent at the β2 receptor compared to at least one of (preferably all of) the β1, α1 or dopamine (D2) receptors.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a mono-, di- or tri-: hydrochloride (for example a mono-hydrochloride or dihydrochloride), hydrobromide (for example a mono-hydrobromide or a dihydrobromide), phosphate, sulphate, acetate, diacetate, fumarate, maleate, malonate, tartrate, lactate, citrate, pyruvate, succinate, oxalate, methanesulfonate or p-toluenesulfonate. Further examples of acid addition salts are: bisulphate, benzenesulphonate, ethanesulphonate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate and 2-naphthalenesulphonate.

The present invention covers all permissible ratios of compound of formula (I) to pharmaceutically acceptable salt, for example mono-hydrobromide, dihydrobromide, bis-malonate or a hemi-salt (such as a hemi-fumarate).

The compounds of the invention may exist as solvates (such as hydrates) and the present invention covers all such solvates.

Halogen includes fluorine, chlorine, bromine and iodine.

Alkyl groups and moieties are straight or branched chain and are, for example, methyl, ethyl, n-propyl, iso-propyl, n-butyl, iso-butyl, tert-butyl, n-pentyl or n-hexyl.

Cycloalkyl is monocyclic and is, for example, cyclopropyl, cyclopentyl or cyclohexyl.

Heterocyclyl is a non-aromatic ring comprising 1 or 2 heteroatoms independently selected from nitrogen, oxygen and sulphur. Heterocyclyl is, for example, pyrrolidinyl, piperidinyl, piperazinyl, morpholinyl, thiomorpholinyl, thiomorpholinyl S-oxide, thiomorpholinyl S-dioxide, tetrahydrofuranyl, tetrahydrothienyl or tetrahydropyranyl.

When R$^3$ and R$^4$ join to form a 4- to 12-membered (for example 5- or 6-membered) monocyclic or bicyclic ring (for example mono-cyclic ring) said ring is, for example, pyrrolidinyl, piperidinyl, piperazinyl, morpholinyl, thiomorpholinyl, thiomorpholinyl S-oxide or thiomorpholinyl S-dioxide. It can additionally be azepanyl or 1,3-dihydro-iso-indolyl.

Aryl is, for example, phenyl or naphthyl. In one aspect of the invention aryl is phenyl.

Heteroaryl is an aromatic heterocycle (for example 5- or 6-membered), optionally fused to one or more other rings, comprising at least one heteroatom selected from the group comprising nitrogen, oxygen and sulfur; or an N-oxide thereof, or an S-oxide or S-dioxide thereof. Heteroaryl is, for example, furyl, thienyl (also known as thiophenyl), pyrrolyl, thiazolyl, isothiazolyl, pyrazolyl, oxazolyl, isoxazolyl, imidazolyl, 1,2,3-triazolyl, 1,2,4-triazolyl, pyridinyl, pyrimidinyl, pyridazinyl, pyrazinyl, 1,2,3-triazinyl, 1,2,4-triazinyl, 1,3,5-triazinyl, indolyl, benzo[b]furyl (also known as benzfuryl), benz[b]thienyl (also known as benzthienyl or benzthiophenyl), indazolyl, benzimidazolyl, benztriazolyl, benzoxazolyl, benzthiazolyl, 1,2,3-benzothiadiazolyl, an imidazopyridinyl (such as imidazo[1,2-a]pyridinyl), thieno[3,2-b]pyridin-6-yl, 1,2,3-benzoxadiazolyl (also known as benzo[1,2,3]thiadiazolyl), 2,1,3-benzothiadiazolyl, benzofurazan (also known as 2,1,3-benzoxadiazolyl), quinoxalinyl, a pyrazolopyridine (for example 1H-pyrazolo[3,4-b]pyridinyl), a purine, quinolinyl, isoquinolinyl, cinnolinyl, a naphthyridinyl (for example [1,6]naphthyridinyl or [1,8]naphthyridinyl), a benzothiazinyl, 4H-benzo[1,4]thiazinyl (for example in a 4H-benzo[1,4]thiazin-3-one-yl moiety); or an N-oxide thereof (such as a pyridine N-oxide), or an S-oxide or S-dioxide thereof. In one aspect of the invention heteroaryl is pyridinyl or indolyl.

In one particular aspect the present invention provides a compound of formula (I):

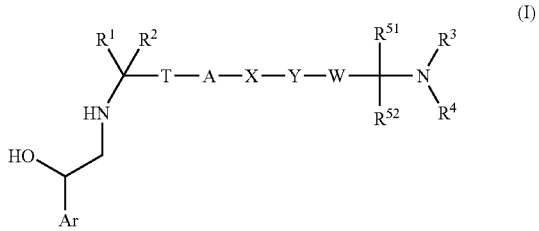

(I)

wherein

Ar is

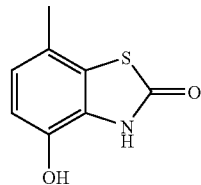

R$^1$ and R$^2$ are, independently, hydrogen or C$_{1-6}$ alkyl;

T is a bond, CR$^{33}$R$^{34}$, CR$^{35}$R$^{36}$CR$^{37}$R$^{38}$ or CR$^{39}$R$^{40}$CR$^{41}$R$^{42}$CR$^{43}$R$^{44}$;

W is a bond, CR$^{45}$R$^{46}$ or CR$^{47}$R$^{48}$CR$^{49}$R$^{50}$;

A is a bond, optionally substituted aryl or optionally substituted heteroaryl;

X is a bond;

Y a bond, optionally substituted aryl or optionally substituted heteroaryl;

but A and Y not both a bond;

R$^3$ and R$^4$ are, independently, hydrogen, C$_{1-6}$ alkyl (optionally substituted by C$_{1-6}$ alkoxy, optionally substituted aryl or optionally substituted heteroaryl), heterocyclyl (optionally substituted by C$_{1-6}$ alkyl, C$_{1-6}$ alkoxy, optionally substituted aryl or optionally substituted heteroaryl) or C$_{3-6}$ cycloalkyl (optionally substituted by $C_{1-6}$ alkyl, $C_{1-6}$ alkoxy, optionally substituted aryl or optionally substituted heteroaryl); or $R^3$ and $R^4$ join to form a 4- or 12-membered monocyclic or bicyclic ring optionally substituted by $C_{1-6}$ alkyl (optionally substituted by $NR^{55}R^{56}$) or $C_{1-6}$ alkoxy, said ring being optionally fused to an optionally substituted aryl or optionally substituted heteroaryl group; all the foregoing phenyl, aryl and heteroaryl groups are, independently, optionally substituted by halogen, $CF_3$, $OCF_3$, cyano, $CO_2H$, OH, nitro, $C_{1-6}$ alkyl, $C_{3-6}$ cycloalkyl, $C_{1-6}$ alkoxy, $C(O)(C_{1-6}$ alkyl), $C(O)_2(C_{1-6}$ alkyl), $S(O)_rR^{25}$, $NR^{26}S(O)_2R^{27}$, $S(O)_2NR^{28}R^{29}$, NHC$(O)R^{30}$, $C(O)NR^{31}R^{32}$ or $NR^{53}R^{54}$;

r is 0, 1 or 2;

$R^{26}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$ or $R^{56}$ are, independently, hydrogen or $C_{1-6}$ alkyl;

$R^{25}$ and $R^{27}$ are, independently $C_{1-6}$ alkyl;

or a pharmaceutically acceptable salt thereof.

In a further aspect the present invention provides a compound of formula (I) wherein $R^1$ and $R^2$ are, independently, hydrogen or methyl. In a still further aspect the present invention provides a compound of formula (I) wherein $R^1$ and $R^2$ are both hydrogen.

In another aspect the present invention provides a compound of formula (I) wherein T is $CH_2$ or $CH_2CH_2$. In yet another aspect the present invention provides a compound of formula (I) wherein T is $CH_2$.

In a further aspect the present invention provides a compound of formula (I) wherein A is optionally substituted phenyl (for example unsubstituted phenyl or phenyl substituted by one or more of the same or different: halogen, $CF_3$, $OCF_3$, $C_{1-6}$ alkyl, $C_{1-6}$ alkoxy or $S(O)_2(C_{1-4}$ alkyl)). In a still further aspect A is unsubstituted phenyl.

In a still further aspect the present invention provides a compound of formula (I) wherein A is optionally substituted phenyl and T and X are meta or para disposed (for example meta disposed) on the phenyl ring of A. In a still further aspect A is optionally substituted phenyl and T and X are meta or para disposed (for example meta disposed) on the phenyl ring of A; Y is a bond; and W is a bond or $CH_2$ (for example W is a bond).

In another aspect the present invention provides a compound of formula (I) wherein Y is a bond or optionally substituted phenyl (for example unsubstituted phenyl or phenyl substituted by one or more of the same or different: halogen, $CF_3$, $OCF_3$, $C_{1-6}$ alkyl, $C_{1-6}$ alkoxy or $S(O)_2(C_{1-4}$ alkyl)). In a further aspect Y is a bond.

In yet another aspect the present invention provides a compound of formula (I) wherein $R^{51}$ and $R^{52}$ are, independently, hydrogen or methyl. In a still further aspect the present invention provides a compound of formula (I) wherein $R^{51}$ and $R^{52}$ are both hydrogen.

In a still further aspect the present invention provides a compound of formula (I) wherein W is a bond. In another aspect the present invention provides a compound of formula (I) wherein W is $CH_2$.

In a further aspect the present invention provides a compound of formula (I) wherein $R^3$ is hydrogen.

In a still further aspect the present invention provides a compound of formula (I) wherein $R^4$ is $C_{1-6}$ alkyl substituted by one or more of: $C_{1-6}$ alkoxy, optionally substituted phenyl (for example unsubstituted phenyl or phenyl substituted by 1 or 2 of: halogen, $C_{1-4}$ alkyl, $C_{1-4}$ alkoxy, cyano, $CF_3$ or $OCF_3$) or optionally substituted heteroaryl (for example optionally substituted indolyl or optionally substituted pyridinyl); or $R^4$ is $C_{3-6}$ cycloalkyl substituted by optionally substituted phenyl (for example phenyl optionally substituted by halogen).

In a further aspect the present invention provides a compound of formula (I) wherein $R^4$ is $C_{1-6}$ alkyl substituted by one or more of: $C_{1-6}$ alkoxy, optionally substituted phenyl (for example phenyl optionally substituted by halogen or $C_{1-4}$ alkoxy) or optionally substituted heteroaryl (for example optionally substituted indolyl or optionally substituted pyridinyl); or $R^4$ is $C_{3-6}$ cycloalkyl substituted by optionally substituted phenyl (for example phenyl optionally substituted by halogen).

In a still further aspect the present invention provides a compound of formula (I) wherein $R^4$ is $C_{1-6}$ alkyl (such as $C_{1-4}$ alkyl, for example $CH_2$) substituted by optionally substituted phenyl (for example unsubstituted phenyl or phenyl substituted by 1 or 2 of: halogen, $C_{1-4}$ alkyl, $C_{1-4}$ alkoxy, cyano, $CF_3$ or $OCF_3$).

In another aspect the present invention provides a compound of formula (I) wherein $R^4$ is unsubstituted benzyl or benzyl wherein the phenyl ring is substituted by 1 or 2 (for example 1) of: halogen, $C_{1-4}$ alkyl or $C_{1-4}$ alkoxy.

In yet another aspect the present invention provides a compound of formula (I) wherein $R^3$ and $R^4$ join to form a 4- or 12-membered monocyclic or bicyclic ring optionally substituted by $C_{1-6}$ alkyl (optionally substituted by $NR^{55}R^{56}$) or $C_{1-6}$ alkoxy, said ring being optionally fused to an optionally substituted aryl or optionally substituted heteroaryl group. $R^{55}$ and $R^{56}$ are, independently, hydrogen or $C_{1-6}$ alkyl (for example hydrogen or $C_{1-4}$ alkyl).

In another aspect the present invention provides a compound of formula (I) wherein $R^3$ and $R^4$ join to form a 4- to 12-membered monocyclic or bicyclic ring optionally substituted by $C_{1-6}$ alkyl (optionally substituted by $NR^{55}R^{56}$) or $C_{1-6}$ alkoxy, said ring being optionally fused to an optionally substituted aryl or optionally substituted heteroaryl group. $R^{55}$ and $R^{56}$ are, independently, hydrogen or $C_{1-6}$ alkyl (for example hydrogen or $C_{1-4}$ alkyl).

In a further aspect the present invention provides a compound of formula (I) wherein $R^3$ and $R^4$ join to form a 4- to 12-membered monocyclic ring (for example a 5-, 6-, 7- or 8-membered ring; such as a 5- or 6-membered ring) which is unsubstituted.

In another aspect the present invention provides a compound of formula (I) wherein $R^3$ and $R^4$ join to form a 5-membered ring, said ring being fused to an optionally substituted phenyl group. Thus $R^3$ and $R^4$, and the nitrogen to which they are attached, form, for example, a 1,3-dihydroisoindol-2-yl group.

In yet another aspect the present invention provides a compound of formula (I) wherein the asterisked carbon in the representation of formula (I) shown below has the (R) absolute stereochemistry.

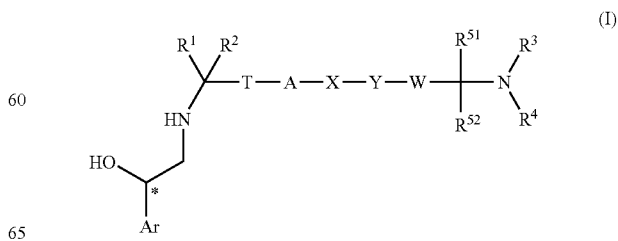

An example of a compound of the invention is:

7-{2-[2-(3-{[2-(2,6-Dichloro-phenyl)-ethylamino]-methyl}-phenyl)-ethylamino]-1R-hydroxy-ethyl}-4-hydroxy-3H-benzothiazol-2-one;

7-[2-(2-{3-[(2,2-Diphenyl-ethylamino)-methyl]-phenyl}-ethylamino)-1R-hydroxy-ethyl]-4-hydroxy-3H-benzothiazol-2-one;

7-[2-(2-{3-[(2-Chloro-benzylamino)-methyl]-phenyl}-ethylamino)-1R-hydroxy-ethyl]-4-hydroxy-3H-benzothiazol-2-one;

7-{2-[2-(3-{[2-(2-Fluoro-phenyl)-ethylamino]-methyl}-phenyl)-ethylamino]-1R-hydroxy-ethyl}-4-hydroxy-3H-benzothiazol-2-one;

4-Hydroxy-7-[1R-hydroxy-2-(2-{3-[(2-methoxy-1-methyl-ethylamino)-methyl]-phenyl}-ethylamino)-ethyl]-3H-benzothiazol-2-one;

4-Hydroxy-7-{1R-hydroxy-2-[2-(3-{[2-(7-methyl-1H-indol-3-yl)-ethylamino]-methyl}-phenyl)-ethylamino]-ethyl}-3H-benzothiazol-2-one;

7-{2-[2-(3-{[2-(2-Chloro-phenyl)-ethylamino]-methyl}-phenyl)-ethylamino]-1R-hydroxy-ethyl}-4-hydroxy-3H-benzothiazol-2-one;

7-{2-[2-(3-{[2-(2-Methoxyphenyl)-ethylamino]-methyl}-phenyl)-ethylamino]-1R-hydroxy-ethyl}-4-hydroxy-3H-benzothiazol-2-one;

4-Hydroxy-7-[1R-hydroxy-2-(2-{3-[(2R-phenylcycloprop-1S-ylamino)-methyl]-phenyl}-ethylamino)-ethyl]-3H-benzothiazol-2-one;

7-{2-[2-(3-{[2S-(4-Fluoro-phenyl)-cycloprop-1R-ylamino]-methyl}-phenyl)-ethylamino]-1R-hydroxy-ethyl}-4-hydroxy-3H-benzothiazol-2-one;

4-Hydroxy-7-[1R-hydroxy-2-(2-{3-[(2-pyridin-2-yl-ethylamino)-methyl]-phenyl}-ethylamino)-ethyl]-3H-benzothiazol-2-one;

4-Hydroxy-7-[1R-hydroxy-2-(2-{3-[(2-methoxy-2-methyl-propylamino)methyl]-phenyl}ethylamino)ethyl]-3H-benzothiazol-2-one;

4-Hydroxy-7-[1R-hydroxy-2-(2-{3-[(2-methoxy-ethylamino)-methyl]-phenyl}-ethylamino)-ethyl]-3H-benzothiazol-2-one;

7-{2-[3-(3-{[2-(2,6-Dichloro-phenyl)-ethylamino]-methyl}-phenyl)-propylamino]-1R-hydroxy-ethyl}-4-hydroxy-3H-benzothiazol-2-one;

7-{2-[2-(3-{[2-(2,6-Dichloro-phenyl)-ethylamino]-methyl}-phenyl)-1-methyl-ethylamino]-1R-hydroxy-ethyl}-4-hydroxy-3H-benzothiazol-2-one;

4-Hydroxy-7-(1R-hydroxy-2-{2-[4-(2-phenylethyl)aminomethyl)phenyl]-ethylamino}ethyl)-3H-benzothiazol-2-one;

7-{2-[2-(4-{[2-(2,6-Dichloro-phenyl)-ethylamino]-methyl}-phenyl)-ethylamino]-1R-hydroxy-ethyl}-4-hydroxy-3H-benzothiazol-2-one;

7-{2-[2-(4-{[2-(2-Fluorophenyl)ethylamino]methyl}phenyl)ethylamino]-1R-hydroxyethyl}-4-hydroxy-3H-benzothiazol-2-one;

7-{2-[2-(4-{[2,2-diphenylethylamino]methyl}phenyl)ethylamino]-1R-hydroxyethyl}-4-hydroxy-3H-benzothiazol-2-one;

4-Hydroxy-7-{2-[2-(4-{[2-(2-methoxyphenyl)ethylamino]methyl}phenyl)ethylamino]-1R-hydroxy-ethyl}-3H-benzothiazol-2-one;

4-Hydroxy-7-{1R-hydroxy-2-[2-(4-{[2-(7-methyl-1H-indol-3-yl)-ethylamino]methyl}-phenyl)ethylamino]ethyl}-3H-benzothiazol-2-one;

4-Hydroxy-7-[1R-hydroxy-2-(2-{4-[(2-(2-pyridyl)ethylamino)methyl]phenyl}-ethylamino)ethyl]-3H-benzothiazol-2-one;

4-Hydroxy-7-[1R-hydroxy-2-(2-{4-[(2S-(4-fluorophenyl-1-cycloprop-1R-ylamino)methyl]phenyl}ethylamino)ethyl]-3H-benzothiazol-2-one;

4-Hydroxy-7-[1R-hydroxy-2-(2-{4-[(2S-phenyl-propylamino)-methyl]-phenyl}-ethylamino)-ethyl]-3H-benzothiazol-2-one;

7-{2-[2-(2-{[2-(2-Fluoro-phenyl)-ethylamino]-methyl}-phenyl)-ethylamino]-1R-hydroxy-ethyl}-4-hydroxy-3H-benzothiazol-2-one;

4-Hydroxy-7-[1-hydroxy-2-(2-{2'-[(3-isopropoxy-propylamino)-methyl]-biphenyl-4-yl}-ethylamino)-ethyl]-3H-benzothiazol-2-one;

4-hydroxy-7-[1R-hydroxy-2-({2-[2'-({[1R-phenylethyl]amino}methyl)biphenyl-4-yl]ethyl}amino)ethyl]-1,3-benzothiazol-2(3H)-one;

7-(2-{2-[3'-(1,3-Dihydro-iso-indol-2-ylmethyl)-biphenyl-4-yl]-ethylamino}-1R-hydroxy-ethyl)-4-hydroxy-3H-benzothiazol-2-one;

7-(2-{2-[3'-(Benzylamino-methyl)-biphenyl-3-yl]-ethylamino}-1R-hydroxy-ethyl)-4-hydroxy-3H-benzothiazol-2-one;

7-{2-[2-(3-{[2-(2-Fluoro-phenyl)-ethylamino]-methyl}-4-methoxy-phenyl)-ethylamino]-1R-hydroxy-ethyl}-4-hydroxy-3H-benzothiazol-2-one;

4-Hydroxy-7-[1R-hydroxy-2-(2-{3-[(3-phenyl-propylamino)-methyl]-phenyl}-ethylamino)-ethyl]-3H-benzothiazol-2-one;

4-Hydroxy-7-{1R-hydroxy-2-[2-(3-piperidin-1-ylmethyl-phenyl)-ethylamino]-ethyl}-3H-benzothiazol-2-one;

4-Hydroxy-7-(1R-hydroxy-2-{2-[3-(4-phenyl-piperidin-1-ylmethyl)-phenyl]-ethylamino}-ethyl)-3H-benzothiazol-2-one;

4-Hydroxy-7-[1R-hydroxy-2-(2-{3-[(methyl-phenethyl-amino)-methyl]-phenyl}-ethylamino)-ethyl]-3H-benzothiazol-2-one;

4-hydroxy-7-[(1R)-1-hydroxy-2-({2-[3-({[(1S)-2-methoxy-1-methylethyl]amino}methyl)phenyl]ethyl}amino)ethyl]-1,3-benzothiazol-2(3H)-one;

4-Hydroxy-7-[1R-hydroxy-2-({2-[3-({[2-methoxy]phenyl-1-methylethyl]amino}methyl)phenyl]ethyl}amino)ethyl]-1,3-benzothiazol-2(3H)-one;

4-Hydroxy-7-[1R-hydroxy-2-{2-[3-(isobutylaminomethyl)phenyl]-ethylamino}ethyl)]-3H-benzothiazol-2-one;

4-Hydroxy-7-[1R-hydroxy-2-(2-{3-[(3-iso-butoxypropylamino)methyl]phenyl}ethylamino)ethyl]-3H-benzothiazol-2-one;

4-Hydroxy-7-[1R-hydroxy-2-(2-{2'-[(2-pyridin-2-yl-ethylamino)-methyl]-biphenyl-4-yl}-ethylamino)-ethyl]-3H-benzothiazol-2-one;

4-Hydroxy-7-{1R-hydroxy-2-[2-(3-{[2-(1-oxy-pyridin-2-yl)-ethylamino]-methyl}-phenyl)-ethylamino]-ethyl}-3H-benzothiazol-2-one;

4-Hydroxy-7-[1R-hydroxy-2-(2-{3-[2-(2-methoxy-ethylamino)-ethyl]-phenyl}-ethylamino)-ethyl]-3H-benzothiazol-2-one;

4-Hydroxy-7-{1R-hydroxy-2-[2-(3-{2-[(pyridin-2-ylmethyl)-amino]-ethyl}-phenyl)-ethylamino]-ethyl}-3H-benzothiazol-2-one;

7-{2-[2-(3-{2-[2-(2-Fluoro-phenyl)-ethylamino]-ethyl}-phenyl)-ethylamino]-1R-hydroxy-ethyl}-4-hydroxy-3H-benzothiazol-2-one;

7-(2-{2-[3-(2-Cyclohexylamino-ethyl)-phenyl]-ethylamino}-1R-hydroxy-ethyl)-4-hydroxy-3H-benzothiazol-2-one;

4-Hydroxy-7-[1R-hydroxy-2-(2-{3-[2-(2-methoxy-benzylamino)-ethyl]-phenyl}-ethylamino)-ethyl]-3H-benzothiazol-2-one;

4-Hydroxy-7-{1R-hydroxy-2-[2-(3-{2-[2-(2-methoxy-phenyl)-ethylamino]-ethyl}-phenyl)-ethylamino]-ethyl}-3H-benzothiazol-2-one;

7-(2-{2-[3-(2-Azepan-1-yl-ethyl)-phenyl]-ethylamino}-1R-hydroxy-ethyl)-4-hydroxy-3H-benzothiazol-2-one;

4-Hydroxy-7-[1R-hydroxy-2-(2-{3-[2-(1S-methoxymethyl-3-methyl-butylamino)-ethyl]-phenyl}-ethylamino)-ethyl]-3H-benzothiazol-2-one;

4-Hydroxy-7-[1R-hydroxy-2-(2-{3-[(1S-methoxymethyl-3-methyl-butylamino)-methyl]-phenyl}-ethylamino)-ethyl]-3H-benzothiazol-2-one;

4-Hydroxy-7-[1R-hydroxy-2-(2-{3-[(2-methoxy-benzylamino)-methyl]-phenyl}-ethylamino)-ethyl]-3H-benzothiazol-2-one;

4-Hydroxy-7-{1R-hydroxy-2-[2-(3-pyrrolidin-1-ylmethyl-phenyl)-ethylamino]-ethyl}-3H-benzothiazol-2-one;

4-Hydroxy-7-{1R-hydroxy-2-(2-{4-piperidin-1-ylmethyl}phenyl)ethylamino)-ethyl}-3H-benzothiazol-2-one;

4-Hydroxy-7-{1R-hydroxy-2-[2-(4-isopropylaminomethyl)phenyl]ethylamino}-ethyl)-3H-benzothiazol-2-one;

4-Hydroxy-7-{1R-hydroxy-2-[2-(4-aminomethyl)phenyl]ethylamino}-ethyl)-3H-benzothiazol-2-one;

4-Hydroxy-7-{1R-hydroxy-2-[2-(4-{2-methoxy}ethylaminomethyl)phenyl]-ethylamino}-ethyl)-3H-benzothiazol-2-one;

4-Hydroxy-7-{1R-hydroxy-2-[2-(3-{2-hydroxyethylamino}methyl)phenyl]ethylamino}ethyl)-3H-benzothiazol-2-one;

4-Hydroxy-7-[1R-hydroxy-2-(2-{3-[(3-pyridin-2-yl-propylamino)-methyl]-phenyl}-ethylamino)-ethyl]-3H-benzothiazol-2-one;

4-Hydroxy-7-{1R-hydroxy-2-[2-(3-{[2-(2-hydroxy-phenyl)-ethylamino]-methyl}-phenyl)-ethylamino]-ethyl}-3H-benzothiazol-2-one;

4-Hydroxy-7-[1-hydroxy-2-(2-{3-[(2-hydroxy-benzylamino)-methyl]-phenyl}-ethylamino)-ethyl]-3H-benzothiazol-2-one;

7-[2-(2-{3-[(2-Fluoro-benzylamino)-methyl]-phenyl}-ethylamino)-1R-hydroxy-ethyl]-4-hydroxy-3H-benzothiazol-2-one;

4-Hydroxy-7-{1R-hydroxy-2-[2-(3-{[(pyridin-2-ylmethyl)-amino]-methyl}-phenyl)-ethylamino]-ethyl}-3H-benzothiazol-2-one;

4-Hydroxy-7-[1R-hydroxy-2-(2-{4-[(2-methoxy-benzylamino)-methyl]-phenyl}-ethylamino)-ethyl]-3H-benzothiazol-2-one;

4-Hydroxy-7-[1R-hydroxy-2-(2-{3-[(3-propoxy-propylamino)-methyl]-phenyl}-ethylamino)-ethyl]-3H-benzothiazol-2-one;

4-Hydroxy-7-[1R-hydroxy-2-(2-{3-[(3-isopropoxy-propylamino)-methyl]-phenyl}-ethylamino)-ethyl]-3H-benzothiazol-2-one;

4-Hydroxy-7-[1R-hydroxy-2-(2-{3-[(3-methoxy-benzylamino)-methyl]-phenyl}-ethylamino)-ethyl]-3H-benzothiazol-2-one;

7-[2-(2-{3-[(2-Ethoxy-benzylamino)-methyl]-phenyl}-ethylamino)-1R-hydroxy-ethyl]-4-hydroxy-3H-benzothiazol-2-one;

4-Hydroxy-7-[1R-hydroxy-2-(2-{3-[(4-methoxy-benzylamino)-methyl]-phenyl}-ethylamino)-ethyl]-3H-benzothiazol-2-one;

4-Hydroxy-7-{1R-hydroxy-2-[2-(3-{[[(2-methoxy-benzyl)-methyl-amino]-methyl}-phenyl)-ethylamino]-ethyl}-3H-benzothiazol-2-one;

4-Hydroxy-7-[1R-hydroxy-2-(2-{3-[(2-methoxy-benzylamino)-methyl]-phenyl}-ethylamino)-ethyl]-3H-benzothiazol-2-one;

4-Hydroxy-7-[1R-hydroxy-2-(2-{3-[(2-methoxy-benzylamino)-methyl]-phenyl}-ethylamino)-ethyl]-3H-benzothiazol-2-one;

7-{2-[2-(3-Azepan-1-ylmethyl-phenyl)-ethylamino]-1R-hydroxy-ethyl}-4-hydroxy-3H-benzothiazol-2-one;

4-Hydroxy-7-{1R-hydroxy-2-[2-(3-morpholin-4-ylmethyl-phenyl)-ethylamino]-ethyl}-3H-benzothiazol-2-one;

4-Hydroxy-7-{1R-hydroxy-2-[2-(3-piperidin-1-ylmethyl-phenyl)-ethylamino]-ethyl}-3H-benzothiazol-2-one;

4-Hydroxy-7-[1R-hydroxy-2-(2-{3-[(2-pyridin-2-yl-ethylamino)-methyl]-phenyl}-ethylamino)-ethyl]-3H-benzothiazol-2-one;

4-Hydroxy-7-[1R-hydroxy-2-(2-{3-[(1R-methoxymethyl-2-methyl-propylamino)-methyl]-phenyl}-ethylamino)-ethyl]-3H-benzothiazol-2-one;

4-Hydroxy-7-[1R-hydroxy-2-(2-{3-[(1R-methoxymethyl-2-methyl-propylamino)-methyl]-phenyl}-ethylamino)-ethyl]-3H-benzothiazol-2-one;

4-Hydroxy-7-[1R-hydroxy-2-(2-{3-[(1R-methoxymethyl-propylamino)-methyl]-phenyl}-ethylamino)-ethyl]-3H-benzothiazol-2-one;

4-Hydroxy-7-[1R-hydroxy-2-(2-{3-[(1S-methoxymethyl-propylamino)-methyl]-phenyl}-ethylamino)-ethyl]-3H-benzothiazol-2-one; or, 4-Hydroxy-7-{1R-hydroxy-2-[2-(3-piperazin-1-ylmethyl-phenyl)-ethylamino]-ethyl}-3H-benzothiazol-2-one;

or a pharmaceutically acceptable salt thereof.

The present invention further provides each of the compounds listed above as an individual compound, or a pharmaceutically acceptable salt thereof.

The present invention further provides a process for the preparation of a compound of formula (I) or a pharmaceutically acceptable salt thereof as defined above which comprises:

(a) when $R^1$ represents hydrogen and $R^3$ and $R^4$ do not represent hydrogen, reacting a compound of formula (II)

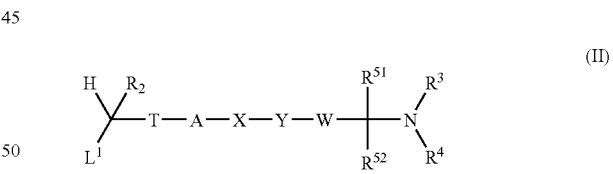

wherein $L^1$ represents a leaving group (e.g. chlorine, bromine, iodine, methanesulfonate or para-toluenesulfonate) and $R^2$, $R^3$, $R^4$, T, A, X, Y, W, $R^{51}$ and $R^{52}$ are as defined in formula (I), with a compound of formula (III), or a suitable salt thereof (e.g. hydrobromide or hydrochloride salt)

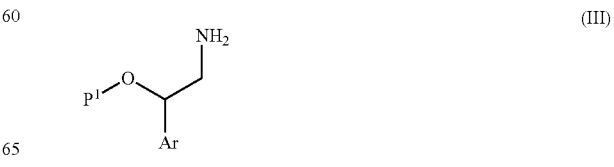

wherein Ar is as defined in formula (I) and $P^1$ is hydrogen or a protective group (e.g. tert-butyldimethyl silyl) in the presence of a base (e.g. potassium carbonate, triethylamine or diisopropylethylamine), followed by removal of the protective group (e.g. using hydrofluoric acid-pyridine complex); or (b) when $R^1$ represents hydrogen and $R^3$ or $R^4$ do not represent hydrogen, reacting a compound of formula (IV), or a suitable salt thereof

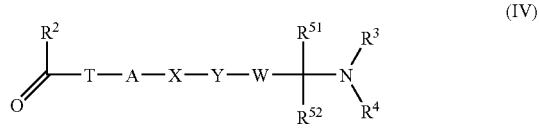

(IV)

wherein $R^2$, $R^3$, $R^4$, T, A, X, Y, W, $R^{51}$ and $R^{52}$ are as defined in formula (I), with a compound of formula (III) or a suitable salt thereof in the presence of a suitable reducing agent (e.g. sodium cyanoborohydride, sodium triacetoxyborohydride, or hydrogen in the presence of a suitable palladium on carbon or palladium oxide catalyst); or (c) when $R^1$ represents hydrogen and $R^3$ represents hydrogen, reacting a compound of formula (V)

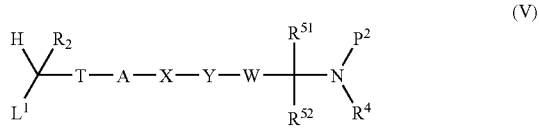

(V)

wherein $L^1$ represents a leaving group (e.g. chlorine, bromine, iodine, methanesulfonate or para-toluenesulfonate), $P^2$ represents a protective group (e.g. tert-butylcarbamate) and $R^2$, $R^1$, T, A, X, Y, W, $R^{51}$ and $R^{52}$ are as defined in formula (I), with a compound of formula (III), or a suitable salt thereof (e.g. hydrobromide or hydrochloride salt), in the presence of a base (e.g. potassium carbonate, triethylamine or diisopropylethylamine) followed by removal of the protective group (e.g. treatment with hydrochloric or trifluoroacetic acid); or (d) when $R^1$ represents hydrogen and $R^3$ represents hydrogen, reacting a compound of formula (VI)

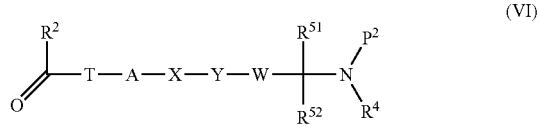

(VI)

wherein $R^2$, $R^4$, T, A, X, Y, W, $R^{51}$ and $R^{52}$ are as defined in formula (I), $P^2$ represents a protective group (e.g. tert-Butyl-carbamate) with a compound of formula (III), or a suitable salt thereof, in the presence of a suitable reducing agent (e.g. sodium cyanoborohydride, sodium triacetoxyborohydride, or hydrogen in the presence of a suitable palladium on carbon or palladium oxide catalyst), followed by removal of the protective group (e.g. treatment with hydrochloric or trifluoroacetic acid); or (e) when $R^3$ and $R^4$ do not represent hydrogen, reacting a compound of formula (VII), or a suitable salt thereof

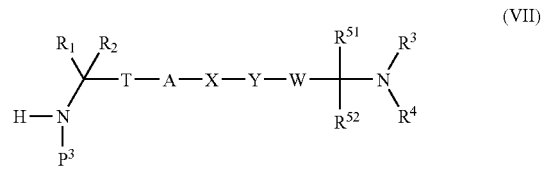

(VII)

wherein $R^1$, $R^2$, $R^3$, $R^4$, T, A, X, Y, W, $R^{51}$ and $R^{52}$ are as defined in formula (I), $P^3$ represents hydrogen or an activating group (e.g. 3-nitrophenylsulfonyl) with a compound of formula (VIII), or a suitable salt thereof,

(VIII)

wherein Ar is as defined in formula (I), $L^2$ represents a leaving group (e.g. chlorine, bromine, iodine, methanesulfonate or para-toluenesulfonate) and $P^1$ is as defined in compound of formula (III) in the presence of a base (e.g. when $P^3$ is hydrogen, potassium carbonate, triethylamine, diisopropylethylamine and, when $P^3$ is 3-nitrophenylsulfonyl, sodium hydride or lithium di-iso-propylamide), followed by removal of the protective groups (e.g. using hydrofluoric acid-pyridine complex, thiophenol, thioacetic acid); or with a compound of formula (IX), or a suitable salt thereof,

(IX)

wherein Ar is as defined in formula (I) in the presence of a base (e.g. when $P^3$ is hydrogen, potassium carbonate, triethylamine, diisopropylethylamine and, when $P^3$ is 3-nitrophenylsulfonyl, sodium hydride or lithium di-iso-propylamide), followed by removal of the protective groups (e.g. trifluoroacetic acid, thiophenol, thioacetic acid); or with a compound of formula (X), or a suitable salt thereof,

(X)

wherein Ar is as defined in formula (I), $L^2$ represents a leaving group (e.g. chlorine, bromine, iodine, methanesulfonate or para-toluenesulfonate) in the presence of a base (e.g. when $P^3$ is hydrogen, potassium carbonate, triethylamine, diisopropylethylamine and, when $P^3$ is 3-nitrophenylsulfonyl, sodium hydride or lithium di-iso-propylamide), followed by reduction of the ketone (e.g. using sodium borohydride or a borane/chiral catalyst complex), followed by removal of the protective groups (e.g. trifluoroacetic acid, thiophenol, thioacetic acid); or (f) when $R^3$ represents hydrogen, reacting a compound of formula (XI)

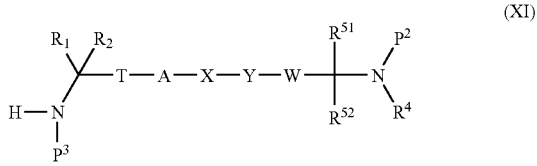

wherein $R^1$, $R^2$, $R^4$, T, A, X, Y, W, $R^{51}$ and $R^{52}$ are as defined in formula (I), $P^2$ represents a protective group (e.g. tert-Butylcarbamate) with a compound of formula (VIII), (IX) or (X), or a suitable salt thereof, in the presence of a base (e.g. when $P^3$ is hydrogen, potassium carbonate, triethylamine, diisopropylethylamine and when $P^3$ is 3-nitrophenylsulfonyl, sodium hydride or lithium di-iso-propylamide), followed by removal of the protective groups (e.g. using trifluoroacetic acid, thiophenol, thioacetic acid); or (g) when $R^{51}$ and $R^{52}$ each represents hydrogen, reacting a compound of formula (XII)

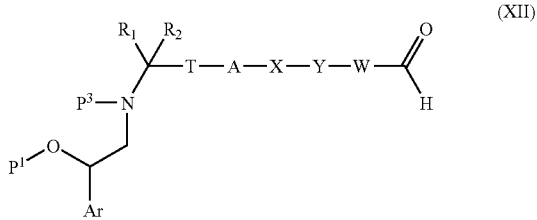

wherein Ar, $R^1$, $R^2$, T, A, X, Y, and W are as defined in formula (I), $P^1$ is as defined in compound of formula (III), $P^3$ represents a protective group (e.g. tert-butylcarbamate or 3-nitrophenylsulfonyl) with a compound of formula (XIII), or a suitable salt thereof,

wherein $R^3$ and $R^4$ are as defined in formula (I), in the presence of a suitable reducing agent (e.g. sodium cyanoborohydride, sodium triacetoxyborohydride, or hydrogen in the presence of a suitable palladium on carbon or palladium oxide catalyst), followed by removal of the protective groups (e.g. treatment with hydrochloric or trifluoroacetic acid; thiophenol, thioacetic acid); or (h) when $R^{51}$ and $R^{52}$ each represents hydrogen, reacting a compound of formula (XIV)

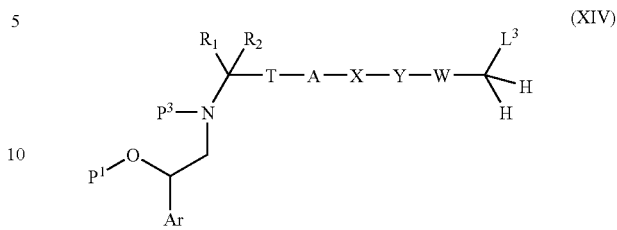

wherein Ar, $R^1$, $R^2$, T, A, X, and W are as defined in formula (I), $P^1$ is as defined in compound of formula (III), $P^3$ represents a protective group (e.g. tert-Butylcarbamate or 3-nitrophenylsulfonyl), $L^3$ represents a leaving group (e.g. chlorine, bromine, iodine, methanesulfonate or para-toluenesulfonate), with a compound of formula (XIII) or a suitable salt thereof, in the presence of a base (e.g. potassium carbonate, triethylamine, diisopropylethylamine), followed by removal of the protective groups (e.g. trifluoroacetic acid, thiophenol, thioacetic acid); or (i) when $R^1$ and $R^2$ each represents hydrogen and $R^3$ or $R^4$ do not represent hydrogen, reacting a compound of formula (XV), or a suitable salt thereof,

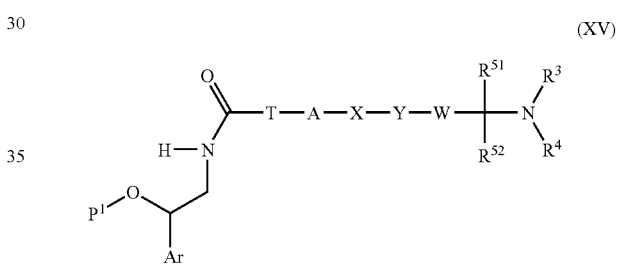

wherein $R^3$, $R^4$, T, A, X, Y W, $R^{51}$ and $R^{52}$ are as defined in formula (I) and $P^1$ is as defined in formula (III) with a suitable reducing agent (e.g. lithium aluminium hydride or borane tetrahydrofuran complex), followed by removal of the protective group (e.g. using hydrofluoric acid-pyridine complex); or, (j) when $R^1$ and $R^2$ each represents hydrogen and $R^3$ represents hydrogen, reacting a compound of formula (XVI)

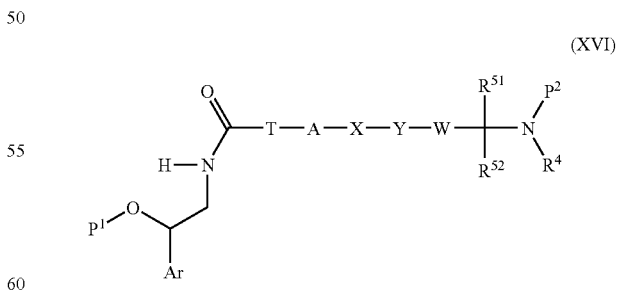

wherein $R^4$, T, A, X, Y, W, $R^{51}$ and $R^{52}$ are as defined in formula (I) and $P^2$ is as defined in compound of formula (XI) with a suitable reducing agent (e.g. lithium aluminium hydride or borane tetrahydrofuran complex), followed by removal of the protective group (e.g. using hydrofluoric acid-pyridine complex); or, and optionally after (a), (b), (c), (d), (e), (f), (g), (h), (i) or (j) carrying out one or more of the following:

a) converting the compound obtained to a further compound of the invention b) forming a pharmaceutically acceptable salt of the compound.

In process (a), (c), (e) and (f), the reaction may conveniently be carried out in an organic solvent such as N,N-dimethylformamide, ethanol, n-butanol or dimethyl sulfoxide, at a temperature, for example, in the range from 50 to 140° C.

In process (b), (d) and (g), the reaction may conveniently be carried out in an organic solvent such as methanol, ethanol, dichloromethane, acetic acid N-methylpyrrolidinone, or N,N-dimethylformamide containing up to 10% w of water and acetic acid.

In process (i) and (j), the reaction may conveniently be carried out in an organic solvent such as tetrahydrofuran, at a temperature, for example, in the range from 0 to 80° C.

Compounds of formula (II) may be prepared by reacting a compound of formula (XVII), or a suitable salt thereof,

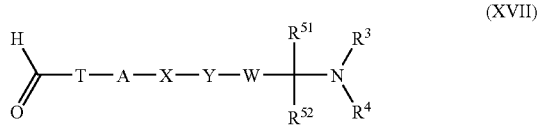

(XVII)

wherein $R^3$, $R^4$, T, A, X, Y, W, $R^{51}$ and $R^{52}$ are as defined in formula (II), with a compound of formula (XVIII)

$R^2$—Mt (XVIII)

wherein $R^2$ is as defined in formula (II) and Mt represents a metal such as lithium or magnesium, or aluminium or boron (e.g. methyllithium, methylmagnesium bromide, lithium aluminium hydride, sodium borohydride) in an organic solvent, for example, tetrahydrofuran or ether, at a temperature, for example in the range from 0 to 60° C., followed by conversion of the resulting hydroxyl group into a suitable leaving group (e.g. chlorine, bromine, iodine, methanesulfonate or para-toluenesulfonate).

Compounds of formula (IV) may be prepared by reacting a compound of formula (XVII) with a compound of formula (XVIII) in an organic solvent, for example, tetrahydrofuran or ether, at a temperature, for example in the range from 0 to 60° C., followed by oxidation of the resulting hydroxyl group with a suitable oxidating agent (e.g. Swern reagent).

Compounds of formula (V) may be prepared by reacting a compound of formula (XIX)

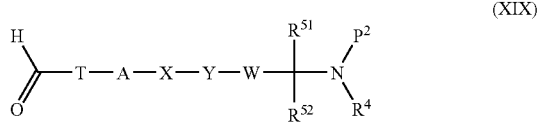

(XIX)

wherein $P^2$, $R^4$, T, A, X, Y, W, $R^{51}$ and $R^{52}$ are as defined in formula (V), with a compound of formula (XVIII) in an organic solvent, for example, tetrahydrofuran or ether, at a temperature, for example in the range from 0 to 60° C., followed by conversion of the resulting hydroxyl group into a suitable leaving group (e.g. chlorine, bromine, iodine, methanesulfonate or para-toluenesulfonate).

Compounds of formula (VI) may be prepared by reacting a compound of formula (XVIII) with a compound of formula (XIX), followed by oxidation of the resulting hydroxyl group with a suitable oxidating agent (e.g. Swern reagent, Dess-Martin reagent or pyridiniumchlorochromate) in an organic solvent such as dichloromethane, N,N-dimethylformamide or dimethylsulfoxide at a temperature, for example in the range from −78 to 60° C.

Compounds of formula (VII) in which $R^1$ represents hydrogen and $R^2$, $R^3$, $R^4$, T, A, X, Y, W, $R^{51}$ and $R^{52}$ are as defined in formula (VII) may be prepared by (a) reacting a compound of formula (II) with sodium azide, in an organic solvent for example, tetrahydrofuran, N,N-dimethylformamide or dimethylsulfoxide at a temperature, for example in the range from 25 to 85° C., followed by reduction of the resulting azido compound using a suitable reducing agent (e.g. triphenylphosphine) in an organic solvent for example, tetrahydrofuran and water, and eventually followed by protection of the resulting amine (e.g. treatment with 3-nitrophenylsulfonyl chloride in the presence of a base such as pyridine); or, (b) reacting a compound of formula (IV) with an amine (e.g. benzylamine, α-methyl benzylamine, 4-methoxybenzylamine or 2,4-methoxybenzylamine) followed by reduction of the resulting imine using a suitable reducing agent (e.g. sodium cyanoborohydride or sodium triacetoxyborohydride) in an organic solvent such as methanol, ethanol, dichloromethane, acetic acid, N-methylpyrrolidinone or N,N-dimethylformamide containing up to 10% w of water and acetic acid, followed by removal of the resulting benzyl protective group using the appropriate reagent (e.g. hydrogen and a suitable catalyst (Palladium on carbon or palladium hydroxyde), 2,3-dichloro-5,6-dicyanobenzoquinone (DDQ), or ammonium cerium nitrate (CAN)) in an organic solvent, for example, ethanol, methanol, tetrahydrofuran, dichloromethane, acetonitrile, water, or a mixture thereof, at a temperature ranging from 25 to 80° C., and eventually followed by protection of the resulting amine (e.g. treatment with 3-nitrophenylsulfonyl chloride in the presence of a base such as pyridine);

Compounds of formula (VII) in which $R^1$ and $R^2$, $R^3$, $R^4$, T, A, X, Y, W, $R^{51}$ and $R^{52}$ are as defined in formula (VII) may be prepared by reacting a compound of formula (XX)

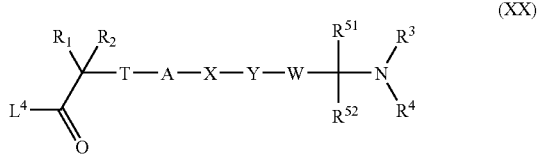

(XX)

wherein $L^4$ is a leaving group (e.g. hydroxyl or chlorine), $R^1$, $R^2$, $R^3$, $R^4$, T, A, X, Y, W, $R^{51}$ and $R^{52}$ are as defined in formula (VII), with reagents such as, when $L^4$ is hydroxyl, diphenylphosphonic azide, in a presence of an amine (e.g. triethylamine), in an organic solvent, for example, tert-butanol, tetrahydrofuran, dichloromethane, water, or a mixture thereof, at a temperature ranging from 25 to 100° C., or when $L^4$ is chlorine, sodium azide, in an organic solvent, for example, ether, tert-butanol, tetrahydrofuran, water, or a mixture thereof, at a temperature ranging from 25 to 100° C. (Angewandte Chemie, 2005, 54, 5188), eventually followed by protection of the resulting amine (e.g. treatment with 3-nitrophenylsulfonyl chloride in the presence of a base such as pyridine).

Compounds of formula (III), (VIII), (IX) and (X) are known in the literature or may be prepared using known techniques.

Compounds of formula (XI) in which $R^1$ represents hydrogen may be prepared by (a) reacting a compound of formula (V) with sodium azide in an organic solvent, for example, tetrahydrofuran, N,N-dimethylformamide or dimethylsulfoxide at a temperature, for example in the range from 25 to 85° C., followed by reduction of the resulting azido compound using a suitable reducing agent (e.g. triphenylphosphine or hydrogen) in an organic solvent for example, tetrahydrofuran and water, eventually followed by protection of the resulting amine (e.g. treatment with 3-nitrophenylsulfonyl chloride in the presence of a base such as pyridine); or, (b) reacting a compound of formula (VI) with an amine (e.g. benzylamine, α-methyl benzylamine, 4-methoxybenzyl amine or 2,4-methoxybenzyl amine), followed by reduction of the resulting imine using a suitable reducing agent (e.g. sodium cyanoborohydride, sodium triacetoxyborohydride) in an organic solvent such as methanol, ethanol, dichloromethane, acetic acid N-methylpyrrolidinone, or N,N-dimethylformamide containing up to 10% w of water and acetic acid, followed by removal of the resulting benzyl protective group using the appropriate reagent (e.g. hydrogen and a suitable catalyst (Palladium on carbon or palladium hydroxide), 2,3-dichloro-5,6-dicyanobenzoquinone (DDQ), or ammonium cerium nitrate (CAN)) in an organic solvent, for example, ethanol, methanol, tetrahydrofuran, dichloromethane, acetonitrile, water, or a mixture thereof, at a temperature ranging from 25 to 80° C., eventually followed by protection of the resulting amine (e.g. treatment with 3-nitrophenylsulfonyl chloride in the presence of a base such as pyridine);

Compounds of formula (XI) may be prepared by reacting a compound of formula (XXI)

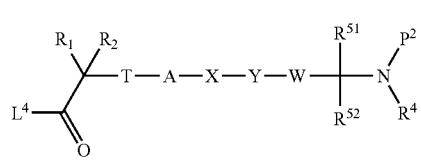

(XXI)

wherein $L^4$ is a leaving group (e.g. hydroxyl or chloride), $R^1$, $R^2$, $P^2$, $R^4$, T, A, X, Y, W, $R^{51}$ and $R^{52}$ are as defined in formula (XI), with reagents such as, when $L^4$ is hydroxyl, diphenylphosphonic azide, in a presence of an amine (e.g. triethylamine), in an organic solvent, for example, tert-butanol, tetrahydrofuran, dichloromethane, water, or a mixture thereof, at a temperature ranging from 25 to 100° C., or when $L^4$ is chlorine, sodium azide, in an organic solvent, for example, ether, tert-butanol, tetrahydrofuran, water, or a mixture thereof, at a temperature ranging from 25 to 100° C. (Angewandte Chemie, 2005, 54, 5188), eventually followed by protection of the resulting amine (e.g. treatment with 3-nitrophenylsulfonyl chloride in the presence of a base such as pyridine).

Compounds of formula (XII) can be prepared by
(a) reacting a compound of formula (XXII)

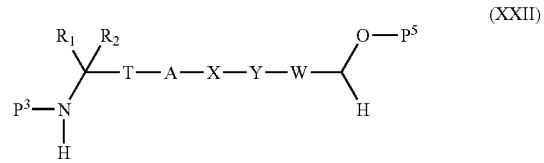

(XXII)

wherein $P^5$ is hydrogen or a protective group (e.g. tert-butyldimethylsilyl, tetrahydropyran) and $R^1$, $R^2$, $P^3$, T, A, X, Y, and W are as defined in formula (XII), with a compound of formula (VIII), (IX) or (X), or a suitable salt thereof, in the presence of a base (e.g. potassium carbonate, triethylamine or diisopropylethylamine when $P^3$ is hydrogen and sodium hydride or lithium di-iso-propylamide when $P^3$ is 3-nitrophenylsulfonyl) in an organic solvent such as N,N-dimethylformamide, N-methylpyrrolidinone, tetrahydrofuran, ethanol, n-butanol or dimethyl sulfoxide, at a temperature, for example, in the range from 50 to 140° C., followed by appropriate selective removal of the protective group (e.g. hydrofluoric acid-pyridine complex, tetrabutylammonium fluoride, diluted hydrochloric acid or amberlyst-15 resin in methanol) and oxidation of the resulting alcohol into the corresponding aldehyde with a suitable oxidating agent (pyridinium chlorochromate, Dess-martin reagent or Swern reagent); or, (b) reacting a compound of formula (XXIII)

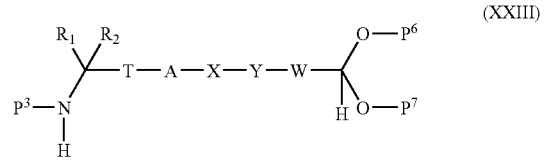

(XXIII)

wherein $P^6$ and $P^7$ represent an acyclic or cyclic carbonyl protective group (e.g. dimethoxy or diethoxy acetal, 1,3-dioxolane or 1,3-dioxane) and $R^1$, $R^2$, $P^3$, T, A, X, Y and W are as defined in formula (XII), with a compound of formula (VIII), (IX) or (X), or a suitable salt thereof, in the presence of a base (e.g. potassium carbonate, triethylamine or diisopropylethylamine when $P^3$ is hydrogen and sodium hydride or lithium di-iso-propylamide when $P^3$ is 3-nitrophenylsulfonyl) in an organic solvent such as N,N-dimethylformamide, N-methylpyrrolidinone, tetrahydrofuran, ethanol, n-butanol or dimethyl sulfoxide, at a temperature, for example, in the range from 50 to 140° C., followed by removal of the protective group (e.g. diluted hydrochloric acid or amberlyst-15 resin in methanol); or, (c) when $R^1$ represents hydrogen, reacting a compound of formula (XXIV)

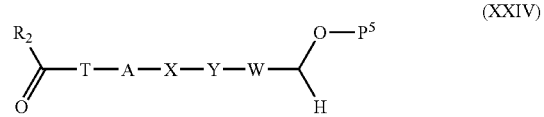

(XXIV)

wherein $P^5$ is hydrogen or a protective group (e.g. tert-butyldimethylsilyl, tetrahydropyran) and $R^2$, T, A, X, Y and W are as defined in formula (XII), with a compound of formula (III), or a suitable salt thereof, in the presence of a suitable reducing agent (e.g. sodium cyanoborohydride, sodium triacetoxyborohydride, or hydrogen in the presence of a suitable palladium on carbon or palladium oxide catalyst) in an organic solvent such as methanol, ethanol, dichloromethane, acetic acid, N-methypyrrolidinone or N,N-dimethylformamide containing up to 10% w of water and acetic acid, followed by appropriate selective removal of the protective group (e.g. hydrofluoric acid-pyridine complex, tetrabutylammonium fluoride, diluted hydrochloric acid or amberlyst-15 resin in methanol) and oxidation of the resulting alcohol into the corresponding aldehyde with a suitable oxidating agent (pyridinium chlorochromate, Dess-Martin reagent or Swern reagent); or, (d) when $R^1$ represents hydrogen, reacting a compound of formula (XXV)

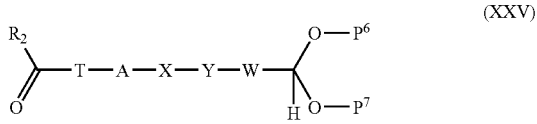

(XXV)

wherein $P^6$ and $P^7$ represent an acyclic or cyclic carbonyl protective group (e.g. dimethoxy or diethoxy acetal, 1,3-dioxolane or 1,3-dioxane) and $R^2$, T, A, X, Y and W are as defined in formula (XII), with a compound of formula (III), or a suitable salt thereof, in the presence of a suitable reducing agent (e.g. sodium cyanoborohydride, sodium triacetoxyborohydride, or hydrogen in the presence of a suitable palladium on carbon or palladium oxide catalyst) in an organic solvent such as methanol, ethanol, dichloromethane, acetic acid, N-methypyrrolidinone or N,N-dimethylformamide containing up to 10% w of water and acetic acid, followed by removal of the protective group (e.g. diluted hydrochloric acid or amberlyst-15 resin in methanol).

(e) when A and Y do not represent a bond, X represents a bond, reacting a compound of formula (XXVI)

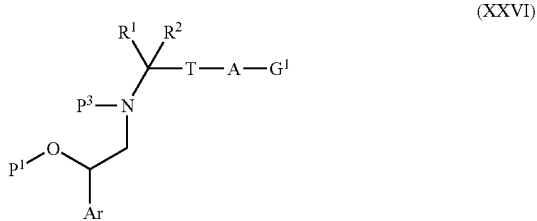

(XXVI)

wherein Ar, T, A, $R^1$, $R^2$, $P^1$ and $P^3$ are as defined in formula (XII), $G^1$ is either a halogen atom (e.g. bromide) or a sulfonate (e.g. triflate, nonaflate), 1—with a compound of formula (XXVII), or a suitable salt thereof,

(XXVII)

wherein Y and W are as defined in formula (XII) and B represents a boronic acid, an acyclic or cyclic boronate functionality (e.g. B(OH)$_2$, B(OMe)$_2$, boronic acid pinacol ester (B(OMe$_2$)$_2$)) or a trifluoroborate salt (e.g. BF$_3$K$^-$) in presence of a suitable metal transition catalyst and eventually of a suitable ligand, 2—with a compound of formula (XXVIII), or a suitable salt thereof,

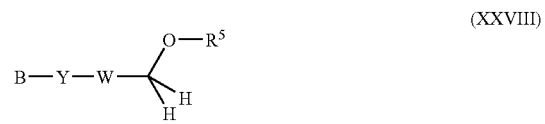

(XXVIII)

wherein Y and W are as defined in formula (XII), B is as defined above and $P^5$ is as defined in formula (XXII) in presence of a suitable metal transition catalyst and eventually of a suitable ligand, eventually followed by appropriate selective removal of the protective group (e.g. hydrofluoric acid-pyridine complex, tetrabutylammonium fluoride, diluted hydrochloric acid or amberlyst-15 resin in methanol) and oxidation of the resulting alcohol into the corresponding aldehyde with a suitable oxidating agent (pyridinium chlorochromate, Dess-Martin reagent or Swern reagent), 3—with a compound of formula (XXIX), or a suitable salt thereof,

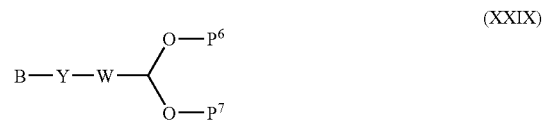

(XXIX)

wherein Y and W are as defined in formula (XII), B is as defined in compound of formula (XXVII) and $P^6$ and $P^7$ are as defined in formula (XXIII), in presence of a suitable metal transition catalyst and eventually of a suitable ligand, followed by removal of the protective group (e.g. diluted hydrochloric acid or amberlyst-15 resin in methanol);

(f) when A and Y do not represent a bond and X represents a bond, reacting a compound of formula (XXX)

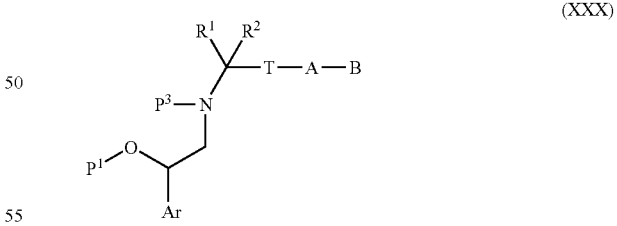

(XXX)

wherein Ar, T, A, $R^1$, $R^2$, $P^1$ and $P^3$ are as defined in formula (XII), B is as defined in compound of formula (XXVII) with a compound of formula (XXXI), (XXXII) or (XXXIII)

(XXXI)

-continued

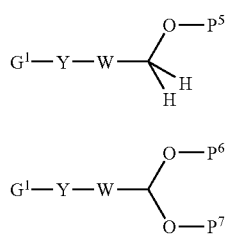
(XXXII)

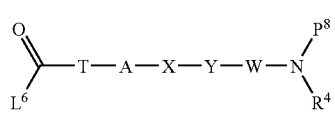
(XXXIII)

wherein Y and W are as defined in compound of formula (XII), $G^1$ is as defined in compound of formula (XXVI), $P^5$ is as defined in compound of formula (XXII) and $P^6$ and $P^7$ are as defined in formula (XXIII), in presence of a suitable metal transition catalyst and eventually of a suitable ligand, followed by removal of the protective group (e.g. diluted hydrochloric acid or amberlyst-15 resin in methanol).

Compounds of formula (XIV) can be prepared by converting compound of formula (XII), or a precursor to compound of formula (XII) as described above, choosing an appropriate sequence of reactions such as, for example, reduction of an aldehyde to an alcohol (e.g. sodium borohydride), appropriate selective removal of the protective group (e.g. hydrofluoric acid-pyridine complex, tetrabutylammonium fluoride, diluted hydrochloric acid or amberlyst-15 resin in methanol) and conversion of an alcohol into a suitable leaving group (e.g. halogen, mesylate, tosylate); or, Compounds of formula (XV) and (XVI) can be prepared by similar methods by (a) reacting a compound of formula (XXXVIII)

(XXXVIII)

wherein T, A, X, Y, W and $R^4$ are as defined in formula (XV), $P^8$ represents either $R^3$ as defined in compound of formula (XV) or $P^2$ as defined in compound of formula (XVI) and $L^6$ represent hydroxyl or a leaving group (e.g. chlorine) with a compound of formula (III), or a suitable salt thereof.

When $L^6$ represents hydroxyl, the reaction is conveniently carried out in the presence of an activating reagent, for example, carbonyldiimidazole or O-(7-azabenzotriazol-1-yl)-N,N,N',N'-tetramethyluroniumhexafluorophosphate (HATU), in an organic solvent, for example, N,N-dimethylformamide or dichloromethane, at a temperature, for example in the range from 0 to 60° C., When $L^6$ represents chlorine, the reaction is conveniently carried out in the presence of a base, for example, triethylamine or diisopropylethylamine in an organic solvent, for example, dichloromethane or tetrahydrofuran at a temperature, for example, in the range from 0 to 25° C. or (b) when A and Y do not represent a bond and X represents a bond, reacting a compound of formula (XXXIX)

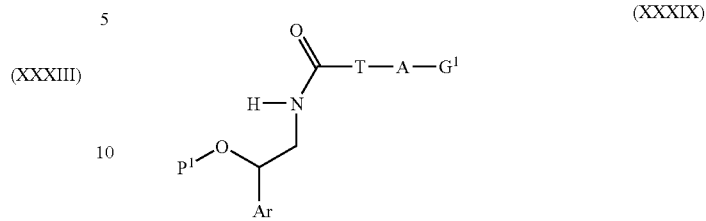
(XXXIX)

wherein Ar, T, A, and $P^1$ are as defined in formula (XV), $G^1$ is as defined in compound of formula (XXVI), 1—with a compound of formula (XXXX)

(XXXX)

$$B-Y-W-N\begin{matrix}P^8\\R^4\end{matrix}$$

wherein Y, $R^4$, W and $P^8$ are as defined in formula (XXXVIII) and B is as defined in compound of formula (XXVII), in presence of a metal transition catalyst and eventually of a suitable ligand, followed by removal of the protective groups (e.g. treatment with hydrofluoric acid, tetra-butylammonium fluoride or trifluoroacetic acid); or, 2—with a compound of formula (XXVII), (XXVIII) or (XXIX) in presence of a suitable metal transition catalyst and eventually of a suitable ligand, eventually followed by selective removal of the protective group and/or an oxidation step, followed by reaction with a compound of formula (XIII), or a suitable salt thereof, in the presence of a suitable reducing agent (e.g. sodium cyanoborohydride, sodium triacetoxyborohydride, or hydrogen in the presence of a suitable palladium on carbon or palladium oxide catalyst), followed by removal of the protective groups (e.g. treatment with hydrofluoric acid, tetra-butylammonium fluoride or trifluoroacetic acid;); or (c) when A and Y do not represent a bond and X represents a bond, reacting a compound of formula (XXXXI)

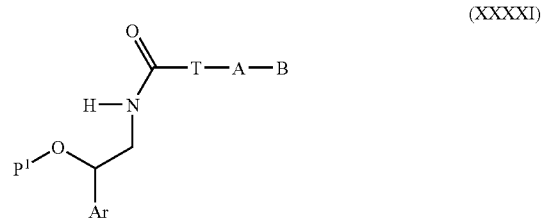
(XXXXI)

wherein Ar, T, A, and $P^1$ are as defined in formula (XV) and B is as defined in compound of formula (XXVII), with a compound of formula (XXXXII)

(XXXXII)

wherein Y, $R^4$, W and $P^8$ are as defined in formula (XXXX) and $G^1$ is as defined in compound of formula (XXV), in presence of a suitable metal transition catalyst and eventually of a suitable ligand, eventually followed by removal of the protective group; or (d) when A and Y do not represent a bond and X represents a bond, reacting a compound of formula (XXXXI) with compound of formula (XXXI), (XXXII) or (XXXIII), in presence of a suitable metal transition catalyst and eventually of a suitable ligand, eventually followed by selective removal of the protective group and/or an oxidation step, followed by reaction with a compound of formula (XIII), or a suitable salt thereof, in the presence of a suitable reducing agent (e.g. sodium cyanoborohydride, sodium triacetoxyborohydride, or hydrogen in the presence of a suitable palladium on carbon or palladium oxide catalyst), followed by removal of the protective groups (e.g. treatment with hydrofluoric acid, tetra-butylammonium fluoride or trifluoroacetic acid).

In the preparation of compounds of formula (XII), (XV) and (XVI), the reactions above involving a metal transition catalyst are well established in the literature (for example: Tetrahedron. Lett. 2006, 47, 1525; Tetrahedron. Lett. 2005, 61, 3835; Tetrahedron. Lett. 2004, 45, 8225 and references cited herein). They can be performed under numerous reaction conditions and may involve a catalyst such as tetrakis(triphenylphosphine)palladium(0), palladium(II)acetate or dichloro-bis-(triphenylphosphine)palladium(II). The reactions eventually require the presence of a suitable ligand such as tri-(phenyl)phosphine, tri-(tert-butyl)phosphine, tri-(o-tolyl)phosphine, S-Phos, X-Phos and are generally performed in the presence of a base such as triethylamine, a carbonate salt (e.g. sodium, potassium, cesium), potassium fluoride, a phosphate salt (e.g. potassium phosphate), in an organic solvent such as toluene, water, ethanol, methanol, tert-butanol, tetrahydrofuran, N,N-dimethylformamide, N-methylpyrrolidinone, or a mixture thereof, and conveniently performed in a range of temperature from 25 to 140° C. In addition, other metal transitions can also be used such as nickel and cobalt (Tetrahedron. Lett. 2005, 46, 2849; Chem. Lett. 2004, 33, 1740 and references cited herein).

Also the process above refers to simple oxidation and reduction steps, these are performed under standard conditions well established in the literature (e.g. Dess-Martin, Swern, pyridiumchlorochromate, pyridiniumsulfurtrioxide complex oxidations). They can be conveniently performed in an organic solvent such as dichloromethane, in a range of temperature from −78 to 50° C. (Annual Reports on the Progress of Chemistry, Section B: Organic Chemistry 2004, 100, 51-70).

Compounds of formula (XVII), (XVIII), (XIX), (XX), (XXI), (XXII), (XXIII), (XXIV), (XXV), (XXVI), (XXVII), (XXVIII), (XXIX), (XXX), (XXXI), (XXXII), (XXXIII), (XXXVIII), (XXXIX), (XXXX), (XXXXI) and (XXXXII) are either commercially available, known in the literature, or can be readily prepare by those skilled in the art using one of the process described above or using known techniques.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

Compounds of formula (I) can be converted into further compounds of formula (I) using standard procedures.

The compounds of formula (I) and their pharmaceutically acceptable salts can be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g. migraine, rhinitis and eczema.

Thus, the present invention provides a compound of formula (I) or a pharmaceutically-acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating, or reducing the risk of, an inflammatory disease or condition (including a reversible obstructive airways disease or condition) which comprises administering to a patient in need thereof a therapeutically effective amount of a compound of formula (I) or a pharmaceutically acceptable salt thereof as hereinbefore defined.

In particular, the compounds of this invention may be used in the treatment of adult respiratory distress syndrome (ARDS), pulmonary emphysema, bronchitis, bronchiectasis, chronic obstructive pulmonary disease (COPD), asthma and rhinitis.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Dry powder formulations and pressurized HFA aerosols of the compounds of the invention may be administered by oral or nasal inhalation. For inhalation, the compound is desirably finely divided. The finely divided compound preferably has a mass median diameter of less than 10 μm, and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

The invention therefore further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with the following agents: non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and $CX_3CR1$ for the $C-X_3-C$ family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrolate, ipratropium bromide, tiotropium bromide, oxitropium bromide, pirenzepine or telenzepine.

The present invention further relates to the combination of a compound of the invention, or a pharmaceutically acceptable salt thereof, and a chromone, such as sodium chromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amityptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof. A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; (xxvii) inhibitor of transcription factor activation such as NFkB, API or STATS; or (xxviii) a glucocorticoid receptor (GR-receptor) agonist.

Where such a combination is to be administered by inhalation, then the one or more agents in addition to a compound of formula (I), or a pharmaceutically acceptable salt thereof, can be selected from the list comprising:

a PDE4 inhibitor including an inhibitor of the isoform PDE4D;

a glucocorticoid receptor agonist, {for example a non-steroidal glucocorticoid receptor agonist, or steroidal glucocorticoid receptor agonist (such as budesonide)};

a muscarinic receptor antagonist (for example a M1, M2 or M3 antagonist, such as a selective M3 antagonist) such as ipratropium bromide, tiotropium bromide, oxitropium bromide, pirenzepine, telenzepine or a glycopyrromium bromide (such as R,R-glycopyrronium bromide or a mixture of R,S- and S,R-glycopyrronium bromide);

a modulator of chemokine receptor function (such as a CCR1 receptor antagonist); or, an inhibitor of p38 kinase function.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4- fluorophenyl)-7-methoxy-6-(3-morpholinopropoxy)quinazolin-4-amine (gefitinib, AZD1839), N-(3-ethynylphenyl)-6,7-bis (2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);
(vi) a vascular damaging agent such as combretastatin A4, or a compound disclosed in WO 99/02166, WO 00/40529, WO 00/41669, WO 01/92224, WO 02/04434 or WO 02/08213;
(vii) an agent used in antisense therapy, for example one directed to one of the targets listed above, such as ISIS 2503, an anti-ras antisense;
(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or
(ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The present invention will now be further explained by reference to the following illustrative examples.

General Methods $^1$H NMR spectra were recorded on a Varian Inova 400 MHz or a Varian Mercury-VX 300 MHz instrument. The central peaks of chloroform-d ($\delta_H$ 7.27 ppm), dimethylsulfoxide-d$_6$ ($\delta_H$ 2.50 ppm), acetonitrile-d$_3$ ($\delta_H$ 1.95 ppm) or methanol-d$_4$ ($\delta_H$ 3.31 ppm) were used as internal references. Column chromatography was carried out using silica gel (0.040-0.63 mm, pre-packed biotage KP-Sil cartridges). Unless stated otherwise, starting materials were commercially available. All solvents and commercial reagents were of laboratory grade and were used as received.

Compounds were named using the Autonom software.

The following method was used for LC/MS analysis: Instrument Agilent 1100; Column Waters Symmetry C$_{18}$, 2.1×50 mm; Mass APCI or multimode (APcI+ESI; Flow rate 1 ml/min; Wavelength 220 nm; Solvent A: water+0.1% TFA; Solvent B: acetonitrile+0.1% TFA; Gradient 5-95%/B over 2.5 min.

Purification by reversed phase preparative HPLC was carried out using a gradient of acetonitrile in 0.1% aqueous TFA solution using either Method A on a SunFire™ prep C18 OBD™ 5 µm 19×50 mm column (Waters Corporation) at a flow rate of 20 mL/min. or Method B on a SunFire™ prep C8 OBD™ 5 µm 30×100 mm column (Waters Corporation) at a flow rate of 35 mL/min or Method C SymmetryPrep® C8 Column 5 µm 19×50 mm (Waters Corporation) at a flow rate of 20 mL/min.

The abbreviations or terms used in the examples have the following meanings:
SCX: Silica based solid phase extraction with a sulfonic acid sorbent
Tosic-65A: Polymer based solid phase extraction with a sulfonic acid sorbent.
Both of the above resins are conditioned before use by washing with the appropriate solvent.

HPLC: High performance liquid chromatography
DMF: N,N-Dimethylformamide

EXAMPLE 1

7-{2-[2-(3-{[2-(2,6-Dichloro-phenyl)-ethylamino]-methyl}-phenyl)-ethylamino]-1R-hydroxy-ethyl}-4-hydroxy-3H-benzothiazol-2-one bis-trifluoroacetate salt

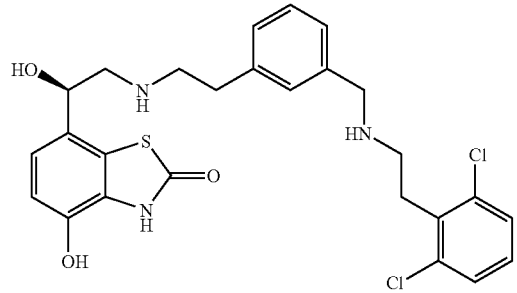

a) (3-Formyl-phenyl)-acetic acid ethyl ester

N-bromosuccinimide (1.78 g) and 2,2'-azobis(2-methyl-propionitrile) (16 mg) were added to a solution of ethyl-3-methylphenylacetate (1.76 mL) in chloroform (18 mL) and heated to reflux for 3 hours. On cooling the mixture was diluted with chloroform (40 mL), washed sequentially with saturated aqueous sodium bicarbonate solution (2×50 mL), brine (50 mL), dried (sodium sulfate) and concentrated. The residue was dissolved in nitrogen degassed dimethylsulfoxide (50 mL) and sodium bicarbonate (13.5 g) added. The mixture was heated at 100° C., under nitrogen for 30 min. The reaction was cooled in an ice-bath and poured into brine (300 mL). The aqueous phase was extracted with diethyl ether (3×300 mL). The combined organics were dried (sodium sulfate) and concentrated. Purification on silica, eluting with 10% diethyl ether in iso-hexane, to afford the subtitle compound as a yellow oil (1.23 g).

$^1$H NMR (400 MHz, CDCl$_3$) δ 10.04 (s, 1H), 7.82-7.78 (m, 2H), 7.59-7.48 (m, 2H), 4.17 (q, 2H), 3.70 (s, 2H), 1.26 (t, 3H).

b) [3-({tert-Butoxycarbonyl-[2-(2,6-dichloro-phenyl)-ethyl]-amino}-methyl)-phenyl]-acetic acid 2-(2,6-Dichlorophenyl)ethylamine (0.27 g) was added to a solution of (3-formyl-phenyl)-acetic acid ethyl ester (0.29 g) and acetic acid (90 µL) in methanol (10 mL), stirred at room temperature, under nitrogen. After 1 hour, sodium triacetoxyborohydride (0.45 g) was added and stirred for 18 hours, under nitrogen, then evaporated. The residue was dissolved in ethanol (5 mL) and applied to a conditioned SCX cartridge (10 g Varian). The cartridge was washed with ethanol (3×20 mL) and then eluted with a mixture of ethanol and 0.880 ammonia solution [4:1] (2×15 mL). The combined elution fractions were concentrated, the residue was dissolved in dimethylformamide (5 mL) and a solution of di-tert-butyl dicarbonate (0.49 g) in dimethylformamide (0.3 mL) was added. The reaction mixture was stirred for 18 hours at room temperature. The reaction was poured in to water and extracted with ethyl acetate (3×50 mL). The combined organics were washed sequentially with saturated aqueous sodium bicarbonate solution (50 mL), brine (50 mL), dried (magnesium sulfate) and evaporated. The residue was dissolved in tetrahydrofuran (10 mL) and a solution of lithium hydroxide (216 mg) in water (5 mL) added. The resulting mixture stirred for 18 hours at room temperature, under nitrogen. The pH was adjusted to pH~4 with acetic acid and the mixture concentrated to ~2 mL. The residue was extracted with ethyl acetate (3×10 mL), the organics were combined, washed with brine (10 mL), dried (magnesium sulfate) and concentrated to give the subtitle compound as a gum (205 mg).

m/z 437 (M−H)− (APCI)

$^1$H NMR (300 MHz, CDCl$_3$) δ 7.33-7.21 (m, 3H), 7.22-7.01 (m, 4H), 4.52-4.27 (m, 2H), 3.63 (s, 2H), 3.42-3.26 (m, 2H), 3.25-3.10 (m, 2H), 1.48 (s, 9H). CO$_2$H not seen.

c) 7-{2-[2-(3-{[2-(2,6-Dichloro-phenyl)-ethylamino]-methyl}-phenyl)-ethylamino]-1R-hydroxy-ethyl}-4-hydroxy-3H-benzothiazol-2-one bis-trifluoroacetate salt

[3-({tert-Butoxycarbonyl-[2-(2,6-dichloro-phenyl)-ethyl]-amino}-methyl)-phenyl]-acetic acid (205 mg), 7-(2-amino-1R-hydroxy-ethyl)-4-hydroxy-3H-benzothiazol-2-one hydrochloride (129 mg), 4-dimethylaminopyridine (143 mg) and 1-(3-dimethylaminopropyl)-3-ethylcarbodiimide hydrochloride (107 mg) were combined in dimethylformamide (5 mL). The resulting mixture was stirred for 18 hours, under nitrogen. The reaction was diluted with methanol (5 mL) and loaded onto a conditioned SCX cartridge (10 g Varian). The cartridge was washed with methanol (3×20 mL) and the combined washings concentrated. A portion of the residue (150 mg) was dissolved in dry tetrahydrofuran (10 mL) and heated to reflux, under nitrogen. Borane-tetrahydrofuran complex (1M in tetrahydrofuran, 0.28 mL) was added dropwise and heating continued at reflux for 1 hour. On cooling, a few drops of 0.880 ammonia solution were added and the reaction mixture concentrated. The residue was suspended in dichloromethane (2 mL) and trifluoroacetic acid (0.5 mL) added. The reaction mixture was stirred for 20 min and concentrated. Purification by HPLC method C to give the title compound as a white solid (17 mg).

m/z 532 (M+H)+ (Agilent multimode)

$^1$H NMR (400 MHz, DMSO) δ 11.69 (s, 1H), 10.21 (s, 1H), 9.21 (s, 2H), 8.83 (s, 2H), 7.51 (d, 2H), 7.46-7.41 (m, 2H), 7.39-7.29 (m, 3H), 6.94 (d, 1H), 6.78 (d, 1H), 6.53-6.49 (m, 1H), 4.94-4.87 (m, 1H), 4.28-4.21 (m, 2H), 3.32-3.23 (m, 4H), 3.19-2.91 (m, 6H).

EXAMPLE 2

7-[2-(2-{3-[(2,2-Diphenyl-ethylamino)-methyl]-phenyl}-ethylamino)-1R-hydroxy-ethyl]-4-hydroxy-3H-benzothiazol-2-one bis-trifluoroacetate salt

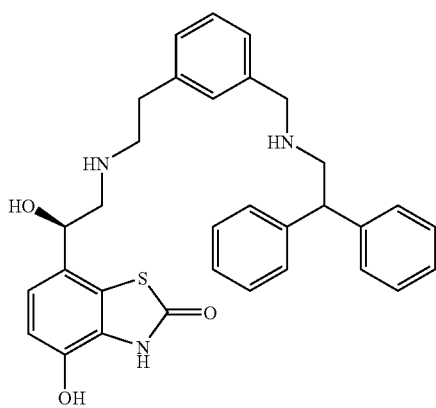

a) (3-{[tert-Butoxycarbonyl-(2,2-diphenyl-ethyl)-amino]-methyl}-phenyl)-acetic acid Prepared from (3-formyl-phenyl)-acetic acid ethyl ester (Example 1, step a, 290 mg) and 2,2-diphenethylamine (280 mg) using the method of Example 1 (step b), to give the subtitle compound as an oil (314 mg).

m/z 444 (M−H)− (APCI)

b) 2-{3-[(2,2-Diphenyl-ethylamino)-methyl]-phenyl}-N-[2R-hydroxy-2-(4-hydroxy-2-oxo-2,3-dihydro-benzothiazol-7-yl)-ethyl]-acetamide 1-(3-Dimethylaminopropyl)-3-ethylcarbodiimide hydrochloride (160 mg) was added to a solution of 7-(2-amino-1R-hydroxy-ethyl)-4-hydroxy-3h-benzothiazol-2-one hydrochloride (190 mg), (3-{[tert-butoxycarbonyl-(2,2-diphenyl-ethyl)-amino]-methyl}-phenyl)-acetic acid (314 mg) and 4-dimethylaminopyridine (210 mg) in dimethylformamide (10 mL) and stirred for 18 hours. The reaction was concentrated, the residue dissolved in methanol and loaded onto a conditioned SCX cartridge (10 g, Varian). The cartridge was washed with methanol (50 mL) and concentrated. The residue was dissolved in dichloromethane (5 mL) and trifluoroacetic acid (0.5 mL) was added, the resulting mixture was stirred for 30 minutes then concentrated. Purification on silica, eluting with a gradient of methanol (2.5% to 7.5%) in dichloromethane, gave the subtitle compound as a pale brown solid (130 mg).

m/z 554 (M+H)+ (APCI)

$^1$H NMR (400 MHz, DMSO) δ 11.55 (s, 1H), 10.00 (s, 1H), 8.97 (s, 2H), 8.15 (t, 1H), 7.37-7.30 (m, 11H), 7.27-7.21 (m, 3H), 6.81 (d, 1H), 6.71 (d, 1H), 4.56 (dd, 1H), 4.46 (t, 1H), 4.15-4.10 (m, 2H), 3.70-3.63 (m, 2H), 3.42 (s, 2H), 3.29-3.20 (m, 1H), 3.18-3.10 (m, 1H).

c) 7-[2-(2-{3-[(2,2-Diphenyl-ethylamino)-methyl]-phenyl}-ethylamino)-1R-hydroxy-ethyl]-4-hydroxy-3H-benzothiazol-2-one bis-trifluoroacetate salt Borane-tetrahydrofuran complex (1M solution in tetrahydrofuran, 1.2 mL) was added over 5 hours, to a solution of 2-{3-[(2,2-diphenyl-ethylamino)-methyl]-phenyl}-N-[2R-hydroxy-2-(4-hydroxy-2-oxo-2,3-dihydro-benzothiazol-7-yl)-ethyl]-acetamide (120 mg) in dry tetrahydrofuran (3 mL), at 50° C. The reaction was cooled to room temperature, quenched with water and concentrated. The residue was redissolved in propan-2-ol and loaded onto conditioned Tosic-65A resin (5 g, Argonaut). The resin was washed with acetonitrile:propan-2-ol [1:1] (50 mL) and eluted with 0.880 ammonia solution in propan-2-ol [1:4] (30 mL). The eluted fraction was evaporated and purified by HPLC Method C to give the title compound as a white solid (4.9 mg).

m/z 540 (M+H)+ (Agilent multimode)

$^1$H NMR (400 MHz, DMSO) δ 11.69 (s, 1H), 10.23 (s, 1H), 8.99-8.71 (m, 4H), 7.44-7.20 (m, 12H), 7.14-6.95 (m, 2H), 6.93 (d, 1H), 6.78 (d, 1H), 6.52-6.48 (m, 1H), 5.75 (s, 1H), 4.90 (s, 1H), 4.44-4.32 (m, 1H), 4.15 (s, 2H), 3.73-3.60 (m, 1H), 3.44-2.81 (m, 6H).

EXAMPLE 3

7-[2-(2-{3-[(2-Chloro-benzylamino)-methyl]-phenyl}-ethylamino)-1R-hydroxy-ethyl]-4-hydroxy-3H-benzothiazol-2-one bis-trifluoroacetate salt

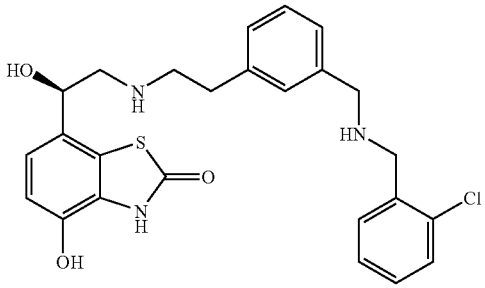

a) (2-Chlorobenzyl)-[3-(2-hydroxy-ethyl)-benzyl]-carbamic acid tert-butyl ester 2-Chlorobenzylamine (0.28 g) was added to a solution of (3-formyl-phenyl)-acetic acid ethyl ester (Example 1, step a)(0.38 g,) and acetic acid (114 µL) in ethanol (10 mL). After 1 hour, sodium triacetoxyborohydride (1.27 g) was added and the reaction mixture stirred for 18 hours. A few drops of 0.880 ammonia solution were added and the reaction concentrated. The residue was dissolved in ethanol (5 mL) and loaded onto a conditioned SCX cartridge (10 g Varian). The cartridge was washed with ethanol (3×20 mL) and eluted with ethanol/0.880 ammonia solution [4:1] (2×15 mL). The combined elution fractions were evaporated. The residue was dissolved in dimethylformamide (5 mL) and a solution of di-tert-butyl dicarbonate (0.48 g) in dimethylformamide (5 mL) added. The resulting mixture was stirred for 18 hours, then evaporated. The residue was dissolved in ethanol (10 mL) and calcium chloride (0.44 g) added, followed by sodium borohydride (0.30 g). The reaction mixture was stirred for 3 hours at room temperature. 2M Aqueous potassium carbonate solution (20 mL) was added and the reaction concentrated to ~20 mL. The aqueous suspension was extracted with ethyl acetate (3×100 mL). The combined organics were washed with brine (100 mL), dried (magnesium sulfate) and concentrated. Purification on silica, eluting with iso-hexane/ethyl acetate [4:1], to afford the subtitle compound as a pale yellow oil (330 mg).

m/z 376 (M+H)$^+$ (APCI)

$^1$H NMR (300 MHz, DMSO, 90° C.) δ 7.40-7.36 (m, 1H), 7.33-7.17 (m, 4H), 7.12-7.00 (m, 3H), 4.46 (s, 2H), 4.37 (s, 2H), 4.25 (t, 1H), 3.61 (td, 2H), 2.70 (t, 2H), 1.39 (s, 9H).

b) 7-[2-(2-{3-[(2-Chloro-benzylamino)-methyl]-phenyl}-ethylamino)-1R-hydroxy-ethyl]-4-hydroxy-3H-benzothiazol-2-one bis-trifluoroacetate salt Dess-Martin periodinane (450 mg) was added to a solution of the (2-chlorobenzyl)-[3-(2-hydroxyethyl)-benzyl]-carbamic acid tert-butyl ester (330 mg) in dry dichloromethane (30 mL) and stirred, under nitrogen, for 1 hour. The reaction was poured onto a mixture of ethyl acetate (30 mL), saturated aqueous sodium thiosulfate solution (30 mL) and saturated aqueous sodium bicarbonate solution (30 mL), and was stirred vigorously for 10 minutes. The aqueous phase was separated and extracted with ethyl acetate (30 mL). The combined organics were washed with water (50 mL), dried (magnesium sulfate) and evaporated. A portion of the crude aldehyde (220 mg) was dissolved in methanol (10 mL) and 7-(2-amino-1R-hydroxy-ethyl)-4-hydroxy-3H-benzothiazol-2-one hydrochloride (100 mg) was added followed by acetic acid (22 µL) and stirred under nitrogen. After 1 hour, sodium cyanoborohydride (36 mg) was added and the reaction stirred for 18 hours. The reaction was quenched with a few drops of 0.880 ammonia solution and concentrated. The residue was dissolved in acetonitrile/propan-2-ol [1:1] and loaded onto conditioned Tosic-65A resin (2 g, Argonaut). The resin was washed with acetonitrile/propan-2-ol [1:1] (50 mL) and eluted with propan-2-ol/0.880 ammonia solution [4:1] (30 mL). The elution fraction was concentrated. The residue was dissolved in dichloromethane (5 mL) and trifluoroacetic acid (2 mL) was added, stirred for 20 minutes and concentrated. Purification by HPLC, method A, and subsequent trituration with diethyl ether afforded the title compound (98 mg).

m/z 484 (M+H)$^+$ (Agilent multimode)

$^1$H NMR (500 MHz, DMSO) δ 11.67 (s, 1H), 10.28 (s, 1H), 9.49 (s, 2H), 9.00 (s, 1H), 8.84 (s, 1H), 7.62 (d, 1H), 7.55 (d, 1H), 7.50-7.28 (m, 6H), 6.93 (d, 1H), 6.78 (d, 1H), 6.51 (s, 1H), 4.91 (d, 1H), 4.33-4.18 (m, 4H), 3.24-2.91 (m, 6H).

EXAMPLE 4

7-{2-[2-(3-{[2-(2-Fluoro-phenyl)-ethylamino]-methyl}-phenyl)-ethylamino]-1R-hydroxy-ethyl}-4-hydroxy-3H-benzothiazol-2-one bis-trifluoroacetate salt

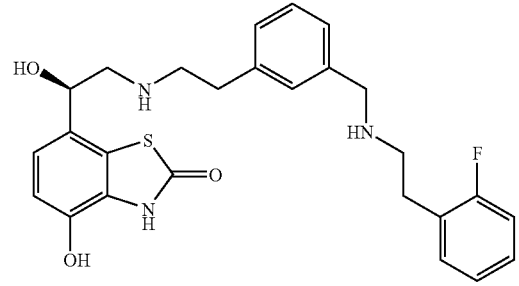

a) [2-(2-Fluoro-phenyl)-ethyl]-[3-(2-hydroxy-ethyl)-benzyl]-carbamic acid tert-butyl ester Prepared from 2-(2-fluorophenyl)ethylamine (0.28 g) and (3-formyl-phenyl)-acetic acid ethyl ester (Example 1, step a, 0.38 g) using the method of Example 3 (step a), to give the subtitle compound as a pale yellow oil (277 mg).

m/z 374 (M+H)$^+$ (APCI)

$^1$H NMR (300 MHz, DMSO, 90° C.) δ 7.29-6.99 (m, 8H), 3.67-3.56 (m, 2H), 3.36 (t, 2H), 2.99 (s, 2H), 2.78 (t, 2H), 2.72 (t, 2H), 1.36 (s, 9H). OH not seen.

b) 7-{2-[2-(3-{[2-(2-Fluoro-phenyl)-ethylamino]-methyl}-phenyl)-ethylamino]-1R-hydroxy-ethyl}-4-hydroxy-3H-benzothiazol-2-one bis-trifluoroacetate salt Prepared from [2-(2-fluoro-phenyl)-ethyl]-[3-(2-hydroxy-ethyl)-benzyl]-carbamic acid tert-butyl ester (0.277 g) and 7-(2-amino-1R-hydroxy-ethyl)-4-hydroxy-3H-benzothiazol-2-one hydrochloride (0.1 g) using the method of Example 3, step b, to give the title compound as a white solid (75 mg).

m/z 482 (M+H)+ (Agilent multimode)

¹H NMR (500 MHz, DMSO, 90° C.) δ 11.67 (s, 1H), 10.28 (s, 1H), 9.23-8.77 (m, 4H), 7.49-7.01 (m, 8H), 6.93 (d, 1H), 6.78 (d, 1H), 6.51 (s, 1H), 4.92 (d, 1H), 4.19 (s, 2H), 3.23-2.91 (m, 10H).

EXAMPLE 5

4-Hydroxy-7-[1R-hydroxy-2-(2-{3-[(2-methoxy-1R-methyl-ethylamino)-methyl]-phenyl}-ethylamino)-ethyl]-3H-benzothiazol-2-one bis-trifluoroacetate salt and 4-Hydroxy-7-[1R-hydroxy-2-(2-{3-[(2-methoxy-5-methyl-ethylamino)-methyl]-phenyl}-ethylamino)-ethyl]-3H-benzothiazol-2-one bis-trifluoroacetate salt

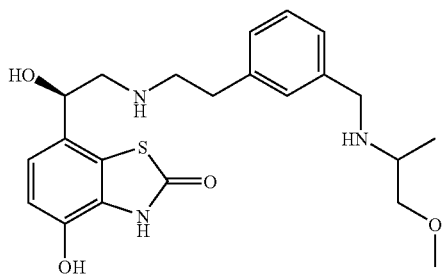

a) [3-(2-Hydroxy-ethyl)-benzyl]-(2-methoxy-1-methyl-ethyl)-carbamic acid tert-butyl ester Prepared from 2-amino-1-methoxypropane (180 mg) and (3-formyl-phenyl)-acetic acid ethyl ester (Example 1, step a, 380 mg) using the method of Example 3 (step a), to give the subtitle compound as a pale yellow oil (152 mg).

m/z 324 (M+H)+ (APCI)

¹H NMR (300 MHz, DMSO) δ 7.22-7.14 (m, 1H), 7.11-7.02 (m, 3H), 4.31 (d, 2H), 4.26-4.21 (m, 1H), 4.10-3.96 (m, 1H), 3.61 (dt, 2H), 3.39 (dd, 1H), 3.25 (dd, 1H), 3.17 (s, 3H), 2.71 (t, 2H), 1.36 (s, 9H) 1.03 (d, 3H).

b) 4-Hydroxy-7-[1R-hydroxy-2-(2-{3-[(2-methoxy-1-methyl-ethylamino)-methyl]-phenyl}-ethylamino)-ethyl]-3H-benzothiazol-2-one bis-trifluoroacetate salt Prepared from [3-(2-hydroxy-ethyl)-benzyl]-(2-methoxy-1-methyl-ethyl)-carbamic acid tert-butyl ester (152 mg) and 7-(2-amino-1R-hydroxy-ethyl)-4-hydroxy-3H-benzothiazol-2-one hydrochloride (0.1 g) using the method of Example 3 (step b), to give the title compound as a white solid (121 mg).

m/z 432 (M+H)+ (Agilent multimode)

¹H NMR (300 MHz, DMSO, 90° C.) δ 7.43-7.34 (m, 3H), 7.33-7.25 (m, 1H), 6.94 (d, 1H), 6.77 (d, 1H), 4.93 (dd, 1H), 4.15 (s, 2H), 3.56-3.52 (m, 2H), 3.44-3.34 (m, 2H), 3.29-3.19 (m, 3H), 3.16-3.08 (m, 3H), 3.06-2.98 (m, 2H), 1.27 (d, 3H). 7H exchangeable not seen at elevated temperature.

EXAMPLE 6

4-Hydroxy-7-{1R-hydroxy-2-[2-(3-{[2-(7-methyl-1H-indol-3-yl)-ethylamino]-methyl}-phenyl)-ethylamino]-ethyl}-3H-benzothiazol-2-one bis-trifluoroacetate salt

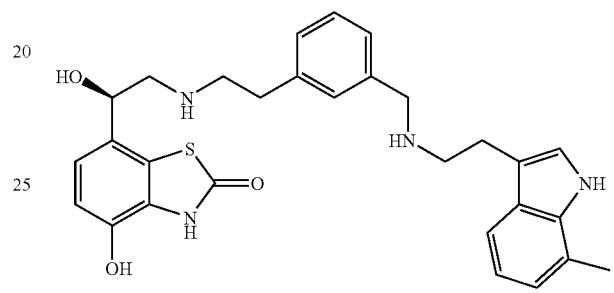

a) [3-(2-Hydroxy-ethyl)-benzyl]-[2-(7-methyl-1H-indol-3-yl)-ethyl]-carbamic acid tert-butyl ester Prepared from 7-methyltryptamine (350 mg). and (3-formyl-phenyl)-acetic acid ethyl ester (Example 1, step a, 380 mg) using the method of Example 3 (step a). Purification on silica, eluting with a gradient of iso-hexane/ethyl acetate [1:1 to 0:1], to give the subtitle compound as a pale brown oil (440 mg).

m/z 409 (M+H)+ (APCI)

¹H NMR (300 MHz, DMSO, 90° C.) δ 10.45 (s, 1H), 7.30-7.16 (m, 2H), 7.11-7.00 (m, 4H), 6.89-6.82 (m, 2H), 4.35 (s, 2H), 4.24 (t, 1H), 3.66-3.58 (m, 2H), 3.43-3.35 (m, 2H), 2.89-2.81 (m, 2H), 2.71 (t, 2H), 2.42 (s, 3H), 1.39 (s, 9H).

b) 4-Hydroxy-7-{1R-hydroxy-2-[2-(3-{[2-(7-methyl-1H-indol-3-yl)-ethylamino]-methyl}-phenyl)-ethylamino]-ethyl}-3H-benzothiazol-2-one bis-trifluoroacetate salt Prepared from [3-(2-hydroxy-ethyl)-benzyl]-[2-(7-methyl-1H-indol-3-yl)-ethyl]-carbamic acid tert-butyl ester (200 mg) and 7-(2-amino-1R-hydroxy-ethyl)-4-hydroxy-3H-benzothiazol-2-one hydrochloride (0.1 g) using the method of Example 3 (step b), to give the title compound as a tan solid (37 mg).

m/z 517 (M+H)+ (Agilent multimode)

¹H NMR (300 MHz, DMSO, 90° C.) 10.65 (s, 1H), 7.41-7.27 (m, 5H), 7.16 (d, 1H), 6.96-6.87 (m, 3H), 6.77 (d, 1H), 4.91 (dd, 1H), 4.19 (s, 2H), 3.28-2.93 (m, 10H), 2.44 (s, 3H). 7H exchangeable not seen at elevated temperature.

EXAMPLE 7

7-{2-[2-(3-{[2-(2-Chloro-phenyl)-ethylamino]-methyl}-phenyl)-ethylamino]-1R-hydroxy-ethyl}-4-hydroxy-3H-benzothiazol-2-one bis-trifluoroacetate salt

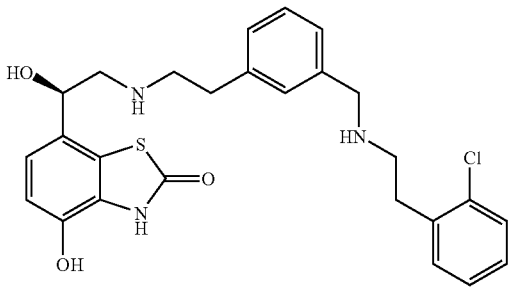

a) [2-(2-Chloro-phenyl)-ethyl]-[3-(2-hydroxy-ethyl)-benzyl]-carbamic acid tert-butyl ester Prepared from 2-(2-chlorophenyl)ethylamine (310 mg) and (3-formyl-phenyl)-acetic acid ethyl ester (Example 1, step a, 380 mg) using the method of Example 3 (step a), to give the subtitle compound as a pale yellow oil (180 mg).

m/z 390 (M+H)+ (APCI)
1H NMR (300 MHz, DMSO, 90° C.) δ 7.39-7.32 (m, 1H), 7.25-7.17 (m, 4H), 7.12-7.00 (m, 3H), 4.32 (s, 2H), 4.25 (t, 1H), 3.62 (td, 2H), 3.37 (t, 2H), 2.88 (t, 2H), 2.71 (t, 2H), 1.37 (s, 9H).

b) 7-{2-[2-(3-{[2-(2-Chloro-phenyl)-ethylamino]-methyl}-phenyl)-ethylamino]-1R-hydroxy-ethyl}-4-hydroxy-3H-benzothiazol-2-one bis-trifluoroacetate Prepared from [2-(2-chloro-phenyl)-ethyl]-[3-(2-hydroxy-ethyl)-benzyl]-carbamic acid tert-butyl ester (200 mg) and 7-(2-amino-1R-hydroxy-ethyl)-4-hydroxy-3H-benzothiazol-2-one hydrochloride (0.1 g) using the method of Example 3 (step b), to give the title compound as a white solid (90 mg).

m/z 498 (M+H)+ (Agilent multimode)
1H NMR (300 MHz, DMSO, 90° C.) δ 7.48-7.11 (m, 8H), 6.94 (d, 1H), 6.77 (d, 1H), 4.95-4.86 (m, 1H), 4.18 (s, 2H), 3.27-3.05 (m, 10H). 7H exchangeable not seen at elevated temperature.

EXAMPLE 8

7-{2-[2-(3-{[2-(2-Methoxyphenyl)-ethylamino]-methyl}-phenyl)-ethylamino]-1R-hydroxy-ethyl}-4-hydroxy-3H-benzothiazol-2-one bis-trifluoroacetate salt

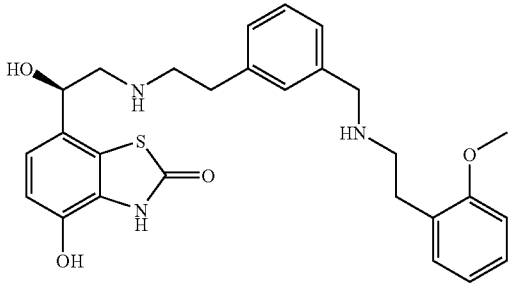

a) [2-(2-Methoxyphenyl)-ethyl]-[3-(2-hydroxy-ethyl)-benzyl]-carbamic acid tert-butyl ester Prepared from 2-(2-methoxyphenyl)ethylamine (300 mg) and (3-formyl-phenyl)-acetic acid ethyl ester (Example 1, step a, 380 mg) using the method of Example 3 (step a) to give the subtitle compound as a pale yellow oil (277 mg).

m/z 386 (M+H)+ (APCI)
1H NMR (300 MHz, DMSO, 90° C.) δ 7.24-7.13 (m, 2H), 7.10-6.99 (m, 4H), 6.92 (d, 1H), 6.86-6.80 (m, 1H), 4.29 (s, 2H), 4.25 (t, 1H), 3.76 (s, 3H), 3.61 (dt, 2H), 3.30 (t, 2H), 2.77-2.68 (m, 4H), 1.38 (s, 9H).

b) 7-{2-[2-(3-{[2-(2-Methoxy-phenyl)-ethylamino]-methyl}-phenyl)-ethylamino]-1R-hydroxy-ethyl}-4-hydroxy-3H-benzothiazol-2-one bis-trifluoroacetate salt Prepared from [2-(2-methoxyphenyl)-ethyl]-[3-(2-hydroxy-ethyl)-benzyl]-carbamic acid tert-butyl ester (275 mg) and 7-(2-amino-1R-hydroxy-ethyl)-4-hydroxy-3H-benzothiazol-2-one hydrochloride (0.1 g) using the method of Example 3 (step b), to give the title compound as a white solid (85 mg).

m/z 494 (M+H)+ (Agilent multimode)
1H NMR (300 MHz, DMSO, 90° C.) δ 7.49-7.23 (m, 5H), 7.19 (d, 1H), 7.06-6.90 (m, 3H), 6.81 (d, 1H), 4.96 (dd, 1H), 4.20 (s, 2H), 3.82 (s, 3H), 3.34-2.93 (m, 10H). 7H exchangeable not seen at elevated temperature.

EXAMPLE 9

4-Hydroxy-7-[1R-hydroxy-2-(2-{3-[(2R-phenylcycloprop-1S-ylamino)-methyl]-phenyl}-ethylamino)-ethyl]-3H-benzothiazol-2-one bis-trifluoroacetate salt

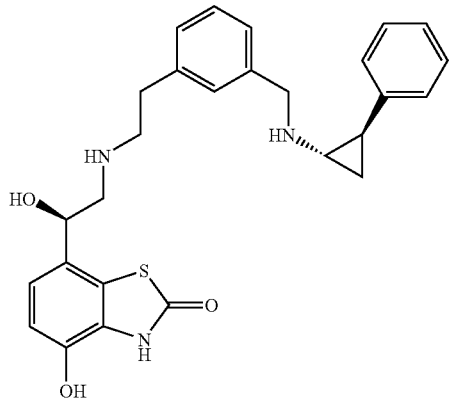

a) [3-(2-Hydroxy-ethyl)-benzyl]-(2R-phenyl-cycloprop-1S-yl)-carbamic acid tert-butyl ester Prepared from 1S,2R-(2-phenyl)cyclopropylamine (−)-tartrate salt [J. Med. Chem. (1986), 29(10), 2044-7] (270 mg) and (3-formyl-phenyl)-acetic acid ethyl ester (Example, 1 step a, 380 mg) using the method of Example 3 (step a), to give the subtitle compound as a pale yellow oil (100 mg).

m/z 368 (M+H)+ (APCI)
1H NMR (300 MHz, DMSO, 90° C.) δ 7.25-7.00 (m, 9H), 4.47 (d, 1H), 4.35 (d, 1H), 4.23 (t, 1H), 3.59 (td, 2H), 2.69 (t,

2H), 2.64-2.58 (m, 1H), 2.18-2.09 (m, 1H), 1.37 (s, 9H), 1.27 (dddd, 1H), 1.16-1.08 (m, 1H).

b) 4-Hydroxy-7-[1R-hydroxy-2-(2-{3-[(2R-phenyl-cycloprop-1S-ylamino)-methyl]-phenyl}-ethylamino)-ethyl]-3H-benzothiazol-2-one bis-trifluoroacetate salt Prepared from [3-(2-hydroxy-ethyl)-benzyl]-(2R-phenyl-cycloprop-1S-yl)-carbamic acid tert-butyl ester (100 mg) and 7-(2-amino-1R-hydroxy-ethyl)-4-hydroxy-3H-benzothiazol-2-one hydrochloride (70 mg) using the method of Example 3 (step b), to give the title compound as a white solid (64 mg).

m/z 476 (M+H)+ (Agilent multimode)

$^1$H NMR (300 MHz, DMSO, 90° C.) δ 7.39-7.14 (m, 7H), 7.08 (d, 2H), 6.94 (d, 1H), 6.77 (d, 1H), 4.90 (dd, 1H), 4.22 (s, 2H), 3.22-2.90 (m, 6H), 2.85-2.77 (m, 1H), 2.41-2.31 (m, 1H), 1.46-1.36 (m, 1H), 1.27-1.18 (m, 1H). 7H not seen at elevated temperature.

EXAMPLE 10

7-{2-[2-(3-{[2S-(4-Fluoro-phenyl)-cycloprop-1R-ylamino]-methyl}-phenyl)-ethylamino]-1R-hydroxy-ethyl}-4-hydroxy-3H-benzothiazol-2-one bis-trifluoroacetate salt

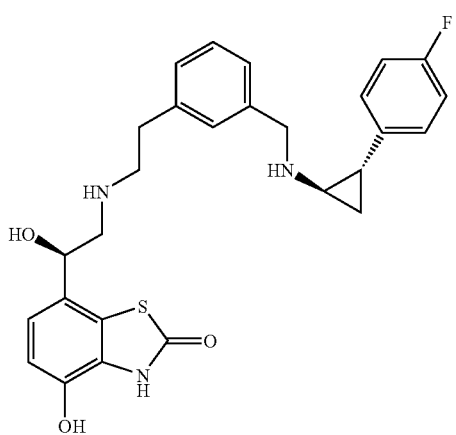

a) (2S-(4-Fluorophenyl)-cycloprop-1R-yl)-[3-(2-hydroxy-ethyl)-benzyl]-carbamic acid tert-butyl ester Prepared from 1R,2S-[2-(4-fluorophenyl)]cyclopropylamine (+)-tartrate salt [WO2000034283] (600 mg) and (3-formyl-phenyl)-acetic acid ethyl ester (Example 1 step a, 380 mg) using the method of (Example 3 step a) to give the subtitle compound as a yellow oil (226 mg).

m/z 386 (M+H)+ (APCI)

$^1$H NMR (300 MHz, DMSO, 90° C.) δ 7.24-7.17 (m, 1H), 7.13-6.95 (m, 7H), 4.47 (d, 1H), 4.34 (d, 1H), 4.24 (t, 1H), 3.65-3.56 (m, 2H), 2.70 (t, 2H), 2.61-2.54 (m, 1H), 2.19-2.10 (m, 1H), 1.31-1.22 (m, 1H), 1.15-1.06 (m, 1H), 1.37 (s, 9H).

b) (7-{2-[2-(3-{[2S-(4-Fluoro-phenyl)-cycloprop-1R-ylamino]-methyl}-phenyl)-ethylamino]-1R-hydroxy-ethyl}-4-hydroxy-3H-benzothiazol-2-one bis-trifluoroacetate salt Prepared from (2S-(4-fluorophenyl)-cycloprop-1R-yl)-[3-(2-hydroxy-ethyl)-benzyl]-carbamic acid tert-butyl ester (226 mg) and 7-(2-amino-1R-hydroxy-ethyl)-4-hydroxy-3H-benzothiazol-2-one hydrochloride (100 mg) using the method of (Example 3 step b), to give the title compound as a white solid (131 mg).

m/z 494 (M+H)+ (Agilent multimode)

$^1$H NMR (300 MHz, DMSO, 90° C.) δ 7.41-7.31 (m, 3H), 7.31-7.24 (m, 1H), 7.17-7.00 (m, 4H), 6.94 (d, 1H), 6.78 (d, 1H), 4.97-4.89 (m, 1H), 4.25 (s, 2H), 3.27-3.08 (m, 4H), 3.04-2.92 (m, 2H), 2.87-2.78 (m, 1H), 2.45-2.37 (m, 1H), 1.50-1.39 (m, 1H), 1.28-1.17 (m, 1H). 7H exchangeable not seen at elevated temperature.

EXAMPLE 11

4-Hydroxy-7-[1R-hydroxy-2-(2-{3-[(2-pyridin-2-yl-ethylamino)-methyl]-phenyl}-ethylamino)-ethyl]-3H-benzothiazol-2-one bis-trifluoroacetate

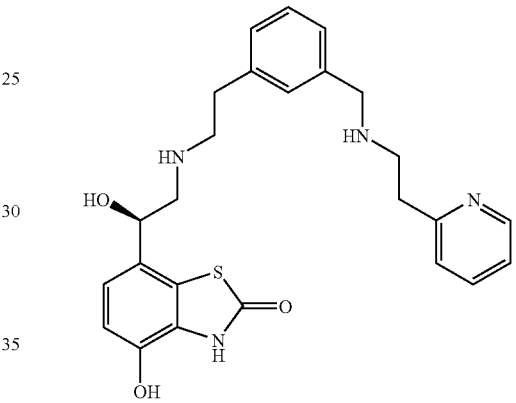

a) [3-(2-Hydroxy-ethyl)-benzyl]-(2-pyridin-2-yl-ethyl)-carbamic acid tert-butyl ester Prepared from 2-(2-aminoethyl)pyridine (240 mg) and (3-formyl-phenyl)-acetic acid ethyl ester (Example 1, step a, 380 mg) using the method of Example 3 (step a), to give the subtitle compound as a yellow oil (100 mg).

m/z 357 (M+H)+ (APCI)

$^1$H NMR (300 MHz, DMSO, 90° C.) δ 8.48-8.43 (m, 1H), 7.64 (td, 1H), 7.24-7.12 (m, 3H), 7.11-6.99 (m, 3H), 4.31 (s, 2H), 4.25 (t, 1H), 3.62 (td, 2H), 3.50 (t, 2H), 2.90 (t, 2H), 2.71 (t, 2H), 1.37 (s, 9H).

b) 4-Hydroxy-7-[1R-hydroxy-2-(2-{3-[(2-pyridin-2-yl-ethylamino)-methyl]-phenyl}-ethylamino)-ethyl]-3H-benzothiazol-2-one bis-trifluoroacetate salt Prepared from [3-(2-hydroxy-ethyl)-benzyl]-(2-pyridin-2-yl-ethyl)-carbamic acid tert-butyl ester (100 mg) and 7-(2-amino-1R-hydroxy-ethyl)-4-hydroxy-3H-benzothiazol-2-one hydrochloride (50 mg) using the method of Example 3 (step b), to give the title compound as a white solid (36 mg).

m/z 465 (M+H)+ (Agilent multimode)

$^1$H NMR (400 MHz, DMSO, 90° C.) δ 11.67 (s, 1H), 10.23 (s, 1H), 9.25-8.94 (m, 3H), 8.93 (s, 1H), 8.57 (s, 1H), 7.82 (t,

1H), 7.47-7.27 (m, 6H), 6.93 (d, 1H), 6.78 (d, 1H), 6.56 (s, 1H), 4.95-4.87 (m, 1H), 4.22 (s, 2H), 3.40-3.29 (m, 2H), 3.22-2.93 (m, 8H).

EXAMPLE 12

4-Hydroxy-7-[1R-hydroxy-2-(2-{3-[(2-methoxy-2-methyl-propylamino)methyl]-phenyl}ethylamino)ethyl]-3H-benzothiazol-2-one bis-hydrochloride salt

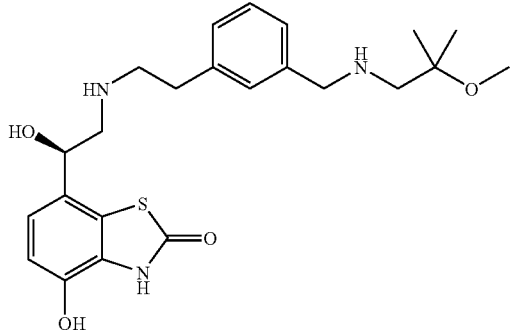

a) [3-(2-Hydroxyethyl)benzyl]-[(2-methoxy-2-methyl)propyl]carbamic acid tert-butyl ester Prepared from 2-methoxy-2-methylpropylamine oxalate salt hemihydrate (607 mg) and (3-formyl-phenyl)-acetic acid ethyl ester (Example 1, step a, 356 mg) using the method of Example 3 (step a), to give the subtitle compound as a water-white oil (454 mg).

$^1$H NMR (300 MHz, CDCl3) δ 7.28-7.23 (m, 1H), 7.11-7.07 (m, 3H), 4.63-4.59 (m, 2H), 3.85 (q, 2H), 3.30-3.20 (m, 2H), 3.16 (s, 3H), 2.86 (t, 2H), 1.49-1.41 (m, 9H), 1.16 (s, 6H). OH not seen.

b) 4-Hydroxy-7-[1R-hydroxy-2-(2-{3-[(2-methoxy-2-methyl-propylamino)methyl]-phenyl}ethylamino)ethyl]-3H-benzothiazol-2-one bis-hydrochloride salt Prepared from [3-(2-hydroxyethyl)benzyl]-[(2-methoxy-2-methyl)propyl]carbamic acid tert-butyl ester (153 mg) and 7-(2-amino-1-(R)-hydroxy-ethyl)-4-hydroxy-3H-benzothiazol-2-one hydrochloride (100 mg) using the method of Example 3 (step b). Purification by HPLC using method A. The trifluoroacetate salt was taken up in a little acetonitrile, treated with an excess of 2M ethereal hydrogen chloride and evaporated. The residue was again taken up in acetonitrile, treated with an excess of 2M ethereal hydrogen chloride and evaporated. The residue was triturated with a little ether and filtered off to give the title compound as a white solid (80 mg).

m/z 446 (M+H)$^+$ (Agilent multimode)

$^1$H NMR (300 MHz, DMSO) δ 11.70 (s, 1H), 10.27 (s, 1H), 9.42 (s, 1H), 8.99 (s, 3H), 7.49-7.46 (m, 2H), 7.40 (t, 1H), 7.30 (d, 1H), 6.93 (d, 1H), 6.80 (d, 1H), 6.47 (s, 1H), 5.03-5.00 (m, 1H), 4.12 (s, 2H), 3.21-3.16 (m, 2H), 3.07 (s, 3H), 3.07-3.00 (m, 4H), 2.85-2.82 (m, 2H), 1.16 (s, 6H).

EXAMPLE 13

4-Hydroxy-7-[1R-hydroxy-2-(2-{3-[(2-methoxy-ethylamino)-methyl]-phenyl}-ethylamino)-ethyl]-3H-benzothiazol-2-one di-hydrochloride salt

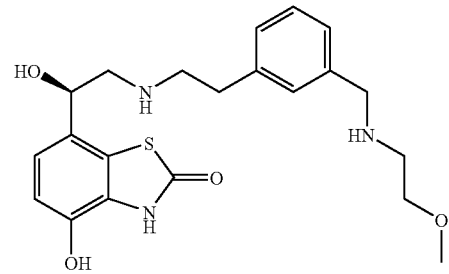

a) [3-(2-Hydroxy-ethyl)-benzyl]-(2-methoxy-ethyl)-carbamic acid tert-butyl ester Prepared from 2-methoxyethylamine (0.16 mL) and (3-formyl-phenyl)-acetic acid ethyl ester (Example 1, step a, 110 mg) using the method of Example 3 (step a) to give the subtitle compound as a pale yellow oil (200 mg).

m/z 310 (M+H)$^+$ (APCI)

b) 4-Hydroxy-7-[1R-hydroxy-2-(2-{3-[(2-methoxy-ethylamino)-methyl]-phenyl}-ethylamino)-ethyl]-3H-benzothiazol-2-one di-hydrochloride Prepared from [3-(2-Hydroxy-ethyl)-benzyl]-(2-methoxy-ethyl)-carbamic acid tert-butyl is ester (250 mg) and 7-(2-amino-1R-hydroxy-ethyl)-4-hydroxy-3H-benzothiazol-2-one hydrochloride (100 mg) using the method of Example 3 (step b), to give a gum. Treatment with 2M hydrogen chloride in diethyl ether solution afforded the title compound, as a white solid (82 mg).

m/z 418 (M+H)$^+$ (Agilent multimode)

$^1$H NMR (400 MHz, DMSO, 90° C.) δ 7.50 (s, 1H), 7.42 (d, 1H), 7.39-7.34 (m, 1H), 7.29 (d, 1H), 6.95 (d, 1H), 6.78 (d, 1H), 5.02 (dd, 1H), 4.12 (s, 2H), 3.66 (t, 2H), 3.30 (s, 3H), 3.24 (t, 2H), 3.11-3.03 (m, 6H).

EXAMPLE 14

7-{2-[3-(3-{[2-(2,6-Dichloro-phenyl)-ethylamino]-methyl}-phenyl)-propylamino]-1R-hydroxy-ethyl}-4-hydroxy-3H-benzothiazol-2-one bis-trifluoroacetate salt

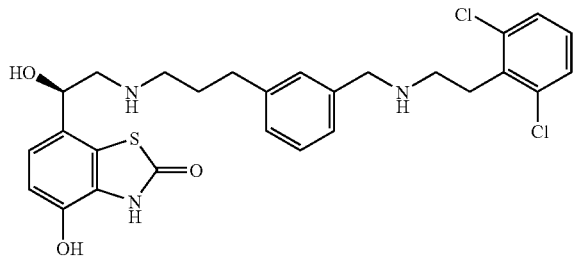

a) [2-(2,6-Dichloro-phenyl)-ethyl]-(3-iodo-benzyl)-amine 2-(2,6-Dichlorophenyl)ethylamine (1.0 g) and 3-iodobenzaldehyde (1.2 g) were combined in dichloromethane (50 mL). After 1 hour, sodium triacetoxyborohydride (2.2 g) was added. After 3.5 hours, the reaction mixture was poured onto 1M aqueous sodium hydroxide (200 mL) and extracted twice with dichloromethane. The organics were combined, dried (sodium sulfate) and evaporated to give the subtitle product, as an oil (2.0 g).
$^1$H NMR (300 MHz, CDCl$_3$) δ 7.70 (s, 1H), 7.57 (d, 1H), 7.32-7.21 (m, 3H), 7.12-7.01 (m, 2H), 3.81 (s, 2H), 3.16 (t, 2H), 2.86 (t, 2H). NH not seen.

b) [2-(2,6-Dichloro-phenyl)-ethyl]-(3-iodo-benzyl)-carbamic acid tert-butyl ester Di-tert-butyl dicarbonate (1.5 g) was added to a solution of [2-(2,6-dichloro-phenyl)-ethyl]-(3-iodo-benzyl)-amine (2.0 g) in dichloromethane (50 mL). After 18 hours the reaction mixture was evaporated. Purification on silica, eluting with a gradient of iso-hexane/dichloromethane [1:1 to 0:1] afforded the subtitle product as an oil (2.3 g).
$^1$H NMR (300 MHz, CDCl$_3$) δ 7.61-7.55 (m, 2H), 7.29-7.24 (m, 3H), 7.11-7.01 (m, 2H), 4.48-4.22 (m, 2H), 3.52-3.31 (m, 2H), 3.27-3.10 (m, 2H), 1.45 (s, 9H).

c) [2-(2,6-Dichloro-phenyl)-ethyl]-[3-(3-oxo-propyl)-benzyl]-carbamic acid tert-butyl ester

[2-(2,6-Dichloro-phenyl)-ethyl]-(3-iodo-benzyl)-carbamic acid tert-butyl ester (506 mg), tetrabutylammonium chloride (280 mg), sodium bicarbonate (210 mg), allyl alcohol (100 μL) and toluene (20 mL) were charged to a flask, followed by palladium acetate (10 mg) and the resultant mixture heated to 80° C., under nitrogen for 5 hours. On cooling, the reaction was filtered, the filtrate diluted with toluene and extracted sequentially, twice with water, once with brine, dried (magnesium sulfate) and evaporated. Purification on silica, eluting with a gradient of iso-hexane/ethyl acetate [4:1 to 2:1], gave the subtitle product as an oil (300 mg).
$^1$H NMR (500 MHz, CDCl$_3$) δ 9.82 (s, 1H), 7.31-7.19 (m, 3H), 7.14-7.00 (m, 4H), 4.47 (s, 2H), 3.49-3.31 (m, 2H), 3.26-3.12 (m, 2H), 2.93 (t, 2H), 2.76 (t, 2H), 1.47 (s, 9H).

d) 7-{2-[3-(3-{[2-(2,6-Dichloro-phenyl)-ethylamino]-methyl}-phenyl)-propylamino]-1R-hydroxy-ethyl}-4-hydroxy-3H-benzothiazol-2-one bis-trifluoroacetate salt

[2-(2,6-Dichloro-phenyl)-ethyl]-[3-(3-oxo-propyl)-benzyl]-carbamic acid tert-butyl ester (146 mg), 7-(2-amino-1R-hydroxy-ethyl)-4-hydroxy-3H-benzothiazol-2-one hydrochloride (100 mg) and acetic acid (25 μL) were combined in methanol (10 mL). After 1.5 hours, sodium cyanoborohydride (40 mg) was added. After 2 hours 0.880 ammonia solution (0.3 mL) was added and the reaction mixture concentrated and loaded onto conditioned Tosic-65A resin (3.3 g, Argonaut) in acetonitrile/propan-2-ol [1:1]. The resin was washed with acetonitrile/propan-2-ol [1:1] (50 mL) and eluted propan-2-ol/0.880 ammonia solution [4:1] (50 mL). The elution fraction was evaporated, treated with trifluoroacetic acid/acetonitrile [1:1] (10 mL) for 30 minutes and evaporated. Purification by HPLC method A, evaporation and trituration with diethyl ether gave the title product, as a white solid (70 mg).

m/z 546 (M+H)$^+$ (Agilent multimode)
$^1$H NMR (300 MHz, DMSO, 90° C.) δ 7.48-7.24 (m, 7H), 6.93 (d, 1H), 6.76 (d, J=8.2 Hz, 1H), 4.89 (dd, 1H), 4.22 (s, 2H), 3.35-3.28 (m, 2H), 3.13-2.98 (m, 6H), 2.69 (t, 2H), 2.05-1.91 (m, 2H). 7H exchangeable protons not seen at elevated temperature.

EXAMPLE 15

7-{2-[2-(3-{[2-(2,6-Dichloro-phenyl)-ethylamino]-methyl}-phenyl)-1-methyl-ethylamino]-1R-hydroxy-ethyl}-4-hydroxy-3H-benzothiazol-2-one bis-trifluoroacetate salt

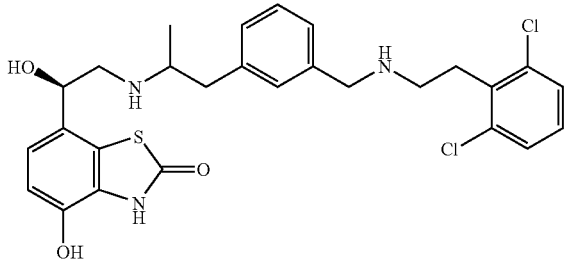

a) [2-(2,6-Dichloro-phenyl)-ethyl]-[3-(2-oxo-propyl)-benzyl]-carbamic acid tert-butyl ester

[2-(2,6-Dichloro-phenyl)-ethyl]-(3-iodo-benzyl)-carbamic acid tert-butyl ester (Example 14, step b) (500 mg), tributyltin methoxide (350 μL), isoprenyl acetate (170 μL), tri-o-tolylphosphine (30 mg) and toluene (20 mL) were charged to a flask and the solution degassed with nitrogen for 5 minutes. Palladium acetate (10 mg) was added and the resultant mixture heated to 100° C., under nitrogen, for 3 hours. On cooling, potassium fluoride (580 mg) in water (3 mL) was added, stir at room temperature for 18 hours. The solids were filtered off, and the filter cake washed with ethyl acetate. The filtrate was evaporated and purified on silica, eluting with a gradient of iso-hexane/ethyl acetate [4:1 to 2:1], to give the subtitle product as an oil (230 mg).
$^1$H NMR (300 MHz, CDCl$_3$, 50° C.) δ 7.31-7.21 (m, 3H), 7.20-7.02 (m, 4H), 4.44 (s, 2H), 3.65 (s, 2H), 3.41 (s, 2H), 3.19 (t, 2H), 2.11 (s, 3H), 1.45 (s, 9H).

b) 7-{2-[2-(3-{[2-(2,6-Dichloro-phenyl)-ethylamino]-methyl}-phenyl)-1-methyl-ethylamino]-1R-hydroxy-ethyl}-4-hydroxy-3H-benzothiazol-2-one bis-trifluoroacetate salt

[2-(2,6-Dichloro-phenyl)-ethyl]-[3-(2-oxo-propyl)-benzyl]-carbamic acid tert-butyl ester (210 mg), 7-(2-amino-1R-hydroxy-ethyl)-4-hydroxy-3H-benzothiazol-2-one hydrochloride (100 mg) were combined in N-methylpyrrolidin-2-one (5 mL). After 30 minutes, sodium triacetoxyborohydride (250 mg) was added. After 3 hours, the reaction mixture was diluted with acetonitrile (5 mL) and loaded onto conditioned Tosic-65A resin (4.0 g, Argonaut). The resin was washed with acetonitrile (50 mL) and eluted acetonitrile/0.880 ammonia solution [4:1] (50 mL). The elution fraction was evaporated, treated with trifluoroacetic acid/acetonitrile [1:1] (10 mL) for 30 min and evaporated. Purification HPLC method A, evaporation and trituration with diethyl ether gave the title product as a white solid (120 mg).

m/z 546 (M+H)⁺ (Agilent multimode)

$^1$H NMR (300 MHz, DMSO, 90° C.) δ 7.48-7.37 (m, 5H), 7.36-7.28 (m, 2H), 6.97 (dd, 1H), 6.79 (d, 1H), 4.95 (td, 1H), 4.24 (s, 2H), 3.60-3.45 (m, 1H), 3.37-3.23 (m, 3H), 3.19-3.13 (m, 2H), 3.12-3.04 (m, 2H), 2.71 (dt, 1H), 1.15 (dd, 3H). 7H exchangeable protons not seen at elevated temperature.

EXAMPLE 16

4-Hydroxy-7-(1R-hydroxy-2-{2-[4-(2-phenylethyl)aminomethyl)phenyl]ethylamino}ethyl)-3H-benzothiazol-2-one bis-trifluoroacetate salt

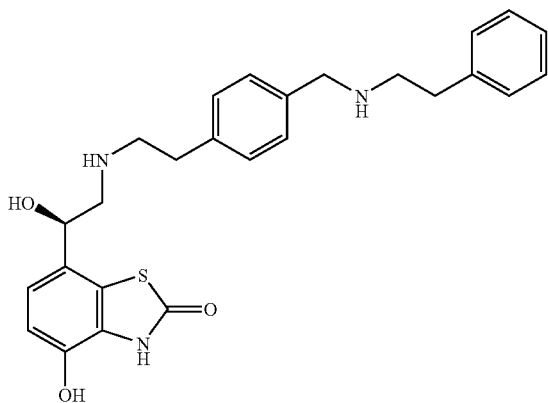

a) (4-Formylphenyl)acetic acid methyl ester

Acetyl chloride (5 mL) was added cautiously to solution of (4-hydroxymethylphenyl)acetic acid (5.78 g) in methanol (200 mL), stirred for 18 hours and evaporated. The residue was dissolved in dichloromethane (100 mL) and treated with manganese (IV) oxide (29.47 g), stirred for 18 hours and filtered through Celite. The filter pad was washed with dichloromethane and the combined filtrates evaporated. Purification on silica, eluting with 20% diethyl ether in iso-hexane, afforded the subtitle compound as a white solid (3.60 g).

$^1$H NMR (300 MHz, CDCl₃) δ 10.01 (s, 1H), 7.86 (d, 2H), 7.46 (d, 2H), 3.72 (s, 5H).

b) [4-(2-Hydroxyethyl)benzyl]-(2-phenylethyl)carbamic acid tert-butyl ester (4-Formylphenyl)acetic acid methyl ester (356 mg), 2-phenylethylamine (364 mg) and acetic acid (114 µL) were combined in ethanol (10 mL). After 1 hour, sodium triacetoxyborohydride (636 mg) was added and stirred for 18 hours. The reaction mixture was loaded onto a conditioned SCX cartridge (10 g Varian) and washed with methanol (50 mL), then eluted with methanol/0.880 ammonia solution [9:1] (50 mL) and the elution fraction evaporated. The residue was dissolved in N,N-dimethylformamide (10 mL) and triethylamine (418 µL) added, followed by di-tert-butyl dicarbonate (655 mg) and stirred for 18 hours. The mixture was diluted with ethyl acetate, washed thrice with water and evaporated. The residue was dissolved in ethanol (20 mL), treated with anhydrous calcium chloride (444 mg), followed by portionwise addition of sodium borohydride (302 mg) and stirred overnight. The mixture was quenched with 2M aqueous potassium carbonate solution (20 mL) and concentrated. The residue was partitioned between ethyl acetate and water. The organics were separated, dried (magnesium sulfate) and evaporated.

Purification on silica, eluting with 40% diethyl ether in iso-hexane, afforded the subtitle compound as an oil (477 mg).

$^1$H NMR (400 MHz, CDCl₃) δ 7.29-7.11 (m, 9H), 4.37-4.29 (m, 2H), 3.85 (q, 2H), 3.40-3.33 (m, 2H), 2.85 (t, 2H), 2.82-2.76 (m, 2H), 1.47 (s, 9H). OH not seen.

c) N-[4-(2-Oxoethyl)benzyl]-N-(2-phenylethyl)carbamic acid tert-butyl ester

[4-(2-Hydroxyethyl)benzyl]-(2-phenylethyl)carbamic acid tert-butyl ester (238 mg) in dichloromethane (10 mL) was treated with Dess-Martin periodinane (341 mg) and stirred for 1 hour. The reaction mixture was added to a mixture of ethyl acetate (10 mL), saturated aqueous sodium thiosulphate solution (10 mL) and saturated aqueous sodium bicarbonate (10 mL), and the mixture was stirred vigorously for 10 minutes. The phases were separated. The aqueous layer was extracted with ethyl acetate and the combined organics were washed with water, dried (magnesium sulfate) and evaporated to give the subtitle compound as an oil (232 mg).

$^1$H NMR (400 MHz, CDCl₃) δ 9.73 (t, 1H), 7.29-7.12 (m, 9H), 4.38-4.30 (m, 2H), 3.67 (d, 2H), 3.40-3.34 (m, 2H), 2.85-2.73 (m, 2H), 1.47 (s, 9H).

d) 4-Hydroxy-7-(1R-hydroxy-2-{2-[4-(2-phenylethyl)aminomethyl)phenyl]-ethylamino}-ethyl)-3H-benzothiazol-2-one bis-trifluoroacetate salt 7-(2-Amino-1R-hydroxy-ethyl)-4-hydroxy-3H-benzothiazol-2-one hydrochloride (100 mg), N-[4-(2-oxoethyl)benzyl]-N-(2-phenylethyl)carbamic acid tert-butyl ester (162 mg) and acetic acid (22 µL) were combined in methanol (10 mL). After 1 hour, sodium cyanoborohydride (36 mg) was added and stirred for 18 hours. The reaction mixture was treated with a few drops of 0.880 ammonia solution and evaporated. The residue was taken up in acetonitrile/iso-propanol [1:1] and loaded onto a conditioned Tosic-65A resin (5 g, Argonaut). The resin was washed with acetonitrile/isopropanol [1:1] (50 mL) then eluted with iso-propanol/acetonitrile/0.880 ammonia solution [2:2:1] (50 mL) and the elution fraction evaporated. The residue was taken up in trifluoroacetic acid (5 mL), allowed to stand for 10 min and evaporated. Purification by HPLC method A, evaporation and trituration with diethyl ether afforded the title compound as a white solid (95 mg).

m/z 464 (M+H)⁺ (Agilent multimode)

$^1$H NMR (400 MHz, DMSO) δ 11.67 (s, 1H), 10.30 (s, 1H), 9.14 (s, 2H), 9.00-8.82 (m, 2H), 7.46 (d, 2H), 7.36-7.23 (m, 7H), 6.93 (d, 1H), 6.78 (d, 1H), 6.62-6.40 (m, 1H), 4.93-4.90 (m, 1H), 4.18 (s, 2H), 3.17-2.93 (m, 10H).

EXAMPLE 17

7-{2-[2-(4-{[2-(2,6-Dichloro-phenyl)-ethylamino]-methyl}-phenyl)-ethylamino]-1R-hydroxy-ethyl}-4-hydroxy-3H-benzothiazol-2-one bis-trifluoroacetate salt

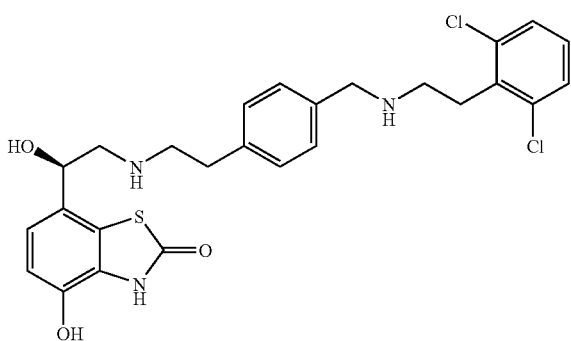

a) [4-({tert-Butoxycarbonyl-[2-(2,6-dichloro-phenyl)-ethyl]-amino}-methyl)-phenyl]-acetic acid (4-Formylphenyl)-acetic acid ethyl ester (Example 16, step a, 0.44 g) was added to a solution of acetic acid (0.14 mL), trimethylorthoformate (2.53 g) and 2-(2,6-dichlorophenyl) ethylamine (0.54 mL) in dimethylformamide (10 mL) and stirred at room temperature, under nitrogen. After 1 hour, sodium triacetoxyborohydride (0.79 g) was added and the resulting mixture stirred for 18 hours, then concentrated. The residue was dissolved in methanol (5 mL) and loaded onto conditioned Tosic-65A resin (5 g, Argonaut). The resin was washed with methanol (3×20 mL) and then eluted with 3M methanolic ammonia solution (2×15 mL). The combined elution fractions were evaporated. The residue was dissolved in dichloromethane (10 mL) and di-tert-butyl dicarbonate (0.42 g) was added. The mixture was stirred at room temperature, under nitrogen, for 18 hours. Purification on silica, eluting with a gradient of iso-hexane/ethyl acetate [1:0 to 9:1] to give a clear oil. The oil was dissolved in tetrahydrofuran (4 mL) and a solution of lithium hydroxide (21 mg) in water (2 mL) was added and stirred for 18 hours, under nitrogen. The pH was adjusted to pH~4 with acetic acid and the mixture concentrated to ~2 mL. The aqueous residue was extracted with ethyl acetate (3×10 mL), the organics combined, washed with brine (10 mL), dried (magnesium sulfate) and evaporated, to give the subtitle compound as a gum (350 mg).

m/z 437 (M−H)⁻ (APCI)

¹H NMR (400 MHz, CDCl₃) δ 7.29-7.17 (m, 6H), 7.08 (t, 1H), 4.51-4.30 (m, 2H), 3.63 (s, 2H), 3.39-3.12 (m, 2H), 2.09 (s, 2H), 1.45 (s, 9H). CO₂H not seen.

b) [2-(2,6-Dichloro-phenyl)-ethyl]-(4-{[2R-hydroxy-2-(4-hydroxy-2-oxo-2,3-dihydro-benzothiazol-7-yl)-ethylcarbamoyl]-methyl}-benzyl)-carbamic acid tert-butyl ester

[4-({tert-Butoxycarbonyl-[2-(2,6-dichloro-phenyl)-ethyl]-amino}-methyl)-phenyl]-acetic acid (44 mg), 7-(2-amino-1R-hydroxy-ethyl)-4-hydroxy-3H-benzothiazol-2-one hydrochloride (26 mg), 1-hydroxybenzotriazole (16 mg), di-isopropylethylamine (0.04 mL), and 1-(3-dimethylaminopropyl)-3-ethylcarbodiimide hydrochloride (23 mg) were combined in dimethylformamide (0.5 mL) and stirred for 18 hours, under nitrogen. The reaction mixture was concentrated and partitioned between ethyl acetate (10 mL) and water (10 mL). The organic phase was separated and washed sequentially with water (10 mL), saturated aqueous sodium bicarbonate solution (10 mL), brine (2×10 mL), dried (magnesium sulfate) and evaporated, to give the subtitle compound as a light brown solid (33 mg) m/z 647 (M+H)⁺ APCI ¹H NMR (400 MHz, DMSO) δ 8.06 (t, 1H), 7.43 (d, 2H), 7.28 (t, 1H), 7.21-7.05 (m, 4H), 6.77 (d, 1H), 6.67 (d, 1H), 4.57-4.51 (m, 1H), 4.40-4.33 (m, 2H), 3.45-3.05 (m, 8H), 1.38-1.24 (m, 9H).

c) 7-{2-[2-(4-{[2-(2,6-Dichloro-phenyl)-ethylamino]-methyl}-phenyl)-ethylamino]-1R-hydroxy-ethyl}-4-hydroxy-3H-benzothiazol-2-one bis-trifluoroacetate salt Borane-tetrahydrofuran complex (1M solution in tetrahydrofuran, 0.28 mL) was added to a solution of [2-(2,6-dichloro-phenyl)-ethyl]-(4-{[2R-hydroxy-2-(4-hydroxy-2-oxo-2,3-dihydro-benzothiazol-7-yl)-ethylcarbamoyl]-methyl}-benzyl)-carbamic acid tert-butyl ester (30 mg) in dry tetrahydrofuran (2 mL) at 70° C. under nitrogen. After 1 hour, a few drops of 0.880 ammonia solution were added and the reaction mixture concentrated. The residue was suspended in dichloromethane (2 mL) and trifluoroacetic acid (0.5 mL) added. The resulting mixture was stirred for 20 minutes and concentrated. Purification by HPLC method C, to give the title compound as a tan solid (9.5 mg).

m/z 532 (M+H)⁺ (Agilent multimode)

¹H NMR (300 MHz, CD₃OD) δ 7.51 (d, 2H), 7.45-7.35 (m, 4H), 7.28 (dd, 1H), 6.99 (d, 1H), 6.77 (d, 1H), 5.02 (dd, 1H), 4.28 (s, 2H), 3.47-3.37 (m, 2H), 3.37-3.27 (m, 3H), 3.26-3.16 (m, 3H), 3.13-3.03 (m, 2H).

EXAMPLE 18

7-{2-[2-(4-{[2-(2-Fluorophenyl)ethylamino]methyl}phenyl)ethylamino]-1R-hydroxyethyl}-4-hydroxy-3H-benzothiazol-2-one bis-trifluoroacetate salt

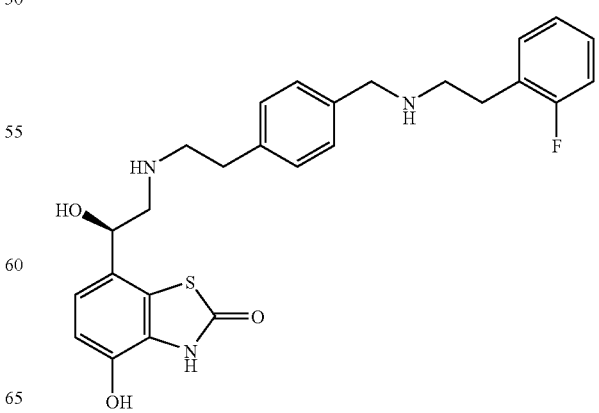

a) [2-(2-Fluorophenyl)ethyl]-[4-(2-hydroxyethyl)benzyl]-carbamic acid tert-butyl ester Prepared from 2-(2-fluorophenyl)ethylamine (278 mg) and (4-formylphenyl)acetic acid methyl ester (Example 16, step a) (374 mg) using the method of Example 16 (step b), to give the subtitle compound as an oil (237 mg).

$^1$H NMR (400 MHz, CDCl$_3$) δ 7.20-7.15 (m, 6H), 7.05-6.97 (m, 2H), 4.39-4.30 (m, 2H), 3.85 (t, 2H), 3.42-3.33 (m, 2H), 2.88-2.79 (m, 2H), 2.85 (t, 2H), 1.45 (s, 9H). OH not seen.

b) 7-{2-[2-(4-{[2-(2-Fluorophenyl)ethylamino]-methyl}-phenyl)-ethylamino]-1R-hydroxy-ethyl}-4-hydroxy-3H-benzothiazol-2-one bis-trifluoroacetate salt

[2-(2-Fluorophenyl)ethyl]-[4-(2-hydroxyethyl)benzyl]-carbamic acid tert-butyl ester (237 mg) in dichloromethane (1 mL) was added to a vigorously stirred suspension of pyridinium chlorochromate (205 mg) and anhydrous sodium acetate (15 mg) in dichloromethane (2 mL). After 1.5 hours, the reaction was diluted with diethyl ether (10 mL) and stirred for 30 minutes. The reaction mixture was filtered through Celite, the pad was washed with diethyl ether and the combined filtrates were evaporated. The residue was dissolved in methanol (8 mL) and 7-(2-amino-1R-hydroxy-ethyl)-4-hydroxy-3H-benzothiazol-2-one hydrochloride (166 mg) added, followed by acetic acid (64 µL). After 1 hour, sodium cyanoborohydride (60 mg) was added and stirred for 18 hours. The mixture was quenched with a few drops of 5M methanolic ammonia solution and evaporated. The residue was taken up in dichloromethane and shaken with water to give an emulsion. The emulsion could not be separated by the addition of ethyl acetate, salt or methanol, so was evaporated. The residue was taken up in acetonitrile/isopropanol [1:1] and loaded onto a conditioned SCX cartridge (10 g Varian). The cartridge was washed sequentially with acetonitrile/isopropanol [1:1], 20% water in acetonitrile, acetonitrile and eluted with isopropanol/acetonitrile/0.880 ammonia solution [2:2:1]. Analysis showed desired compound in the washings, all were combined and evaporated. The residue was dissolved in trifluoroacetic acid (10 mL), allowed to stand for 10 minutes and evaporated. Purification by HPLC method C and then method A. Evaporation and subsequent trituration with diethyl ether afforded the title compound as a white solid (27 mg).

m/z 482 (M+H)$^+$ (Agilent multimode)

$^1$H NMR (300 MHz, DMSO) δ 11.67 (s, 1H), 10.28 (s, 1H), 9.13-8.85 (m, 4H), 7.46 (d, 2H), 7.34-7.31 (m, 3H), 7.23-7.16 (m, 2H), 6.93 (d, 1H), 6.78 (d, 1H), 6.57 (s, 1H), 6.50-6.49 (m, 1H), 4.94-4.89 (m, 1H), 4.19 (s, 2H), 3.19-2.97 (m, 10H).

EXAMPLE 19

7-{2-[2-(4-{[2,2-diphenylethylamino]methyl}phenyl)ethylamino]-1R-hydroxyethyl}-4-hydroxy-3H-benzothiazol-2-one bis-trifluoroacetate salt

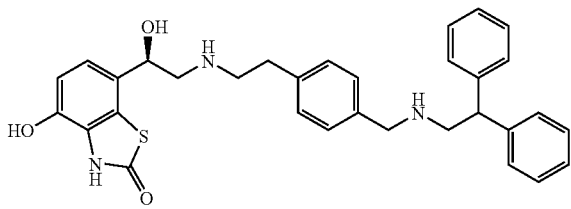

a) N-[2,2-Diphenylethyl]-[4-(2-hydroxyethyl)-benzyl]carbamic acid tert-butyl ester Prepared from 2,2-diphenylethylamine (395 mg) and (4-formylphenyl)acetic acid methyl ester (Example 16, step a, 374 mg) using the method of Example 16 (step b), to give the subtitle compound as an oil (496 mg).

$^1$H NMR (400 MHz, CDCl$_3$) δ 7.30-7.03 (m, 14H), 4.45-4.29 (m, 1H), 4.14-4.03 (m, 2H), 3.87-3.74 (m, 4H), 2.84 (t, 2H), 1.43 (d, 9H). OH not seen.

b) 7-{2-[2-(4-{[2,2-diphenylethylamino]methyl}phenyl)ethylamino]-1R-hydroxyethyl}-4-hydroxy-3H-benzothiazol-2-one bis-trifluoroacetate salt Prepared by the method of Example 16 (step c), using N-[2,2-diphenylethyl]-[4-(2-hydroxyethyl)-benzyl]carbamic acid tert-butyl ester (196 mg). Purification by HPLC method B, afforded the title compound as a white solid (96 mg).

m/z 540 (M+H)$^+$ (Agilent multimode)

$^1$H NMR (300 MHz, DMSO) δ 11.67 (s, 1H), 10.27 (s, 1H), 8.93-8.80 (m, 4H), 7.43 (d, 2H), 7.35-7.21 (m, 10H), 7.29 (d, 2H), 6.93 (d, 1H), 6.78 (d, 1H), 6.49 (d, 1H), 4.93-4.87 (m, 1H), 4.40 (t, 1H), 4.15 (s, 2H), 3.66-3.64 (m, 2H), 3.20-2.87 (m, 6H).

EXAMPLE 20

4-Hydroxy-7-{2-[2-(4-{[2-(2-methoxyphenyl)ethylamino]methyl}phenyl)ethylamino]-1R-hydroxyethyl}-3H-benzothiazol-2-one bis-trifluoroacetate salt

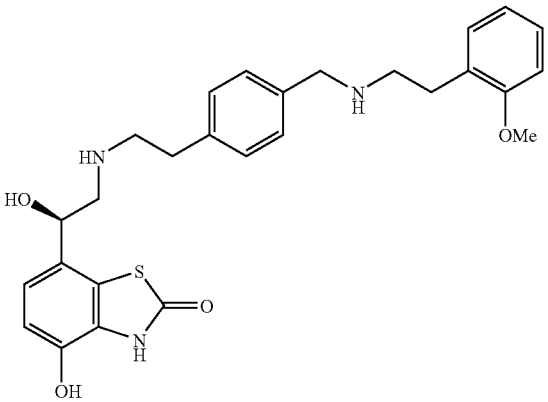

a) N-[4-(2-Hydroxyethyl)benzyl]-N-[2-(2-methoxyphenyl)ethyl]carbamic acid tert-butyl ester Prepared from 2-(2-methoxyphenyl)ethylamine (302 mg) and (4-formylphenyl)acetic acid methyl ester (Example 16, step a) (374 mg) using the method of Example 16 (step b), to give the subtitle compound as an oil (327 mg).

$^1$H NMR (400 MHz, CDCl$_3$) δ 7.20-7.03 (m, 6H), 6.88-6.81 (m, 2H), 4.37-4.28 (m, 2H), 3.84 (q, 2H), 3.80 (s, 3H), 3.38-3.31 (m, 2H), 2.87-2.78 (m, 2H), 2.85 (t, 2H), 1.47 (s, 9H). OH not seen.

b) 4-Hydroxy-7-{2-[2-(4-{[2-(2-methoxyphenyl)ethylamino]methyl}phenyl)ethylamino]-1R-hydroxy-ethyl}-3H-benzothiazol-2-one bis-trifluoroacetate salt Prepared from N-[4-(2-hydroxyethyl)benzyl]-N-[2-(2-methoxyphenyl)ethyl]carbamic acid tert-butyl ester (327 mg) and 7-(2-amino-1R-hydroxy-ethyl)-4-hydroxy-3H-benzothiazol-2-one hydrochloride (100 mg) using the method of Example 16 (step c and d). Purification by HPLC method B, to give the title compound as a white solid (70 mg).

m/z 494 (M+H)$^+$ (Agilent multimode)

$^1$H NMR (300 MHz, DMSO) δ 11.70 (s, 1H), 10.22 (s, 1H), 8.94-8.80 (m, 4H), 7.45 (d, 2H), 7.32 (d, 2H), 7.29-7.24 (m, 1H), 7.17-7.14 (m, 1H), 7.00 (d, 1H), 6.95-6.89 (m, 2H), 6.77 (d, 1H), 6.49-6.48 (m, 1H), 4.92-4.87 (m, 1H), 4.19-4.15 (m, 2H), 3.78 (s, 3H), 3.20-2.89 (m, 10H).

EXAMPLE 21

4-Hydroxy-7-{1R-hydroxy-2-[2-(4-{[2-(7-methyl-1H-indol-3-yl)-ethylamino]methyl}-phenyl)ethylamino]ethyl}-3H-benzothiazol-2-one bis-trifluoroacetate salt

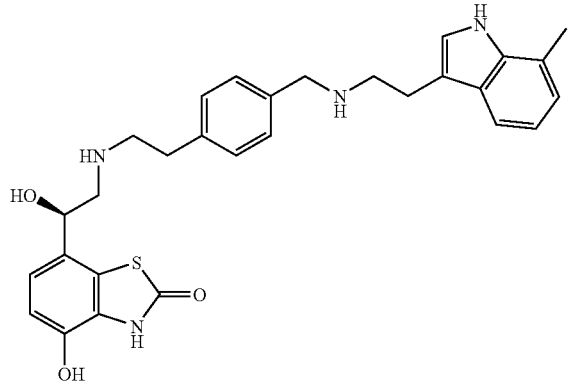

a) N-[4-(2-hydroxyethyl)benzyl]-N-[2-(7-methyl-1H-indole-3-yl)ethyl carbamic acid tert-butyl ester Prepared from 7-methyltryptamine (348 mg) and (4-formylphenyl)acetic acid methyl ester (Example 16, step a, 374 mg) using the method of Example 16 (step b). Purification on silica, eluting diethyl ether, to give the subtitle compound as an oil (293 mg).

$^1$H NMR (300 MHz, CDCl$_3$) δ 7.88 (s, 1H), 7.40-7.37 (m, 1H), 7.16-6.93 (m, 7H), 4.41-4.35 (m, 2H), 3.88-3.81 (m, 2H), 3.52-3.40 (m, 2H), 3.01-2.89 (m, 2H), 2.85 (t, 2H), 2.47 (s, 3H), 1.46 (s, 9H). OH not seen.

b) 4-Hydroxy-7-{1R-hydroxy-2-[2-(4-{[2-(7-methyl-1H-indol-3-yl)ethylamino]methyl}-phenyl)ethylamino]ethyl}-3H-benzothiazol-2-one bis-trifluoroacetate salt Prepared from N-[4-(2-hydroxyethyl)benzyl]-N-[2-(7-methyl-1H-indol-3-yl)ethyl carbamic acid tert-butyl ester (293 mg) and 7-(2-amino-1R-hydroxy-ethyl)-4-hydroxy-3H-benzothiazol-2-one hydrochloride (100 mg) using the method of Example 16 (step c and d). Purification by HPLC method A, to give the title compound as a white solid (18 mg).

m/z 517 (M+H)$^+$ (Agilent multimode)

$^1$H NMR (300 MHz, DMSO) δ 11.68 (s, 1H), 10.92 (s, 1H), 10.21 (s, 1H), 8.96-8.69 (m, 4H), 7.46 (d, 2H), 7.35-7.31 (m, 3H), 7.21 (d, 1H), 6.92-6.90 (m, 3H), 6.77 (d, 1H), 6.49-6.47 (m, 1H), 4.92-4.86 (m, 1H), 4.21-4.18 (m, 2H), 3.19-2.90 (m, 10H), 2.44 (s, 3H).

EXAMPLE 22

4-Hydroxy-7-[1R-hydroxy-2-(2-{4-[(2-(2-pyridyl)ethylamino)methyl]phenyl}-ethylamino)ethyl]-3H-benzothiazol-2-one tris-trifluoroacetate salt

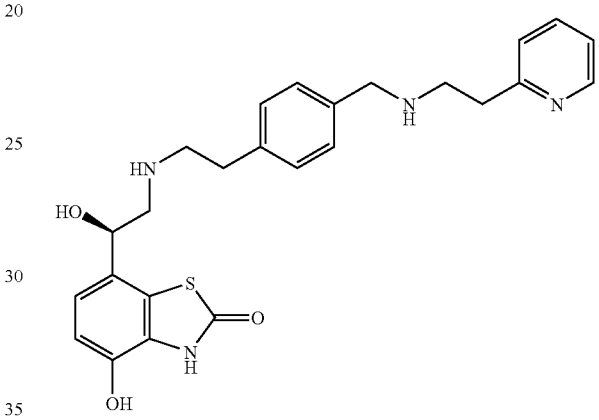

a) N-[4-(2-hydroxyethyl)benzyl]-N-[2-(2-pyridyl)ethyl]carbamic acid tert-butyl ester Prepared from 2-(2-aminoethyl)pyridine (0.244 g) and (4-formylphenyl)acetic acid methyl ester (Example 16, step a, 374 mg) using the method of Example 16 (step b). Purification on silica, eluting 1% triethylamine in ethyl acetate, afforded the subtitle compound as a pale yellow oil (191 mg).

$^1$H NMR (300 MHz, CDCl$_3$) δ 8.52-8.50 (m, 1H), 7.58 (td, 1H), 7.16-7.10 (m, 6H), 4.36-4.31 (m, 2H), 3.86-3.83 (m, 2H), 3.60-3.49 (m, 2H), 3.05-2.92 (m, 2H), 2.84 (t, 2H), 1.45 (s, 9H). OH not seen.

b) 4-Hydroxy-7-{1R-hydroxy-2-[2-(4-{[2-(2-pyridyl)ethylamino]methyl}-phenyl)ethylamino]ethyl}-3H-benzothiazol-2-one tris-trifluoroacetate salt Prepared from N-[4-(2-hydroxyethyl)benzyl]-N-[2-(2-pyridyl)ethyl]carbamic acid tert-butyl ester (191 mg) and 7-(2-amino-1R-hydroxy-ethyl)-4-hydroxy-3H-benzothiazol-2-one hydrochloride (100 mg) using the method of Example 16 (step c and d). Purification by HPLC method B, to give the title compound as a white solid (61 mg).

m/z 465 (M+H)$^+$ (Agilent multimode)

$^1$H NMR (300 MHz, DMSO) δ 11.68 (s, 1H), 10.20 (s, 1H), 9.01-8.90 (m, 2H), 8.83-8.71 (m, 3H), 8.52 (d, 1H), 7.80 (td,

1H), 7.47 (d, 2H), 7.34-7.30 (m, 4H), 6.93 (d, 1H), 6.77 (d, 1H), 6.52-6.45 (m, 1H), 4.91-4.86 (m, 1H), 4.23-4.19 (m, 2H), 3.33-2.94 (m, 10H).

EXAMPLE 23

4-Hydroxy-7-[1R-hydroxy-2-(2-{4-[(2S-(4-fluorophenyl-1-cycloprop-1R-ylamino)methyl]phenyl}ethylamino)ethyl]-3H-benzothiazol-2-one bis-trifluoroacetate salt

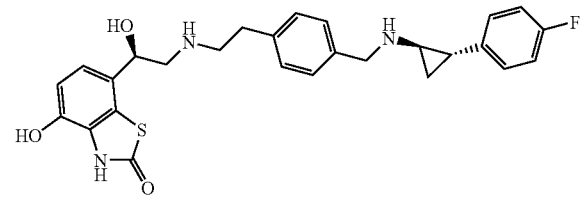

a) N-[2S-(4-Fluorophenyl)-cycloprop-1R-yl]-N-[4-(2-hydroxyethyl)benzyl]-carbamic acid tert-butyl ester Prepared from 1R,2S-2-(4-fluorophenyl)cyclopropylamine (+)-tartrate salt [WO2000034283] (302 mg) and (4-formylphenyl)acetic acid methyl ester (Example 16, step a, 374 mg) using the method of Example 16 (step b). Purification on silica, eluting 1% triethylamine in ethyl acetate, to give the subtitle compound as a pale yellow oil (112 mg).

$^1$H NMR (500 MHz, CDCl$_3$) δ 7.20-7.16 (m, 4H), 7.04-7.00 (m, 2H), 6.91 (t, 2H), 4.59 (d, 1H), 4.33 (d, 1H), 3.85 (q, 2H), 2.85 (t, 2H), 2.60 (quin, 1H), 2.15-2.12 (m, 1H), 1.43 (s, 9H), 1.35 (t, 1H), 1.28-1.24 (m, 1H). OH not seen.

b) 4-Hydroxy-7-[1R-hydroxy-2-(2-{4-[(2S-(4-fluorophenyl-1-cycloprop-1R-ylamino)methyl]phenyl}ethylamino)ethyl]-3H-benzothiazol-2-one bis-trifluoroacetate salt Prepared from N-[2S-(4-Fluorophenyl)-cycloprop-1R-yl]-N-[4-(2-hydroxyethyl)benzyl]-carbamic acid tert-butyl ester (112 mg) and 7-(2-Amino-1R-hydroxy-ethyl)-4-hydroxy-3H-benzothiazol-2-one hydrochloride (100 mg) using the method of Example 16 (step c and d). Purification by HPLC method A, to give the title compound as a white solid (44 mg).

m/z 494 (M+H)$^+$ (Agilent multimode)

$^1$H NMR (300 MHz, DMSO, 90° C.) δ 7.41 (d, 2H), 7.26 (d, 2H), 7.14-7.03 (m, 4H), 6.94 (d, 1H), 6.77 (d, 1H), 4.92-4.88 (m, 1H), 4.21 (s, 2H), 3.24-2.94 (m, 7H), 2.37-2.30 (m, 1H), 1.42-1.34 (m, 1H), 1.26-1.17 (m, 1H). 7H exchangeable not seen at elevated temperature.

EXAMPLE 24

4-Hydroxy-7-[1R-hydroxy-2-(2-{4-[(2S-phenyl-propylamino)-methyl]-phenyl}-ethylamino)-ethyl]-3H-benzothiazol-2-one bis-trifluoroacetate salt

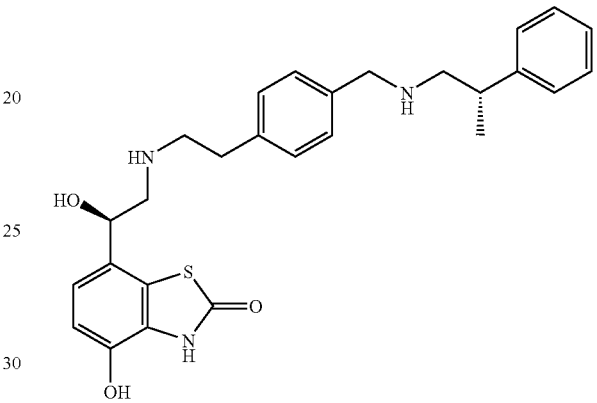

a) N-[4-(2-hydroxyethyl)benzyl]-N-(2S-phenylpropyl)carbamic acid tert-butyl ester The subtitle compound was prepared from 2S-phenyl-1-propylamine (406 mg) and (4-formylphenyl)acetic acid methyl ester (Example 16, step a, 356 mg) using the method of Example 16 (step b), to give the subtitle compound as an oil (338 mg).

$^1$H NMR (400 MHz, CDCl$_3$) δ 7.31-7.03 (m, 9H), 4.45-4.02 (m, 1H), 3.84 (q, 2H), 3.51-3.27 (m, 1H), 3.21-3.06 (m, 3H), 2.84 (t, 2H), 1.46-1.42 (m, 9H), 1.24 (d, 3H). OH not seen.

b) 4-Hydroxy-7-[1R-hydroxy-2-(2-{4-[(2S-phenyl-propylamino)-methyl]-phenyl}-ethylamino)-ethyl]-3H-benzothiazol-2-one bis-trifluoroacetate salt Prepared from N-[4-(2-hydroxyethyl)benzyl]-N-(2S-phenylpropyl)carbamic acid tert-butyl ester (168 mg) and 7-(2-amino-1R-hydroxy-ethyl)-4-hydroxy-3H-benzothiazol-2-one hydrochloride (100 mg) using the method of Example 16 (step c & d). Purification by HPLC method A, afforded the title compound as a white solid (69 mg).

m/z 478 (M+H)$^+$ (Agilent multimode)

$^1$H NMR (300 MHz, DMSO) δ 11.68 (s, 1H), 10.21 (s, 1H), 8.89-8.62 (m, 4H), 7.43 (d, 2H), 7.38-7.26 (m, 7H), 6.93 (d,

1H), 6.77 (d, 1H), 6.49-6.48 (m, 1H), 4.91-4.87 (m, 1H), 4.13-4.10 (m, 2H), 3.21-2.97 (m, 9H), 1.26 (d, 3H).

EXAMPLE 25

7-{2-[2-(2-{[2-(2-Fluoro-phenyl)-ethylamino]-methyl}-phenyl)-ethylamino]-1R-hydroxy-ethyl}-4-hydroxy-3H-benzothiazol-2-one bis-trifluoroacetate salt

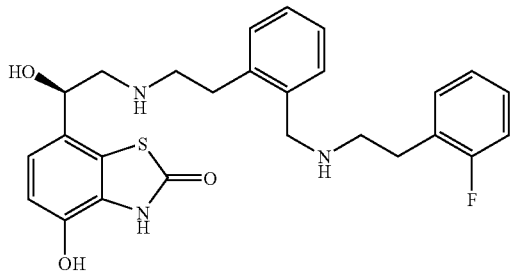

a) 2-(2-Hydroxymethyl-phenyl)-ethanol

Borane-tetrahydrofuran complex (1M solution in tetrahydrofuran, 100 mL) was added dropwise over 10 minutes, to a solution of 2-carboxymethyl-benzoic acid (6 g) in dry tetrahydrofuran (100 mL) at 0° C., under nitrogen. The resulting mixture was stirred at 0-5° C. for 20 minutes, then warmed to room temperature for 1 hour. Saturated citric acid solution (150 mL) was added and the reaction concentrated to ~150 mL. The aqueous phase was extracted with ethyl acetate (3×150 mL). The combined organics were washed sequentially with 1M aqueous sodium hydroxide solution (150 mL), water (150 mL), brine (150 mL), dried (sodium sulfate) and evaporated to give the subtitle compound as yellow oil (3.5 g).
$^1$H NMR (400 MHz, CDCl$_3$) δ 7.33-7.19 (m, 4H), 4.62 (s, 2H), 3.86 (t, 2H), 2.93 (t, 2H). 2 OH not seen.

b) Iso-chroman-1-ol

Manganese(IV) oxide (1.43 g) was added to a solution of 2-(2-hydroxymethyl-phenyl)-ethanol (0.5 g) in dichloromethane (25 mL) and stirred for 18 hours under nitrogen. The reaction was filtered through celite, the filter pad washed with dichloromethane (2×20 mL), and the combined filtrates evaporated. Purification on silica, eluting with a gradient of iso-hexane:ethyl acetate [1:0 to 4:1], afforded the subtitle compound as a yellow oil (263 mg).
$^1$H NMR (300 MHz, CDCl$_3$) δ 7.35-7.10 (m, 4H), 6.00-5.93 (m, 1H), 4.22 (td, 1H), 3.95 (ddd, 1H), 3.03-2.92 (m, 2H), 2.68 (dt, 1H).

c) [2-(2-Fluoro-phenyl)-ethyl]-[2-(2-hydroxy-ethyl)-benzyl]-carbamic acid tert-butyl ester 2-(2-Fluoro-phenyl)-ethylamine (0.34 mL) was added to a solution of iso-chroman-1-ol (0.26 g) and acetic acid (0.1 mL) in methanol (5 mL). After stirring for 1 hour, sodium cyanoborohydride (0.17 g) was added and stirred for 18 hours. A few drops of 0.880 ammonia solution was added and the resulting mixture concentrated. The residue was dissolved in methanol (5 mL) and loaded onto a conditioned SCX cartridge (10 g Varian). The cartridge was washed with methanol (3×20 mL), then eluted with a methanolic ammonia solution (2×15 mL) and the combined elution fractions evaporated. The residue was dissolved in dimethylformamide (5 mL) and triethylamine (0.37 mL) added, followed by di-tert-butyl dicarbonate (0.57 g) and the resulting mixture was stirred for 72 hours. The reaction was concentrated, partitioned between ethyl acetate (50 mL) and saturated aqueous sodium bicarbonate solution (50 mL). The organic phase was separated and the aqueous phase extracted with ethyl acetate (2×50 mL). The combined organics were washed sequentially with water (50 mL), brine (50 mL), dried (magnesium sulfate) and concentrated. Purification on silica, eluting with a gradient of iso-hexane:ethyl acetate [1:0 to 4:1], afforded the subtitle compound as a yellow oil (250 mg).
m/z 374 (M+H)$^+$ (APCI)
$^1$H NMR (400 MHz, DMSO, 90° C.) δ 7.29-7.00 (m, 8H), 4.44 (s, 2H), 4.30 (t, 1H), 3.59 (dd, 2H), 3.32 (t, 2H), 2.84-2.70 (m, 4H), 1.36 (s, 9H).

d) 7-{2-[2-(2-{[2-(2-Fluoro-phenyl)-ethylamino]-methyl}-phenyl)-ethylamino]-1R-hydroxy-ethyl}-4-hydroxy-3H-benzothiazol-2-one bis-trifluoroacetate salt Prepared from [2-(2-fluoro-phenyl)-ethyl]-[2-(2-hydroxy-ethyl)-benzyl]-carbamic acid tert-butyl ester (250 mg) and 7-(2-amino-1R-hydroxy-ethyl)-4-hydroxy-3H-benzothiazol-2-one hydrochloride (0.1 g) using the method of Example 3 (step b), to give the title compound as a white solid (64 mg).
m/z 482 (M+H)$^+$ (Agilent multimode)
$^1$H NMR (400 MHz, DMSO, 90° C.) δ 7.53 (d, 1H), 7.42-7.25 (m, 5H), 7.20-7.12 (m, 2H), 6.93 (d, 1H), 6.77 (d, 1H), 4.95-4.91 (m, 1H), 4.25 (s, 2H), 3.32-3.02 (m, 10H).

EXAMPLE 26

4-Hydroxy-7-[1-hydroxy-2-(2-{2'-[(3-isopropoxy-propylamino)-methyl]-biphenyl-4-yl}-ethylamino)-ethyl]-3H-benzothiazol-2-one bis-trifluoroacetate salt

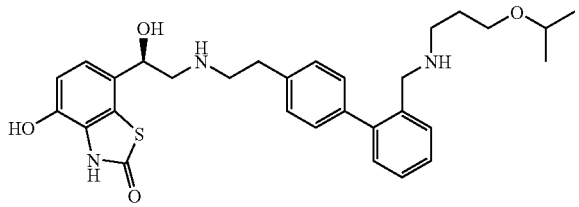

a) (2'-Formyl-biphenyl-4-yl)-acetic acid methyl ester

Methyl (4-bromophenyl)acetate (5.9 g), (2-formylphenyl) boronic acid (5.0 g) and potassium carbonate (10.8 g) were combined in a mixture of toluene and methanol [9:1] (50 mL). The resulting mixture was degassed by bubbling nitrogen though for 1 hour. Tetrakis(triphenylphosphine)palladium(0) (1.5 g) was added and the reaction heated to reflux for 12 hours, under nitrogen. The reaction mixture was filtered through a pad of Celite, the filter pad was washed with ethyl acetate and the combined filtrates evaporated. Purification on silica, eluting with a gradient 0 to 10% ethyl acetate in iso-hexane.

¹H NMR (300 MHz, CDCl₃) δ 10.00 (s, 1H), 8.01 (dd, 1H), 7.64 (dt, 1H), 7.50 (t, 1H), 7.46-7.29 (m, 5H), 3.74 (s, 3H), 3.71 (s, 2H).

b) [4'-(2-Hydroxy-ethyl)-biphenyl-2-ylmethyl]-(3-isopropoxy-propyl)-carbamic acid tert-butyl ester Acetic acid (115 μL) was added to a mixture of (2'-formyl-biphenyl-4-yl)-acetic acid methyl ester (0.530 g) and 3-isopropoxypropyl-1-amine (0.234 g) in methanol (7.5 mL) at room temperature. After 1 hour, sodium triacetoxyborohydride (0.640 g) was added and the mixture stirred for 18 hours at room temperature. The reaction was loaded onto a conditioned SCX cartridge (10 g Varian). The cartridge was washed with methanol (2×20 mL), then eluted with a mixture methanol/7N ammonia solution in methanol (4:1 mixture, 3×20 mL) and the combined elution fractions evaporated. The residue was dissolved in dichloromethane (10 mL) and di-tert-butyl dicarbonate (0.57 g), triethylamine (0.60 mL) and 4-dimethylaminopyridine (2 mg) added, stirred for 18 hours and then evaporated. The residue was dissolved in dry ethanol (35 mL) and anhydrous calcium chloride (575 mg) was added. The reaction mixture was cooled to 0° C. and sodium borohydride (390 mg) was cautiously added. The resulting mixture was allowed to warm to room temperature and stirred until consumption of ester by HPLC (~3 hours). The reaction mixture was quenched with 2M aqueous potassium carbonate solution. The ethanol was evaporated and the resulting suspension was diluted with water (50 mL) and extracted with ethyl acetate (3×100 mL). The combined organics were washed with brine (100 mL), dried (magnesium sulfate) and evaporated. Purification on silica, eluting with 30% ethyl acetate in iso-hexane, to give the subtitle compound as a clear oil (360 mg).

m/z 428 (M+H)⁺ (APCI)

¹H NMR (300 MHz, CDCl₃) δ 7.39-7.14 (m, 8H), 4.50-4.29 (m, 2H), 3.92 (t, 2H), 3.43 (septet, 1H), 3.34-2.99 (m, 4H), 2.92 (t, 2H), 1.66-1.52 (m, 2H), 1.51-1.30 (m, 9H), 1.05 (d, 6H).

c) 4-Hydroxy-7-(1R-hydroxy-2-{[2-(2'-{[(3-isopropoxypropyl)amino]methyl}biphenyl-4-yl)ethyl]amino}ethyl)-1,3-benzothiazol-2(3H)-one bis-trifluoroacetate salt Prepared from [4'-(2-hydroxy-ethyl)-biphenyl-2-ylmethyl]-(3-isopropoxy-propyl)-carbamic acid tert-butyl ester (360 mg) and 7-(2-amino-1R-hydroxy-ethyl)-4-hydroxy-3H-benzothiazol-2-one hydrochloride (0.1 g) using the method of Example 3 (step b), to give the title compound the title compound (85 mg).

m/z 536 (M+H)⁺ (Agilent multimode)

¹H NMR (300 MHz, DMSO, 90° C.) δ 7.69 (t, 1H), 7.57-7.48 (m, 2H), 7.41 (d, 2H), 7.36 (d, 2H), 7.35-7.30 (m, 1H), 6.99 (d, 1H), 6.82 (d, 1H), 4.96 (t, 1H), 4.14 (s, 2H), 3.58-3.46 (m, 1H), 3.39 (t, 2H), 3.35-3.27 (m, 2H), 3.15 (m, 4H), 2.88 (t, 2H), 1.74 (quin, 2H), 1.08 (d, 6H). 7H exchangeable not seen at elevated temperature.

EXAMPLE 27

4-hydroxy-7-[1R-hydroxy-2-({2-[2'-({[1R-phenyl-ethyl]amino}methyl)biphenyl-4-yl]ethyl}amino)ethyl]-1,3-benzothiazol-2(3R)-one bis-trifluoroacetate salt

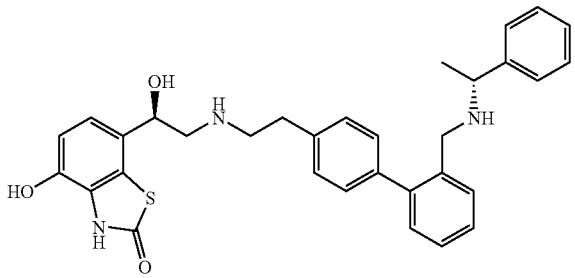

a) [4'-(2-Hydroxy-ethyl)-biphenyl-2-ylmethyl]-(1R-phenyl-ethyl)-carbamic acid tert-butyl ester Prepared following the procedure described in Example 26 (Step b).

m/z 432 (M+H)⁺ (APCI)

¹H NMR (300 MHz, CDCl₃) δ 7.22 (m, 13H), 4.50-4.22 (m, 1H), 4.18-3.97 (m, 1H), 3.91 (q, 2H), 2.91 (t, 2H), 1.55 (s, 3H), 1.55 (s, 9H), 1.30 (m, 2H).

b) 4-Hydroxy-7-[1R-hydroxy-2-({2-[2'-({[1R-phenylethyl]amino}methyl)biphenyl-4-yl]ethyl}amino)ethyl]-1,3-benzothiazol-2(3H)-one bis-trifluoroacetate salt Prepared from [4'-(2-hydroxy-ethyl)-biphenyl-2-ylmethyl]-(1R-phenyl-ethyl)-carbamic acid tert-butyl ester using the method of Example 18 (step b), to give the title compound.

m/z 540 (M+H)⁺ (Agilent multimode)

¹H NMR (300 MHz, DMSO, 90° C.) δ 7.71-7.62 (m, 1H), 7.49-7.42 (m, 2H), 7.36-7.27 (m, 5H), 7.26-7.20 (m, 1H), 7.20 (d, 2H), 7.13 (d, 2H), 6.97 (d, 1H), 6.78 (d, 1H), 4.93 (m, 1H), 4.29-4.18 (m, 1H), 3.98 (d, 1H), 3.81 (d, 1H), 3.26 (t, 2H), 3.20-3.00 (m, 4H), 1.47 (d, 3H). 7H exchangeable not seen at elevated temperature.

EXAMPLE 28

7-(2-{2-[3'-(1,3-Dihydro-iso-indol-2-ylmethyl)-biphenyl-4-yl]-ethylamino}-1R-hydroxy-ethyl)-4-hydroxy-3H-benzothiazol-2-one bis-trifluoroacetate salt

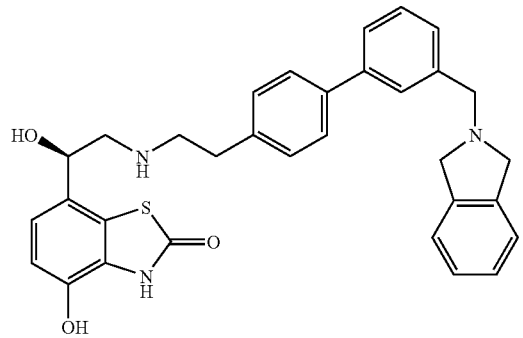

a) (4-Bromo-phenyl)-acetic acid methyl ester

Acetyl chloride (10 g) was added dropwise over 5 minutes to methanol (250 mL). After 5 minutes, (4-bromo-phenyl)-acetic acid (15 g) was added. The resulting mixture was stirred for 96 hours, concentrated and the residue azeotroped with toluene (×2) to give the subtitle compound as a yellow oil (16 g).

$^1$H NMR (400 MHz, CDCl$_3$) δ 7.50-7.41 (m, 2H), 7.19-7.10 (m, 2H), 3.69 (s, 3H), 3.58 (s, 2H).

b) (3'-Formyl-biphenyl-4-yl)-acetic acid methyl ester

3-Formylphenylboronic acid (2.25 g), potassium carbonate (4.15 g) and tetrakis(triphenylphosphine)palladium(0) (0.58 g) was added to a solution of (4-bromophenyl)-acetic acid methyl ester (2.3 g) in a nitrogen degassed mixture of toluene and methanol [9:1] (20 mL) and heated to reflux for 18 hours. On cooling the reaction was filtered through a pad of Celite, the pad was washed with ethyl acetate (2×50 mL) and the combined filtrates were concentrated. Purification on silica, eluting with iso-hexane/ethyl acetate [1:0 to 4:1], afforded the subtitle compound as yellow oil (2.45 g)

$^1$H NMR (400 MHz, CDCl$_3$) δ 10.09 (s, 1H), 8.09 (t, 1H), 7.87-7.83 (m, 2H), 7.63-7.57 (m, 3H), 7.40 (d, 2H), 3.73 (s, 3H), 3.70 (s, 2H).

c) [3'-(1,3-Dihydro-iso-indol-2-ylmethyl)-biphenyl-4-yl]-acetic acid methyl ester (3'-Formyl-biphenyl-4-yl)-acetic acid methyl ester (1.22 g), acetic acid (0.23 mL) and iso-indoline (0.48 g) were combined in methanol (10 mL). After 1 hour, sodium triacetoxyborohydride (1.27 g) was added and stirred for 18 hours, at room temperature, under nitrogen. The reaction was quenched with 0.880 ammonia solution and concentrated. The residue was dissolved in methanol and loaded onto a conditioned SCX cartridge (50 g Varian). The cartridge was washed with methanol (3×50 mL), then eluted with methanolic ammonia solution (2×50 mL) and the combined elution fractions evaporated. Purification on silica, eluting with triethylamine/ethyl acetate/iso-hexane [1:19:80], to give the subtitle compound as a dark brown oil (450 mg).

m/z 358 (M+H)$^+$ (APCI)

$^1$H NMR (400 MHz, CDCl$_3$) δ 7.64 (s, 1H), 7.58 (dt, 2H), 7.50 (dt, 1H), 7.44-7.37 (m, 2H), 7.34 (d, 2H), 7.18 (s, 4H), 3.97 (s, 2H), 3.97 (s, 4H), 3.71 (s, 3H), 3.67 (s, 2H).

d) [3'-(1,3-Dihydro-iso-indol-2-ylmethyl)-biphenyl-4-yl]-acetic acid

Lithium hydroxide (126 mg) in water (5 mL) was added to a solution of [3'-(1,3-dihydro-iso-indol-2-ylmethyl)-biphenyl-4-yl]-acetic acid methyl ester (0.47 g) in tetrahydrofuran (10 mL) and stirred at room temperature for 72 hour. The reaction mixture was acidified with glacial acetic acid and evaporated. The residue was partitioned between ethyl acetate (20 mL) and water (20 mL). The aqueous was separated and extracted with ethyl acetate (2×20 mL). The combined organics were washed with brine (20 mL), dried (sodium sulfate) and evaporated to give a the subtitle compound as a brown oil (450 mg).

m/z 342 (M−H)$^-$ (APCI)

1H NMR (300 MHz, DMSO) δ 7.95-7.61 (m, 3H), 7.58-7.47 (m, 2H), 7.41-7.25 (m, 7H), 4.44 (s, 4H), 3.62 (s, 2H), 3.17 (s, 2H).

e) 2-[3'-(1,3-Dihydro-iso-indol-2-ylmethyl)-biphenyl-4-yl]-ethanol

Borane-tetrahydrofuran complex (1M in tetrahydrofuran) (1.0 mL) was added to a solution of [3'-(1,3-dihydro-iso-indol-2-ylmethyl)-biphenyl-4-yl]-acetic acid (0.444 g) in tetrahydrofuran (30 mL) and stirred at room temperature, under nitrogen, for 3 hours, then evaporated The residue was dissolved in methanol and loaded onto a conditioned SCX cartridge (10 g Varian). The cartridge was washed with methanol (3×20 mL) and then eluted with methanolic ammonia solution (2×20 mL). The combined eluents were concentrated to give the subtitle compound as a dark brown oil (165 mg)

m/z 330 (M+H)$^+$ (APCI)

$^1$H NMR (400 MHz, CDCl$_3$) δ 7.60-7.28 (m, 9H), 7.25-7.16 (m, 3H), 4.47 (d, 2H), 4.36 (d, 2H), 4.20 (s, 2H), 4.02-3.88 (m, 2H), 2.93 (t, 2H).

f) 7-(2-{2-[3'-(1,3-Dihydro-iso-indol-2-ylmethyl)-biphenyl-4-yl]-ethylamino}-1R-hydroxy-ethyl)-4-hydroxy-3H-benzothiazol-2-one bis-trifluoroacetate salt Pyridinium chlorochromate (0.16 g) was added to a solution of 2-[3'-(1,3-dihydro-iso-indol-2-ylmethyl)-biphenyl-4-yl]-ethanol (0.16 g) and sodium acetate (12 mg) in dichloromethane (10 mL) and stirred under nitrogen for 2 hours. The reaction was filtered through a pad of celite and the filtrate evaporated. The residue was dissolved in methanol and 7-(2-amino-1R-hydroxy-ethyl)-4-hydroxy-3H-benzothiazol-2-one hydrochloride (100 mg) was added followed by acetic acid (0.03 mL). After stirring for 1 hour, sodium cyanoborohydride (41 mg) was added and stirred for 18 hours. The reaction mixture was loaded onto conditioned Tosic-65A resin (2 g Argonaut). The resin was washed with methanol (3×50 mL) and the eluted with methanolic ammonia solution (2×30 mL). The combined elution fractions were evaporated and the residue purified by HPLC method A, to give the title compound as a white solid (23 mg).

m/z 538 (M+H)$^+$ (Agilent multimode)

$^1$H NMR (400 MHz, DMSO, 90° C.) δ 7.74 (s, 1H), 7.64 (d, 3H), 7.52-7.42 (m, 2H), 7.38-7.22 (m, 6H), 6.94 (d, 1H), 6.77 (t, 1H), 4.94-4.88 (m, 1H), 3.30-2.80 (m, 12H).

EXAMPLE 29

7-(2-{2-[3'-(Benzylamino-methyl)-biphenyl-3-yl]-ethylamino}-1R-hydroxy-ethyl)-4-hydroxy-3H-benzothiazol-2-one bis-trifluoroacetate salt

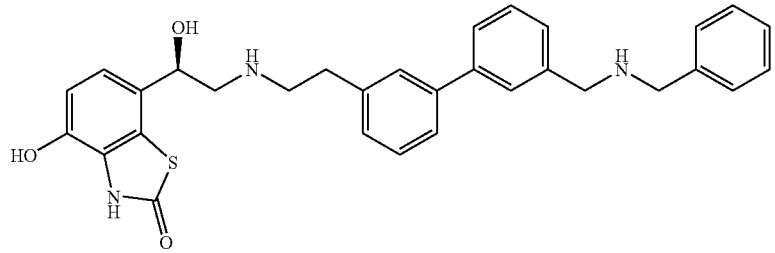

a) (3-Bromo-phenyl)-acetic acid methyl ester

Acetyl chloride (5 mL) was added to a solution of (3-bromo-phenyl)-acetic acid (10 g) in methanol (250 mL). Evaporation after 24 hours afforded the subtitle product, as an oil (10.9 g).

$^1$H NMR (300 MHz, CDCl$_3$) δ 7.46-7.37 (m, 2H), 7.23-7.16 (m, 2H), 3.70 (s, 3H), 3.60 (s, 2H).

b) (3'-Formyl-biphenyl-3-yl)-acetic acid methyl ester

A mixture of (3-bromo-phenyl)-acetic acid methyl ester (5 g), 3-formyl phenyl boronic acid (5 g) and potassium carbonate (9 g) in toluene/methanol [10:1] (33 mL) was degassed with nitrogen for 1 hour. Tetrakis(triphenylphosphine)palladium(0) (1.3 g) was washed with ethanol, under nitrogen, until golden in colour and added to the mixture. The resultant mixture was heated to reflux for 24 hours. On cooling, the reaction was diluted with iso-hexane/diethyl ether [4:1] (100 mL) and filtered through a Celite pad. The filtrate was evaporated and the residue purified on silica, eluting iso-hexane/ethyl acetate [4:1] to give the subtitle product, as an oil (3.7 g).

$^1$H NMR (300 MHz, CDCl$_3$) δ 10.09 (s, 1H), 8.10 (t, 1H), 7.88 (d, 1H), 7.85 (s, 1H), 7.61 (t, 1H), 7.57-7.52 (m, 2H), 7.44 (t, 1H), 7.33 (d, 1H), 3.72 (s, 5H).

c) Benzyl-[3'-(2-hydroxy-ethyl)-biphenyl-3-ylmethyl]-carbamic acid tert-butyl ester Benzylamine (214 mg), (3'-formyl-biphenyl-3-yl)-acetic acid methyl ester (510 mg) and acetic acid (114 μl) were combined in methanol (5 mL). After 1 hour, sodium triacetoxyborohydride (1.3 g) was added, followed by methanol (5 mL). After 24 hours, the reaction mixture was quenched onto saturated aqueous bicarbonate solution and extracted twice with dichloromethane. The organic extracts were combined and evaporated. The resultant residue was loaded onto a conditioned SCX cartridge (10 g Varian) and washed with methanol (50 mL), then eluted with methanol/0.880 ammonia soon [9:1] (50 mL). The elution fraction was evaporated and the residue was dissolved in tetrahydrofuran (10 mL). 2M Lithium borohydride in tetrahydrofuran (1.5 mL) was added and heated to reflux for 2 hours. Methanol (10 mL) was added and heating continued for a further 1 hour. Concentrated hydrochloric acid (2 mL) was added and heating continued for a further 1 hour, cooled and concentrated. The residue was loaded in methanol onto a conditioned SCX cartridge (10 g Varian), washed with methanol (50 mL), then eluted with methanol/0.880 ammonia solution [9:1] (50 mL). The elution fraction was evaporated and the residue dissolved in dichloromethane/methanol [9:1] (20 mL) and di-tert-butyl dicarbonate (400 mg) added. After 72 hours, the reaction mixture was evaporated and the residue purified on silica, eluting with a gradient of methanol (0-4%) in dichloromethane, to give the subtitle product, as an oil (340 mg).

$^1$H NMR (300 MHz, CDCl$_3$, 50° C.) δ 7.51-7.15 (m, 13H), 4.44 (d, 2H), 3.96-3.84 (m, 2H), 3.72-3.52 (m, 2H), 2.98-2.87 (m, 2H), 1.50 (s, 9H). (OH not seen).

d) 7-(2-{2-[3'-(Benzylamino-methyl)-biphenyl-3-yl]-ethylamino}-1R-hydroxy-ethyl)-4-hydroxy-3H-benzothiazol-2-one bis-trifluoroacetate salt Dess-Martin periodinane (415 mg) was added to a solution of benzyl-[3'-(2-hydroxy-ethyl)-biphenyl-3-ylmethyl]-carbamic acid tert-butyl ester (340 mg) in dichloromethane. After 75 minutes the reaction mixture was poured on to a mixture of: sodium thiosulfate (15 g); water (15 mL); saturated aqueous sodium bicarbonate (35 mL) and ethyl acetate (35 mL). Stirred vigorously for 30 minutes. The mixture was diluted with ethyl acetate and extracted twice with brine, dried (magnesium sulfate) and evaporated. The residue was dissolved in methanol (10 mL), then 7-(2-amino-1R-hydroxy-ethyl)-4-hydroxy-3H-benzothiazol-2-one hydrochloride (100 mg) and acetic acid (25 μL) added. After 1 hour, sodium cyanoborohydride (50 mg) was added. After 18 hours, 0.880 ammonia solution (0.5 mL) was added and the reaction mixture concentrated. The residue was loaded onto conditioned Tosic-65A resin (3.3 g, Argonaut) in acetonitrile/propan-2-ol [1:1]. The resin was washed with acetonitrile/propan-2-ol [1:1] (50 mL) and eluted propan-2-ol/0.880 ammonia solution [4:1] (100 mL). The elution fraction was evaporated, treated with trifluoroacetic acid/dichloromethane [1:1] (10 mL) for 30 minutes and evaporated. Purification by HPLC method A, evaporation and trituration with diethyl ether gave the title product, as a white solid (15 mg).

m/z 526 (M+H)$^+$ (Agilent multimode)

$^1$H NMR (300 MHz, DMSO, 90° C.) δ 7.81 (s, 1H), 7.73 (d, 1H), 7.62-7.42 (m, 10H), 7.31 (d, 1H), 6.97 (d, 1H), 6.81 (d,

J=9.0 Hz, 1H), 4.97 (t, 1H), 4.29 (s, 2H), 4.25 (s, 2H), 3.44-3.30 (m, 2H), 3.23-3.05 (m, 4H). 7H exchangeable not seen at elevated temperature.

EXAMPLE 30

7-{2-[2-(3-{[2-(2-Fluoro-phenyl)-ethylamino]-methyl}-4-methoxy-phenyl)-ethylamino]-1R-hydroxy-ethyl}-4-hydroxy-3H-benzothiazol-2-one bis-trifluoroacetate salt

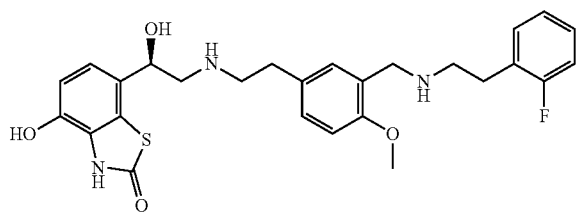

a) (3-Bromomethyl-4-methoxy-phenyl)-acetic acid

N-Bromosuccinimide (1.0 g) and 2,2'-azobis(2-methyl-propionitrile) (20 mg) were added to a solution of (4-methoxy-3-methyl-phenyl)-acetic acid (1.1 g) in chloroform (25 mL) and heated to reflux for 4 hours. On cooling, the mixture was evaporated, the residue dissolved in ethyl acetate, washed sequentially with 2M aqueous hydrochloric acid (2×50 mL), brine (50 mL), dried (magnesium sulfate) and concentrated to give the subtitle compound as an oil (1.4 g).

$^1$H NMR (400 MHz, CDCl$_3$) δ 7.26-7.18 (m, 2H), 6.88 (d, 1H), 4.69 (s, 2H), 3.90 (s, 3H), 3.59 (s, 2H). CO$_2$H not seen b) (3-Formyl-4-methoxy-phenyl)-acetic acid

Copper(II) nitrate trihydrate (3.3 g) was added to (3-bromomethyl-4-methoxy-phenyl)-acetic acid (1.4 g) in water (50 mL) and heated to reflux for 75 minutes. On cooling the reaction mixture was acidified with 2M aqueous hydrochloric acid and extracted with ethyl acetate. The organic phase was separated and washed sequentially with 2M aqueous hydrochloric acid (2×50 mL), brine (50 mL), dried (magnesium sulfate) and concentrated. Purification on silica, eluting iso-hexane/ethyl acetate [4:1 to 1:1 to 0:1], to give the subtitle compound as a solid (0.26 g).

$^1$H NMR (300 MHz, CDCl$_3$) δ 10.45 (s, 1H), 9.91 (s, 1H), 7.73 (d, 1H), 7.49 (dd, 1H), 6.98 (d, 1H), 3.94 (s, 3H), 3.64 (s, 2H).

c) (3-{[2-(2-Fluoro-phenyl)-ethylamino]-methyl}-4-methoxy-phenyl)-acetic acid methyl ester 2-(2-Fluorophenyl)ethylamine (180 mg) in dichloromethane (5 mL) was added to (3-formyl-4-methoxy-phenyl)-acetic acid (260 mg). After 30 minutes, sodium triacetoxyborohydride (0.5 g) was added. After a further 2.5 hours, the reaction mixture was evaporated and the residue loaded onto a conditioned SCX cartridge (10 g Varian). The cartridge was washed with methanol (50 mL) and then eluted with a mixture of methanol/0.880 ammonia solution [4:1] (50 mL). The elution fraction was concentrated, the residue was dissolved in methanol (100 mL) and tri-methylchlorosilane (2 mL) added. After 18 hours, the reaction mixture was evaporated and the residue purified on silica, eluting iso-hexane/ethyl acetate [4:1 to 1:1 to 0:1]+1% triethylamine, to give the subtitle compound as an oil (0.30 g).

m/z 332 (M+H)$^+$ (APCI)

$^1$H NMR (300 MHz, CDCl$_3$) δ 7.25-7.00 (m, 6H), 6.80 (d, 1H), 3.80 (s, 2H), 3.75 (s, 3H), 3.70 (s, 3H), 2.90 (s, 6H). NH not seen.

d) [3-({tert-Butoxycarbonyl-[2-(2-fluoro-phenyl)-ethyl]-amino}-methyl)-4-methoxy-phenyl]-acetic acid methyl ester Di-tert-butyl dicarbonate (0.30 g) was added to a solution of (3-{[2-(2-fluoro-phenyl)-ethylamino]-methyl}-4-methoxy-phenyl)-acetic acid methyl ester (0.30 g) in dichloromethane (10 mL). After 2 hours, the reaction was concentrated and purified on silica, eluting with a gradient of methanol (0% to 1%) in dichloromethane, to give the subtitle compound as an oil (0.25 g).

$^1$H NMR (300 MHz, CDCl$_3$) δ 7.26-6.95 (m, 6H), 6.80 (d, 1H), 4.34 (s, 2H), 3.81 (s, 3H), 3.66 (s, 3H), 3.54 (s, 2H), 3.50-3.30 (m, 2H), 2.90-2.75 (m, 2H), 1.43 (s, 9H).

e) [2-(2-Fluoro-phenyl)-ethyl]-[5-(2-hydroxy-ethyl)-2-methoxy-benzyl]-carbamic acid tert-butyl ester 2M Lithium borohydride in tetrahydrofuran (1.5 mL) was added to a solution of [3-({tert-butoxycarbonyl-[2-(2-fluoro-phenyl)-ethyl]-amino}-methyl)-4-methoxy-phenyl]-acetic acid methyl ester (0.25 g) in tetrahydrofuran (5 mL), at 0° C. under nitrogen. After 4 hours, the reaction was quenched by the addition of ethyl acetate. The reaction was diluted with ethyl acetate and extracted sequentially twice with saturated aqueous sodium bicarbonate solution, brine, dried (magnesium sulfate) and evaporated. Purification on silica, eluting with a gradient of methanol (0% to 1%) in dichloromethane, to give the subtitle compound as an oil (0.25 g).

m/z 404 (M+H)$^+$ (APCI)

$^1$H NMR (300 MHz, CDCl$_3$) δ 7.26-7.00 (m, 6H), 6.79 (d, 1H), 4.40 (d, 2H), 3.85-3.77 (m, 5H), 3.50-3.30 (s, 3H), 3.54 (m, 2H), 2.90-2.75 (m, 4H), 1.44 (s, 9H).

f) 7-{2-[2-(3-{[2-(2-Fluoro-phenyl)-ethylamino]-methyl}-4-methoxy-phenyl)-ethylamino]-1R-hydroxy-ethyl}-4-hydroxy-3H-benzothiazol-2-one bis-trifluoroacetate salt Prepared from [2-(2-fluoro-phenyl)-ethyl]-[5-(2-hydroxy-ethyl)-2-methoxy-benzyl]-carbamic acid tert-butyl ester (0.25 g) and 7-(2-amino-1R-hydroxy-ethyl)-4-hydroxy-3H-benzothiazol-2-one hydrochloride (0.1 g) using the method of Example 3 (step b), to give the title compound as a white solid (52 mg).

m/z 512 (M+H)$^+$ (Agilent multimode)

$^1$H NMR (300 MHz, DMSO, 90° C.) δ 7.35-7.25 (m, 4H), 7.20-7.10 (m, 2H), 7.05 (d, 1H), 6.93 (d, 1H), 6.77 (d, 1H), 4.90 (dd, 1H), 4.13 (s, 2H), 3.83 (s, 3H), 3.23-2.88 (m, 10H). 7H exchangeable not seen at elevated temperature.

EXAMPLE 31

4-Hydroxy-7-[1R-hydroxy-2-(2-{3-[(3-phenyl-propylamino)-methyl]-phenyl}-ethylamino)-ethyl]-3H-benzothiazol-2-one bis-trifluoroacetate salt

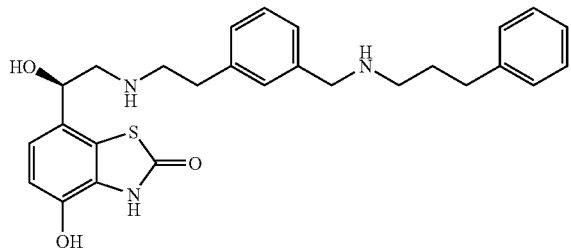

a) (3-{[tert-Butoxycarbonyl-(3-phenyl-propyl)-amino]-methyl}-phenyl)-acetic acid methyl ester Sodium triacetoxyborohydride (2.0 g) was added to a solution of 3-phenylpropyl-1-amine (0.6 g) and (3-formyl-phenyl)-acetic acid methyl ester (0.52 g) in dichloromethane (10 mL). After 4 hours, the reaction mixture was poured on to saturated aqueous sodium bicarbonate solution and extracted with dichloromethane (2×50 mL). The combined organics were dried (sodium sulfate), filtered and di-tert-butyl dicarbonate (1.0 g) added to the filtrate. After 18 hours, the reaction mixture was evaporated and the residue purified on silica, eluting with methanol (1%) in dichloromethane, to give the subtitle compound as an oil (0.93 g).

$^1$H NMR (400 MHz, CDCl$_3$) δ 7.30-7.23 (m, 2H), 7.20-7.10 (m, 7H), 4.42 (d, 2H), 3.69 (s, 3H), 3.60 (s, 2H), 3.15 (q, 2H), 2.56 (t, 2H), 1.85-1.77 (m, 2H), 1.44 (s, 9H).

b) [3-(2-Hydroxy-ethyl)-benzyl]-(3-phenyl-propyl)-carbamic acid tert-butyl ester Prepared from (3-{[tert-butoxycarbonyl-(3-phenyl-propyl)-amino]-methyl}-phenyl)-acetic acid methyl ester (0.93 g) using the method of Example 30 (step e), to give the subtitle compound as an oil (666 mg).

m/z 314 (M+2H−tBu)$^+$ (APCI)

$^1$H NMR (300 MHz, CDCl$_3$) δ 7.31-7.22 (m, 2H), 7.22-7.01 (m, 7H), 4.41 (s, 2H), 3.84 (q, 2H), 3.22 (d, 2H), 2.85 (t, 2H), 2.57 (t, 2H), 1.83 (s, 2H), 1.45 (s, 9H), 1.34 (t, 1H).

c) 4-Hydroxy-7-[1R-hydroxy-2-(2-{3-[(3-phenyl-propylamino)-methyl]-phenyl}-ethylamino)-ethyl]-3H-benzothiazol-2-one bis-trifluoroacetate salt Prepared from [3-(2-hydroxy-ethyl)-benzyl]-(3-phenyl-propyl)-carbamic acid tert-butyl ester (220 mg) and 7-(2-amino-1R-hydroxy-ethyl)-4-hydroxy-3H-benzothiazol-2-one hydrochloride (100 mg) using the method of Example 30 (step f), to give the title compound as a white solid (59 mg).

m/z 478 (M+1)$^+$ (Agilent multimode)

$^1$H NMR (300 MHz, DMSO, 90° C.) δ 7.44-7.13 (m, 9H), 6.94 (d, 1H), 6.77 (d, 1H), 4.89 (t, 1H), 4.11 (s, 2H), 3.27-2.83 (m, 8H), 2.66 (t, 2H), 1.95 (quintet, 2H). 7H exchangeable not seen at elevated temperature.

EXAMPLE 32

4-Hydroxy-7-{1R-hydroxy-2-[2-(3-piperidin-1-ylmethyl-phenyl)-ethylamino]-ethyl}-3H-benzothiazol-2-one bis-trifluoroacetate salt

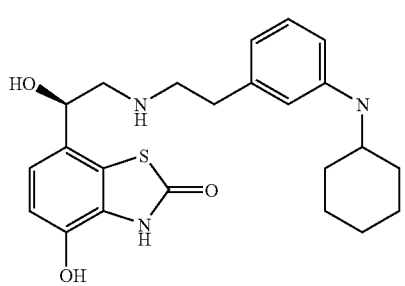

a) 1-Boranyl-1-[3-(2-hydroxy-ethyl)-benzyl]-piperidinium (3-Formyl-phenyl)-acetic acid methyl ester (0.64 g), acetic acid (0.18 mL) and piperidine (0.29 mL) were combined in dichloromethane (10 mL). After 1 hour, sodium triacetoxyborohydride (0.95 g) was added and the reaction stirred overnight. After 24 hours, the solvent was evaporated. The resultant residue was loaded onto a conditioned SCX cartridge (10 g Varian) and washed with methanol (50 mL), then eluted with methanolic ammonia solution (50 mL). The elution fraction was evaporated and the residue was dissolved in ethanol (10 mL). Calcium chloride anhydrous (0.67 g) was added followed by sodium borohydride (0.45 g) and the resulting mixture stirred overnight. Aqueous potassium carbonate solution (2M, 50 mL) was added and the ethanol evaporated. The aqueous was extracted with ethyl acetate (3×50 mL) and the combined organics washed with water (50 mL), brine (50 mL), dried (sodium sulfate) and evaporated. The residue was redissolved in tetrahydrofuran (10 mL) and cooled to 0° C., under nitrogen. Borane-methyl sulfide complex (2M solution in tetrahydrofuran, 2.25 mL) was added and the resulting mixture stirred for 5 minutes. The tetrahydrofuran was evaporated and the residue purified on silica, eluting with diethyl ether/iso-hexane [1:1 to 1:0] to give subtitle product, as an oil (133 mg).

$^1$H NMR (400 MHz, CDCl$_3$) δ 7.34-7.28 (m, 2H), 7.27-7.23 (m, 2H), 3.99 (s, 2H), 3.88 (q, 2H), 2.96-2.86 (m, 4H), 2.69-2.60 (m, 2H), 2.22-2.10 (m, 2H), 1.71-1.56 (m, 3H), 1.35-1.26 (m, 1H).

b) 4-Hydroxy-7-{1R-hydroxy-2-[2-(3-piperidin-1-ylmethyl-phenyl)-ethylamino]-ethyl}-3H-benzothiazol-2-one bis-trifluoroacetate salt Dess-Martin periodinane (292 mg) was added to a solution of 1-boranyl-1-[3-(2-hydroxy-ethyl)-benzyl]-piperidinium (133 mg) in dichloromethane (4 mL). After 75 minutes, the reaction mixture was poured onto a mixture of: sodium thiosulfate (10 g); water (10 mL); saturated aqueous sodium bicarbonate (100 mL) and ethyl acetate (20 mL) and was stirred vigorously for 10 minutes. The mixture was separated and the aqueous extracted with ethyl acetate (20 mL). The combined organics were washed with water (20 mL), brine (20 mL), dried (magnesium sulfate) and evaporated. The residue was dissolved in methanol (10 mL), then 7-(2-amino-1R-hydroxy-ethyl)-4-hydroxy-3H-benzothiazol-2-one hydrochloride (100 mg) and acetic acid (24 µL) added. After 1 hour, sodium cyanoborohydride (36 mg) was added. After 18 hours, 0.880 ammonia solution (0.5 mL) was added and the reaction mixture concentrated under vacuum. The residue was loaded onto conditioned Tosic-65A resin (3.3 g, Argonaut) in acetonitrile/propan-2-ol [1:1]. The resin was washed with acetonitrile/propan-2-ol [1:1] (50 mL) and eluted propan-2-ol/0.880 ammonia solution [4:1] (100 mL). The elution fraction was evaporated, and the residue redissolved in tetrahydrofuran (10 mL). Ethylenediamine (0.25 mL) was added and the mixture refluxed for 5 min and evaporated. The residue was treated with trifluoroacetic acid (1 mL) and evaporated. Purification by HPLC method A, evaporation and trituration with diethyl ether gave the title product, as a white solid (48 mg).

m/z 428 (M+H)+ (Agilent multimode)

1H NMR (300 MHz, DMSO, 90° C.) δ 7.44-7.28 (m, 4H), 6.93 (d, 1H), 6.77 (d, 1H), 4.97-4.88 (m, 1H), 4.22 (s, 2H), 3.35-2.92 (m, 10H), 1.84-1.66 (m, 4H), 1.63-1.45 (m, 2H). 6H exchangeable not seen at elevated temperature

EXAMPLE 33

4-Hydroxy-7-(1R-hydroxy-2-{2-[3-(4-phenyl-piperidin-1-ylmethyl)-phenyl]-ethylamino}-ethyl)-3H-benzothiazol-2-one bis-trifluoroacetate salt

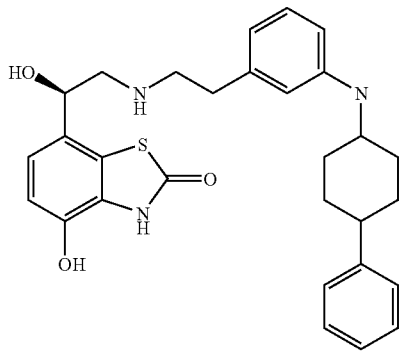

1-Boranyl-1-[3-(2-hydroxy-ethyl)-benzyl]-4-phenyl-piperidinium (3-Formyl-phenyl)-acetic acid methyl ester (0.64 g), acetic acid (0.18 mL) and 4-phenyl-piperidine (0.48 mL) were combined in dichloromethane (10 mL). After 1 hour, sodium triacetoxyborohydride (0.95 g) was added and the reaction stirred overnight. After 24 hours, the solvent was evaporated. The resultant residue was loaded onto a conditioned SCX cartridge (10 g, Varian) and washed with methanol (50 mL), then eluted with methanolic ammonia solution (2M, 50 mL). The elution fraction was evaporated and the residue was dissolved in ethanol (10 mL). Calcium chloride anhydrous (0.67 g) was added followed by sodium borohydride (0.45 g) and the resulting mixture stirred overnight. An aqueous potassium carbonate solution (2M, 50 mL) was added and the ethanol evaporated. The aqueous was extracted with ethyl acetate (3×50 mL) and the combined organics washed with water (50 mL), brine (50 mL), dried (sodium sulfate) and evaporated. The residue was redissolved in tetrahydrofuran (10 mL) and cooled to 0° C., under nitrogen. Borane-methyl sulfide complex (2M solution in tetrahydrofuran, 2.25 mL) was added and the resulting mixture stirred for 5 min. The tetrahydrofuran was evaporated and the residue purified on silica, eluting with diethyl ether: iso-hexane [1:1 to 1:0] to give subtitle product, as an oil 193 mg.

1H NMR (300 MHz, CDCl3) δ 7.39-7.14 (m, 9H), 4.09 (s, 2H), 3.95-3.87 (m, 2H), 3.05 (d, 2H), 2.92 (t, 2H), 2.75-2.58 (m, 4H), 2.45-2.33 (m, 1H), 1.72-1.60 (m, 2H)

b) 4-Hydroxy-7-(1R-hydroxy-2-{2-[3-(4-phenyl-piperidin-1-ylmethyl)-phenyl]-ethylamino}-ethyl)-3H-benzothiazol-2-one bis-trifluoroacetate salt Dess-Martin periodinane (320 mg) was added to a solution of 1-boranyl-1-[3-(2-hydroxy-ethyl)-benzyl]-4-phenyl-piperidinium (193 mg) in dichloromethane (4 mL). After 75 minutes, the reaction mixture was poured onto a mixture of: sodium thiosulfate (10 g); water (10 mL); saturated aqueous sodium bicarbonate (10 mL) and ethyl acetate (20 mL). Stirred vigorously for 10 minutes. The mixture was separated and the aqueous extracted with ethyl acetate (20 mL). The combined organics were washed with water (20 mL), brine (20 mL), dried (magnesium sulfate) and evaporated. The residue was dissolved in methanol (10 mL), then 7-(2-amino-1R-hydroxy-ethyl)-4-hydroxy-3H-benzothiazol-2-one hydrochloride (100 mg) and acetic acid (24 µL) were added. After 1 hour, sodium cyanoborohydride (36 mg) was added. After 18 hours, 0.880 ammonia solution (0.5 mL) was added and the reaction mixture concentrated under vacuum. The residue was loaded onto conditioned Tosic-65A resin (3.3 g, Argonaut) in acetonitrile/propan-2-ol [1:1]. The resin was washed with acetonitrile/propan-2-ol [1:1] (50 mL) and eluted with propan-2-ol/0.880 ammonia solution [4:1] (100 mL). The elution fraction was evaporated, and the residue redissolved in tetrahydrofuran (10 mL), ethylenediamine (0.25 mL) was added and the mixture refluxed for 5 min and evaporated. The residue was treated with trifluoroacetic acid and evaporated. Purification by HPLC method A, evaporation and trituration with diethyl ether gave the title product, as a white solid (82 mg).

m/z 504 (M+H)+ (Agilent multimode)

1H NMR (300 MHz, DMSO, 90° C.) δ 7.46-7.27 (m, 6H), 7.21 (t, 3H), 6.94 (d, 1H), 6.77 (d, 1H), 4.96-4.88 (m, 1H), 4.29 (s, 2H), 3.47-3.37 (m, 2H), 3.31-3.22 (m, 2H), 3.16-2.97 (m, 6H), 2.89-2.75 (m, 1H), 2.05-1.90 (m, 4H)). 6H exchangeable not seen at elevated temperature

EXAMPLE 34

4-Hydroxy-7-[1R-hydroxy-2-(2-{3-[(methyl-phenethyl-amino)-methyl]-phenyl}-ethylamino)-ethyl]-3H-benzothiazol-2-one bis-trifluoroacetic acid salt

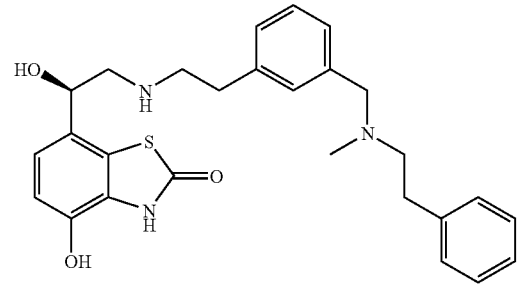

a) N-Boranyl-2-{3-[(Methyl-phenethyl-ammonium)-methyl]-phenyl}-ethanol (3-Formyl-phenyl)-acetic acid methyl ester (0.64 g), acetic acid (0.18 mL) and methyl-phenethyl-amine (0.44 mL were combined in dichloromethane (10 mL). After 1 hour, sodium triacetoxyborohydride (0.95 g) was added and the reaction stirred overnight. After 24 hours, the solvent was evaporated. The resultant residue was loaded onto a conditioned SCX cartridge (10 g Varian) and washed with methanol (50 mL), then eluted with methanolic ammonia solution (2M, 50 mL). The elution fraction was evaporated and the residue was dissolved in ethanol (10 mL). Calcium chloride anhydrous (0.67 g) was then added followed by sodium borohydride (0.45 g) and the resulting mixture stirred overnight. An aqueous potassium carbonate solution (2M, 50 mL) was added and the ethanol evaporated. The aqueous was extracted with ethyl acetate (3×50 mL) and the combined organics washed with water (50 mL), brine (50 mL), dried over sodium sulfate, filtered, and evaporated. The residue was redissolved in tetrahydrofuran (10 mL) and cooled to 0° C. under $N_2$. Borane-methyl sulfide complex (2M soln in THF, 2.25 mL) was added and the resulting mixture stirred for 5 min. The tetrahydrofuran was evaporated and the residue purified on silica, eluting with diethyl ether: iso-hexane [1:1 to 1:0], to give subtitle product, as an oil (446 mg).

$^1$H NMR (300 MHz, $CDCl_3$) δ 7.38-7.16 (m, 9H), 4.12 (d, 1H), 3.99 (d, 1H), 3.85 (t, 2H), 3.28-3.11 (m, 2H), 2.91-2.73 (m, 4H), 2.54 (s, 3H).

b) 4-Hydroxy-7-[1R-hydroxy-2-(2-{3-[(methyl-phenethyl-amino)-methyl]-phenyl}-ethylamino)-ethyl]-3H-benzothiazol-2-one bis-trifluoroacetate salt Dess-Martin periodinane (455 mg) was added to a solution of N-boranyl-2-{3-[(methyl-phenethyl-ammonium)-methyl]-phenyl}-ethanol (253 mg) in dichloromethane (4 mL). After 75 minutes, the reaction mixture was poured onto a mixture of: sodium thiosulfate (10 g); water (10 mL); saturated aqueous sodium bicarbonate (100 mL) and ethyl acetate (20 mL). Stirred vigorously for 10 minutes. The mixture was separated and the aqueous extracted with ethyl acetate (20 mL). The combined organics were washed with water (20 mL), brine (20 mL), dried (magnesium sulfate) and evaporated. The residue was dissolved in methanol (10 mL), then 7-(2-amino-1R-hydroxy-ethyl)-4-hydroxy-3H-benzothiazol-2-one hydrochloride (100 mg) and acetic acid (24 µL) added. After 1 hour, sodium cyanoborohydride (36 mg) was added. After 18 hours, 0.880 ammonia solution (0.5 mL) was added and the reaction mixture concentrated. The residue was loaded onto conditioned Tosic-65A resin (3.3 g, Argonaut) in acetonitrile/propan-2-ol [1:1]. The resin was washed with acetonitrile/propan-2-ol [1:1] (50 mL) and eluted propan-2-ol/0.880 ammonia solution [4:1] (100 mL). The elution fraction was evaporated, and the residue redissolved in tetrahydrofuran (10 mL), ethylenediamine (0.25 mL) was added and the mixture refluxed for 5 minutes and evaporated. The residue was treated with trifluoroacetic acid and evaporated. Purification by HPLC method A, evaporation and trituration with diethyl ether, to give the title product as a white solid (16.3 mg).

m/z 478 (M+H)$^+$ (Agilent multimode)

$^1$H NMR (300 MHz, DMSO, 90° C.) δ 7.44-7.15 (m, 9H), 6.94 (d, 1H), 6.77 (d, 1H), 4.95-4.86 (m, 1H), 4.22-4.09 (m, 2H), 3.28-2.90 (m, 11H), 2.67-2.60 (m, 2H). 6H exchangeable not seen at elevated temperature

EXAMPLE 35

4-Hydroxy-7-[1R-hydroxy-2-({2-[3-({[-2-methoxy-1S-methylethyl]amino}methyl)phenyl]ethyl}amino)ethyl]-1,3-benzothiazol-2(3H)-one bis-hydrochloride

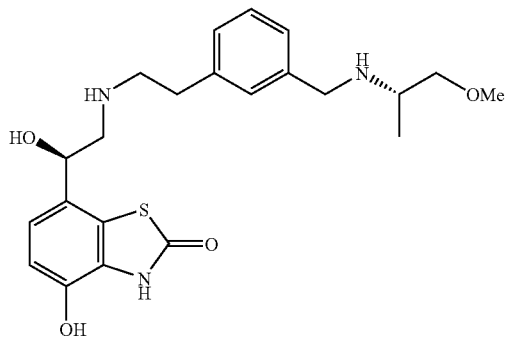

a) [3-(2-Hydroxyethyl)benzyl]-(2-methoxy-1S-methylethyl)carbamic acid tert-butyl ester Prepared from 1S-methoxy-2-propylamine (0.267 g) and (3-formyl-phenyl)-acetic acid ethyl ester (Example 1, step a, 356 mg) using the method of Example 3 (step a). Purification on silica, eluting with 60% diethyl ether/iso-hexane gave the subtitle compound as a colourless oil (280 mg).

$^1$H NMR (300 MHz, $CDCL_3$) δ 7.26-7.22 (m, 1H), 7.13-7.07 (m, 3H), 4.51-4.28 (m, 3H), 4.04-3.95 (m, 1H), 3.85 (q, 2H), 3.44-3.38 (m, 1H), 3.24 (s, 3H), 2.85 (t, 2H), 1.49-1.36 (m, 9H), 1.11 (d, 3H)

b) 4-Hydroxy-7-[1R-hydroxy-2-({2-[3-({[1S-2-methoxy-1-methylethyl]amino}methyl)phenyl]ethyl}amino)ethyl]-1,3-benzothiazol-2(3H)-one bis-hydrochloride Prepared from [3-(2-hydroxyethyl)benzyl]-(2-methoxy-1S-methylethyl)carbamic acid tert-butyl ester (280 mg) and 7-(2-amino-1R-hydroxy-ethyl)-4-hydroxy-3H-benzothiazol-2-one hydrochloride (0.1 g) using the method of Example 3 (step b). The residue was purified by HPLC method B. The purified material was dissolved in acetonitrile (2 mL), treated with an excess of 2M ethereal hydrogen chloride solution and evaporated. The residue was re-dissolved acetonitrile, treated with an excess of 2M ethereal hydrogen chloride solution a second time and evaporated. The residue was triturated with diethyl ether and filtered to give the title compound as a white solid (100 mg)

m/z 432 (M+H)$^+$ (Agilent multimode)

$^1$H NMR (400 MHz, DMSO) δ 11.70 (s, 1H), 10.22 (s, 1H), 9.17 (s, 2H), 9.00-8.88 (m, 2H), 7.47-7.39 (m, 3H), 7.31-7.29 (m, 1H), 6.94 (d, 1H), 6.79 (d, 1H), 6.48 (s, 1H), 4.99-4.97 (m,

1H), 4.15 (s, 2H), 3.59-3.50 (m, 6H), 3.33 (s, 3H), 3.21-3.17 (m, 1H), 3.10-3.06 (m, 2H), 1.28 (d, 3H).

EXAMPLE 36

4-Hydroxy-7-[1R-hydroxy-2-(2-{3-[(2-methoxy-benzylamino)-methyl]-phenyl}-ethylamino)-ethyl]-3H-benzothiazol-2-one bis-trifluoroacetate salt

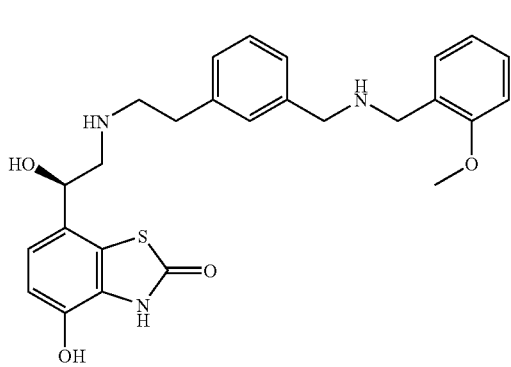

a) [3-(2-Hydroxyethyl)benzyl]-(2-methoxybenzyl) carbamic acid tert-butyl ester Prepared from 2-methoxybenzylamine (0.411 g) and (3-formyl-phenyl)-acetic acid ethyl ester (Example 1 step a)(356 mg) using the method of Example 3 (step a). Purification on silica, eluting with 60% diethyl ether/iso-hexane gave the subtitle compound as a pale yellow oil (504 mg).

$^1$H NMR (300 MHz, CDCl$_3$) δ 7.28-7.05 (m, 7H), 6.93 (t, 1H), 6.84 (d, 1H), 4.49-4.38 (m, 4H), 3.84 (q, 2H), 3.78 (s, 3H), 2.84 (t, 2H), 1.47-1.47 (m, 9H).

b) 4-Hydroxy-7-[1R-hydroxy-2-(2-{3-[(2-methoxy-benzylamino)methyl]phenyl}ethylamino)ethyl]-3H-benzothiazol-2-one bis-trifluoroacetate salt Prepared from [3-(2-hydroxyethyl)benzyl]-(2-methoxybenzyl)carbamic acid tert-butyl ester (252 mg) and 7-(2-amino-1R-hydroxy-ethyl)-4-hydroxy-3H-benzothiazol-2-one hydrochloride (0.1 g) using the method of Example 3 (step b). The crude product was purified by HPLC method B. The purified material was dissolved in acetonitrile (2 mL), evaporated and the residue was triturated with diethyl ether and filtered to give the title compound as a white solid (81 mg).

m/z 480 (M+H)$^+$ (Agilent multimode)

$^1$H NMR (400 MHz, DMSO, 90° C.) δ 7.39-7.30 (m, 6H), 7.06 (d, 1H), 6.99-6.92 (m, 2H), 6.77 (d, 1H), 4.93-4.90 (m, 1H), 4.14 (s, 2H), 4.09 (s, 2H), 3.81 (s, 3H), 3.25-3.00 (m, 6H). 7H exchangeable not seen at elevated temperature.

EXAMPLE 37

4-Hydroxy-7-[1R-hydroxy-2-{2-[3-(isobutylaminomethyl)phenyl]-ethylamino}ethyl)]-3H-benzothiazol-2-one bis-hydrochloride

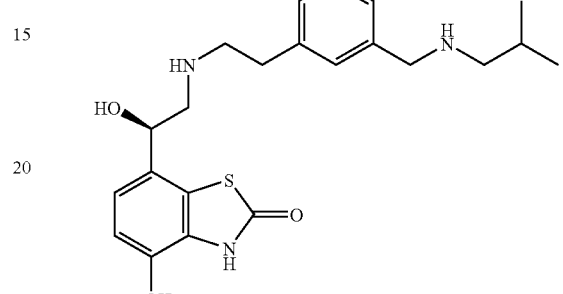

a) [3-(2-Hydroxyethyl)benzyl]-(iso-butyl)carbamic acid tert-butyl ester

Prepared from iso-butylamine (1.182 g) and (3-formyl-phenyl)-acetic acid ethyl ester (Example 1, step a, 356 mg) using the method of Example 16 (step b). Purification on silica, eluting with diethyl ether/iso-hexane [1:1], gave the subtitle compound as a pale yellow oil (451 mg).

$^1$H NMR (300 MHz, CDCl$_3$) δ 7.29-7.24 (m, 1H), 7.13-7.07 (m, 3H), 4.45-4.41 (m, 2H), 3.86 (q, 2H), 3.07-2.98 (m, 2H), 2.86 (t, 2H), 1.92 (s, 1H), 1.48-1.43 (m, 9H), 0.87 (d, 6H).

b) 4-Hydroxy-7-[1R-hydroxy-2-{2-[3-(isobutylaminomethyl)phenyl]-ethylamino}ethyl)]-3H-benzothiazol-2-one bis-hydrochloride Prepared from [3-(2-hydroxyethyl)benzyl]-(iso-butyl)carbamic acid tert-butyl ester (225 mg) and 7-(2-amino-1R-hydroxy-ethyl)-4-hydroxy-3H-benzothiazol-2-one hydrochloride (100 mg) using the method of Example 3 (step b). The crude product was purified by HPLC method A. The purified material was dissolved in acetonitrile (2 mL), treated with a drop of concentrated hydrochloric acid and evaporated. The residue was dissolved acetonitrile/iso-propanol [1:1] mixture, treated with a drop of concentrated hydrochloric acid and evaporated. The residue was triturated with diethyl ether, filtered and dried, to give the title compound as a white solid (27 mg).

m/z 416 (M+H)$^+$ (Agilent multimode)

$^1$H NMR (400 MHz, DMSO) δ 11.70 (s, 1H), 10.24 (s, 1H), 9.40 (s, 1H), 9.22 (s, 2H), 8.95 (s, 1H), 7.51-7.25 (m, 5H), 6.93 (d, 1H), 6.80 (d, 1H), 6.46 (s, 1H), 5.04-5.00 (m, 1H), 4.10 (t, 2H), 3.23-3.16 (m, 3H), 3.07-3.01 (m, 4H), 2.72-2.67 (m, 2H), 2.04 (septet, 1H), 0.94 (d, 6H).

EXAMPLE 38

4-Hydroxy-7-[1R-hydroxy-2-(2-{3-[(3-iso-butoxypropylamino)methyl]phenyl}-ethylamino)ethyl]-3H-benzothiazol-2-one bis-hydrochloride

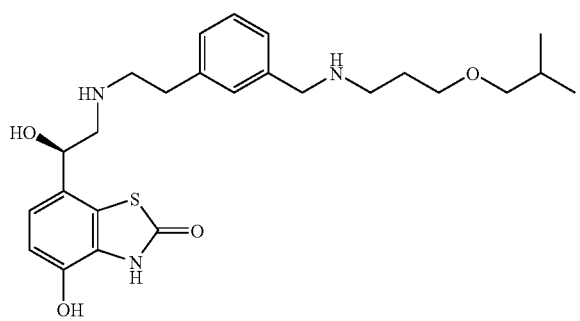

a) [3-(2-Hydroxyethyl)benzyl]-(3-iso-butoxypropyl) carbamic acid tert-butyl ester Prepared from 3-(iso-butoxy)propylamine (0.393 g) and (3-formyl-phenyl)-acetic acid ethyl ester (Example 1, step a, 356 mg) using the method of Example 16 (step b). Purification on silica, eluting with diethyl ether/iso-hexane [3:2], gave the subtitle compound as an oil (464 mg).

$^1$H NMR (300 MHz, CDCl$_3$) δ 7.29-7.24 (m, 1H), 7.14-7.08 (m, 3H), 4.43 (s, 2H), 3.85 (q, 2H), 3.40-3.36 (m, 2H), 3.25 (s, 2H), 3.12 (d, 2H), 2.85 (t, 2H), 1.86-1.74 (m, 3H), 1.51-1.41 (m, 9H), 0.88 (d, 6H).

b) 4-Hydroxy-7-[1R-hydroxy-2-(2-{3-[(3-iso-butoxypropylamino)methyl]phenyl}-ethylamino)ethyl]-3H-benzothiazol-2-one bis-hydrochloride Prepared from [3-(2-hydroxyethyl)benzyl]-(3-iso-butoxypropyl)carbamic acid tert-butyl ester (232 mg) and 7-(2-amino-1R-hydroxy-ethyl)-4-hydroxy-3H-benzothiazol-2-one hydrochloride (100 mg) using the method of Example 3 (step b). The crude product was purified by HPLC method B. The purified material was dissolved in acetonitrile (2 mL), treated with a drop of concentrated hydrochloric acid and evaporated. The residue was dissolved in acetonitrile/isopropanol [1:1] mixture, treated with a drop of concentrated hydrochloric acid and evaporated. The residue was triturated with diethyl ether, filtered and dried, to give the title compound as a white solid (54 mg).

m/z 474 (M+H)$^+$ (Agilent multimode)

$^1$H NMR (400 MHz, DMSO) δ 11.69 (s, 1H), 10.21 (s, 1H), 9.28-9.14 (m, 3H), 8.94-8.85 (m, 1H), 7.46-7.28 (m, 4H), 6.93 (d, 1H), 6.79 (d, 1H), 6.47 (s, 1H), 5.01-4.97 (m, 1H), 4.13-4.10 (m, 2H), 3.42 (t, 2H), 3.22-3.15 (m, 2H), 3.12 (d, 2H), 3.09-2.91 (m, 6H), 1.94-1.87 (m, 2H), 1.81-1.71 (m, 1H), 0.83 (d, 6H)

EXAMPLE 39

4-Hydroxy-7-[1R-hydroxy-2-(2-{2'-[(2-pyridin-2-yl-ethylamino)-methyl]-biphenyl-4-yl}-ethylamino)-ethyl]-3H-benzothiazol-2-one tris-trifluoroacetate salt

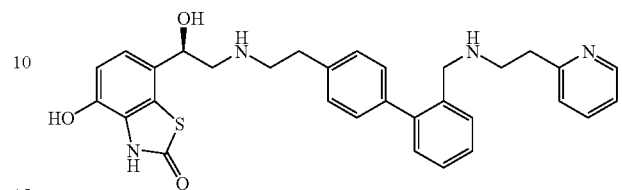

a) [4'-(2-Hydroxy-ethyl)-biphenyl-2-ylmethyl]-(2-pyridin-2-yl-ethyl)-carbamic acid tert-butyl ester Prepared from (2'-formyl-biphenyl-4-yl)-acetic acid methyl ester (Example 26, step a, 533 mg) and 2-(2-aminoethyl)pyridine) (244 mg) following the procedure described in Example 26 (step b). Purification on silica, eluting with a gradient of methanol (0-10%) in dichloromethane, afforded the subtitle compound as an oil (300 mg).

m/z 433 (M+H)$^+$ (APCI)

$^1$H NMR (300 MHz, CDCl$_3$) δ 8.41 (d, 1H), 7.51 (td, 1H), 7.34-7.14 (m, 9H), 7.05 (dd, 2H), 4.31 (d, 2H), 3.93 (q, 2H), 3.38 (d, 2H), 2.93 (t, 2H), 2.85-2.67 (m, 2H), 1.41 (s, 9H).

b) 4-Hydroxy-7-[1R-hydroxy-2-(2-{2'-[(2-pyridin-2-yl-ethylamino)-methyl]-biphenyl-4-yl}-ethylamino)-ethyl]-3H-benzothiazol-2-one tris-trifluoroacetate salt Prepared from [4'-(2-hydroxy-ethyl)-biphenyl-2-ylmethyl]-(2-pyridin-2-yl-ethyl)-carbamic acid tert-butyl ester (250 mg) and 7-(2-amino-1-R-hydroxy-ethyl)-4-hydroxy-3H-benzothiazol-2-one hydrochloride (108 mg) using the method of Example 3 (step b), (sodium sulfate as drying agent) to give the title compound as a white solid (10 mg).

m/z 541 (M+H)$^+$ (Agilent multimode)

$^1$H NMR (300 MHz, DMSO, 90° C.) δ 8.44 (d, 1H), 7.77-7.65 (m, 2H), 7.54-7.17 (m, 9H), 6.95 (d, 1H), 6.78 (d, 1H), 4.95 (dd, 1H), 4.19 (s, 2H), 3.33-3.20 (m, 4H), 3.18-3.12 (m, 2H), 3.10-2.99 (m, 4H). 8H exchangeable not seen at 90° C.

EXAMPLE 40

4-Hydroxy-7-{1R-hydroxy-2-[2-(3-{[2-(1-oxy-pyridin-2-yl)-ethylamino]-methyl}-phenyl)-ethylamino]-ethyl}-3H-benzothiazol-2-one bis-trifluoroacetate salt

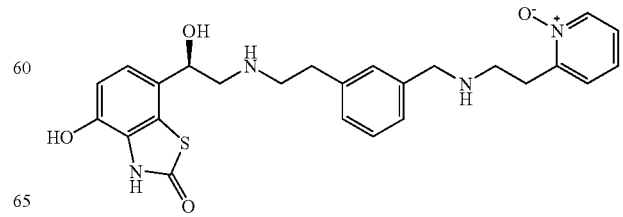

a) [3-(2-Hydroxy-ethyl)-benzyl]-[2-(1-oxy-pyridin-2-yl)-ethyl]-carbamic acid tert-butyl ester Di-tert-butyl dicarbonate (275 mg) was added to a solution of 2-{3-[(2-pyridin-2-yl-ethylamino)-methyl]-phenyl}-ethanol (Example 11, step a, 260 mg) in dichloromethane (10 mL). After 1.5 hours, 3-chloroperoxybenzoic acid (70% grade, 300 mg) was added. After a further 1.5 hours, the reaction mixture was treated with saturated aqueous sodium thiosulfate solution and extracted with ethyl acetate. The organic phase was separated and washed sequentially with saturated aqueous sodium bicarbonate and brine, then dried (magnesium sulfate) and evaporated, to give the subtitle compound as a clear oil (450 mg).
$^1$H NMR (300 MHz, CDCl$_3$) δ 8.18 (s, 1H), 7.26-7.03 (m, 7H), 4.40 (s, 2H), 3.90 (t, 2H), 3.58 (s, 2H), 3.08 (d, 2H), 2.84 (t, 2H), 1.49 (s, 9H), OH not seen.

b) 4-Hydroxy-7-{1R-hydroxy-2-[2-(3-{[2-(1-oxy-pyridin-2-yl)-ethylamino]-methyl}-phenyl)-ethylamino]-ethyl}-3H-benzothiazol-2-one bis-trifluoroacetate salt Prepared from [3-(2-hydroxy-ethyl)-benzyl]-[2-(1-oxy-pyridin-2-yl)-ethyl]-carbamic acid tert-butyl ester (300 mg) and 7-(2-amino-1R-hydroxy-ethyl)-4-hydroxy-3H-benzothiazol-2-one hydrochloride (110 mg) using the method of Example 3 (step b), to give the title compound as a white solid (35 mg).
m/z 481 (M+H)$^+$ (Agilent multimode)
$^1$H NMR (300 MHz, DMSO) δ 11.67 (s, 1H), 9.43 (s, 2H), 9.23 (s, 1H), 8.94 (s, 1H), 8.35 (s, 1H), 7.54 (t, 1H), 7.47-7.38 (m, 5H), 7.37-7.30 (m, 1H), 6.96 (d, 1H), 6.82 (d, 1H), 5.02-4.93 (m, 1H), 4.22 (s, 2H), 3.50-2.91 (m, 10H).

EXAMPLE 41

4-Hydroxy-7-[1R-hydroxy-2-(2-{3-[2-(2-methoxy-ethylamino)-ethyl]-phenyl}-ethylamino)-ethyl]-3H-benzothiazol-2-one-bis-trifluoroacetate salt

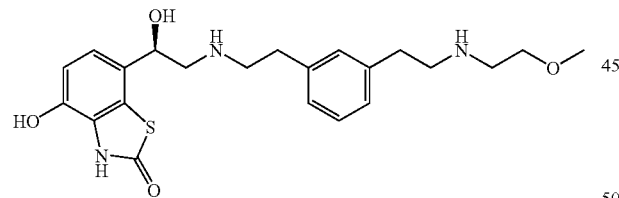

a) (3-{2-[tert-Butoxycarbonyl-(2-methoxy-ethyl)-amino]-ethyl}-phenyl)-acetic acid ethyl ester Dess-Martin periodinane (1.5 g) was added, at 0° C., to a solution of [3-(2-hydroxy-ethyl)-phenyl]-acetic acid ethyl ester (700 mg) [prepared according to EP1577291] in dry dichloromethane (50 mL). After 2 hours, the reaction was poured onto a mixture of ethyl acetate (100 mL), sodium thiosulfate (13 g), water (50 mL) and saturated aqueous sodium bicarbonate solution (100 mL), and was stirred vigorously for 10 minutes. The aqueous phase was separated and extracted with ethyl acetate (30 mL). The combined organics were washed with water (50 mL), dried over magnesium sulfate and evaporated. A portion of the crude aldehyde (220 mg) was dissolved in dichloromethane (2 mL) and 2-methoxyethylamine (170 mg) added, followed by sodium triacetoxyborohydride (430 mg). After 2 hours, the reaction mixture was diluted with dichloromethane and extracted with saturated aqueous sodium bicarbonate solution. The organic phase was separated, dried over sodium sulfate and added to di-tert-butyl dicarbonate (450 mg). After 24 h, the reaction was purified on silica, eluting with a gradient of ethanol (0-2%) in dichloromethane, to give the subtitle compound as an oil (240 mg).
$^1$H NMR (300 MHz, CDCl$_3$) δ 7.24 (t, 1H), 7.18-7.05 (m, 3H), 4.15 (q, 2H), 3.58 (s, 2H), 3.51-3.38 (m, 4H), 3.38-3.26 (m, 5H), 2.87-2.77 (m, 2H), 1.45 (s, 9H), 1.25 (t, 3H).

b) {2-[3-(2-Hydroxy-ethyl)-phenyl]-ethyl}-(2-methoxy-ethyl)-carbamic acid tert-butyl ester 2M Lithium borohydride in tetrahydrofuran solution (0.7 mL) was added to a solution of (3-{2-[tert-butoxycarbonyl-(2-methoxy-ethyl)-amino]-ethyl}-phenyl)-acetic acid ethyl ester (230 mg) in tetrahydrofuran (10 mL) and heated to reflux for 1 hour. On cooling, the reaction was diluted with ethyl acetate and extracted sequentially, twice with saturated aqueous sodium bicarbonate solution, once with brine, dried over magnesium sulfate and evaporated, to give the subtitle compound as an oil (200 mg).
$^1$H NMR (300 MHz, CDCl$_3$) δ 7.23 (t, 1H), 7.15-7.00 (m, 3H), 3.85 (q, 2H), 3.52-3.22 (m, 9H), 2.89-2.77 (m, 4H), 1.45 (s, 1H), 1.42 (s, 9H).

c) 4-Hydroxy-7-[1R-hydroxy-2-(2-{3-[2-(2-methoxy-ethylamino)-ethyl]-phenyl}-ethylamino)-ethyl]-3H-benzothiazol-2-one bis-trifluoroacetate salt Prepared from {2-[3-(2-hydroxy-ethyl)-phenyl]-ethyl}-(2-methoxy-ethyl)-carbamic acid tert-butyl ester (200 mg) and 7-(2-amino-1R-hydroxy-ethyl)-4-hydroxy-3H-benzothiazol-2-one hydrochloride (110 mg) using the method of Example 3 (step b), to give the title compound as a white solid (35 mg).
m/z 432 (M+H)$^+$ (Agilent multimode)
$^1$H NMR (300 MHz, DMSO) δ 11.67 (s, 1H), 10.31 (s, 1H), 8.99 (s, 1H), 8.81 (s, 3H), 7.29 (d, 1H), 7.21-7.07 (m, 3H), 6.93 (d, 1H), 6.78 (d, 1H), 6.51 (s, 1H), 4.91 (s, 1H), 3.59 (s, 2H), 3.32 (s, 3H), 3.16 (s, 8H), 2.93 (s, 4H).

EXAMPLE 42

4-Hydroxy-7-{1R-hydroxy-2-[2-(3-{2-[(pyridin-2-ylmethyl)-amino]-ethyl}-phenyl)-ethylamino]-ethyl}-3H-benzothiazol-2-one tris-trifluoroacetate salt

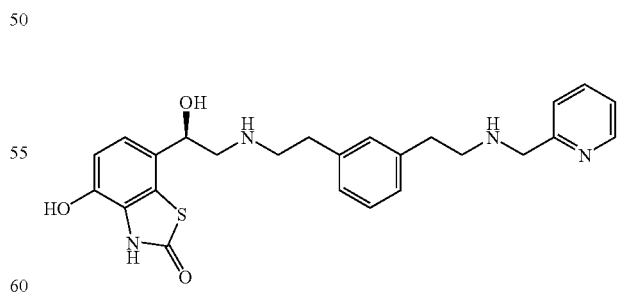

a) {3-[2-(tert-Butoxycarbonyl-pyridin-2-ylmethyl-amino)-ethyl]-phenyl}-acetic acid ethyl ester Prepared from 2-aminomethylpyridine (220 mg) and [3-(2-hydroxy-ethyl)-phenyl]-acetic acid ethyl ester (220 mg)

using the method of Example 41 (step a), to give the subtitle compound as an oil (280 mg).

¹H NMR (300 MHz, CDCl₃) δ 8.53 (ddd, 1H), 7.64 (td, 1H), 7.25-7.01 (m, 6H), 4.51 (d, 2H), 4.14 (q, 2H), 3.56 (s, 2H), 3.54-3.40 (m, 2H), 2.91-2.74 (m, 2H), 1.44 (d, 9H), 1.24 (t, 3H). Rotamers in solution.

b) {2-[3-(2-Hydroxy-ethyl)-phenyl]-ethyl}-pyridin-2-ylmethyl-carbamic acid tert-butyl ester Prepared from {3-[2-(tert-butoxycarbonyl-pyridin-2-ylmethyl-amino)-ethyl]-phenyl}-acetic acid ethyl ester (0.27 g) using the method of Example 41 (step b), to give the subtitle compound as an oil (280 mg).

¹H NMR (300 MHz, CDCl₃) δ 8.75 (d, 0.5H), 8.53 (d, 0.5H), 7.89 (t, 0.5H), 7.64 (td, 0.5H), 7.44-7.28 (m, 2H), 7.25-6.95 (m, 4H), 4.70 (dd, 2H), 4.25 (t, 2H), 3.58-3.40 (m, 2H), 2.97-2.73 (m, 4H), 1.42 (d, 9H). Rotamers in solution.

c) 4-Hydroxy-7-{1R-hydroxy-2-[2-(3-{2-[(pyridin-2-ylmethyl)-amino]-ethyl}-phenyl)-ethylamino]-ethyl}-3H-benzothiazol-2-one tris-trifluoroacetate salt Prepared from {2-[3-(2-hydroxy-ethyl)-phenyl]-ethyl}-pyridin-2-ylmethyl-carbamic acid tert-butyl ester (200 mg) and 7-(2-amino-1R-hydroxy-ethyl)-4-hydroxy-3H-benzothiazol-2-one hydrochloride (110 mg) using the method of Example 3 (step b), to give the title compound as a white solid (75 mg).

m/z 465 (M+H)⁺ (Agilent multimode)

¹H NMR (300 MHz, DMSO) δ 11.67 (s, 1H), 10.31 (s, 1H), 9.31 (s, 2H), 8.98 (s, 1H), 8.81 (s, 1H), 8.66 (s, 1H), 7.91 (t, 1H), 7.53-7.42 (m, 2H), 7.31 (t, 1H), 7.19-7.07 (m, 3H), 6.93 (d, 1H), 6.78 (d, 1H), 6.49 (s, 1H), 4.91 (s, 1H), 4.39 (s, 2H), 3.29-2.85 (m, 10H).

EXAMPLE 43

7-{2-[2-(3-{2-[2-(2-Fluoro-phenyl)-ethylamino]-ethyl}-phenyl)-ethylamino]-1R-hydroxy-ethyl}-4-hydroxy-3H-benzothiazol-2-one bis-hydrochlore salt

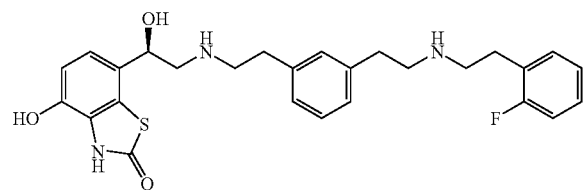

a) [3-(2-{tert-Butoxycarbonyl-[2-(2-fluoro-phenyl)-ethyl]-amino}-ethyl)-phenyl]-acetic acid ethyl ester Prepared from 2-(2-fluorophenyl)ethylamine (222 mg) and [3-(2-hydroxy-ethyl)-phenyl]-acetic acid ethyl ester (220 mg) using the method of Example 41 (step a), to give the subtitle compound as an oil (100 mg).

¹H NMR (300 MHz, CDCl₃) δ 7.31-6.95 (m, 8H), 4.14 (q, 2H), 3.57 (s, 2H), 3.43-3.26 (m, 4H), 3.00-2.67 (m, 4H), 1.42 (s, 9H), 1.24 (t, 3H).

b) [2-(2-Fluoro-phenyl)-ethyl]-{2-[3-(2-hydroxy-ethyl)-phenyl]-ethyl}-carbamic acid tert-butyl ester Prepared from [3-(2-{tert-butoxycarbonyl-[2-(2-fluoro-phenyl)-ethyl]-amino}-ethyl)-phenyl]-acetic acid ethyl ester (100 mg) using the method of Example 41 (step b), to give the subtitle compound as an oil (90 mg).

¹H NMR (500 MHz, DMSO, 90° C.) δ 7.42-6.95 (m, 8H), 4.31 (s, 1H), 3.70 (s, 2H), 3.40 (q, 4H), 2.86 (t, 2H), 2.82-2.76 (m, 4H), 2.56 (s, 9H).

c) 7-{2-[2-(3-{2-[2-(2-Fluoro-phenyl)-ethylamino]-ethyl}-phenyl)-ethylamino]-1R-hydroxy-ethyl}-4-hydroxy-3H-benzothiazol-2-one bis-hydrochloride salt Prepared from [2-(2-fluoro-phenyl)-ethyl]-{2-[3-(2-hydroxy-ethyl)-phenyl]-ethyl}-carbamic acid tert-butyl ester (90 mg) and 7-(2-amino-1R-hydroxy-ethyl)-4-hydroxy-3H-benzothiazol-2-one hydrochloride (55 mg) using the method of Example 3 (step b). The trifluoroacetate salt, from HPLC, was treated with 2M hydrochloric acid in diethylether (4 mL) and evaporated to give the title compound as a white solid (20 mg).

m/z 496 (M+H)⁺ (Agilent multimode)

¹H NMR (300 MHz, DMSO) δ 11.70 (s, 1H), 10.27 (s, 1H), 9.30 (s, 3H), 8.90 (s, 1H), 7.41-7.26 (m, 3H), 7.25-7.09 (m, 5H), 6.93 (d, 1H), 6.80 (d, 1H), 5.62 (s, 1H), 5.00 (t, 1H), 3.24-2.91 (m, 14H).

EXAMPLE 44

7-(2-{2-[3-(2-Cyclohexylamino-ethyl)-phenyl]-ethylamino}-1R-hydroxy-ethyl)-4-hydroxy-3H-benzothiazol-2-one bis-hydrochloride salt

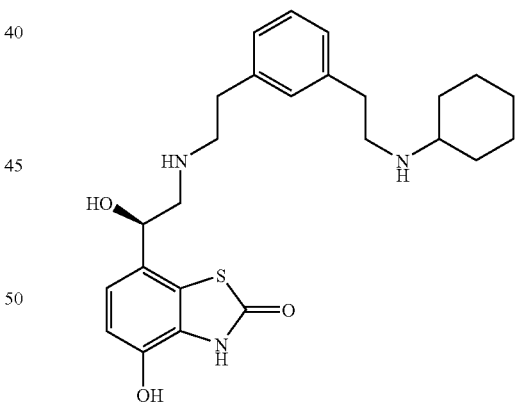

a) (3-Cyclohexylcarbamoylmethyl-phenyl)-acetic acid

Cyclohexylamine (510 mg), (3-carboxymethyl-phenyl)-acetic acid (1.0 g), 1-hydroxybenzotriazole (700 mg) and Hunigs base (0.9 mL) were added to a round bottomed flask and dissolved in dichloromethane (40 mL) at room temperature. The mixture was stirred at room temperature for 5 minutes then 1-(3-dimethylaminopropyl)-3-ethylcarbodiimide hydrochloride (990 mg) was added. The reaction was stirred at room temperature for 3 hours. The mixture was diluted with dichloromethane (40 mL) and washed with 2M hydrochloric acid (2×40 mL). The organic layer was isolated and extracted with 2M sodium hydroxide (2×40 mL). The basic extract was isolated, acidified with 2M hydrochloric acid and extracted with dichloromethane (2×40 mL). The dichloromethane extracts were combined, dried over anhydrous sodium sulphate, filtered and concentrated to give 626 mg of the sub-titled product as a white solid.

m/z 276 (M+H)$^+$ (APCI)

$^1$H NMR (400 MHz, CDCl$_3$) δ 7.32-7.27 (m, 1H), 7.21-7.14 (m, 3H), 5.33-5.30 (m, 1H), 3.79-3.69 (m, 1H), 3.64 (s, 2H), 3.54 (s, 2H), 1.84-1.80 (m, 2H), 1.61-1.54 (m, 3H), 1.36-1.26 (m, 2H), 1.12-0.96 (m, 3H).

b) 2-[3-(2-Cyclohexylamino-ethyl)-phenyl]-ethanol (3-Cyclohexylcarbamoylmethyl-phenyl)-acetic acid (620 mg) was dissolved in dry dichloromethane (25 mL) and treated with borane-methyl sulphide complex (2M, 12 mL) at room temperature. The reaction was stirred at room temperature for 1 hour and at reflux for a further 1 hour. The mixture was cooled, quenched with methanol and treated with 2M hydrochloric acid (25 mL). The acidified mixture was heated at reflux for 10 minutes, cooled and basified with 2M sodium hydroxide. The basic mixture was extracted with dichloromethane (2×50 mL). The organic extracts were combined, dried over anhydrous sodium sulphate, filtered and concentrated to yield 500 mg of the sub-titled compound as an oil.

m/z 248 [M+H]$^+$ (APCI)

$^1$H NMR (400 MHz, CDCl$_3$) δ 7.26 (t, 1H), 7.06 (d, 3H), 3.85 (t, 2H), 2.91-2.83 (m, 4H), 2.79-2.75 (m, 2H), 2.41 (quintet, 1H), 1.87 (d, 2H), 1.72 (d, 2H), 1.60 (d, 1H), 1.29-1.11 (m, 3H), 1.09-0.99 (m, 2H).

c) Cyclohexyl-{2-[3-(2-hydroxy-ethyl)-phenyl]-ethyl}-carbamic acid tert-butyl ester 2-[3-(2-Cyclohexylamino-ethyl)-phenyl]-ethanol (360 mg) was dissolved in dichloromethane (18 mL) and treated with di-tert-butyl dicarbonate (320 mg) at room temperature. The resultant solution was stirred at room temperature for 2 hours. The mixture was then concentrated and the collected residue was purified on silica, eluting with dichloromethane: ethyl acetate 8:1, to give 460 g of the sub-titled compound as an oil.

m/z 248 [M+H]$^+$ (APCI)

d) 7-(2-{2-[3-(2-Cyclohexylamino-ethyl)-phenyl]-ethylamino}-1R-hydroxy-ethyl)-4-hydroxy-3H-benzothiazol-2-one bis-hydrochloride salt Cyclohexyl-{2-[3-(2-hydroxy-ethyl)-phenyl]-ethyl}-carbamic acid tert-butyl ester (200 mg) was dissolved in dry dichloromethane (20 mL) and treated with Dess-Martin periodinane (300 mg) at room temperature. The resultant mixture was stirred under nitrogen at room temperature for 1 hour. The reaction mixture was diluted with ethyl acetate (40 mL) and quenched with saturated sodium thiosulphate (20 mL) and saturated sodium bicarbonate. The bi-phasic mixture was stirred for 10 minutes and the organic layer was separated. The remaining aqueous layer was extracted with ethyl acetate (2×20 mL). The organic extracts were combined, washed with brine, dried over anhydrous sodium sulphate, filtered and concentrated to give an oil. The isolated oil was dissolved in methanol (10 mL) and added to a stirred solution of 7-(2-amino-1-hydroxy-ethyl)-4-hydroxy-3H-benzothiazol-2-one hydrochloride (130 g), dissolved in methanol (10 mL) and acetic acid (40 mL), under nitrogen. The mixture was stirred at room temperature for 5 minutes then sodium cyanoborohydride (40 mg) was added and the reaction was stirred at room temperature for a further 4 hours. The reaction mixture was quenched with 0.880 ammonia and concentrated. The isolated residue was dissolved in iso-propanol: acetonitrile (5:1, 5 mL) and adsorbed onto Tosic-65A resin. The resin was washed with iso-propanol:acetonitrile (5:1) and eluted with iso-propanol:0.880 ammonia. The basic eluent was concentrated and the isolated residue was dissolved in trifluoroacetic acid, concentrated and purified by preparatory HPLC, using a SymmetryPrep® C8 Column 5 μm 19×50 mm, to give an oil. The oil was dissolved in acetonitrile and treated with 2M hydrochloric acid, in diethyl ether, to give 79 mg of the titled compound as a white solid.

m/z 456 (M+H)$^+$ (Agilent multimode+)

$^1$H NMR (400 MHz, DMSO) δ 11.70 (s, 1H), 10.24 (s, 1H), 9.28 (bs, 1H), 9.04 (bs, 2H), 8.85 (bs, 1H), 7.30 (t, 1H), 7.15 (t, 1H), 6.93 (d, 1H), 6.80 (d, 1H), 6.47 (bs, 1H), 4.99 (t, 1H), 3.17-2.95 (m, 10H), 2.06 (d, 2H), 1.76 (d, 2H), 1.61 (d, 1H), 1.39-1.08 (m, 6H).

EXAMPLE 45

4-Hydroxy-7-[1R-hydroxy-2-(2-{3-[2-(2-methoxy-benzylamino)-ethyl]-phenyl}-ethylamino)-ethyl]-3H-benzothiazol-2-one bis-hydrochloride salt

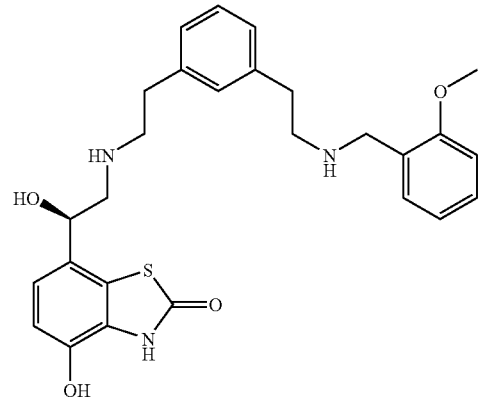

a) {3-[(2-Methoxy-benzylcarbamoyl)-methyl]-phenyl}-acetic acid

Prepared from 2-methoxy-benzylamine (1.4 g), (3-carboxymethyl-phenyl)-acetic acid (2 g), 1-hydroxybenzotriazole (1.4 g), Hunigs base (1.8 mL), 1-(3-dimethylaminopropyl)-3-ethylcarbodiimide hydrochloride (2.0 g), using the method of Example 44 (step a), to give 990 mg of the sub-titled compound as a white solid.

m/z 314 (M+H)$^+$ (APCI)

$^1$H NMR (400 MHz, DMSO) δ 12.32 (bs, 1H), 8.31 (t, 1H), 7.24-7.18 (m, 2H), 7.15-7.09 (m, 4H), 6.94 (d, 1H), 6.86 (t, 1H), 4.21 (d, 2H), 3.76 (s, 3H), 3.51 (s, 2H), 3.45 (s, 2H).

b) 2-{3-[2-(2-Methoxy-benzylamino)-ethyl]-phenyl}-ethanol

Prepared from {3-[(2-methoxy-benzylcarbamoyl)-methyl]-phenyl}-acetic acid (3.0 g) and borane-methyl sulphide complex (2M, 48 mL) using the method of Example 44 (step b) to give 2.7 g of the sub-titled compound as an oil.

m/z 286 (M+H)$^+$ (APCI)

c) {2-[3-(2-Hydroxy-ethyl)-phenyl]-ethyl}-(2-methoxy-benzyl)-carbamic acid tert-butyl ester Prepared from 2-{3-[2-(2-methoxy-benzylamino)-ethyl]-phenyl}-ethanol (2.7 g) and di-tert-butyl dicarbonate (2.1 g) using the method of Example 44 (step c). The compound was purified on silica, eluting with dichloromethane:ethyl acetate 5:1 to give 3.5 g of the sub-titled compound as an oil.

m/z 286 (M+H)$^+$ (APCI)–Boc group fragments in mass analyser.

d) 4-Hydroxy-7-[1R-hydroxy-2-(2-{3-[2-(2-methoxy-benzylamino)-ethyl]-phenyl}-ethylamino)-ethyl]-3H-benzothiazol-2-one bis-hydrochloride salt Prepared from {2-[3-(2-hydroxy-ethyl)-phenyl]-ethyl}-(2-methoxy-benzyl)-carbamic acid tert-butyl ester (200 mg), Dess-Martin periodinane (260 mg), 7-(2-amino-1-hydroxy-ethyl)-4-hydroxy-3H-benzothiazol-2-one hydrochloride (110 mg) and sodium cyanoborohydride (36 mg) using the method of Example 44 (step d) to give 126 mg of the titled product as a white solid.

m/z 494 (M+H)$^+$ (Agilent multimode+)

$^1$H NMR (400 MHz, DMSO) δ 11.71 (s, 1H), 10.28 (bs, 1H), 9.36 (bs, 1H), 9.22 (bs, 2H), 8.92 (bs, 1H), 7.50 (t, 1H), 7.43 (t, 1H), 7.30 (t, 1H), 7.14-7.09 (m, 4H), 7.1 (d, 1H), 7.00 (t, 1H), 6.93 (d, 1H), 6.8 (d, 1H), 5.01 (t, 1H), 4.14 (t, 2H), 3.79 (s, 3H), 3.17-3.00 (m, 10H).

EXAMPLE 46

4-Hydroxy-7-{1R-hydroxy-2-[2-(3-{2-[2-(2-methoxy-phenyl)-ethylamino]-ethyl}-phenyl)-ethylamino]-ethyl}-3H-benzothiazol-2-one bis-hydrochloride salt

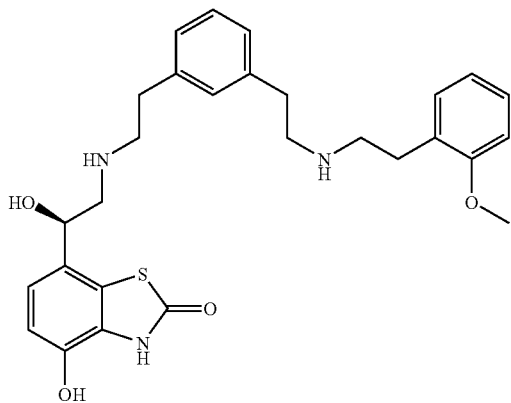

a) (3-{[2-(2-Methoxy-phenyl)-ethylcarbamoyl]-methyl}-phenyl)-acetic acid

Prepared from (3-carboxymethyl-phenyl)-acetic acid (2.00 g), 2-(2-methoxy-phenyl)-ethylamine (1.60 g), 1-hydroxybenzotriazole (1.40 g), Hunigs base (1.8 mL), 1-(3-dimethylaminopropyl)-3-ethylcarbodiimide hydrochloride (2.00 g), using the method of Example 44 (step a), to give 1.03 g of the sub-titled compound as a white solid.

m/z 328 (M+H)$^+$ (APCI)

$^1$H NMR (400 MHz, CDCl$_3$) δ 7.26 (t, 1H), 7.20-7.15 (m, 2H), 7.07 (t, 2H), 6.95 (d, 1H), 6.81 (t, 2H), 5.65 (bs, 1H), 3.70 (s, 3H), 3.59 (s, 2H), 3.50 (s, 2H), 3.48-3.41 (m, 2H), 2.74 (t, 2H).

b) 2-(3-{2-[2-(2-Methoxy-phenyl)-ethylamino]-ethyl}-phenyl)-ethanol

Prepared from (3-{[2-(2-methoxy-phenyl)-ethylcarbamoyl]-methyl}-phenyl)-acetic acid (1.03 g) and borane-methyl sulphide complex (2M, 15 mL) using the method of Example 44 (step b) to give 890 mg of the sub-titled compound as an oil.

m/z 300 (M+H)$^+$ (APCI)

c) {2-[3-(2-Hydroxy-ethyl)-phenyl]-ethyl}-[2-(2-methoxyphenyl)-ethyl]-carbamic acid tert-butyl ester Prepared from 2-(3-{2-[2-(2-Methoxy-phenyl)-ethylamino]-ethyl}-phenyl)-ethanol (900 mg) and di-tert-butyl dicarbonate (700 mg) using the method of Example 44 (step c). The compound was purified on silica, eluting with dichloromethane:ethyl acetate 5:1 to give 1.13 g of the sub-titled compound as an oil.

m/z 300 (M+H)$^+$ (APCI)–Boc group fragments in mass analyser $^1$H NMR (400 MHz, CDCl$_3$) δ 7.19 (t, 2H), 7.11-7.05 (m, 4H), 6.89-6.83 (m, 2H), 3.85-3.78 (m, 5H), 3.40-3.30 (m, 4H), 2.84-2.79 (m, 6H), 1.39 (s, 9H).

d) 4-Hydroxy-7-{1R-hydroxy-2-[2-(3-{2-[2-(2-methoxy-phenyl)-ethylamino]-ethyl}-phenyl)-ethylamino]-ethyl}-3H-benzothiazol-2-one bis-hydrochloride salt Prepared from {2-[3-(2-hydroxy-ethyl)-phenyl]-ethyl}-[2-(2-methoxy-phenyl)-ethyl]-carbamic acid tert-butyl ester (200 mg), Dess-Martin periodinane (250 mg), 7-(2-amino-1-hydroxy-ethyl)-4-hydroxy-3H-benzothiazol-2-one hydrochloride (110 mg) and sodium cyanoborohydride (34 mg) using the method of Example 44 (step d) to give 106 mg of the titled compound as a white solid.

m/z 508 (M+H)$^+$ (Agilent multimode+)

$^1$H NMR (400 MHz, DMSO) d 11.70 (s, 1H), 10.26 (bs, 1H), 9.83 (bs, 1H), 9.23 (bs, 2H), 8.93 (bs, 2H), 7.31-7.23 (m,

2H), 7.17 (t, 4H), 6.99 (d, 1H), 6.91 (t, 2H), 6.80 (d, 1H), 5.01 (t, 1H), 3.79 (s, 3H), 3.15-2.98 (m, 14H).

EXAMPLE 47

7-(2-{2-[3-(2-Azepan-1-yl-ethyl)-phenyl]-ethylamino}-1R-hydroxy-ethyl)-4-hydroxy-3H-benzothiazol-2-one bis-hydrochloride salt

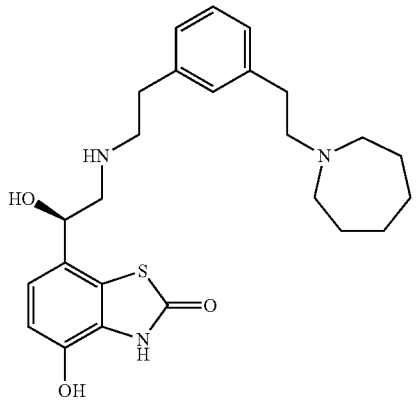

a) [3-(2-Azepan-1-yl-2-oxo-ethyl)-phenyl]-acetic acid

Prepared from (3-carboxymethyl-phenyl)-acetic acid (990 mg), azepane (500 g), 1-hydroxybenzotriazole (690 mg), Hunigs base (0.89 mL), 1-(3-dimethylaminopropyl)-3-ethylcarbodiimide hydrochloride (980 mg), using the method of Example 44 (step a), to give 700 mg of the sub-titled compound as a solid.

m/z 276 (M+H)$^+$ (APCI)

$^1$H NMR (400 MHz, CDCl$_3$) δ 7.37 (t, 1H), 7.27-7.14 (m, 3H), 3.72 (s, 2H), 3.59 (s, 2H), 3.54-3.46 (m, 2H), 3.42 (t, 2H), 1.70 (quintet, 2H), 1.60 (quintet, 2H), 1.54-1.44 (m, 4H).

b) 2-[3-(2-Azepan-1-yl-ethyl)-phenyl]-ethanol

Prepared from [3-(2-azepan-1-yl-2-oxo-ethyl)-phenyl]-acetic acid (700 mg) and borane-methyl sulphide complex (2M, 14.5 mL) using the method of Example 44 (step b) to give 540 mg of the sub-titled compound as an oil.

m/z 248 (M+H)$^+$ (APCI)

$^1$H NMR (400 MHz, CDCl$_3$) δ 7.25-7.21 (m, 1H), 7.06 (t, 3H), 3.85 (t, H), 2.86 (t, 2H), 2.79-2.55 (m, 8H), 1.74-1.52 (m, 8H).

c) (2-{3-[2-(Azepan-1-yl-κN)ethyl]phenyl}ethanol)(trihydrido)boron

2-[3-(2-Azepan-1-yl-ethyl)-phenyl]-ethanol (540 mg) was dissolved in dry tetrahydrofuran (20 mL) and cooled to 0° C. Borane-methyl sulphide complex (2M, 1.7 mL) was added to the cooled solution dropwise. The reaction was stirred at 0° C. for 10 minutes and then quenched with methanol. The reaction mixture was concentrated and the isolated residue was purified on silica, eluting with ethyl acetate:dichloromethane (1:7) to give 450 mg of the sub-titled as a white solid.

m/z 248 (M+H)$^+$ (APCI)–Borane complex broken down in mass analyser.

d) 7-(2-{2-[3-(2-Azepan-1-yl-ethyl)-phenyl]-ethylamino}-1R-hydroxy-ethyl)-4-hydroxy-3H-benzothiazol-2-one bis-hydrochloride salt (2-{3-[2-(Azepan-1-yl-κN)ethyl]phenyl}ethanol)(trihydrido)boron (200 mg) was dissolved in dry dichloromethane (20 mL) and treated with Dess-Martin periodinane (390 mg) at room temperature. The resultant mixture was stirred under nitrogen at room temperature for 1 hour. The reaction mixture was diluted with ethyl acetate (40 mL) and quenched with saturated sodium thiosulphate (20 mL) and saturated sodium bicarbonate. The bi-phasic mixture was stirred for 10 minutes and the organic layer was separated. The remaining aqueous layer was extracted with ethyl acetate (2×20 mL). The organic extracts were combined, washed with brine, dried over anhydrous sodium sulphate, filtered and concentrated to give an oil. The isolated oil was dissolved in methanol (10 mL) and added to a stirred solution of 7-(2-amino-1-hydroxy-ethyl)-4-hydroxy-3H-benzothiazol-2-one hydrochloride (160 mg), dissolved in methanol (10 mL) and acetic acid (40 mL), under nitrogen. The mixture was stirred at room temperature for 5 minutes then sodium cyanoborohydride (53 mg) was added and the reaction was stirred at room temperature for a further 4 hours. The reaction mixture was quenched with 0.880 ammonia and concentrated. The isolated residue was dissolved in iso-propanol:acetonitrile (5:1, 5 mL) and adsorbed onto Tosic-65A resin. The resin was washed with iso-propanol:acetonitrile (5:1) and eluted with iso-propanol:0.880 ammonia. The basic eluent was concentrated and the isolated residue was dissolved in dry tetrahydrofuran (20 mL) and treated with ethylene diamine (0.2 mL). The mixture was stirred at reflux for 5 minutes then cooled to room temperature and concentrated. The collected residue was dissolved in trifluoroacetic acid, concentrated and purified by preparatory HPLC, using a SymmetryPrep® C8 Column 5 μm 19×50 mm, to give an oil. The oil was dissolved in acetonitrile and treated with 2M hydrochloric acid, in diethyl ether, to give 61 mg of the titled compound as a white solid.

m/z 456 (M+H)$^+$ (Agilent multimode+)

$^1$H NMR (400 MHz, DMSO) δ 11.68 (s, 1H), 10.64 (bs, 1H), 10.22 (s, 1H), 9.28 (bs, 1H), 8.88 (bs, 1H), 7.28 (t, 1H), 7.13 (t, 3H), 6.91 (d, 1H), 6.78 (d, 1H), 6.44 (bs, 1H), 4.97 (t, 1H), 3.39 (bs, 2H), 3.23-2.95 (m, 12H), 1.82 (bs, 4H), 1.65-1.56 (m, 4H).

EXAMPLE 48

4-Hydroxy-7-[1R-hydroxy-2-(2-{3-[2-(1S-methoxymethyl-3-methyl-butylamino)-ethyl]-phenyl}-ethylamino)-ethyl]-3H-benzothiazol-2-one bis-hydrochloride salt

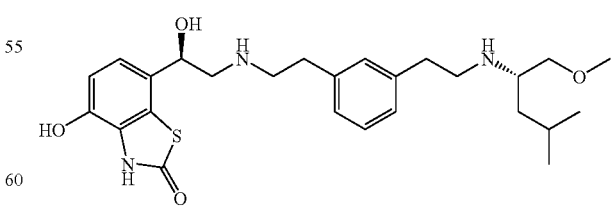

a) 1S-Methoxymethyl-3-methyl-butylamine

Sodium hydride (380 mg) was washed with hexane and suspended in dry tetrahydrofuran (8 mL) under nitrogen. A solution of (S)-2-amino-4-methyl-pentan-1-ol (1.0 g), dissolved in dry tetrahydrofuran (20 mL), was added to the stirred suspension dropwise at room temperature. The resultant mixture was stirred at room temperature for 2 hours, then methyl iodide (1.2 g) was added dropwise and the reaction was stirred at room temperature for a further 2 hours. The mixture was diluted with ethyl acetate (50 mL) and washed with brine (50 mL). The organic layer was isolated and the remaining aqueous layer was extracted with ethyl acetate (2×25 mL). The organic extracts were combined, dried over anhydrous sodium sulphate, filtered and concentrated to give 700 mg of the sub-titled product as a crude mixture.

m/z 132 (M+H)+ (APCI)

b) {3-[((S)-1-Methoxymethyl-3-methyl-butylcarbamoyl)-methyl]-phenyl}-acetic acid Prepared from (3-carboxymethyl-phenyl)-acetic acid (560 mg), 1S-methoxymethyl-3-methyl-butylamine (380 mg), 1-hydroxybenzotriazole (390 mg), Hunigs base (0.45 mL), 1-(3-dimethylaminopropyl)-3-ethylcarbodiimide hydrochloride (560 mg), using the method of Example 44 (step a), to give 270 mg of the sub-titled compound as an oil.

m/z 294 (M+H)+ (APCI)

c) 2-{3-[2-(1S-Methoxymethyl-3-methyl-butylamino)-ethyl]-phenyl}-ethanol

Prepared from {3-[(1S-methoxymethyl-3-methyl-butylcarbamoyl)-methyl]-phenyl}-acetic acid (270 mg) and borane-methyl sulphide complex (2M, 4.5 mL) using the method of Example 44 (step b) to give 210 mg of the sub-titled compound as an oil.

m/z 280 (M+H)+ (APCI)

d) {2-[3-(2-Hydroxy-ethyl)-phenyl]-ethyl}-((S)-1-methoxymethyl-3-methyl-butyl)-carbamic acid tert-butyl ester Prepared from 2-{3-[2-(1S-methoxymethyl-3-methyl-butylamino)-ethyl]-phenyl}-ethanol (210 mg) and di-tert-butyl dicarbonate (160 mg) using the method of Example 44 (step c). The compound was purified on silica, eluting with dichloromethane:ethyl acetate 6:1 to give 0.15 g of the sub-titled compound as an oil.

m/z 280 (M+H)+ (APCI)–Boc group fragments in mass analyser

1H NMR (400 MHz, CDCl3) δ 7.24 (d, 1H), 7.12-7.05 (m, 3H), 4.11 (d, 2H), 3.45-3.22 (m, 6H), 2.96 (s, 2H), 2.88-2.78 (m, 3H), 1.64 (s, 1H), 1.54 (d, 1H), 0.92 (q, 6H).

e) 4-Hydroxy-7-[(R)-1R-hydroxy-2-(2-{3-[2-(S-methoxyethyl-3-methyl-butylamino)-ethyl]-phenyl}-ethylamino)-ethyl]-3H-benzothiazol-2-one bis-hydrochloride salt Prepared from {2-[3-(2-hydroxy-ethyl)-phenyl]-ethyl}-(1S-methoxymethyl-3-methyl-butyl)-carbamic acid tert-butyl ester (150 mg), Dess-Martin periodinane (200 mg), 7-(2-amino-1R-hydroxy-ethyl)-4-hydroxy-3H-benzothiazol-2-one hydrochloride (84 mg) and sodium cyanoborohydride (30 mg) using the method of Example 44 (step d) to give 45 mg of the titled compound as a white solid.

m/z 488 (M+H)+ (Agilent multimode+)

1H NMR (400 MHz, DMSO) δ 11.72 (s, 1H), 10.29 (bs, 1H), 9.47 (bs, 1H), 9.12-8.97 (m, 3H), 7.30 (t, 1H), 7.15 (s, 3H), 6.93 (d, 1H), 6.82 (d, 1H), 5.03 (t, 1H), 3.67-3.52 (m, 3H), 3.32 (s, 3H), 3.25-3.30 (m, 1H), 3.20-3.15 (m, 4H), 3.06-2.99 (m, 6H), 1.69-1.64 (m, 1H), 1.60-1.49 (m, 2H), 0.89 (q, 6H).

EXAMPLE 49

4-Hydroxy-7-[1R-hydroxy-2-(2-{3-[(1S-methoxymethyl-3-methyl-butylamino)-methyl]-phenyl}-ethylamino)-ethyl]-3H-benzothiazol-2-one bis-hydrochloride salt

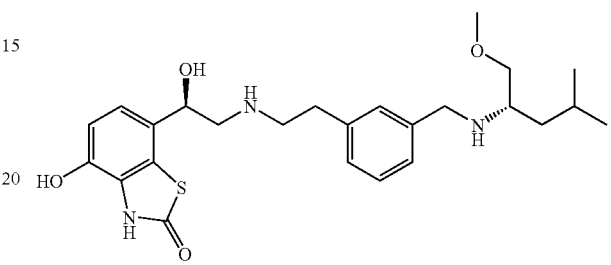

a) 2-{3-[(1S-Methoxymethyl-3-methyl-butylamino)-methyl]-phenyl}-ethanol

3-[2-(Tetrahydro-pyran-2-yloxy)-ethyl]-benzaldehyde (350 mg) and 1S-methoxymethyl-3-methyl-butylamine (250 mg) were dissolved in dichloroethane (15 mL) and acetic acid (0.25 mL) and stirred at room temperature for 10 minutes. Sodium triacetoxyborohydride (1.2 g) was added to the mixture and the reaction was stirred at room temperature for a further 3 hours. The mixture was partitioned between saturated sodium bicarbonate (25 mL) and dichloromethane (25 mL) and the organic layer was isolated. The remaining aqueous layer was extracted with dichloromethane (2×15 mL). The organic extracts were combined, dried over anhydrous sodium sulphate, filtered and concentrated. The isolated residue was dissolved in methanol and adsorbed to an SCX column. The SCX was washed with methanol and the crude product was eluted from the column with methanolic ammonia (0.7M). The basic eluent was concentrated to give 120 mg of the sub-titled compound as an oil (crude product).

m/z 266 (M+H)+ b) [3-(2-Hydroxy-ethyl)-benzyl]-(1S-methoxymethyl-3-methyl-butyl)-carbamic acid tert-butyl ester Prepared from 2-{3-[(1S-methoxymethyl-3-methyl-butylamino)-methyl]-phenyl}-ethanol (120 mg) and di-tert-butyl dicarbonate (100 mg) using the method of Example 44 (step c). The compound was purified on silica, eluting with dichloromethane:ethyl acetate 4:1 to give 110 mg of the sub-titled compound as an oil.

m/z 266 (M+H)+ (APCI)–Boc group fragments in mass analyser.

c) 4-Hydroxy-7-[(R)-1-hydroxy-2-(2-{3-[((S)-1-methoxymethyl-3-methyl-butylamino)-methyl]-phenyl}-ethylamino)-ethyl]-3H-benzothiazol-2-one bis-hydrochloride salt Prepared from [3-(2-hydroxy-ethyl)-benzyl]-(1S-methoxymethyl-3-methyl-butyl)-carbamic acid tert-butyl ester (110 mg), Dess-Martin periodinane (150 mg), 7-(2-amino- 1R-hydroxy-ethyl)-4-hydroxy-3H-benzothiazol-2-one hydrochloride (63 mg) and sodium cyanoborohydride (20 mg) using the method of Example 44 (step d) to give 45 mg of the titled compound as a white solid.

m/z 474 (M+H)+ (Agilent multimode+)

$^1$H NMR (400 MHz, DMSO) δ 11.69 (bs, 1H), 10.24 (bs, 1H), 9.50 (bs, 1H), 9.22 (bs, 2H), 8.97 (bs, 1H), 7.49 (s, 1H), 7.44 (d, 1H), 7.36 (t, 1H), 7.26 (d, 1H), 6.91 (d, 1H), 6.78 (d, 1H), 5.01 (t, 1H), 4.12 (bs, 2H), 3.63-3.53 (m, 3H), 3.29 (s, 3H), 3.20-3.15 (m, 3H), 3.03-3.01 (m, 4H), 1.62-1.51 (m, 3H), 0.84 (d, 3H), 0.79 (d, 3H).

EXAMPLE 50

4-Hydroxy-7-[1R-hydroxy-2-(2-{3-[(2-methoxy-benzylamino)-methyl]-phenyl}-ethylamino)-ethyl]-3H-benzothiazol-2-one bis-malonate salt

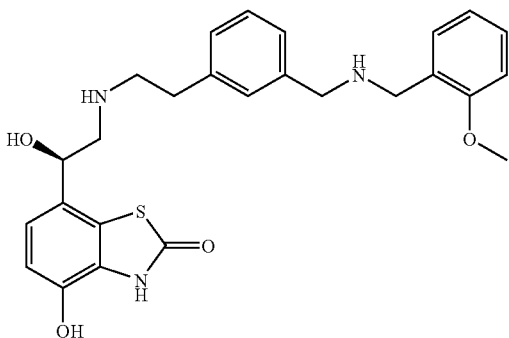

a) 3-[2-(Tetrahydro-pyran-2-yloxy)-ethyl]-benzaldehyde

To a solution of 2-[2-(3-bromo-phenyl)-ethoxy]-tetrahydro-pyran (20 g) in anhydrous tetrahydrofuran (300 mL) at −78° C. was added n-butyl lithium (2.5M in hexanes, 33.6 ml) dropwise over 5 minutes. The dark solution was kept at −78° C. for 30 minutes then N,N-dimethylformamide (16.35 ml) was added. The mixture was stirred −78° C. for half hour then quenched with aqueous ammonium acetate, and allowed to warm to room temperature. The resulting mixture was extracted with ethyl acetate, and the organics washed with brine, dried over sodium sulfate and concentrated in vacuo to give a yellow/orange oil (16.0 g). The material was used in the next step without further purification.

$^1$H NMR (400 MHz, DMSO) δ 10.00 (s, 1H), 7.80 (s, 1H), 7.76 (d, 1H), 7.61 (d, 1H), 7.53 (t, 1H), 4.59-4.56 (m, 1H), 3.84 (dt, 1H), 3.66-3.53 (m, 2H), 3.40-3.33 (m, 1H), 2.94 (t, 2H), 1.74-1.54 (m, 2H), 1.51-1.32 (m, 4H).

b) (2-Methoxy-benzyl)-{3-[2-(tetrahydro-pyran-2-yloxy)-ethyl]-benzyl}-amine

To a solution of 3-[2-(tetrahydro-pyran-2-yloxy)-ethyl]-benzaldehyde (10 g) and 2-methoxybenzylamine (6 g) in toluene (150 mL) was added TsOH (100 mg). The mixture was heated at reflux in a Dean-Stark apparatus for a couple of hours. About 1 mL water was displaced. The reaction was checked by TLC, iso-hexane/EtOAc (4/1, Rf ~0.5). The mixture was cooled and washed with aqueous bicarbornate, then concentrated in vacuo. The residue was azeotroped twice with toluene and was taken up in ethanol (150 ml). The solution was cooled to 0° C. and sodium borohydride (1.65 g) was added slowly. The reaction was left to warm to room temperature and was stirred overnight. Water was added (150 mL) and ethanol removed under vacuum. The residue was partitioned between aqueous bicarbonate and ethyl acetate. The organic layers were dried over sodium sulfate and concentrated in vacuo to give a yellow oil (6.5 g). The material was used in the next step without further purification.

$^1$H NMR (300 MHz, DMSO) δ 7.33 (dd, 1H), 7.27-7.13 (m, 4H), 7.09 (d, 1H), 6.94 (d, 1H), 6.89 (d, 1H), 4.56 (t, 1H), 3.85-3.72 (m, 1H), 3.76 (s, 3H), 3.76 (s, 2H), 3.64 (s, 2H), 3.70-3.49 (m, 4H), 3.41-3.28 (m, 1H), 2.81 (t, 1H), 2.50 (quintet, 1H), 1.75-1.29 (m, 4H).

c) (2-Methoxy-benzyl)-{3-[2-(tetrahydro-pyran-2-yloxy)-ethyl]-benzyl}-carbamic acid tert-butyl ester To a solution of (2-methoxybenzyl)-{3-[2-(tetrahydro-pyran-2-yloxy)-ethyl]-benzyl}-amine (15 g) in dichloromethane (200 mL) at 0° C. was added N,N-diisopropylamine (3.7 ml) and di-tert-butyl dicarbonate (4.2 g). The reaction was stirred for 4 hour and allowed to warm to room temperature. The reaction was partitioned between dichloromethane and aqueous bicarbonate. The organic layer was washed with brine, dried over sodium sulfate then concentrated in vacuo to give a yellow oil (18.1 g). The material was used in the next step without further purification.

[M+H−BOC] 356 d) (2-Methoxy-benzyl)-{3-[2-(hydroxy)-ethyl]-benzyl}-carbamic acid tert-butyl ester (2-Methoxy-benzyl)-{3-[2-(tetrahydro-pyran-2-yloxy)-ethyl]-benzyl}-carbamic acid tert-butyl ester (51 g) was dissolved in a mixture of THF (250 mL), AcOH (225 mL) and water (150 mL) and the resulting mixture refluxed for a total of 10 hours. The majority of the tetrahydrofuran and acetic acid was evaporated and the pH of was adjusted to 8 using saturated aqueous sodium bicarbonate solution. The aqueous phase was extracted with ethyl acetate (3×250 mL) and the combined organics were washed with water (250 mL), brine (250 mL), dried over sodium sulfate, filtered and evaporated. The crude material was purified in two portions by column chromatography eluting with dichloromethane:ethyl acetate (95:5 to 80:20 gradient) to give a yellow oil (total of 17.2 g).

$^1$H NMR (300 MHz, DMSO) δ 7.30-7.18 (m, 2H), 7.11 (d, 2H), 7.07-6.88 (m, 4H), 4.63 (t, 1H), 4.40-4.23 (m, 4H), 3.76 (s, 3H), 3.58 (td, 2H), 2.70 (t, 2H), 1.39 (s, 9H).

e) 4-hydroxy-7-[1R-hydroxy-2-(2-{3-[(2-methoxy-benzylamino)-methyl]-phenyl}-ethylamino)-ethyl]-3H-benzothiazol-2-one A vigorously stirred solution of 4-hydroxy-7-[1R-hydroxy-2-(2-{3-[(2-methoxy-benzylamino)-methyl]-phenyl}-ethylamino)-ethyl]-3H-benzothiazol-2-one bis-trifluoroacetate prepared according to procedure from (2-methoxy-benzyl)-{3-[2-(hydroxy)-ethyl]-benzyl}-carbamic acid tert-butyl ester as described in Example 36 (step b, 56 mg) in water (3 mL) was treated dropwise with 1 drop of concentrated aqueous ammonia. After stirring for 2 minutes, the resultant precipitate was filtered off and washed with water before being dried under vacuum at room temperature. Yield 26 mg m/z 480 (M+1H)+ (Agilent multimode)

$^1$H NMR (400 MHz, DMSO) δ 7.23 (d, 1H), 7.24-7.14 (m, 4H), 7.04 (d, 1H), 6.96-6.89 (m, 2H), 6.85 (d, 1H), 6.68 (d,

1H), 4.61-4.58 (m, 1H), 3.76 (s, 3H), 3.67 (s, 2H), 3.65 (s, 2H), 2.80-2.74 (m, 2H), 2.72-2.63 (m, 4H). 5 exchangeable protons not seen at elevated temperature.

f) 4-Hydroxy-7-[1R-hydroxy-2-(2-{3-[(2-methoxy-benzylamino)-methyl]-phenyl}-ethylamino)-ethyl]-3H-benzothiazol-2-one bis-malonate salt To a solution 4-hydroxy-7-[1R-hydroxy-2-(2-{3-[(2-methoxy-benzylamino)-methyl]-phenyl}-ethylamino)-ethyl]-3H-benzothiazol-2-one (100 mg) in a mixture of ethanol (2 mL) and acetonitrile (10 mL) at reflux (~90° C.) was added dropwise a solution of malonic acid (65 mg) in ethanol (0.5 mL). Precipitate formed during addition but redissolved on complete addition of acid. Acetonitrile was added until slight cloudiness persisted then the mixture refluxed until the solution cleared. The solution was cooled to ~70-80° C. and seed crystals added (~1 mg). The mixture was allowed to cool to room temperature and stirred slowly under nitrogen overnight. The solution was further cooled in an ice bath for 2 hours. The solid was collected by filtration, washed with acetonitrile, then with ether (twice) and dried at 50° C. under high vacuum to give yield 93 mg of the title compound.

[M+H]+ 480

$^1$H NMR (400 MHz, DMSO) δ 7.41-7.28 (m, 4H), 7.31 (s, 1H), 7.24 (d, 1H), 7.05 (d, 1H), 6.97 (t, 1H), 6.92 (d, 1H), 6.76 (d, 1H), 4.89-4.82 (m, 1H), 4.01 (s, 2H), 3.94 (s, 2H), 3.79 (s, 3H), 3.14 (t, 2H), 3.09-2.86 (m, 4H), 2.80 (s, 4H). 7 exchangeable protons not observed.

EXAMPLE 51

4-Hydroxy-7-{1R-hydroxy-2-[2-(3-pyrrolidin-1-ylmethyl-phenyl)-ethylamino]-ethyl}-3H-benzothiazol-2-one bis-hydrochloride salt

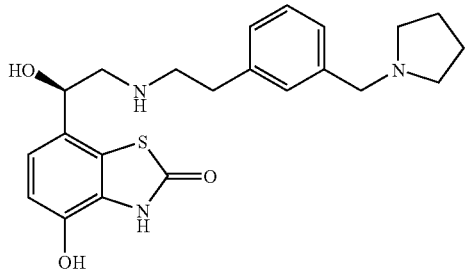

a) Trihydrido(2-{3-[2-(pyrrolidin-1-yl-κN)ethyl]phenyl}ethanol)boron (3-Formyl-phenyl)-acetic acid methyl ester (Example 1, step a, 540 mg), acetic acid (0.18 mL) and pyrrolidine (230 mg) were combined in methanol (10 mL), sodium triacetoxyborohydride (950 mg) was then added. After 24 hours, the solvent was evaporated. The resultant residue was loaded onto a conditioned SCX cartridge (50 g, Varian) and washed with methanol (250 mL), then eluted with methanolic ammonia solution (2M, 150 mL). The elution fraction was evaporated and the residue was dissolved in ethanol (10 mL). Calcium chloride anhydrous (11.0 g) was added followed by sodium borohydride (680 mg) and the resulting mixture stirred overnight. An aqueous potassium carbonate solution (2M, 50 mL) was added and the mixture filtered. The filtrate was extracted with ethyl acetate (3×50 mL) and the combined organics washed with water (50 mL), brine (50 mL), dried over sodium sulfate and evaporated. The residue was redissolved in tetrahydrofuran (10 mL) and cooled to 0° C., under nitrogen. Borane-methyl sulfide complex (2M solution in tetrahydrofuran, 4.5 mL) was added and the resulting mixture stirred for 5 minutes. The tetrahydrofuran was evaporated and the residue purified is on silica, eluting with diethyl ether:isohexane [0:1 to 1:1] to give subtitle product, as an oil 420 mg.

$^1$H NMR (300 MHz, CDCl$_3$) δ 7.36-7.20 (m, 4H), 4.02 (s, 2H), 3.88 (q, 2H), 3.14-3.03 (m, 2H), 2.94-2.79 (m, 4H), 2.23-2.11 (m, 2H), 1.84-1.72 (m, 2H). +4 exchangeable protons not seen.

b) 4-Hydroxy-7-{1R-hydroxy-2-[2-(3-pyrrolidin-1-ylmethyl-phenyl)-ethylamino]-ethyl}-3H-benzothiazol-2-one bis-hydrochloride salt Dess-Martin periodinane (194 mg) was added to a solution of trihydrido(2-{3-[2-(pyrrolidin-1-yl-κN)ethyl]phenyl}ethanol)boron (84 mg) in dichloromethane (15 mL). After 60 minutes, the reaction mixture was poured onto a mixture of: sodium thiosulfate (15 g); water (15 mL); saturated aqueous sodium bicarbonate (15 mL) and ethyl acetate (15 mL). Stirred vigorously for 10 minutes. The mixture was separated and the aqueous extracted with ethyl acetate (2×15 mL). The combined organics were washed with water (20 mL), brine (20 mL), dried (sodium sulfate) and evaporated. The residue was dissolved in methanol (5 mL), then (R)-7-(2-amino-1-hydroxy-ethyl)-4-hydroxy-3H-benzothiazol-2-one hydrochloride (100 mg) and acetic acid (20 μL) were added. After 1 hour, sodium cyanoborohydride (36 mg) was added. After 18 hours the reaction mixture was concentrated under vacuum. The residue was loaded onto conditioned Tosic-65A resin (3.3 g, Argonaut) in acetonitrile:propan-2-ol [1:1]. The resin was washed with acetonitrile:propan-2-ol [1:1] (50 mL) and eluted with propan-2-ol:0.880 ammonia solution [4:1] (100 mL). The elution fraction was evaporated, and the residue redissolved in tetrahydrofuran (10 mL) ethylenediamine (0.23 mL) was added and the mixture was refluxed for 5 minutes then concentrated. The residue was azeotroped with toluene twice, treated with trifluoroacetic acid and evaporated. Purification by HPLC method B. The purified material was dissolved in acetonitrile (2 mL), treated with an excess of 2M ethereal hydrogen chloride solution and evaporated and trituration with diethyl ether gave the title product, as a white solid (40 mg).

m/z 414 (M+H)+ (Agilent multimode)

1H NMR (400 MHz, DMSO 25C) δ 11.67 (s, 1H), 11.07 (s, 1H), 10.26 (s, 1H), 9.33 (s, 1H), 8.92 (s, 1H), 7.51 (s, 1H), 7.45 (d, 1H), 7.37 (t, 1H), 7.31-7.25 (m, 1H), 6.90 (d, 1H), 6.77 (d, 1H), 6.43 (s, 1H), 4.98 (dd, 1H), 4.28 (d, 2H), 4.05-

3.80 (m, 2H), 3.32-3.15 (m, 4H), 3.09-2.92 (m, 4H), 2.04-1.90 (m, 2H), 1.90-1.76 (m, 2H).

EXAMPLE 52

4-Hydroxy-7-{1R-hydroxy-2-(2-{4-piperidin-1-ylmethyl}phenyl)ethylamino)-ethyl}-3H-benzothiazol-2-one bis-hydrochloride salt

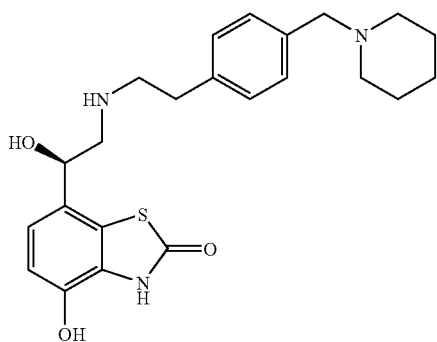

a) 2-(4-Piperidin-1-ylmethylphenyl)ethanol

A solution of piperidine (204 mg) and (4-formylphenyl)acetic acid methyl ester (Example 16, step a, 356 mg) in dichloromethane (10 mL) was stirred for 1 hour, treated with sodium triacetoxyborohydride (636 mg) and stirred overnight. The resultant mixture was loaded onto a conditioned SCX cartridge (10 g, Varian) and washed with methanol (50 mL), then eluted with methanolic ammonia solution (50 mL). The elution fraction was evaporated and the residue was dissolved in ethanol (20 mL), treated with anhydrous calcium chloride (444 mg), followed by sodium borohydride (303 mg) and stirred overnight. The mixture was quenched with aqueous potassium carbonate solution (2M, 20 mL) and concentrated to remove most of the ethanol. The residue was extracted with ethyl acetate and the washed and dried (sodium sulfate) extract was evaporated. The residue was purified on silica, eluting with 5% triethylamine in diethyl ether to give the subtitle product, as a colourless oil (287 mg).

$^1$H NMR (300 MHz, CDCl$_3$) δ 7.26 (d, 2H), 7.17 (d, 2H), 3.86 (t, 2H), 3.44 (s, 2H), 2.86 (t, 2H), 2.38-2.34 (m, 4H), 1.60-1.41 (m, 6H), OH not seen.

b) Methanesulfonic acid 2-(4-piperidin-1-ylmethylphenyl)ethyl ester

A stirred solution of 2-(4-piperidin-1-ylmethylphenyl)ethanol (125 mg) and triethylamine (0.18 mL) in dichloromethane (5 mL) was treated dropwise at 0° C. with methanesulphonyl chloride (71.8 mg, 0.05 mL) and then stirred at room temperature for 3 hours. The mixture was diluted with methylene chloride and washed with water. The dried (sodium sulphate) organic layer was evaporated to give the subtitle compound as a water-white oil (150 mg).

$^1$H NMR (300 MHz, CDCl$_3$) δ 7.29 (d, 2H), 7.18 (d, 2H), 4.41 (t, 2H), 3.47 (s, 2H), 3.04 (t, 2H), 2.85 (s, 3H), 2.43-2.32 (m, 4H), 1.61-1.40 (m, 6H).

c) 4-Hydroxy-7-{1R-hydroxy-2-(2-[4-piperidin-1-ylmethyl]phenyl)ethylamino)-ethyl}-3H-benzothiazol-2-one bis-hydrochloride salt A mixture of 7-(2-amino-1R-hydroxyethyl)-4-hydroxy-3H-benzothiazol-2-one (100 mg), methanesulfonic acid 2-(4-piperidin-1-ylmethylphenyl)ethyl ester (138 mg) and anhydrous sodium carbonate (202 mg) in N,N-dimethylformamide (5 mL) was stirred at 60° C. overnight. The reaction was allowed to cool and evaporated to remove most of the dimethylformamide. The residue was suspended in acetonitrile/iso-propanol [1:1] mixture, filtered and the filtrate was applied to a cartridge of Tosic-65A resin. The resin was washed with acetonitrile/iso-propanol [1:1] mixture and the product was eluted off with a solution of 20% 0.880 ammonia-40% acetonitrile in iso-propanol. The eluents were evaporated and the residue was purified by reversed phase preparative HPLC using Method A. The trifluoroacetate salt was taken up in acetonitrile, treated with an excess of 2M ethereal hydrogen chloride and evaporated. The residue was again taken up in acetonitrile, treated with an excess of 2M ethereal hydrogen chloride and evaporated. The residue was triturated with ether and filtered off to give the title compound as a white solid (7 mg).

m/z 428 (M+H)$^+$ (Agilent multimode)

$^1$H NMR (400 MHz, DMSO) δ 11.69 (s, 1H), 10.34 (s, 1H), 10.23 (s, 1H), 9.17 (s, 1H), 8.86 (s, 1H), 7.55 (d, 2H), 7.34 (d, 2H), 6.93 (d, 1H), 6.79 (d, 1H), 6.47 (s, 1H), 4.96 (s, 1H), 4.22 (d, 2H), 3.27-3.18 (m, 4H), 3.08-3.00 (m, 4H), 2.86-2.73 (m, 2H), 1.76-1.67 (m, 4H), 1.36-1.23 (m, 2H).

EXAMPLE 53

4-Hydroxy-7-{1R-hydroxy-2-[2-(4-isopropylaminomethyl)phenyl]ethylamino}-ethyl)-3H-benzothiazol-2-one bis-trifluoroacetate salt

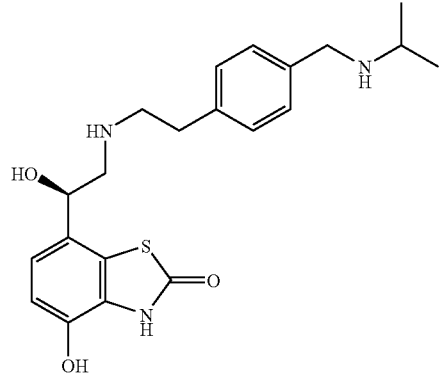

a) [3-(2-Hydroxyethyl)benzyl]-[isopropyl]carbamic acid tert-butyl ester

Prepared from isopropylamine (1.18 g) and (3-formyl-phenyl)-acetic acid ethyl ester (Example 1, step a, 356 mg) using the method of Example 3 (step a), to give the subtitle compound as a colorless oil (520 mg).

$^1$H NMR (300 MHz, CDCl$_3$) δ 7.20-7.14 (m, 4H), 4.33 (s, 2H), 4.22-3.97 (m, 1H), 3.85 (q, 2H), 2.85 (t, 2H), 1.47-1.32 (m, 9H), 1.10 (d, 6H). OH not seen.

b) 4-Hydroxy-7-{1R-hydroxy-2-[2-(4-isopropylaminomethyl)phenyl]ethylamino}-ethyl)-3H-benzothiazol-2-one bis-trifluoroacetate salt Prepared from [3-(2-hydroxyethyl)benzyl]-[isopropyl]carbamic acid tert-butyl ester (200 mg) and 7-(2-amino-1R- hydroxy-ethyl)-4-hydroxy-3H-benzothiazol-2-one hydrochloride (100 mg) using the method of Example 3 (step b). Purification by HPLC using method B gave the title compound as a white solid (120 mg).

m/z 402 (M+H)$^+$ (Agilent multimode)

$^1$H NMR (500 MHz, DMSO) δ 11.67 (s, 1H), 10.26 (s, 1H), 8.92-8.77 (m, 4H), 7.46 (d, 2H), 7.32 (d, 2H), 6.93 (d, 1H), 6.78 (d, 1H), 6.49 (s, 1H), 4.92-4.88 (m, 1H), 4.15-4.11 (m, 2H), 3.32-2.91 (m, 7H), 1.27 (d, 6H).

EXAMPLE 54

4-Hydroxy-7-{1R-hydroxy-2-[2-(4-aminomethyl)phenyl]ethylamino}-ethyl)-3H-benzothiazol-2-one bis-trifluoroacetate salt

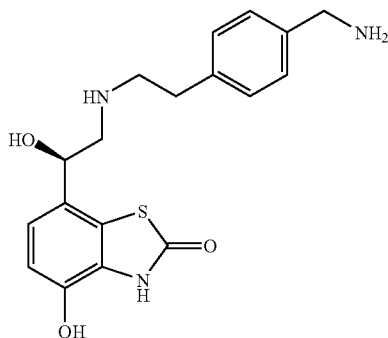

Prepared from 4-(2-hydroxyethyl)benzyl]carbamic acid tert-butyl ester (G. Wayne et al, WO 9422835, 188 mg) and 7-(2-amino-1R-hydroxy-ethyl)-4-hydroxy-3H-benzothiazol-2-one hydrochloride (10 g) using the method of Example 3 (step b). Purification by HPLC using method B gave the title compound as a white solid (97 mg).

m/z 360 (M+H)$^+$ (Agilent multimode)

$^1$H NMR (500 MHz, DMSO) δ 11.67 (s, 1H), 10.30 (s, 1H), 8.91 (d, 2H), 8.25 (s, 3H), 7.41 (d, 2H), 7.29 (d, 2H), 6.93 (d, 1H), 6.78 (d, 1H), 6.50 (br s, 1H), 4.93-4.90 (m, 1H), 4.02-4.01 (m, 2H), 3.17-2.90 (m, 6H).

EXAMPLE 55

4-Hydroxy-7-{1R-hydroxy-2-[2-(4-{2-methoxy}ethylaminomethyl)phenyl]-ethylamino}-ethyl)-3H-benzothiazol-2-one bis-hydrochloride salt

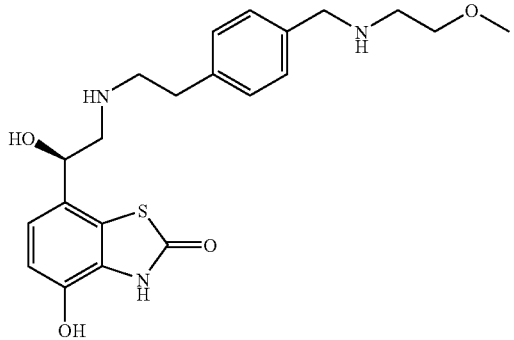

a) [4-(2-hydroxyethyl)benzyl]-[(2-methoxy)ethyl]carbamic acid tert-butyl ester

Prepared from 2-methoxyethylamine (225 mg) and (4-formyl-phenyl)-acetic acid ethyl ester (Example 16, step a, 356 mg) using the method of Example 3 (step a), to give the subtitle compound as a water-white oil (367 mg).

$^1$H NMR (300 MHz, CDCl$_3$) δ 7.20-7.17 (m, 4H), 4.48 (s, 2H), 3.86 (q, 2H), 3.51-3.38 (m, 4H), 3.31 (s, 3H), 2.86 (t, 2H), 1.49-1.45 (m, 9H). OH not seen.

b) 4-Hydroxy-7-{1R-hydroxy-2-[2-(4-{2-methoxy}ethylaminomethyl)phenyl]-ethylamino}-ethyl)-3H-benzothiazol-2-one bis-hydrochloride salt Prepared from [4-(2-hydroxyethyl)benzyl]-[(2-methoxy)ethyl]carbamic acid tert-butyl ester (232 mg) and 7-(2-amino-1R-hydroxy-ethyl)-4-hydroxy-3H-benzothiazol-2-one hydrochloride (100 mg) using the method of Example 3 (step b). Purification by HPLC using method A. The trifluoroacetate salt was taken up in a little acetonitrile/iso-propanol mixture, treated with an excess of 2M ethereal hydrogen chloride and evaporated. The residue was again taken up in acetonitrile/iso-propanol, treated with an excess of 2M ethereal hydrogen chloride and evaporated. The residue was triturated with ether and filtered off to give the title compound as a white solid (52 mg).

m/z 418 (M+H)$^+$ (Agilent multimode)

$^1$H NMR (300 MHz, DMSO) δ 11.71 (s, 1H), 10.27 (s, 1H), 9.37 (s, 3H), 8.94 (s, 1H), 7.51 (d, 2H), 7.30 (d, 2H), 6.93 (d, 1H), 6.81 (d, 1H), 6.47 (br s, 1H), 5.03-4.98 (m, 1H), 4.11 (br s, 2H), 3.62 (t, 2H), 3.28 (s, 3H), 3.19-3.00 (m, 8H).

EXAMPLE 56

4-Hydroxy-7-{1R-hydroxy-2-[2-(3-{2-hydroxyethylamino}methyl)phenyl]ethylamino}ethyl)-3H-benzothiazol-2-one bis-hydrochloride salt

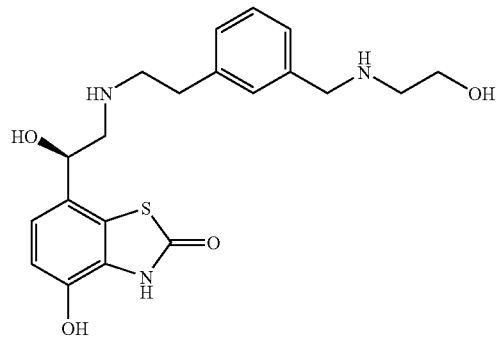

a) [3-(2-hydroxyethyl)benzyl]-[(2-(tert-butyl-dimethylsilanyloxy)ethyl]carbamic acid tert-butyl ester Prepared from 2-(tert-butyl-dimethylsilanyloxy)ethylamine (Matteucci, Mark et al WO 9205186, 421 mg) and (3-formyl-phenyl)-acetic acid ethyl ester (Example 1, step a, 356 mg) using the method of Example 3 (step a), to give the subtitle compound as a colorless oil (316 mg).

$^1$H NMR (300 MHz, CDCl$_3$) δ 7.29-7.24 (m, 2H), 7.13-7.07 (m, 2H), 4.51 (s, 2H), 3.85 (q, 2H), 3.78-3.64 (m, 2H), 3.35-3.21 (m, 2H), 2.86 (t, 2H), 1.49-1.43 (m, 9H), 0.89 (s, 9H), 0.05 (s, 6H) OH not seen.

b) 4-Hydroxy-7-{1R-hydroxy-2-[2-(3-{2-methoxy}ethylaminomethyl)phenyl]-ethylamino}-ethyl)-3H-benzothiazol-2-one bis-hydrochloride salt Prepared from [3-(2-hydroxyethyl)benzyl]-[(2-(tert-butyl-dimethylsilanyloxy)ethyl]-carbamic acid tert-butyl ester (307 mg) and 7-(2-amino-1-(R)-hydroxy-ethyl)-4-hydroxy-3H-benzothiazol-2-one hydrochloride (100 mg) using the method of Example 3 (step b). Purification by HPLC using method B. The trifluoroacetate salt was taken up in a little acetonitrile, treated with an excess of 2M ethereal hydrogen chloride and evaporated. The residue was again taken up in acetonitrile, treated with an excess of 2M ethereal hydrogen chloride and evaporated. The residue was triturated with a little ether and filtered off to give the title compound as a white solid (100 mg).

m/z 404 (M+H)+ (Agilent multimode)

$^1$H NMR (300 MHz, DMSO) δ 11.70 (s, 1H), 10.25 (s, 1H), 9.35 (s, 2H), 9.22 (s, 2H), 8.93 (s, 1H), 7.46-7.37 (m, 3H), 7.29 (d, 1H), 6.93 (d, 1H), 6.80 (d, 1H), 6.47 (s, 1H), 5.02-4.99 (m, 1H), 4.13 (s, 2H), 3.41-3.36 (m, 2H), 3.20-3.16 (m, 2H), 3.07-2.92 (m, 6H).

EXAMPLE 57

4-Hydroxy-7-[1R-hydroxy-2-(2-{3-[(3-pyridin-2-yl-propylamino)-methyl]-phenyl}-ethylamino)-ethyl]-3H-benzothiazol-2-one tris-hydrochloride salt

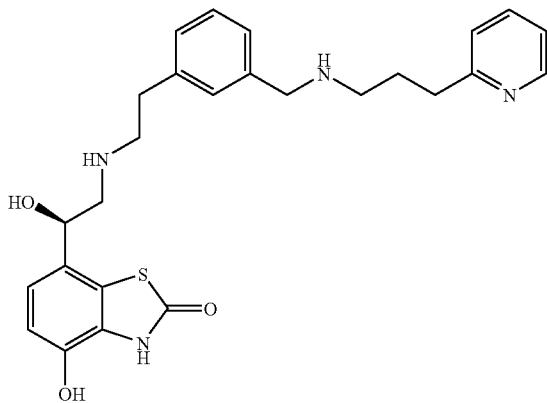

a) [3-(2-Hydroxy-ethyl)-benzyl]-(3-pyridin-2-yl-propyl)-carbamic acid tert-butyl ester A solution of 2-pyridinepropanamine dihydrochloride (940 mg) in 1-methyl-2-pyrrolidone (5 mL) was treated with 3-[2-(tetrahydro-pyran-2-yloxy)-ethyl]-benzaldehyde prepared as described in Example 50 (step a, 500 mg) and stirred for 30 minutes. The reaction mixture was treated with sodium triacetoxyborohydride (1.0 g) and stirred at room temperature for 18 hours. At the end of this time, the mixture was treated with 2M aqueous hydrochloric acid (5 mL) and then stirred for 3 hours before being loaded onto conditioned Tosic-65A resin (5 g, Argonaut). The resin was washed with acetonitrile (100 mL) and eluted with triethylamine:acetonitrile [1:4] (100 mL). The eluted fraction was evaporated and the residue (800 mg) dissolved in dichloromethane (20 mL). To the solution was added di-tert-butyl-dicarbonate (650 mg) and the resultant mixture stirred for 18 hours. The solvents were evaporated under reduced pressure and the residue purified on silica, gradient elution of 0-5% methanol in dichloromethane, to afford the subtitle compound (90 mg).

m/z 371 (M+H)+ (APCI)

b) [3-(2-Oxo-ethyl)-benzyl]-(3-pyridin-2-yl-propyl)-carbamic acid tert-butyl ester A solution of [3-(2-hydroxy-ethyl)-benzyl]-(3-pyridin-2-yl-propyl)-carbamic acid tert-butyl ester (90 mg) in anhydrous dichloromethane (8 mL) under nitrogen was treated with Dess-Martin periodinane (123 mg) and the mixture stirred for 90 minutes. Ethyl acetate (8 mL) was added followed by saturated aqueous sodium thiosulphate (8 mL) and saturated aqueous sodium bicarbonate (8 mL), the resultant mixture was stirred vigorously for 10 minutes before being extracted with ethyl acetate. The organic layer was separated, washed with saturated aqueous sodium bicarbonate, dried and the solvent removed under reduced pressure to yield the sub-titled compound (90 mg).

m/z 369 (M+H)+ (APCI)

c) (3-{2-[2R-Hydroxy-2-(4-hydroxy-2-oxo-2,3-dihydro-benzothiazol-7-yl)-ethylamino]-ethyl}-benzyl)-(3-pyridin-2-yl-propyl)-carbamic acid tert-butyl ester A solution of 7-(2-amino-1-hydroxy-ethyl)-4-hydroxy-3H-benzothiazol-2-one hydrochloride (64 mg) and [3-(2-oxo-ethyl)-benzyl]-(3-pyridin-2-yl-propyl)-carbamic acid tert-butyl ester (81 mg) in methanol (7 mL) was treated with acetic acid (10 mg) followed by sodium cyanoborohydride (23 mg) and the resultant mixture was stirred for 4 hours. At the end of this time, the solvent was removed under reduced pressure and the residue partitioned between a mixture of ethyl acetate (50 mL), saturated aqueous brine (50 mL) and concentrated aqueous ammonia (1 mL). The organic layer was separated, dried and evaporated under reduced pressure. The residue was purified on silica eluting with 1% aqueous ammonia and 9% methanol in dichloromethane to yield the sub-titled compound (53 mg).

m/z 579 (M+H)+ (APCI)

d) 4-Hydroxy-7-[1R-hydroxy-2-(2-{3-[(3-pyridin-2-yl-propylamino)-methyl]-phenyl}-ethylamino)-ethyl]-3H-benzothiazol-2-one tris-hydrochloride salt (3-{2-[2R-Hydroxy-2-(4-hydroxy-2-oxo-2,3-dihydro-benzothiazol-7-yl)-ethylamino]-ethyl}-benzyl)-(3-pyridin-2-yl-propyl)-carbamic acid tert-butyl ester (53 mg) was dissolved in trifluoroacetic acid (2 mL) and the solution allowed to stand at room temperature for 10 minutes. The solvent was evaporated under reduced pressure and the residue was azeotroped with acetonitrile. The residue was dissolved in acetonitrile (100 mL) and treated with a 4M solution of hydrogen chloride in 1,4-dioxane (1 mL). The solvents were evaporated off under reduced pressure and the residue was triturated with diethyl ether. Purification was by HPLC on a Hichrom ACE column (50×21.2 mm) eluting with 5-50% acetonitrile in 0.2% aqueous trifluoroacetic acid. The product was dissolved in acetonitrile (10 mL) and treated with a 4M solution of hydrogen chloride in 1,4-dioxane (1 mL). The solvents were evaporated off under reduced pressure and the residue was triturated with diethyl ether to yield the title compound (22 mg).

m/z 479 (M+H)+ (Agilent multimode)

¹H NMR (400 MHz, DMSO) δ 11.71 (s, 1H), 10.25 (s, 1H), 9.53 (s, 2H), 9.40 (s, 1H), 8.96 (s, 1H), 8.73 (s, 1H), 8.31 (s, 1H), 7.80 (d, 1H), 7.73 (s, 1H), 7.54 (s, 1H), 7.51-7.37 (m, 3H), 7.29 (d, 1H), 6.93 (d, 1H), 6.80 (d, 1H), 6.45 (s, 1H), 5.04-5.01 (m, 1H), 4.12 (s, 2H), 3.22-3.18 (m, 2H), 3.10-3.00 (m, 6H), 2.94 (s, 2H), 2.21-2.15 (m, 2H).

EXAMPLE 58

4-Hydroxy-7-{1R-hydroxy-2-[2-(3-{[2-(2-hydroxy-phenyl)-ethylamino]-methyl}-phenyl)-ethylamino]-ethyl}-3H-benzothiazol-2-one bis-hydrochloride salt

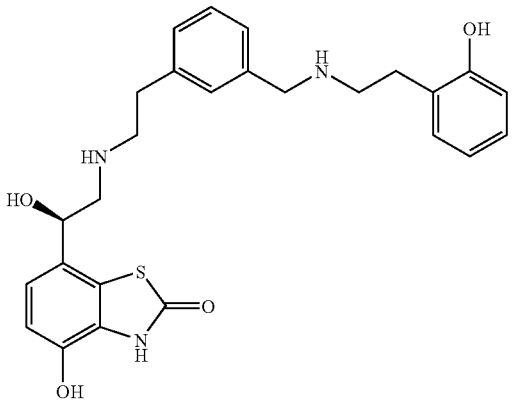

a) [3-({tert-Butoxycarbonyl-[2-(2-hydroxy-phenyl)-ethyl]-amino}-methyl)-phenyl]-acetic acid methyl ester A mixture of 2-hydroxyphenethylamine hydrobromide salt (480 mg) and (3-formylphenyl)acetic acid methyl ester prepared as described in Example 1 (step a, 370 mg) in dichloromethane (10 mL) and 1-methyl-2-pyrrolidone (2 mL) was stirred for 30 minutes and then treated with sodium triacetoxyborohydride (1.02 g) The mixture was stirred for 18 hours and at the end of this time partitioned between ethyl acetate and saturated aqueous sodium bicarbonate, the organic layer was separated, dried and the solvent removed under reduced pressure. The residue was dissolved in dichloromethane (20 mL) and treated with di-tert-butyl-dicarbonate (480 mg). The solution was stirred for 5 hours, at the end of this time the solvent was removed under reduced pressure. The residue was purified on silica eluting with 20% ethyl acetate in isohexane to yield the sub-titled compound (560 mg).

m/z 398 (M−H)− (APCI)

b) [3-(2-Hydroxy-ethyl)-benzyl]-[2-(2-hydroxy-phenyl)-ethyl]-carbamic acid tert-butyl ester A solution of [3-({tert-butoxycarbonyl-[2-(2-hydroxy-phenyl)-ethyl]-amino}-methyl)-phenyl]-acetic acid methyl ester (560 mg) in anhydrous tetrahydrofuran (20 mL) was treated with lithium borohydride (62 mg) and the mixture was heated at 60° C. for 5 hours under nitrogen. The reaction mixture was cooled to room temperature and partitioned between ethyl acetate and saturated aqueous brine, the organic layer was separated, dried and the solvent evaporated under reduced pressure. The residue was purified on silica, eluting with 40% ethyl acetate in isohexane to yield the sub-titled compound (500 mg).

m/z 370 (M−H)− (APCI)

c) [3-(2-Hydroxy-ethyl)-benzyl]-[2-(2-methoxymethoxy-phenyl)-ethyl]-carbamic acid tert-butyl ester A solution of [3-(2-hydroxy-ethyl)-benzyl]-[2-(2-hydroxy-phenyl)-ethyl]-carbamic acid tert-butyl ester (123 mg) in anhydrous N,N-dimethylformamide (2 mL) was treated with sodium hydride (14 mg of 60% grade reagent) and the mixture stirred under nitrogen for 10 minutes. A solution of chloromethyl methyl ether (29 mg) in anhydrous N,N-dimethylformamide (0.5 mL) was added dropwise followed by stirring at room temperature for 30 minutes. The reaction mixture was partitioned between ethyl acetate and saturated aqueous brine, the organic layer was separated, dried and the solvent evaporated under reduced pressure to yield the sub-titled compound (110 mg).

¹H NMR (400 MHz, DMSO) δ 7.26-7.02 (m, 7H), 6.91 (t, 1H), 5.18 (s, 2H), 4.62 (t, 1H), 4.36-4.30 (m, 2H), 3.57 (q, 2H), 3.20-3.40 (m, 2H), 2.75-2.67 (m, 4H), 1.37 (s, 9H).

d) (3-{2-[2R-Hydroxy-2-(4-hydroxy-2-oxo-2,3-dihydro-benzothiazol-7-yl)-ethylamino]-ethyl}-benzyl)-[2-(2-methoxymethoxy-phenyl)-ethyl]-carbamic acid tert-butyl ester A solution of [3-(2-hydroxy-ethyl)-benzyl]-[2-(2-methoxymethoxy-phenyl)-ethyl]-carbamic acid tert-butyl ester (110 mg) anhydrous dichloromethane (3 mL) under nitrogen was treated with Dess-Martin periodinane (135 mg) and the mixture stirred for 60 minutes. Ethyl acetate (3 mL) was added followed by saturated aqueous sodium thiosulphate (3 mL) and saturated aqueous sodium bicarbonate (3 mL), the resultant mixture was stirred vigorously for 10 minutes before being extracted with ethyl acetate. The organic layer was separated, washed with saturated aqueous sodium bicarbonate, dried and the solvent removed under reduced pressure. The residue (100 mg) was dissolved in methanol (1 mL) and added to a solution of 7-(2-amino-1-hydroxy-ethyl)-4-hydroxy-3H-benzothiazol-2-one hydrochloride (70 mg) in methanol (7 mL), the reaction mixture was treated with acetic acid (10 mg) followed by sodium cyanoborohydride (25 mg) and the resultant mixture was stirred for 4 hours. At the end of this time the solvent was removed under reduced pressure and the residue partitioned between a mixture of ethyl acetate (50 mL), saturated aqueous brine (50 mL) and concentrated aqueous ammonia (1 mL). The organic layer was separated, dried and evaporated under reduced pressure. The residue was purified on silica eluting with 1% aqueous ammonia and 9% methanol in dichloromethane to yield the sub-titled compound (56 mg).

m/z 622 (M−H)− (APCI)

e) 4-Hydroxy-7-{1R-hydroxy-2-[2-(3-{[2-(2-hydroxy-phenyl)-ethylamino]-methyl}-phenyl)-ethylamino]-ethyl}-3H-benzothiazol-2-one bis-hydrochloride salt The title compound was prepared from (3-{2-[2-hydroxy-2-(4-hydroxy-2-oxo-2,3-dihydro-benzothiazol-7-yl)-ethylamino]-ethyl}-benzyl)-[2-(2-methoxymethoxy-phenyl)-ethyl]-carbamic acid tert-butyl ester (56 mg) using the method of Example 58 (step d). Yield (19 mg).

m/z 480 (M+H)+ (Agilent multimode)

¹H NMR (400 MHz, DMSO, 90° C.) δ 7.48 (s, 1H), 7.43-7.34 (m, 2H), 7.29 (d, 1H), 7.09-7.02 (m, 2H), 6.95 (d, 1H), 6.85 (d, 1H), 6.78-6.71 (m, 2H), 5.00 (t, 1H), 4.12 (s, 2H), 3.23 (t, 2H), 3.12-2.95 (m, 8H). 8H exchangeable not seen at elevated temperature.

EXAMPLE 59

4-Hydroxy-7-[1-hydroxy-2-(2-{3-[(2-hydroxy-benzylamino)-methyl]-phenyl}-ethylamino)-ethyl]-3H-benzothiazol-2-one bis-hydrochloride salt

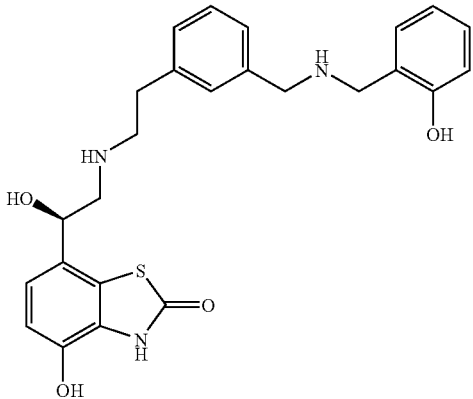

a) {3-[(2-Hydroxy-benzylamino)-methyl]-phenyl}-acetic acid methyl ester

A mixture of 2-hydroxybenzylamine (407 mg) and (3-formylphenyl)acetic acid methyl ester (594 mg) in dichloromethane (10 mL) and 1-methyl-2-pyrrolidone (10 mL) was treated with acetic acid (333 mg) followed by sodium triacetoxyborohydride (1.41 g) and the whole stirred at room temperature for 18 hours. The reaction mixture was partitioned between ethyl acetate and saturated aqueous sodium bicarbonate, the organic layer was washed twice with saturated aqueous brine before being separated, dried and evaporated under reduced pressure to yield the sub-titled compound (0.81 g).

m/z 286 (M+H)+ (APCI)

b) 2-{[3-(2-Hydroxy-ethyl)-benzylamino]-methyl}-phenol

A solution of {3-[(2-hydroxy-benzylamino)-methyl]-phenyl}-acetic acid methyl ester (0.81 g) in anhydrous tetrahydrofuran (20 mL) was treated with lithium borohydride (186 mg) and the whole stirred at room temperature for 30 minutes. The reaction mixture was then heated at 60° C. for 2 hours under nitrogen. After cooling to room temperature the mixture was partitioned between diethyl ether and dilute aqueous hydrochloric acid, the aqueous layer was separated and treated with excess solid sodium bicarbonate. The aqueous layer was extracted three times with dichloromethane and the combined organic washings were dried, filtered and evaporated under reduced pressure to yield the sub-titled compound (400 mg).

m/z 258 (M+H)+ (APCI)

c) (2-Hydroxy-benzyl)-[3-(2-hydroxy-ethyl)-benzyl]-carbamic acid tert-butyl ester A solution of 2-{[3-(2-hydroxy-ethyl)-benzylamino]-methyl}-phenol (400 mg) in dichloromethane (15 mL) was treated with di-tert-butyl-dicarbonate (370 mg) and the solution was stirred at room temperature for 3 days. The solvent was evaporated under reduced pressure and the residue was purified on silica eluting with 40% ethyl acetate in isohexane to yield the sub-titled compound (500 mg).

m/z 356 (M−H)− (APCI)

d) [3-(2-Hydroxy-ethyl)-benzyl]-(2-methoxymethoxy-benzyl)-carbamic acid tert-butyl ester A solution of (2-hydroxy-benzyl)-[3-(2-hydroxy-ethyl)-benzyl]-carbamic acid tert-butyl ester (250 mg) in anhydrous N,N-dimethylformamide (2 mL) was treated with sodium hydride (29 mg of 60% grade reagent) and the mixture stirred under nitrogen for 10 minutes. A solution of chloromethyl methyl ether (62 mg) in anhydrous N,N-dimethylformamide (0.5 mL) was added dropwise followed by stirring at room temperature for 30 minutes. The reaction mixture was partitioned between ethyl acetate and saturated aqueous brine, the organic layer was washed twice with aqueous brine, separated, dried and the solvent evaporated under reduced pressure. The residue was purified on silica eluting with 30% ethyl acetate in isohexane to yield the sub-titled compound (145 mg).

¹H NMR (400 MHz, DMSO) δ 7.26-7.20 (m, 2H), 7.15-6.96 (m, 6H), 5.19 (s, 2H), 4.62 (t, 1H), 4.37-4.32 (m, 4H), 3.57 (q, 2H), 2.69 (t, 2H), 1.39 (s, 9H).

e) (2-Methoxymethoxy-benzyl)-[3-(2-oxo-ethyl)-benzyl]-carbamic acid tert-butyl ester The sub-titled compound was prepared from [3-(2-hydroxy-ethyl)-benzyl]-(2-methoxymethoxy-benzyl)-carbamic acid tert-butyl ester (145 mg) according to the method of Example 3 (step b).

Yield (116 mg).

¹H NMR (400 MHz, CDCl₃) δ 9.72 (s, 1H), 7.34-7.20 (m, 4H), 7.12-6.97 (m, 4H), 5.14 (s, 2H), 4.55-4.35 (m, 4H), 3.65 (s, 2H), 3.42 (s, 3H), 1.47 (s, 9H).

f) 4-Hydroxy-7-[1-hydroxy-2-(2-{3-[(3-hydroxy-benzylamino)-methyl]-phenyl}-ethylamino)-ethyl]-3H-benzothiazol-2-one bis-hydrochloride salt A solution of (2-methoxymethoxy-benzyl)-[3-(2-oxo-ethyl)-benzyl]-carbamic acid tert-butyl ester (116 mg) in methanol (1 mL) was added to a solution of 7-(2-amino-1-hydroxy-ethyl)-4-hydroxy-3H-benzothiazol-2-one hydrochloride (76 mg) in methanol (5 mL), the reaction mixture was treated with acetic acid (20 mg) followed by sodium cyanoborohydride (27 mg) and the resultant mixture was stirred for 5 hours. At the end of this time concentrated aqueous ammonia (0.5 mL) was added, the solvents were then removed under reduced pressure and the residue partitioned between ethyl acetate and saturated aqueous brine. The aqueous layer was re-extracted with ethyl acetate and the combined organic layers were dried, filtered and the solvent removed under reduced pressure. The residue was dissolved in trifluoroacetic acid (5 mL) and the solution allowed to stand at room temperature for 15 minutes, the solvent was evaporated under reduced pressure and the residue azeotroped three times with acetonitrile. Purification was by HPLC on a Hichrom ACE column (50×21.2 mm) column eluting with 5-50% acetonitrile in 0.2% aqueous trifluoroacetic acid. The product was dissolved in acetonitrile (10 mL) and treated with a 4M solution of hydrogen chloride in 1,4-dioxane (2 mL). The solvents were evaporated off under reduced pressure and the residue was triturated with diethyl ether to yield the title compound (50 mg).

m/z 466 (M+H)+ (Agilent multimode)

$^1$H NMR (400 MHz, DMSO) δ 11.70 (s, 1H), 10.23 (d, 2H), 9.33 (s, 3H), 8.92 (s, 1H), 7.44-7.35 (m, 4H), 7.29 (d, 1H), 7.25-7.21 (m, 1H), 6.94 (t, 2H), 6.84 (t, 1H), 6.79 (d, 1H), 6.47 (s, 1H), 5.02-4.99 (m, 1H), 4.12 (s, 2H), 4.03 (s, 2H), 3.19-3.16 (m, 2H), 3.08-2.99 (m, 4H).

EXAMPLE 60

7-[2-(2-{3-[(2-Fluoro-benzylamino)-methyl]-phenyl}-ethylamino)-1R-hydroxy-ethyl]-4-hydroxy-3H-benzothiazol-2-one bis-hydrochloride salt

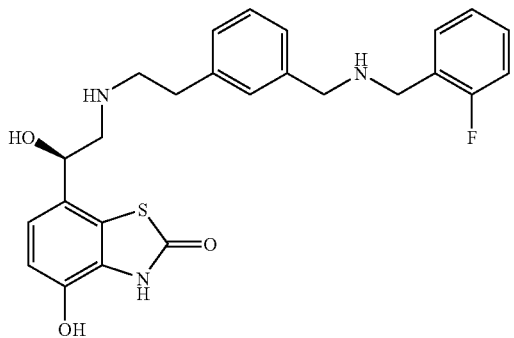

a) (2-Fluoro-benzyl)-[3-(2-hydroxy-ethyl)-benzyl]-carbamic acid tert-butyl ester A mixture of (3-formyl-phenyl)-acetic acid ethyl ester (400 mg), (2-fluorobenzyl)amine (410 mg) and acetic acid (130 mg) in methanol (5 mL) was stirred at room temperature. After 1 h, sodium triacetoxyborohydride (700 mg) was added. After 5 hours, the reaction mixture was neutralised with aqueous ammonia (0.880) and the solution evaporated to dryness. The residue was diluted with toluene and the mixture evaporated. The resulting gum was dissolved in methanol and applied to a SCX cartridge (70 g, varian). The cartridge was eluted with methanol (250 mL) and then 20% ammonia in methanol to collect the reductive amination product. The solution was evaporated and the gum dissolved in ethanol. Anhydrous calcium chloride (730 mg) was added followed by careful portionwise addition of sodium borohydride (500 mg). After 16 hours, the reaction mixture was quenched with 2M aqueous potassium carbonate (20 mL). The solid was removed by filtration, the filtrate evaporated and the residue partitioned between ethyl acetate and brine. The organic solution was dried over magnesium sulphate, filtered and evaporated. Purification was by silica gel chromatography eluting with ethyl acetate:dichloromethane 1:3, then ethyl acetate:dichloromethane 1:3 containing 5% triethylamine, to give 2-{3-[(2-fluoro-benzylamino)-methyl]-phenyl}-ethanol (320 mg). Without further purification the 2-{3-[(2-fluoro-benzylamino)-methyl]-phenyl}-ethanol was dissolved in dichloromethane (5 mL) and di-tert-butyl dicarbonate (300 mg) added. After 3 hours, the solution was applied to a silica gel column eluting with ethyl acetate:dichloromethane 1:9 to give the subtitle compound (300 mg).

$^1$H NMR (400 MHz, CDCl$_3$) δ 7.30-6.95 (m, 8H), 4.50-4.30 (m, 4H), 3.81 (q, 2H), 2.82 (t, 2H), 1.46 (9H, s).

b) 7-[2-(2-{3-[(2-Fluoro-benzylamino)-methyl]-phenyl}-ethylamino)-1R-hydroxy-ethyl]-4-hydroxy-3H-benzothiazol-2-one di-hydrochloride salt Prepared from (2-fluoro-benzyl)-[3-(2-hydroxy-ethyl)-benzyl]-carbamic acid tert-butyl ester (200 mg) and 7-(2-amino-1R-hydroxy-ethyl)-4-hydroxy-3H-benzothiazol-2-one hydrochloride (100 mg) using the method of Example 3 (step b). Purification by preparative HPLC yielded the title compound as the trifluoroacetate salt. The trifluoroacetate salt was dissolved in acetonitrile (0.5 mL). 2M HCl in diethyl ether (1 mL) was added and the title compound, as the dihydrochloride salt, precipitated (30 mg).

m/z 468 (M+H)+

$^1$H NMR (400 MHz, DMSO, 90° C.) δ 7.6-7.2 (m, 8H), 6.93 (d, 1H), 6.76 (d, 1H), 4.91 (dd, 1H), 4.20-4.03 (m, 4H), 3.40-2.90 (m, 6H). 7 exchangeable protons not seen at elevated temperature.

EXAMPLE 61

4-Hydroxy-7-{1R-hydroxy-2-[2-(3-{[(pyridin-2-ylmethyl)-amino]-methyl}-phenyl)-ethylamino]-ethyl}-3H-benzothiazol-2-one bis-hydrochloride salt

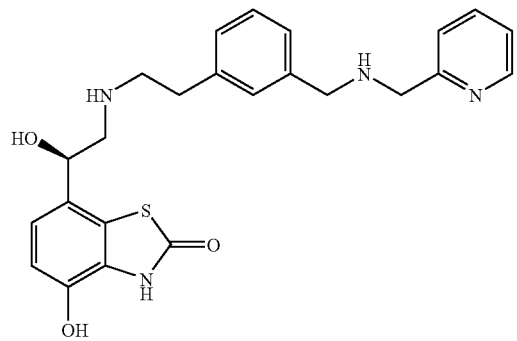

a) [3-(2-Hydroxy-ethyl)-benzyl]-pyridin-2-ylmethyl-carbamic acid tert-butyl ester Prepared from (3-formyl-phenyl)-acetic acid ethyl ester (2.0 g) and (2-aminomethyl)pyridine (1.8 g) using the method of Example 60 (step a) to give the subtitle compound (500 mg).

$^1$H NMR (400 MHz, CDCl$_3$) δ 8.43-8.40 (m, 1H), 7.60-7.55 (m, 1H), 7.30-6.95 (m, 6H), 4.55-4.45 (m, 2H), 4.45-4.35 (m, 2H), 3.80-3.70 (m, 2H), 2.77 (t, 2H), 1.50-1.30 (m 9H)

b) 4-Hydroxy-7-{1R-hydroxy-2-[2-(3-{[(pyridin-2-ylmethyl)-amino]-methyl}-phenyl)-ethylamino]-ethyl}-3H-benzothiazol-2-one bis-hydrochloride salt Prepared from [3-(2-hydroxy-ethyl)-benzyl]-pyridin-2-ylmethyl-carbamic acid tert-butyl ester (100 mg) and 7-(2-amino-1R-hydroxy-ethyl)-4-hydroxy-3H-benzothiazol-2-one hydrochloride (60 mg) using the method of Example 3

(step b). Purification by preparative HPLC yielded the title compound as the trifluoroacetate salt. The trifluoroacetate salt was dissolved in acetonitrile (0.5 mL). 2M HCl in diethyl ether (1 mL) was added and the title compound precipitated as the dihydrochloride salt (25 mg).

m/z 451 (M+H)+

$^1$H NMR (400 MHz, DMSO, 90° C.) δ 11.37 (br s, 1H), 9.19 (br s, 1H), 8.88 (br s, 1H), 8.61 (d, 1H), 7.86 (dt, 1H), 7.52 (d, 1H), 7.47 (s, 1H), 7.45-7.35 (m, 3H), 7.30 (d, 1H), 6.94 (d, 1H), 6.77 (d, 1H), 5.00 (dd, 1H), 4.27 (s, 2H), 4.22 (s, 2H), 3.30-3.20 (m, 2H), 3.15-3.00 (m, 4H). 4 exchangeable protons not seen at elevated temperature.

EXAMPLE 62

4-Hydroxy-7-[1R-hydroxy-2-(2-{4-[(2-methoxy-benzylamino)-methyl]-phenyl}-ethylamino)-ethyl]-3H-benzothiazol-2-one bis-hydrochloride salt

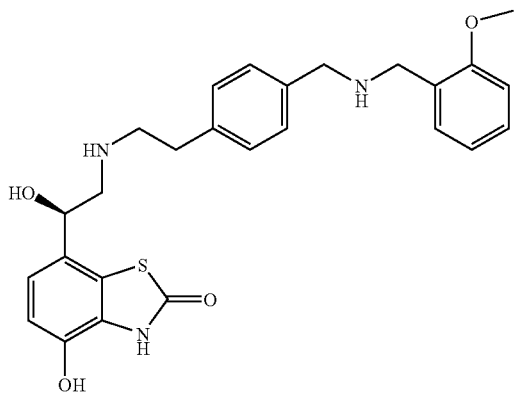

a) [4-(2-Hydroxy-ethyl)-benzyl]-(2-methoxy-benzyl)-carbamic acid tert-butyl ester Prepared from (4-formyl-phenyl)-acetic acid methyl ester (530 mg) and (2-methoxybenzyl)amine (610 mg) using the method of Example 60 (step a) to give the subtitle compound (550 mg).

$^1$H NMR (300 MHz, CDCl$_3$) δ 7.30-7.10 (m, 6H), 6.93 (t, 1H), 6.84 (d, 1H), 4.50-4.30 (m, 4H), 3.90-3.80 (m, 2H), 3.78 (s, 3H), 2.90-2.80 (m, 2H), 1.47 (s, 9H).

b) 4-Hydroxy-7-[1R-hydroxy-2-(2-{4-[(2-methoxy-benzylamino)-methyl]-phenyl}-ethylamino)-ethyl]-3H-benzothiazol-2-one bis-hydrochloride salt Prepared from [4-(2-hydroxy-ethyl)-benzyl]-(2-methoxy-benzyl)-carbamic acid tert-butyl ester (320 g) and 7-(2-amino-1R-hydroxy-ethyl)-4-hydroxy-3H-benzothiazol-2-one hydrochloride (150 mg) using the method of Example 3 (step b). Purification by preparative HPLC yielded the title compound as the trifluoroacetate salt. The trifluoroacetate salt was dissolved in acetonitrile (0.5 mL). 2M HCl in diethyl ether (1 mL) was added and the title compound precipitated as the dihydrochloride salt (110 mg).

m/z 480 (M+H)+

$^1$H NMR (400 MHz, DMSO) δ 11.69 (s, 1H), 10.22 (br s, 1H), 9.36 (br s, 1H), 9.29 (br s, 1H), 7.51 (d, 2H), 7.41 (t, 2H), 7.31 (d, 2H), 7.06 (d, 1H), 6.99 (t, 1H), 6.93 (d, 1H), 6.79 (d, 1H), 5.05-4.95 (m, 1H), 4.20-4.10 (m, 2H), 4.10-4.0 (m, 2H), 3.79 (s, 3H), 3.25-2.90 (m, 6H). 3 exchangeable protons not seen.

EXAMPLE 63

4-Hydroxy-7-[1R-hydroxy-2-(2-{3-[(3-propoxy-propylamino)-methyl]-phenyl}-ethylamino)-ethyl]-3H-benzothiazol-2-one bis-hydrochloride salt

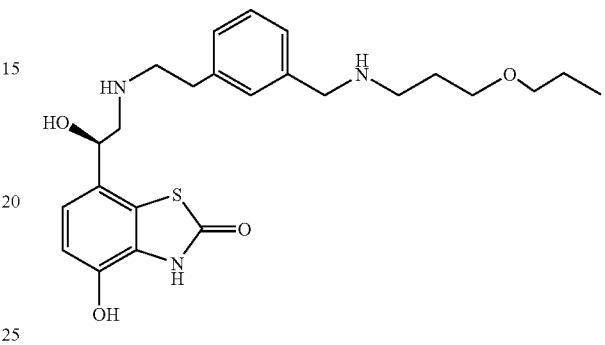

a) [3-(2-Hydroxy-ethyl)-benzyl]-(3-propoxy-propyl)-carbamic acid tert-butyl ester A mixture (3-formyl-phenyl)-acetic acid ethyl ester (530 mg), (3-propoxypropyl)amine (1.5 g) and acetic acid (0.17 mL) in methanol (15 mL) was stirred at room temperature for 15 minutes. Sodium triacetoxyborohydride (950 mg) was added. After 5 hours, the reaction mixture was neutralised with aqueous ammonia (0.880) and the solution evaporated to dryness. The residue was diluted with toluene and the mixture evaporated. The resulting gum was dissolved in methanol and applied to a SCX cartridge (70 g, varian). The cartridge was eluted with methanol (250 mL) and then 20% ammonia in methanol to collect the reductive amination product. Toluene was added and the solution was evaporated. The crude product was dissolved in dichloromethane (20 mL) and di-tert-butyl dicarbonate (1.8 g) added. After 16 hours, the solution was evaporated, the residue dissolved in ethanol (30 mL), anhydrous calcium chloride (11.0 g) added, followed by portionwise addition of sodium borohydride (700 mg). After 16 hours, the reaction mixture was quenched with 2M aqueous potassium carbonate (20 mL), filtered and evaporated. The residue was partitioned between ethyl acetate and brine. The organic solution was dried over sodium sulphate, filtered and evaporated. Purification was by silica gel chromatography eluting with ethyl acetate:dichloromethane 1:4 to give the subtitle compound (300 mg).

$^1$H NMR (400 MHz, CDCl$_3$) δ 7.35-7.30 (m, 1H), 7.20-7.04 (m, 3H), 4.50-4.40 (m, 2H), 3.84 (q, 2H), 3.45-3.35 (m, 2H), 3.32 (t, 2H), 3.30-3.20 (m, 2H), 2.85 (t, 2H), 1.90-1.70 (m, 2H), 1.65-1.50 (m, 2H), 1.50-1.40 (br s, 9H), 0.90 (t, 3H).

b) 4-Hydroxy-7-[1R-hydroxy-2-(2-{3-[(3-propoxy-propylamino)-methyl]-phenyl}-ethylamino)-ethyl]-3H-benzothiazol-2-one bis-hydrochloride salt Prepared from [3-(2-hydroxy-ethyl)-benzyl]-(3-propoxy-propyl)-carbamic acid tert-butyl ester (200 mg) and 7-(2-amino-1R-hydroxy-ethyl)-4-hydroxy-3H-benzothiazol-2-one hydrochloride (150 mg) using the method of Example 3

(step b). Purification by preparative HPLC yielded the title compound as the trifluoroacetate salt. The trifluoroacetate salt was dissolved in acetonitrile (0.5 mL). 2M HCl in diethyl ether (1 mL) was added and the title compound precipitated as the dihydrochloride salt (110 mg).

m/z 460 (M+H)$^+$ $^1$H NMR (400 MHz, DMSO) δ 11.69 (s, 1H) 10.22 (br s, 1H), 9.40-9.20 (m, 2H), 9.0-8.9 (m, 1H), 7.48 (s, 1H), 7.45-7.35 (m, 2H), 7.29 (d, 1H), 6.93 (d, 1H), 6.79 (d, 1H), 5.05-4.95 (m, 1H), 4.20-4.10 (m, 2H), 4.05-3.60 (m, 4H), 3.20-3.10 (m, 2H), 3.10-2.98 (m, 4H), 3.0-2.95 (m, 2H), 2.0-1.90 (m, 2H), 1.50-1.40 (m, 2H), 0.84 (t, 3H). 2 exchangeable protons not seen.

EXAMPLE 64

4-Hydroxy-7-[1R-hydroxy-2-(2-{3-[(3-isopropoxy-propylamino)-methyl]-phenyl}-ethylamino)-ethyl]-3H-benzothiazol-2-one bis-hydrochloride salt

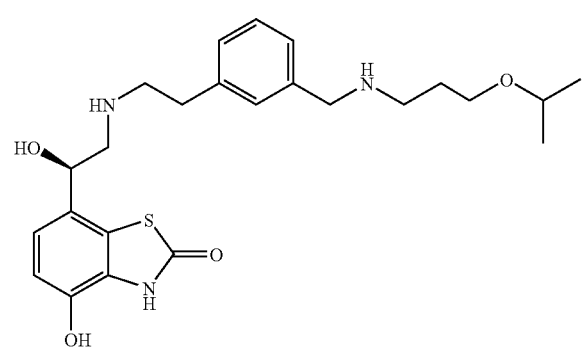

a) [3-(2-Hydroxy-ethyl)-benzyl]-(3-isopropoxy-propyl)-carbamic acid tert-butyl ester Prepared from (3-formyl-phenyl)-acetic acid ethyl ester (530 mg) and (3-isopropoxypropyl)amine (1.5 g) using the method of Example 63 (step a) to give the subtitle compound (300 mg).

$^1$H NMR (400 MHz, CDCl$_3$) δ 7.30-7.22 (m, 2), 7.15-7.05 (m, 2H), 4.50-4.40 (m, 2H), 3.85 (q, 2H), 3.51 (heptet, 1H), 3.42-3.35 (m, 2H), 3.40-3.18 (m, 2H), 2.85 (t, 2H), 1.80-1.70 (m, 2H), 1.55-1.36 (m, 9H), 1.12 (d, 6H).

b) 4-Hydroxy-7-[1R-hydroxy-2-(2-{3-[(3-isopropoxy-propylamino)-methyl]-phenyl}-ethylamino)-ethyl]-3H-benzothiazol-2-one bis-hydrochloride salt Prepared from [3-(2-hydroxy-ethyl)-benzyl]-(3-isopropoxy-propyl)-carbamic acid tert-butyl ester (200 mg) and 7-(2-amino-1R-hydroxy-ethyl)-4-hydroxy-3H-benzothiazol-2-one hydrochloride (150 mg) using the method of Example 3 (step b). Purification by preparative HPLC yielded the title compound as the trifluoroacetate salt. The trifluoroacetate salt was dissolved in acetonitrile (0.5 mL). Hydrogen chloride in diethyl ether (1 mL. 2M) was added and the title compound precipitated as the bis-hydrochloride salt (110 mg).

m/z 460 (M+H)$^+$ $^1$H NMR (400 MHz, DMSO) δ 11.38 (br s, 1H), 9.30-9.00 (m, 3H), 7.51 (s, 1H), 7.50-7.30 (m, 3H), 6.95 (d, 1H), 6.77 (d, 1H), 5.02 (dd, 1H), 4.1 (br s, 2H), 3.55 (m, 1H), 3.50-3.40 (m, 2H), 3.30-3.20 (m, 2H), 3.15-3.05 (m, 4H), 3.0-2.90 (m, 2H), 1.95-1.85 (m, 2H), 1.05 (d, 6H). 3 exchangeable protons not seen.

EXAMPLE 65

4-Hydroxy-7-[1R-hydroxy-2-(2-{3-[(3-methoxy-benzylamino)-methyl]-phenyl}-ethylamino)-ethyl]-3H-benzothiazol-2-one bis-hydrochloride salt

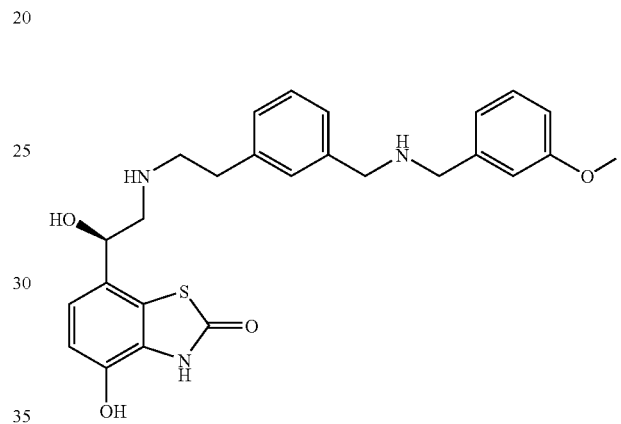

a) [3-(2-Hydroxy-ethyl)-benzyl]-(3-methoxy-benzyl)-carbamic acid tert-butyl ester Prepared from (3-formyl-phenyl)-acetic acid ethyl ester (530 mg) and (3-methoxybenzyl)amine (610 mg) using the method of Example 60 (step a) to give the subtitle compound (500 mg).

$^1$H NMR (300 MHz, CDCl$_3$) δ 7.30-7.00 (m, 5H), 6.90-6.70 (m, 3H), 4.50-4.30 (m, 4H), 3.84 (q, 2H), 3.78 (s, 3H), 2.84 (t, 2H), 1.49 (s, 9H).

b) 4-Hydroxy-7-[1R-hydroxy-2-(2-{3-[(3-methoxy-benzylamino)-methyl]-phenyl}-ethylamino)-ethyl]-3H-benzothiazol-2-one bis-hydrochloride salt Prepared from [3-(2-hydroxy-ethyl)-benzyl]-(3-methoxy-benzyl)-carbamic acid tert-butyl ester (320 mg) and 7-(2-amino-1-R-hydroxy-ethyl)-4-hydroxy-3H-benzothiazol-2-one hydrochloride (150 mg) using the method of Example 3 (step b). Purification by preparative HPLC yielded the title compound as the trifluoroacetate salt. The trifluoroacetate salt was dissolved in acetonitrile (0.5 mL). 2M HCl in diethyl ether (1 mL) was added and the title compound precipitated as the dihydrochloride salt (55 mg).

m/z 480 (M+H)⁺

¹H NMR (300 MHz, DMSO) δ 11.70 (s, 1H), 10.22 (s, 1H), 9.69 (br s, 2H), 9.28 (br s, 1H), 8.91 (br s, 1H), 7.50-7.30 (m, 5H), 7.22 (s, 1H), 7.09 (d, 1H), 7.0-6.90 (m, 2H), 6.79 (d, 1H), 6.46 (br s, 1H), 5.05-4.95 (m, 1H), 4.15-4.07 (m, 4H), 3.78 (s, 3H), 3.22-3.15 (m, 2H), 3.15-2.95 (m, 4H).

EXAMPLE 66

7-[2-(2-{3-[(2-Ethoxy-benzylamino)-methyl]-phenyl}-ethylamino)-1R-hydroxy-ethyl]-4-hydroxy-3H-benzothiazol-2-one bis-hydrochloride salt

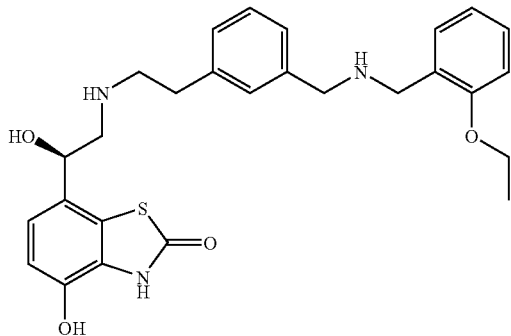

a) (2-Ethoxy-benzyl)-[3-(2-hydroxy-ethyl)-benzyl]-carbamic acid tert-butyl ester Prepared from (3-formyl-phenyl)-acetic acid ethyl ester (530 mg) and (2-ethoxybenzyl)amine (610 mg) using the method of Example 60 (step a) to give the subtitle compound (500 mg).

¹H NMR (300 MHz, CDCl₃) δ 7.30-7.00 (m, 6H), 6.92 (t, 1H), 6.82 (d, 1H), 4.60-4.30 (m, 4H), 3.99 (q, 2H), 3.90-3.80 (m, 2H), 2.84 (t, 2H), 1.46 (s, 9H), 1.36 (t, 3H).

b) 7-[2-(2-{3-[(2-Ethoxy-benzylamino)-methyl]-phenyl}-ethylamino)-1-R-hydroxy-ethyl]-4-hydroxy-3H-benzothiazol-2-one bis-hydrochloride salt Prepared from (2-ethoxy-benzyl)-[3-(2-hydroxy-ethyl)-benzyl]-carbamic acid tert-butyl ester (200 mg) and 7-(2-amino-1R-hydroxy-ethyl)-4-hydroxy-3H-benzothiazol-2-one hydrochloride (150 mg) using the method of Example 3 (step b). Purification by preparative HPLC yielded the title compound as the trifluoroacetate salt. The trifluoroacetate salt was is dissolved in acetonitrile (0.5 mL). 2M HCl in diethyl ether (1 mL) was added and the title compound precipitated as the dihydrochloride salt (130 mg).

m/z 494 (M+H)⁺

¹H NMR (400 MHz, DMSO) δ 11.70 (s, 1H), 10.23 (br s, 1H), 9.40-9.20 (br s, 2H), 9.0-8.95 (br s, 1H), 7.50-7.30 (m, 6H), 7.04 (d, 1H), 6.98 (t, 1H), 6.93 (d, 1H), 6.79 (d, 1H), 5.05-4.95 (m, 1H), 4.30-3.90 (m, 6H), 3.22-3.12 (m, 2H), 3.10-2.95 (m, 4H), 1.29 (t, 3H).

EXAMPLE 67

4-Hydroxy-7-[1-R-hydroxy-2-(2-{3-[(4-methoxy-benzylamino)-methyl]-phenyl}-ethylamino)-ethyl]-3H-benzothiazol-2-one bis-hydrochloride salt

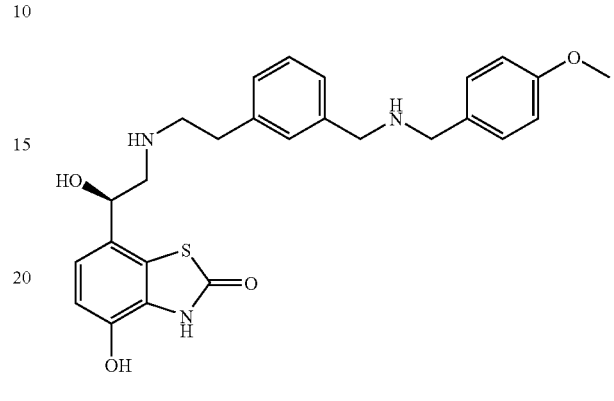

a) [3-(2-Hydroxy-ethyl)-benzyl]-(4-methoxy-benzyl)-carbamic acid tert-butyl ester A mixture of 3-[2-(tetrahydro-2H-pyran-2-yloxy)ethyl] benzaldehyde (Example 50, step a, 400 mg), (4-methoxybenzyl)amine (350 mg), acetic acid (100 mg) and sodium triacetoxyborohydride (600 mg) in methanol (7 mL) was stirred at room temperature. After 16 hours, the reaction mixture was applied directly to a SCX cartridge (70 g, varian) eluting with methanol (250 mL) then 2M ammonia in methanol to collect the 2-(3-{[(4-methoxybenzyl)amino]methyl}phenyl)ethanol (530 mg). The solution was evaporated and the resulting gum dissolved in dry dichloromethane (10 mL) and di-tert-butyl dicarbonate (450 mg) added. After 1 hour, the reaction mixture was applied to a silica gel column eluting with ethyl acetate:dichloromethane 1:6 to give the subtitle product (350 mg).

¹H NMR (400 MHz, CDCl₃) δ 7.35-7.25 (m, 2H), 7.22-7.00 (m, 4H), 6.84 (d, 2H), 4.50-4.30 (m, 4H), 3.85 (q, 2H), 3.80 (s, 3H), 2.85 (t, 2H), 1.49 (s, 9H).

b) 4-Hydroxy-7-[1R-hydroxy-2-(2-{3-[(4-methoxy-benzylamino)-methyl]-phenyl}-ethylamino)-ethyl]-3H-benzothiazol-2-one bis-hydrochloride salt Prepared from [3-(2-hydroxy-ethyl)-benzyl]-(4-methoxy-benzyl)-carbamic acid tert-butyl ester (200 mg) and 7-(2-amino-1R-hydroxy-ethyl)-4-hydroxy-3H-benzothiazol-2-one hydrochloride (150 mg) using the method of Example 3 (step b). Purification by preparative HPLC yielded the title compound as the trifluoroacetate salt. The trifluoroacetate salt was dissolved in acetonitrile (0.5 mL). 2M HCl in diethyl ether (1 mL) was added and the title compound precipitated as the dihydrochloride salt (55 mg).

m/z 480 (M+H)⁺

¹H NMR (400 MHz, DMSO) δ 11.70 (s, 1H), 10.23 (br s, 1H), 9.60 (br s, 2H), 9.34 (br s, 1H), 8.9 (br s, 1H), 7.50-7.30 (m, 6H), 6.98 (d, 2H), 6.92 (d, 1H), 6.79 (d, 1H), 6.45 (br s,

1H), 5.05-4.95 (m, 1H), 4.05-4.00 (m, 4H), 3.77 (s, 3H), 3.20-3.12 (m, 2H), 3.05-2.95 (m, 4H).

EXAMPLE 68

4-Hydroxy-7-{1R-hydroxy-2-[2-(3-{[(2-methoxybenzyl)-methyl-amino]-methyl}-phenyl)-ethylamino]-ethyl}-3H-benzothiazol-2-one bis-hydrochloride salt

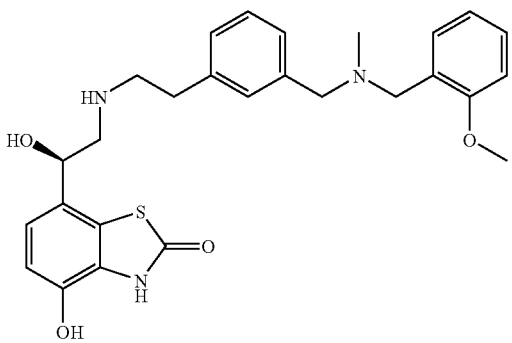

a) 2-(3-{[(2-Methoxybenzyl)(methyl)amino]methyl}phenyl)ethanol

Prepared from 3-[2-(tetrahydro-2H-pyran-2-yloxy)ethyl]benzaldehyde (Example 50, step a, 530 mg) (2-methoxybenzyl)methylamine (610 mg) using the method of Example 67 (step a) to give the subtitle compound (500 mg) and was used directly in the next step without further purification.

m/z 286 (M+H)$^+$ b) N-Boranyl-2-(3-{[(2-methoxybenzyl)(methyl)ammonium]methyl}phenyl)ethanol 2-(3-{[(2-Methoxybenzyl)(methyl)amino]methyl}phenyl)ethanol (500 mg) was dissolved in dry tetrahydrofuran (20 mL) and cooled in an ice bath. Borane-dimethylsulphide complex (2.5 mL of 2M solution in tetrahydrofuran) was added dropwise. After 10 minutes, the reaction was quenched carefully with methanol then the solution was evaporated to dryness. Purification was by silica gel chromatography eluting with ethyl acetate:iso-hexanes 1:2 to give the subtitle compound (300 mg) and was used directly in the next step without further purification.

m/z 286 (M−BH$_3$+H)$^+$ c) 4-Hydroxy-7-{1-hydroxy-2-[2-(3-{[(2-methoxybenzyl)-methyl-amino]-methyl}-phenyl)-ethylamino]-ethyl}-3H-benzothiazol-2-one bis-hydrochloride salt Prepared from N-boranyl-2-(3-{[(2-methoxybenzyl)(methyl)ammonium]methyl}phenyl)-ethanol (300 mg) and 7-(2-amino-1R-hydroxy-ethyl)-4-hydroxy-3H-benzothiazol-2-one hydrochloride (150 mg) using the method of Example 3 (step b). When the reaction was complete the solution was evaporated to dryness, dissolved in tetrahydrofuran (5 mL) and ethylene diamine (0.4 mL). The mixture was heated to 70° C. for 1 minute, cooled and evaporated. The gum was dissolved in iso-propanol and applied to a SCX cartridge (70 g, varian) eluting first with iso-propanol (250 mL) then iso-propanol:20% 0.880 ammonia to collect the product. Purification by preparative HPLC yielded the product as the trifluoroacetate salt. The trifluoroacetate salt was dissolved in acetonitrile (0.5 mL). 2M HCl in diethyl ether (1 mL) was added and the title compound precipitated as the dihydrochloride salt (25 mg).

m/z 494 (M+H)$^+$ $^1$H NMR (400 MHz, DMSO) δ 11.70 (s, 1H), 10.23 (s, 1H), 10.08 (br s, 1H), 9.35 (br s, 1H), 8.93 (br s, 1H), 7.55-7.40 (m, 5H), 7.35 (d, 1H), 7.09 (d, 1H), 7.02 (t, 1H), 6.92 (d, 1H), 6.79 (d, 1H), 6.46 (br s, 1H), 5.05-4.95 (m, 1H), 4.38-4.25 (m, 3H), 4.18-4.08 (m, 1H), 3.78 (s, 3H), 3.22-3.18 (m, 2H), 3.15-3.0 (m, 4H), 2.57 (d, 3H).

EXAMPLE 69

4-Hydroxy-7-[1R-hydroxy-2-(2-{3-[(2-methoxybenzylamino)-methyl]-phenyl}-ethylamino)-ethyl]-3H-benzothiazol-2-one bis-hydrochloride salt

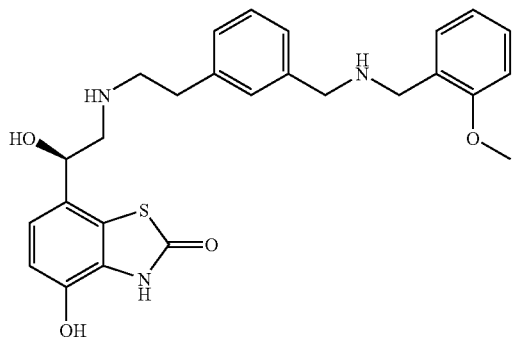

A solution of 4-hydroxy-7-[1-hydroxy-2-(2-{3-[(2-methoxy-benzylamino)-methyl]-phenyl}-ethylamino)-ethyl]-3H-benzothiazol-2-one (Example 50, step e) bis-trifluoroacetate (40 mg) in anhydrous acetonitrile (2 mL) was treated with a 4 molar solution of hydrogen chloride in diethyl ether (2 mL). A solid crashed out and the supernatant solution was removed with a Pasteur pipette, the solid was washed with acetonitrile followed by diethyl ether and dried under high vacuum to yield a white solid (40 mg).

m/z 480 (M+H)$^+$ (Agilent multimode)

$^1$H NMR (400 MHz, DMSO) δ 11.71 (s, 1H), 10.25 (s, 1H), 9.48 (s, 3H), 8.97 (s, 1H), 7.46-7.38 (m, 5H), 7.30 (d, 1H), 7.07 (d, 1H), 6.99 (t, 1H), 6.93 (d, 1H), 6.80 (d, 1H), 6.47 (d,

1H), 5.04-5.02 (m, 1H), 4.12 (s, 2H), 4.04 (s, 2H), 3.80 (s, 3H), 3.21-3.17 (m, 2H), 3.06-3.02 (m, 4H).

EXAMPLE 70

4-Hydroxy-7-[1R-hydroxy-2-(2-{3-[(2-methoxy-benzylamino)-methyl]-phenyl}-ethylamino)-ethyl]-3H-benzothiazol-2-one 1-tartrate salt

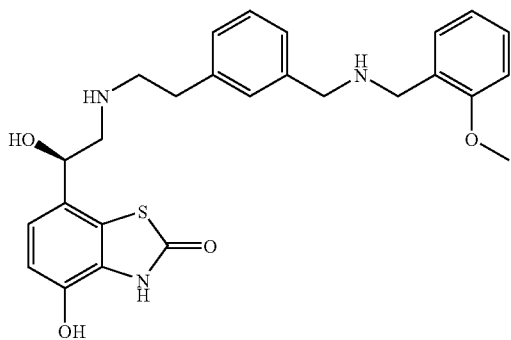

To a solution of 4-hydroxy-7-[1R-hydroxy-2-(2-{3-[(2-methoxy-benzylamino)-methyl]-phenyl}-ethylamino)-ethyl]-3H-benzothiazol-2-one (Example 50, step e, 50 mg) in water (0.25 mL) and ethanol (2 mL) at 100° C. was added dropwise a solution of 1-tartaric acid (16 mg) in water (0.25 mL) and the resulting mixture allowed to cool slowly to room temperature under nitrogen with slow stirring. The solid was collected and washed with ethanol then ether twice. The solid was dried at 40° C. under high vacuum overnight to give the title compound (47 mg).

m/z 480 (M+H)+ (Agilent multimode)
$^1$H NMR (400 MHz, DMSO) δ 7.37-7.32 (m, 2H), 7.31-7.20 (m, 5H), 7.13 (d, 1H), 7.00-6.87 (m, 3H), 6.74 (d, 1H), 4.79 (t, 1H), 3.92 (s, 2H), 3.79 (s, 2H), 3.77 (s, 3H), 3.76 (s, 2H), 3.05-2.97 (m, 2H), 2.94-2.89 (m, 2H), 2.88-2.79 (m, 2H). 9 exchangeables not seen.

EXAMPLE 71

7-{2-[2-(3-Azepan-1-ylmethyl-phenyl)-ethylamino]-1R-hydroxy-ethyl}-4-hydroxy-3H-benzothiazol-2-one bis-hydrochloride salt-

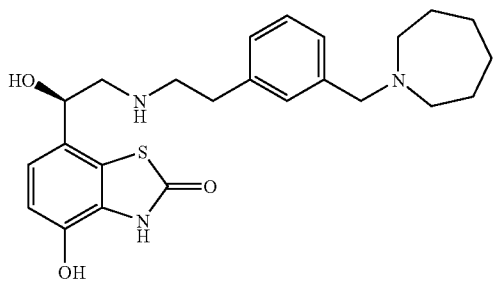

a) (2-{3-[2-(azepan-1-yl-N)ethyl]phenyl}ethanol) (trihydrido)boron (3-Formyl-phenyl)-acetic acid methyl ester (Example 1, step 1, 0.54 g), acetic acid (0.18 mL) and azepane (1 mL) were combined in methanol (10 mL), sodium triacetoxyborohydride (950 mg) was then added. After 24 hours, the solvent was evaporated. The resultant residue was loaded onto a conditioned SCX cartridge (50 g, Varian) and washed with methanol (250 mL), then eluted with methanolic ammonia solution (2M, 150 mL). The elution fraction was evaporated and the residue was dissolved in ethanol (10 mL). Calcium chloride anhydrous (1.0 g) was added followed by sodium borohydride (680 mg) and the resulting mixture stirred overnight. An aqueous potassium carbonate solution (2M, 50 mL) was added and the mixture filtered. The filtrate was extracted with ethyl acetate (3×50 mL) and the combined organics washed with water (50 mL), brine (50 mL), dried (sodium sulfate) and evaporated. The residue was redissolved in tetrahydrofuran (10 mL) and cooled to 0° C., under nitrogen. Borane-methyl sulfide complex (2M solution in tetrahydrofuran, 4.5 mL) was added and the resulting mixture stirred for 5 min. The tetrahydrofuran was evaporated and the residue purified on silica, eluting with diethyl ether: iso-hexane [0:1 to 1:1] to give subtitle product, as an oil 550 mg.

$^1$H NMR (400 MHz, CDCl$_3$) δ 7.35 (s, 1H), 7.32-7.23 (m, 3H), 3.91 (s, 2H), 3.87 (t, 2H), 3.07 (dd, 2H), 2.96 (dd, 2H), 2.89 (t, 2H), 1.93-1.80 (m, 2H), 1.63-1.42 (m, 6H). +1 exchangeable proton not seen.

b) 7-{2-[2-(3-Azepan-1-ylmethyl-phenyl)-ethylamino]1R-hydroxy-ethyl}-4-hydroxy-3H-benzothiazol-2-one bis-hydrochloride salt Dess-Martin periodinane (194 mg) was added to a solution of (2-{3-[2-(azepan-1-yl-κN)ethyl]phenyl}ethanol)(trihydrido)boron (140 mg) in dichloromethane (15 mL). After 60 minutes, the reaction mixture was poured onto a mixture of: sodium thiosulfate (15 g); water (15 mL); saturated aqueous sodium bicarbonate (15 mL) and ethyl acetate (15 mL). Stirred vigorously for 10 minutes. The mixture was separated and the aqueous extracted with ethyl acetate (2×15 mL). The combined organics were washed with water (20 mL), brine (20 mL), dried (sodium sulfate) and evaporated. The residue was dissolved in methanol (5 mL), then 7-(2-amino-1-hydroxy-ethyl)-4-hydroxy-3H-benzothiazol-2-one hydrochloride (100 mg) and acetic acid (20 µL) were added. After 1 hour, sodium cyanoborohydride (36 mg) was added. After 18 hours, the reaction mixture was concentrated under vacuum. The residue was loaded onto conditioned Tosic-65A resin (3.3 g, Argonaut) in acetonitrile/propan-2-ol [1:1]. The resin was washed with acetonitrile:propan-2-ol [1:1] (50 mL) and eluted with propan-2-ol:0.880 ammonia solution [4:1] (100 mL). The elution fraction was evaporated, and the residue redissolved in tetrahydrofuran (10 mL) ethylenediamine (0.23 mL) was added and the mixture was refluxed for 5 min then concentrated. The residue was azeotroped with toluene twice, treated with trifluoroacetic acid and evaporated. Purification by HPLC method B. The purified material was dissolved in acetonitrile (2 mL), treated with an excess of 2M ethereal hydrogen chloride solution and evaporated and trituration with diethyl ether gave the title product, as a white solid (51 mg)

m/z 442 (M+H)+ (Agilent multimode)
1H NMR (400 MHz, DMSO, 90° C.) δ 11.35 (s, 1H), 7.60 (s, 1H), 7.48 (d, 1H), 7.39 (t, 1H), 7.33 (d, 1H), 6.94 (d, 1H), 6.77 (d, 1H), 5.04-4.95 (m, 1H), 4.26 (s, 2H), 3.36-2.99 (m, 10H), 1.84 (s, 4H), 1.63 (s, 4H). 5 exchangeable protons not seen at elevated temperature.

EXAMPLE 72

4-Hydroxy-7-{1R-hydroxy-2-[2-(3-morpholin-4-ylmethyl-phenyl)-ethylamino]-ethyl}-3H-benzothiazol-2-one bis-hydrochloride salt

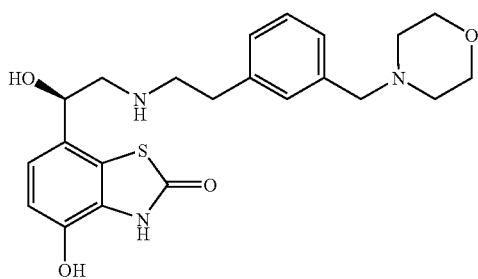

a) Trihydrido(2-{3-[2-(morpholin-4-yl-κN)ethyl]phenyl}ethanol)boron (3-Formyl-phenyl)-acetic acid methyl ester (Example 1, step a, 540 mg), acetic acid (0.18 mL) and morpholine (0.29 mL) were combined in methanol (10 mL), sodium triacetoxyborohydride (950 mg) was then added. After 24 hours, the solvent was evaporated. The resultant residue was loaded onto a conditioned SCX cartridge (50 g, Varian) and washed with methanol (250 mL), then eluted with methanolic ammonia solution (2M, 150 mL). The elution fraction was evaporated and the residue was dissolved in ethanol (10 mL). Calcium chloride anhydrous (1.0 g) was added followed by sodium borohydride (680 mg) and the resulting mixture stirred overnight. An aqueous potassium carbonate solution (2M, 50 mL) was added and the mixture filtered. The filtrate was extracted with ethyl acetate (3×50 mL) and the combined organics washed with water (50 mL), brine (50 mL), dried (sodium sulfate) and evaporated. The residue was redissolved in tetrahydrofuran (10 mL) and cooled to 0° C., under nitrogen. Borane-methyl sulfide complex (2M solution in tetrahydrofuran, 2.25 mL) was added and the resulting mixture stirred for 5 minutes. The tetrahydrofuran was evaporated and the residue purified on silica, eluting with ethyl acetate: isohexane [0:1 to 1:1] to give subtitle product, as an oil 350 mg.

$^1$H NMR (400 MHz, CDCl$_3$) δ 7.38-7.10 (m, 4H), 4.40-4.25 (m, 2H), 4.10-4.01 (m, 2H), 3.98-3.82 (m, 2H), 3.75-3.57 (m, 2H), 2.94-2.68 (m, 4H), 2.50-2.38 (m, 2H). +4 exchangeable protons not seen.

b) 4-Hydroxy-7-{1R-hydroxy-2-[2-(3-morpholin-4-ylmethyl-phenyl)-ethylamino]-ethyl}-3H-benzothiazol-2-one bis-hydrochloride salt Dess-Martin periodinane (168 mg) was added to a solution of trihydrido(2-{3-[2-(morpholin-4-yl-κN)ethyl]phenyl}ethanol)boron (90 mg) in dichloromethane (10 mL). After 60 minutes, the reaction mixture was poured onto a mixture of: sodium thiosulfate (10 g); water (10 mL); saturated aqueous sodium bicarbonate (10 mL) and ethyl acetate (20 mL). Stirred vigorously for 10 minutes. The mixture was separated and the aqueous extracted with ethyl acetate (20 mL). The combined organics were washed with water (20 mL) and brine (20 mL), dried (magnesium sulfate) and evaporated. The residue was dissolved in methanol (5 mL), then 7-(2-amino-1R-hydroxy-ethyl)-4-hydroxy-3H-benzothiazol-2-one hydrochloride (110 mg) and acetic acid (20 μL) were added. After 1 hour, sodium cyanoborohydride (31 mg) was added. After 18 hours, the reaction mixture was concentrated under vacuum. The residue was loaded onto conditioned Tosic-65A resin (3.3 g, Argonaut) in acetonitrile:propan-2-ol [1:1]. The resin was washed with acetonitrile:propan-2-ol [1:1] (50 mL) and eluted with propan-2-ol:0.880 ammonia solution [4:1] (100 mL). The elution fraction was evaporated, and the residue redissolved in tetrahydrofuran (10 mL) ethylenediamine (0.23 mL) was added and the mixture was refluxed for 5 minutes then concentrated. The residue was azeotroped with toluene twice, treated with trifluoroacetic acid and evaporated. Purification by HPLC method B. The purified material was dissolved in acetonitrile (2 mL), treated with an excess of 2M ethereal hydrogen chloride solution and evaporated and trituration with diethyl ether gave the title product, as a white solid (51 mg).

m/z 430 (M+H)$^+$ (Agilent multimode)

1H NMR (300 MHz, DMSO, 90° C.) δ 7.57 (s, 1H), 7.47-7.28 (m, 3H), 6.94 (d, 1H), 6.77 (d, 1H), 11.33 (s, 1H), 5.00 (dd, 1H), 4.26-4.13 (m, 2H), 3.88-3.81 (m, 4H), 3.32-2.98 (m, 10H). +5 exchangeable protons not seen.

EXAMPLE 73

4-Hydroxy-7-{1R-hydroxy-2-[2-(3-piperidin-1-ylmethyl-phenyl)-ethylamino]-ethyl}-3H-benzothiazol-2-one bis-hydrochloride

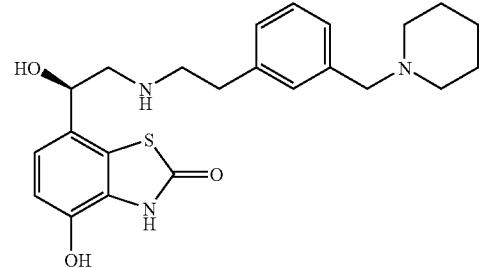

To a solution of boron, trihydro[3-[(1-piperidinyl-κN)methyl]benzeneethanol]- (Example 32, step a, 0.21 g) in dry dichloromethane (15 mL) was added Dess-Martin periodinane (0.45 g) and the resulting mixture was stirred for 1 hour under nitrogen. Saturated sodium thiosulfate solution (15 mL), saturated sodium bicarbonate (15 mL) and ethyl acetate (15 ml) were added and the resulting mixture stirred for 10 minutes. The organic layer was separated and the aqueous extracted with ethyl acetate (2×15 mL). The combined organic phases were washed with water (20 mL) and brine (20 mL), then dried over sodium sulfate, filtered and evaporated. The crude aldehyde was redissolved in methanol (20 ml) and 7-(2-amino-1R-hydroxy-ethyl)-4-hydroxy-3H-benzothiazol-2-one hydrochloride (0.20 g) was added followed by acetic acid (0.045 ml). The resulting mixture was stirred for 5 minutes then sodium cyanoborohydride (0.072 g) was added and the resulting mixture stirred overnight. The reaction was quenched with 0.880 ammonia (few drops) and evaporated to dryness. The residue was redissolved in iso-propyl alcohol and added to Tosic-65A resin (pre-wetted with iso-propyl alcohol) the resin was washed with iso-propyl alcohol (100 mL), eluted with 4:1 iso-propyl alcohol:0.880 ammonia solution and the eluent evaporated. The residue was suspended in THF (10 mL) and ethylenediamine (0.51 ml) was added. The mixture was refluxed for 5 min and evaporated to dryness. The residue was azeotroped with toluene (×2) and treated with trifluoroacetic acid (5 mL). The mixture was evaporated to dryness and the purified by HPLC method B. The fractions were evaporated and redissolved in MeCN (10 mL), 2M HCl in ether solution (2 mL) was added and the solvent removed. The residue was triturated with ether to give the titled compound as a white solid (123 mg).

[M+H]$^+$428

H NMR (300 MHz, DMSO,) δ 11.70 (s, 1H), 10.63-10.48 (m, 1H), 10.31-10.16 (m, 1H), 9.29 (s, 1H), 8.92 (s, 1H), 7.53 (s, 1H), 7.49-7.30 (m, 3H), 6.93 (d, 1H), 6.79 (d, 1H), 6.57 (s, 1H), 5.05-4.93 (m, 1H), 4.22 (d, 2H), 3.29-3.20 (m, 4H), 3.10-2.98 (m, 4H), 2.88-2.76 (m, 2H), 1.82-1.70 (m, 4H), 1.37-1.27 (m, 2H)

EXAMPLE 74

4-Hydroxy-7-[1R-hydroxy-2-(2-{3-[(2-pyridin-2-yl-ethylamino)-methyl]-phenyl}-ethylamino)-ethyl]-3H-benzothiazol-2-one tris-hydrochloride

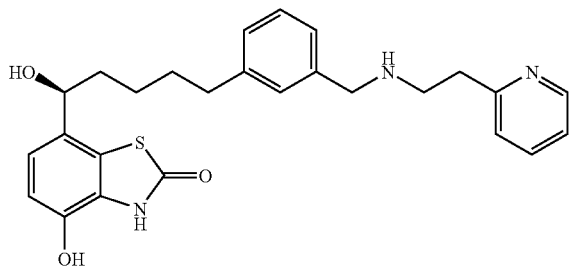

a) (2-Pyridin-2-yl-ethyl)-{3-[2-(tetrahydro-pyran-2-yloxy)-ethyl]-benzyl}-amine

To a solution of 3-[2-(tetrahydro-pyran-2-yloxy)-ethyl]-benzaldehyde (Example 50, step A, 6.1 g) and 2-(2-aminoethyl)pyridine (3.18 g, 3.1 ml) in toluene (150 mL) was added p-toluene sulfonic acid (100 mg). The reaction was heated at reflux in a Dean-Stark apparatus for couple of hours. Around 2 mL water were displaced. The mixture was cooled and washed with aqueous bicarbonate and concentrated in vacuo. The residue was taken up in ethanol (100 ml) and cooled. Sodium borohydride (1.0 g) was added slowly and the reaction left 1 hour to warm to room temperature. Water was added (100 mL) and ethanol removed by distillation. The reaction was partitioned between aqueous bicarbonate and ethyl acetate. The organic layers were dried over sodium sulfate and concentrated in vacuo to give yellow oil (6.5 g). The material was used in the next step without further purification.

$^1$H NMR (400 MHz, DMSO) δ 8.47-8.43 (m, 1H), 7.70-7.62 (m, 1H), 7.27-7.11 (m, 6H), 4.58-4.53 (m, 1H), 3.82-3.73 (m, 1H), 3.67 (s, 2H), 3.65-3.49 (m, 2H), 3.42-3.29 (m, 1H), 2.90-2.75 (m, 6H), 1.73-1.50 (m, 2H), 1.48-1.31 (m, 4H). NH not seen.

b) (2-Pyridin-2-yl-ethyl)-{3-[2-(tetrahydro-pyran-2-yloxy)-ethyl]-benzyl}-carbamic acid tert-butyl ester To a solution of (2-pyridin-2-yl-ethyl)-{3-[2-(tetrahydro-pyran-2-yloxy)-ethyl]-benzyl}-amine (6.5 g) in dichloromethane (200 mL) at 0° C. was added N,N-diisopropylethylamine (3.7 mL) and di-tert-butyl dicarbonate (4.2 g). The reaction was stirred for 4 hour, allowing to warm to room temperature. The reaction partitioned between dichloromethane and aqueous bicarbonate. The organic layer washed with brine, dried over sodium sulfate then concentrated in vacuo to give a yellow oil (7 g). The material was used in the next step without further purification.

$^1$H NMR (400 MHz, DMSO) δ 8.47 (d, 1H), 7.73-7.63 (m, 1H), 7.30-7.00 (m, 6H), 4.58-4.51 (m, 1H), 4.33 (s, 2H), 3.85-3.73 (m, 1H), 3.64-3.28 (m, 3H), 2.95-2.76 (m, 4H), 1.71-1.48 (m, 2H), 1.50-1.23 (m, 15H).

c) [3-(2-Hydroxy-ethyl)-benzyl]-(2-pyridin-2-yl-ethyl)-carbamic acid tert-butyl ester (2-Pyridin-2-yl-ethyl)-{3-[2-(tetrahydro-pyran-2-yloxy)-ethyl]-benzyl}-carbamic acid tert-butyl ester (8 g) in tetrahydrofuran (100 mL) was treated with acetic acid (10 mL) and water (10 mL). The reaction was refluxed for 8 hour. Another 10 mL acetic and 10 mL water were added and the reaction heated at reflux for a further 2 hours. The reaction was cooled and the volatiles removed under vacuum. The reaction mixture was partitioned between aqueous sodium bicarbonate and ethyl acetate. The organic layers were dried over sodium sulfate and concentrated in vacuo. The yellow residue was passed through a plug of silica, eluting with ether then ethyl acetate to elute the desired product (4.1 g).

$^1$H NMR (300 MHz, CDCl$_3$) δ 8.46 (s, 1H), 7.57 (td, 1H), 7.27-7.20 (m, 1H), 7.18-7.01 (m, 5H), 4.38 (s, 2H), 3.86 (t, 2H), 3.64-3.42 (m, 2H), 2.95-2.76 (m, 4H), 1.45 (d, 9H). OH not seen.

d) 4-Hydroxy-7-[1R-hydroxy-2-(2-{3-[(2-pyridin-2-yl-ethylamino)-methyl]-phenyl}-ethylamino)-ethyl]-3H-benzothiazol-2-one tris-hydrochloride To a solution of [3-(2-hydroxy-ethyl)-benzyl]-(2-pyridin-2-yl-ethyl)-carbamic acid tert-butyl ester (0.244 g) in dry dichloromethane (10 ml) was added Dess-Martin periodinane (0.363 g) and the resulting mixture for 1 hour. Saturated sodium thiosulfate solution (10 mL), saturated sodium bicarbonate solution (10 mL) and ethyl acetate (20 mL) were added and the resulting mixture stirred for 10 minutes. The aqueous was separated and extracted with ethyl acetate (20 mL), the combined organics were washed with water (20 mL), dried over MgSO$_4$, filtered and evaporated. The residue was redissolved in methanol (10 ml) and 7-(2-amino-1R-hydroxy-ethyl)-4-hydroxy-3H-benzothiazol-2-one hydrochloride (0.150 g) was added followed by acetic acid (0.034 g, 0.034 ml) and the resulting mixture stirred for 30 minutes. Sodium cyanoborohydride (0.054 g) was added and the resulting mixture stirred overnight. 0.880 ammonia (few drops) was then added and the solvent evaporated. The residue was partioned between water (20 mL) and ethyl acetate (20 mL). The phases were separated and the aqueous extracted with ethyl acetate (2×20 mL). The combined organics were washed with brine (20 mL), dried over sodium sulfate, filtered and the solvent evaporated. The residue was purified by column chromatography eluting with 7M ammonia in methanol solution:DCM. 2:98 to 5:95 gradient. The residue was redissolved in trifluoroacetic acid and stirred for 5 minutes. The trifluoroacetic acid was evaporated and the residue purified by HPLC Method B. The fractions were combined and evaporated and the residue was redissolved in MeCN (10 mL). 2M HCl solution in ether (0.5 ml) was added, the solvent evaporated and the residue was triturated with ether to give 54 mg of white solid.

M/z 465 (M+H)+ (Agilent multimode)

$^1$H NMR (400 MHz, DMSO, 90° C.) δ 11.37 (s, 1H), 8.52 (d, 1H), 7.79 (td, 1.7 Hz, 1H), 7.51 (s, 1H), 7.47-7.27 (m, 5H), 6.95 (d, 1H), 6.77 (d, 1H), 5.01 (dd, 1H), 4.19 (s, 2H), 3.34 (t, 2H), 3.27-3.21 (m, 4H), 3.14-3.00 (m, 4H). 7 exchangeables not seen at elevated temperature.

EXAMPLE 75

4-Hydroxy-7-[1R-hydroxy-2-(2-{3-[(1R-methoxymethyl-2-methyl-propylamino)-methyl]-phenyl}-ethylamino)-ethyl]-3H-benzothiazol-2-one dihydrochloride

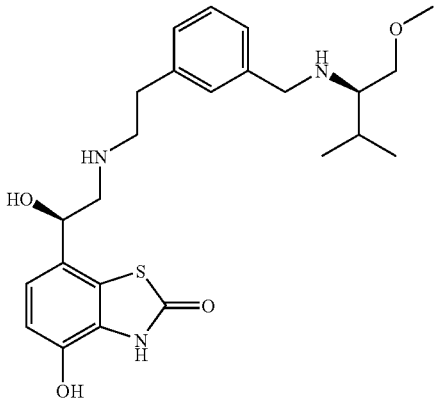

a) (R)-1-Methoxymethyl-2-methyl-propylamine hydrochloride

A solution of (D)-valinol (1.0 g) in anhydrous tetrahydrofuran (15 mL) was added dropwise over 15 minutes to a stirred mixture of sodium hydride (280 mg) in anhydrous tetrahydrofuran (8 mL). The reaction mixture was stirred under nitrogen at room temperature for 2 hours. A solution of methyl iodide (1.38 g) in anhydrous tetrahydrofuran (4 mL) was added dropwise over 10 minutes and the resultant mixture stirred at room temperature under nitrogen for a further 2 hours. Di-tert-butyl dicarbonate (2.33 g) was then added in one portion and stirring continued at room temperature under nitrogen for 2 hours. The mixture was partitioned between ethyl acetate and aqueous brine, the organic layer was dried and the solvent evaporated under reduced pressure. The 'BOC-protected' intermediate was purified on silica eluting with 12% ethyl acetate in isohexane. The resultant material was dissolved in methanol (20 mL) and treated with a 4 molar solution of hydrogen chloride in dioxane (8 mL). This solution was allowed to stand at room temperature for 18 hours, the solvents were then removed under reduced pressure and the residue triturated with diethyl ether to yield the sub-titled compound (0.4 g).

$^1$H NMR (400 MHz, DMSO) δ 7.99 (s, 3H), 3.55-3.42 (m, 2H), 3.31 (s, 3H), 3.03-3.00 (m, 1H), 1.94-1.87 (m, 1H), 0.97-0.91 (m, 6H).

b) (1R-Methoxymethyl-2-methyl-propyl)-{3-[2-(tetrahydro-pyran-2-yloxy)-ethyl]-benzyl}-amine A solution of 3-[2-(tetrahydro-pyran-2-yloxy)-ethyl]-benzaldehyde (Example 50 step a, 0.5 g) in a mixture of dichloromethane (10 mL) and 1-methyl-2-pyrrolidone (2 mL) was treated with 1-methoxymethyl-2-methyl-propylamine hydrochloride (396 mg) followed by sodium triacetoxyborohydride (906 mg) and the mixture stirred at room temperature for 4 hours. The reaction mixture was partitioned between ethyl acetate and aqueous sodium bicarbonate, the organic layer was dried and the solvent evaporated under reduced pressure to yield the subtitled compound (0.6 g).

m/z 336 (M+H)+ (APCI)

c) [3-(2-Hydroxy-ethyl)-benzyl]-(1R-methoxymethyl-2-methyl-propyl)-carbamic acid tert-butyl ester (1R-Methoxymethyl-2-methyl-propyl)-{3-[2-(tetrahydro-pyran-2-yloxy)-ethyl]-benzyl}-amine (0.6 g) was dissolved in dichloromethane (20 mL) and treated with di-tert-butyl dicarbonate (0.6 g), the resultant solution was allowed to stand at room temperature for 18 hours. The solvent was removed under reduced pressure and the residue purified on silica, eluting with 15% ethyl acetate in iso-hexane to yield 0.38 g of intermediate. This material was dissolved in a mixture of tetrahydrofuran (50 mL), water (12.5 mL) and acetic acid (12.5 mL) and the resultant solution refluxed for 4.5 hours. The solvents were removed under reduced pressure and the residue partitioned between ethyl acetate and aqueous sodium bicarbonate, the organic layer was dried and the solvent removed under reduced pressure. The residue was purified on silica eluting with 33% ethyl acetate in isohexane to yield the sub-titled compound (0.27 g).

$^1$H NMR (400 MHz, DMSO 90° C.) δ 7.18-7.03 (m, 4H), 4.36-4.21 (m, 2H), 3.60 (t, 2H), 3.48-3.41 (m, 2H), 3.07 (s, 3H), 2.71 (t, 2H), 1.92-1.86 (m, 1H), 1.34 (s, 9H), 0.88 (d, 3H), 0.76 (d, 3H).

d) (1R-Methoxymethyl-2-methyl-propyl)-[3-(2-oxo-ethyl)-benzyl]-carbamic acid tert-butyl ester The Dess-Martin periodinane (450 mg) was added to a solution of [3-(2-hydroxy-ethyl)-benzyl]-(1R-methoxymethyl-2-methyl-propyl)-carbamic acid tert-butyl ester (0.27 g) in dichloromethane (20 ml) under nitrogen at room temperature. After 1 h, ethyl acetate (10 ml), saturated aqueous sodium thiosulfate (10 ml) and saturated sodium bicarbonate (10 ml). After 10 minutes the aqueous phase was extracted with ethyl acetate. The combined organic fractions were dried with sodium sulfate, filtered and evaporated. Yield 239 mg.

$^1$H NMR (400 MHz, DMSO 90° C.) δ 9.67 (s, 1H), 7.28-7.08 (m, 4H), 4.35 (q, 2H), 3.61 (d, 2H), 3.45-3.39 (m, 2H), 3.06 (s, 3H), 1.95-1.85 (m, 1H), 1.33 (s, 9H), 0.89 (d, 3H), 0.76 (d, 3H).

e) (3-{2R-[2-Hydroxy-2-(4-hydroxy-2-oxo-2,3-dihydro-benzothiazol-7-yl)-ethylamino]-ethyl}-benzyl)-(1R-methoxymethyl-2-methyl-propyl)-carbamic acid tert-butyl ester A solution of 7-(2-amino-1R-hydroxy-ethyl)-4-hydroxy-3H-benzothiazol-2-one acetic acid salt (267 mg) in methanol (20 mL) was treated with acetic acid (41 mg) and then cooled using an ice-water bath. To the reaction mixture was then added dropwise a 1 molar solution of hydrogen chloride in diethyl ether (0.69 mL) followed by in one portion sodium cyanoborohydride (65 mg). This mixture was then treated with a solution of. (1R-methoxymethyl-2-methyl-propyl)-[3-(2-oxo-ethyl)-benzyl]-carbamic acid tert-butyl ester (239 mg) in methanol (2 mL). The reaction mixture was stirred at room temperature for 2.5 hours. At the end of this time most of the methanol was removed under reduced pressure and the residue then added to a vigorously stirred solution of ethyl acetate (50 mL) and aqueous phosphate buffer (pH=7.2, 20 mL). The organic layer was dried and evaporated under reduced pressure. Purification was on silica eluting with 1% aqueous ammonia and 9% methanol in dichloromethane to yield the sub-titled compound (170 mg).

m/z 560.3 (M+H)$^+$ (APCI)

f) 4-Hydroxy-7-[1R-hydroxy-2-(2-{3-[(1R-methoxymethyl-2-methyl-propylamino)-methyl]-phenyl}-ethylamino)-ethyl]-3H-benzothiazol-2-one dihydrochloride A solution of 3-{2-[2R-hydroxy-2-(4-hydroxy-2-oxo-2,3-dihydro-benzothiazol-7-yl)-ethylamino]-ethyl}-benzyl)-(1R-methoxymethyl-2-methyl-propyl)-carbamic acid tert-butyl ester (170 mg) in a mixture of anhydrous dichloromethane (4 mL) and trifluoroacetic acid (4 mL) was allowed to stand at room temperature for 15 minutes. The reaction mixture was then diluted with toluene (50 mL) and the solvents were removed under reduced pressure, the residue was azeotroped with acetonitrile followed by anhydrous ethanol followed by acetonitrile. Purification was by HPLC on a Sunfire column eluting with 5-50% acetonitrile in 0.2% aqueous trifluoroacetic acid. The product was dissolved in acetonitrile (5 mL) and treated with a 1 molar solution of hydrogen chloride in diethyl ether (2 mL).

The mixture was stirred for 5 minutes at room temperature and then diluted with diethyl ether (10 mL), stirring was continued for 15 minutes. At the end of this time the resultant solid was filtered off and washed with diethyl ether. Yield 90 mg.

m/z 460 (M+H)$^+$ (Agilent multimode)

$^1$H NMR (400 MHz, DMSO) δ 11.70 (s, 1H), 10.23 (s, 1H), 9.40 (s, 1H), 9.26 (s, 1H), 8.96 (s, 2H), 7.52 (s, 1H), 7.46 (d, 1H), 7.40 (t, 1H), 7.30 (d, 1H), 6.93 (d, 1H), 6.80 (d, 1H), 6.47 (d, 1H), 5.03-4.99 (m, 1H), 4.21-4.16 (m, 2H), 3.69-3.59 (m, 2H), 3.19 (s, 2H), 3.06-3.02 (m, 4H), 2.20-2.10 (m, 1H), 0.96-0.91 (m, 6H).

EXAMPLE 76

4-Hydroxy-7-[1R-hydroxy-2-(2-{3-[(1S-methoxymethyl-2-methyl-propylamino)-methyl]-phenyl}-ethylamino)-ethyl]-3H-benzothiazol-2-one dihydrochloride

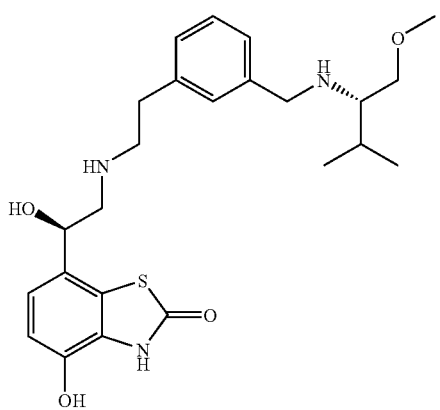

a) (1-Methoxymethyl-2-methyl-propyl)-[3-(2-oxoethyl)-benzyl]-carbamic acid tert-butyl ester The subtitle compound was prepared from (L)-valinol (1 g) by the method of Example 75 steps a, b, c and d. Yield 0.28 g.

$^1$H NMR (400 MHz, DMSO 90° C.) δ 9.67 (s, 1H), 7.28-7.08 (m, 4H), 4.35 (q, 2H), 3.61 (d, 2H), 3.45-3.39 (m, 2H), 3.06 (s, 3H), 1.95-1.85 (m, 1H), 1.33 (s, 9H), 0.89 (d, 3H), 0.76 (d, 3H).

b) 4-Hydroxy-7-[1R-hydroxy-2-(2-{3-[(1S-methoxymethyl-2-methyl-propylamino)-methyl]-phenyl}-ethylamino)-ethyl]-3H-benzothiazol-2-one dihydrochloride The title compound was prepared by the method of Example 75 steps e and f using the product of step a (0.28 g). Yield 0.1 µg $^1$H NMR (400 MHz, DMSO) 11.70 (s, 1H), 10.24 (s, 1H), 9.50-9.40 (br m, 1H), 9.32-9.20 (br m, 1H), 9.04-8.88 (br m, 2H), 7.52 (s, 1H), 7.47 (d, 1H), 7.40 (t, 1H), 7.29 (d, 1H), 6.93 (d, 1H), 6.80 (d, 1H), 6.46 (br s, 1H), 5.06-5.00 (m, 1H), 4.30-4.20 (m, 1H), 4.20-4.10 (m, 1H), 3.70-3.63 (dd, 1H), 3.62-3.58 (dd, 1H), 3.32 (s, 3H), 3.20-3.12 (m, 1H), 3.12-3.00 (m, 4H), 2.20-2.10 (m, 1H), 0.94 (d, 3H), 0.91 (d, 3H).

EXAMPLE 77

4-Hydroxy-7-[1R-hydroxy-2-(2-{3-[(1R-methoxymethyl-propylamino)-methyl]-phenyl}-ethylamino)-ethyl]-3H-benzothiazol-2-one dihydrochloride

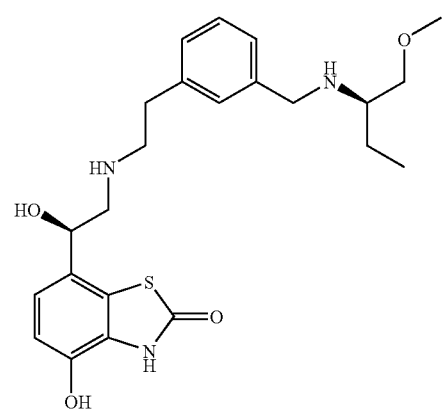

a) (R) 1-Methoxymethyl-propylamine hydrochloride

The sub-titled compound was prepared from (R)-(−)-2-amino-1-butanol (1.0 g) using the method of Example 75, step a. Yield 0.65 g.

$^1$H NMR (400 MHz, DMSO) δ 8.15 (s, 3H), 3.53-3.43 (m, 2H), 3.31 (s, 3H), 3.15-3-10 (m, 1H), 1.63-1.52 (m, 2H), 0.93-0.89 (m, 3H).

b) [3-(2-Hydroxy-ethyl)-benzyl]-(1-methoxymethyl-propyl)-carbamic acid tert-butyl ester The subtitle compound was prepared from the product of step a (0.36 g) by the method of Example 75 steps b and c. Yield 0.18 g.

¹H NMR (400 MHz, DMSO 90° C.) δ 7.19-7.04 (m, 4H), 4.29 (q, 2H), 3.85 (s, 1H), 3.61 (t, 2H), 3.41-3.35 (m, 1H), 3.30-3.23 (m, 1H), 3.13 (s, 3H), 2.71 (t, 2H), 1.51-1.43 (m, 2H), 1.36 (s, 9H), 0.78-0.74 (m, 3H).

c) 4-Hydroxy-7-[1R-hydroxy-2-(2-{3-[(1R-methoxymethyl-propylamino)-methyl]-phenyl}-ethylamino)-ethyl]-3H-benzothiazol-2-one dihydrochloride The title compound was prepared by the method of Example 75 steps d, e and f using the product of step b (0.18 g). Yield 0.025 g ¹H NMR (400 MHz, DMSO) 11.69 (s, 1H), 10.22 (s, 1H), 9.35-9.25 (br s, 1H), 9.15-9.05 (br s, 2H), 8.95-8.85 (br s, 1H), 7.48 (s, 1H), 7.45-7.38 (m, 2H), 7.29 (d, 1H), 6.93 (d, 1H), 6.79 (d, 1H), 6.47 (br s, 1H), 5.02-4.97 (m, 1H), 4.18-4.10 (m, 2H), 3.63 (dd, 1H), 3.58 (dd, 1H), 3.22-2.97 (m, 7H), 1.83-1.70 (m, 1H), 1.70-1.60 (m, 1H), 0.90 (t, 3H).

EXAMPLE 78

4-Hydroxy-7-[1R-hydroxy-2-(2-{3-[(1S-methoxymethyl-propylamino)-methyl]-phenyl}-ethylamino)-ethyl]-3H-benzothiazol-2-one dihydrochloride

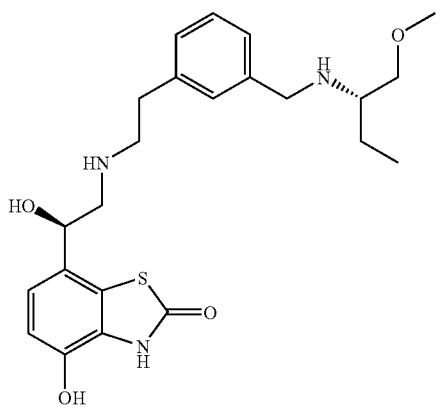

a) (S)-1-Methoxymethyl-propylamine hydrochloride

The sub-titled compound was prepared from (S)-(+)-2-amino-1-butanol (1.0 g) using the method of Example 75, step a. Yield 0.65 g.

¹H NMR (400 MHz, DMSO) δ 8.09 (s, 3H), 3.52-3.40 (m, 2H), 3.31 (s, 3H), 3.15-3.13 (m, 1H), 1.62-1.53 (m, 2H), 0.91 (t, 3H).

b) (1-Methoxymethyl-propyl)-{3-[2-(tetrahydro-pyran-2-yloxy)-ethyl]-benzyl}-amine The sub-titled compound was prepared from (S)-1-methoxymethyl-propylamine hydrochloride (0.36 g) and 3-[2-(tetrahydro-pyran-2-yloxy)-ethyl]-benzaldehyde (Example 50, step a, 0.5 g) using the method of Example 75, step b. Yield 0.6 g.

m/z 322 (M+H)⁺ (APCI)

c) [3-(2-Hydroxy-ethyl)-benzyl]-(1S-methoxymethyl-propyl)-carbamic acid tert-butyl ester The sub-titled compound was prepared from (1-methoxymethyl-propyl)-{3-[2-(tetrahydro-pyran-2-yloxy)-ethyl]-benzyl}-amine (0.6 g) using the method of Example 75, step c. Yield (0.22 g).

¹H NMR (400 MHz, DMSO 90° C.) δ 7.19-7.04 (m, 4H), 4.29 (q, 2H), 3.85 (s, 1H), 3.61 (t, 2H), 3.41-3.35 (m, 1H), 3.30-3.23 (m, 1H), 3.13 (s, 3H), 2.71 (t, 2H), 1.51-1.43 (m, 2H), 1.36 (s, 9H), 0.78-0.74 (m, 3H).

d) (1S-Methoxymethyl-propyl)-[3-(2-oxo-ethyl)-benzyl]-carbamic acid tert-butyl ester The sub-titled compound was prepared from [3-(2-hydroxy-ethyl)-benzyl]-(1-methoxymethyl-propyl)-carbamic acid tert-butyl ester (0.22 g) using the method of Example 75, step d. Yield 0.17 g ¹H NMR (400 MHz) δ 9.65 (s, 1H), 7.31-7.09 (m, 4H), 4.40-4.19 (m, 2H), 4.09 (s, 1H), 3.73 (s, 2H), 3.36-3.24 (m, 2H), 3.10 (s, 3H), 1.50-1.40 (m, 2H), 1.33 (d, 9H), 0.80-0.72 (m, 3H).

e) (3-{2-[2R-Hydroxy-2-(4-hydroxy-2-oxo-2,3-dihydro-benzothiazol-7-yl)-ethylamino]-ethyl}-benzyl)-(1S-methoxymethyl-propyl)-carbamic acid tert-butyl ester The sub-titled compound was prepared from (1-methoxymethyl-propyl)-[3-(2-oxo-ethyl)-benzyl]-carbamic acid tert-butyl ester (0.17 g) and 7-(2-amino-1-hydroxy-ethyl)-4-hydroxy-3H-benzothiazol-2-one acetic acid salt (225 mg) using the method of Example 75, step e. Yield 0.13 g.

m/z 546.3 (M+H)⁺ (APCI)

f) 4-Hydroxy-7-[1R-hydroxy-2-(2-{3-[(1S-methoxymethyl-propylamino)-methyl]-phenyl}-ethylamino)-ethyl]-3H-benzothiazol-2-one dihydrochloride The title compound was prepared from (3-{2-[2-hydroxy-2-(4-hydroxy-2-oxo-2,3-dihydro-benzothiazol-7-yl)-ethylamino]-ethyl}-benzyl)-(1-methoxymethyl-propyl)-carbamic acid tert-butyl ester (0.13 g) using the method of Example 75, step f. Yield 70 mg.

m/z 446 (M+H)⁺ (Agilent multimode)

¹H NMR (400 MHz, DMSO) δ 11.67 (s, 1H), 10.23 (s, 1H), 9.38 (s, 1H), 9.17 (s, 2H), 8.95 (s, 1H), 7.49 (s, 1H), 7.45-7.37 (m, 2H), 7.29 (d, 1H), 6.93 (d, 1H), 6.79 (d, 1H), 6.46 (s, 1H), 5.02-4.98 (m, 1H), 4.14 (s, 2H), 3.63-3.59 (m, 2H), 3.19-3.16 (m, 2H), 3.07-3.01 (m, 4H), 1.80-1.75 (m, 1H), 1.65-1.60 (m, 1H), 0.90 (t, 3H).

EXAMPLE 79

4-Hydroxy-7-{1R-hydroxy-2-[2-(3-piperazin-1-ylmethyl-phenyl)-ethylamino]-ethyl}-3H-benzothiazol-2-one

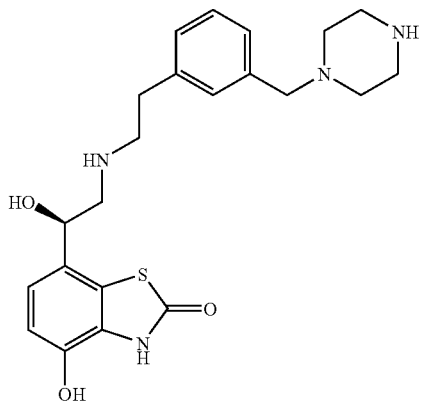

a) Trihydrido (4-κN-[3-(2-Hydroxy-ethyl)-benzyl]-piperazine-1-carboxylic acid tert-butyl ester) boron (3-Formyl-phenyl)-acetic acid methyl ester (Example 1, step 1, 0.54 g), acetic acid (0.18 mL) and Boc-piperazine (0.62 g) were combined in methanol (10 mL), sodium triacetoxyborohydride (950 mg) was then added. After 24 hours, the solvent was evaporated. The resultant residue was loaded onto a conditioned SCX cartridge (50 g, Varian) and washed with methanol (250 mL), then eluted with methanolic ammonia solution (2M, 150 mL). The elution fraction was evaporated and the residue was dissolved in ethanol (10 mL). Calcium chloride anhydrous (1.0 g) was added followed by sodium borohydride (680 mg) and the resulting mixture stirred overnight. An aqueous potassium carbonate solution (2M, 50 mL) was added and the mixture filtered. The filtrate was extracted with ethyl acetate (3×50 mL) and the combined organics washed with water (50 mL), brine (50 mL), dried (sodium sulfate) and evaporated. The residue was redissolved in tetrahydrofuran (10 mL) and cooled to 0° C., under nitrogen. Borane-methyl sulfide complex (2M solution in tetrahydrofuran, 4.5 mL) was added and the resulting mixture stirred for 5 min. The tetrahydrofuran was evaporated and the residue purified on silica, eluting with diethyl ether: iso-hexane [0:1 to 1:1] to give subtitle product, as an oil 550 mg.

$^1$H NMR (299.946 MHz, CDCL3) δ 7.37-7.16 (m, 4H), 4.05 (s, 2H), 3.93-3.66 (m, 6H), 2.94-2.78 (m, 4H), 2.75-2.59 (m, 2H), 1.42 (s, 9H)+1 exchangeable proton not seen.

b) 4-Hydroxy-7-{1R-hydroxy-2-[2-(3-piperazin-1-ylmethyl-phenyl)-ethylamino]-ethyl}-3H-benzothiazol-2-one bis-hydrochloride salt Dess-Martin periodinane (194 mg) was added to a solution of trihydrido (4-κN-[3-(2-hydroxy-ethyl)-benzyl]-piperazine-1-carboxylic acid tert-butyl ester) boron (191 mg) in dichloromethane (15 mL). After 60 minutes, the reaction mixture was poured onto a mixture of: sodium thiosulfate (15 g); water (15 mL); saturated aqueous sodium bicarbonate (15 mL) and ethyl acetate (15 mL). Stirred vigorously for 10 minutes. The mixture was separated and the aqueous extracted with ethyl acetate (2×15 mL). The combined organics were washed with water (20 mL), brine (20 mL), dried (sodium sulfate) and evaporated. The residue was dissolved in methanol (5 mL), then 7-(2-amino-1-hydroxy-ethyl)-4-hydroxy-3H-benzothiazol-2-one hydrochloride (100 mg) and acetic acid (20 μL) were added. After 1 hour, sodium cyanoborohydride (36 mg) was added. After 18 hours, the reaction mixture was concentrated under vacuum. The residue was loaded onto conditioned Tosic-65A resin (3.3 g, Argonaut) in acetonitrile/propan-2-ol [1:1]. The resin was washed with acetonitrile:propan-2-ol [1:1] (50 mL) and eluted with propan-2-ol:880 ammonia solution [4:1] (100 mL). The elution fraction was evaporated, and the residue redissolved in tetrahydrofuran (10 mL) ethylenediamine (0.23 mL) was added and the mixture was refluxed for 5 min then concentrated. The residue was azeotroped with toluene twice, treated with trifluoroacetic acid and evaporated. Purification by HPLC method B. The purified material was dissolved in acetonitrile (2 mL), treated with an excess of 2M ethereal hydrogen chloride solution and evaporated and trituration with diethyl ether gave the title product, as a white solid (50 mg)

m/z 429 (M+H)$^+$ (Agilent multimode)

$^1$H NMR (299.947 MHz, DMSO) δ 11.35 (s, 1H), 7.51-7.22 (m, 4H), 6.94 (d, J=8.5 Hz, 1H), 6.78 (d, J=8.3 Hz, 1H), 5.00 (t, J=6.5 Hz, 1H), 4.06 (s, 2H), 3.46-2.98 (m, 14H), 6 exchangeables not seen at elevated temperature Biological Assays—Experimental Procedures Adrenergic β2 Mediated cAMP Production Cell Preparation H292 cells were grown in RPMI (Roswell Park Memorial Institute) medium containing, 10% (v/v) FBS (foetal bovine serum) and 2 mM L-glutamine. Cells were grown in 225 cm2 flasks containing 25 mL media in a humidified incubator at 37° C., 5% CO$_2$. Cells were harvested from the flask and passaged at a 1 in 10 dilution once per week.

Experimental Method

The media from flasks containing H292 cells was removed, rinsed with 10 mL PBS phosphate buffered saline) and replaced with 10 mL Accutase™ cell detachment solution. Flasks were incubated for 15 minutes in a humidified incubator at 37° C., 5% CO$_2$. The cell suspension was counted and the cells re-suspended in RPMI media (containing 10% (v/v) FBS and 2 mM L-glutamine) at 0.05×10$^6$ cells per mL. 5000 cells in 100 μL were added to each well of a tissue-culture-treated 96-well plate and the cells incubated overnight in a humidified incubator at 37° C., 5% CO$_2$. The culture media was removed, washed twice with 100 μL assay buffer and replaced with 50 μL assay buffer. Cells were rested at room temperature for 20 minutes after which time 25 μL of rolipram (1.2 mM made up in assay buffer containing 2.4% (v/v) dimethylsulphoxide) was added. Cells were incubated with rolipram for 10 minutes after which time test compounds (made up as ×4 concentrated stocks in assay buffer containing 4% (v/v) dimethylsulphoxide) were added and the cells were incubated for 10 minutes at room temperature. Final rolipram concentration in the assay was 300 μM and final vehicle concentration was 1.6% (v/v) dimethylsulphoxide. The reaction was stopped by removing supernatants, washing once with 100 μL assay buffer and replacing with 50 μL lysis buffer. The cell monolayer was frozen at −80° C. for 30 minutes (or overnight).

AlphaScreen™ cAMP Detection

The concentration of cAMP (cyclic adenosine monophosphate) in the cell lysate was determined using the AlphaScreen™ methodology. The frozen cell plate was thawed for 20 minutes on a plate shaker then 10 μL of the cell lysate was transferred to a 96-well white plate. 40 μL of mixed AlphaScreen™ detection beads (containing equal volumes of donor beads (pre-incubated with biotinylated cAMP in the dark for 30 minutes) and acceptor beads), was added to each well and the plate incubated at room temperature for 10 hours in the dark. The AlphaScreen™ signal was measured using an EnVision spectrophotometer (Perkin-Elmer Inc.) with the recommended manufacturer's settings. cAMP concentrations were determined by reference to a calibration curve determined in the same experiment using standard cAMP concentrations (made up in lysis buffer in a 96-well tissue-culture-treated plate and frozen/thawed alongside the test samples) and detected using the same protocol. Concentration response curves for agonists were constructed to determine both the $pEC_{50}$ and Intrinsic Activity. Intrinsic Activity was expressed as a fraction relative to the maximum activity determined for formoterol in each experiment. The results obtained for a representative selection of the compounds of the Examples are shown in Table 1 below.

Selectivity Assays

Adrenergic α1D

Membrane Preparation

Membranes were prepared from human embryonic kidney 293 (HEK293) cells expressing recombinant human $α1_D$ receptor. These were diluted in Assay Buffer (50 mM HEPES, 1 mM EDTA, 0.1% gelatin, pH 7.4) to provide a final concentration of membranes that gave a clear window between maximum and minimum specific binding.

Experimental Method

Assays were performed in U-bottomed 96-well polypropylene plates. 10 μL [$^3$H]-prazosin (0.3 nM final concentration) and 10 μL of test compound (10× final concentration) were added to each test well. For each assay plate 8 replicates were obtained for [$^3$H]-prazosin binding in the presence of 10 μL vehicle (10% (v/v) DMSO in Assay Buffer; defining maximum binding) or 10 μL BMY7378 (10 μM final concentration; defining non-specific binding (NSB)). Membranes were then added to achieve a final volume of 100 μL. The plates were incubated for 2 hours at room temperature and then filtered onto PEI coated GF/B filter plates, pre-soaked for 1 hour in Assay Buffer, using a 96-well plate Tomtec cell harvester. Five washes with 250 μL wash buffer (50 mM HEPES, 1 mM EDTA, pH 7.4) were performed at 4° C. to remove unbound radioactivity. The plates were dried then sealed from underneath using Packard plate sealers and MicroScint-O (50 μL) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^3$H]-prazosin binding) were determined using serial dilutions typically in the range 0.1 nM to 10 μM. Data was fitted to a four parameter logistic equation to determine the compound potency, which was expressed as pIC50 (negative log molar concentration inducing 50% inhibition of [$^3$H]-prazosin binding).

Adrenergic β1

Membrane Preparation

Membranes containing recombinant human adrenergic beta 1 receptors were obtained from Euroscreen. These were diluted in Assay Buffer (50 mM HEPES, 1 mM EDTA, 120 mM NaCl, 0.1% gelatin, pH 7.4) to provide a final concentration of membranes that gave a clear window between maximum and minimum specific binding.

Experimental Method

Assays were performed in U-bottomed 96-well polypropylene plates. 10 μL [$^{125}$I]-Iodocyanopindolol (0.036 nM final concentration) and 10 μL of test compound (10× final concentration) were added to each test well. For each assay plate 8 replicates were obtained for [$^{125}$I]-Iodocyanopindolol binding in the presence of 10 μL vehicle (10% (v/v) DMSO in Assay Buffer; defining maximum binding) or 10 μL Propranolol (10 μM final concentration; defining non-specific binding (NSB)). Membranes were then added to achieve a final volume of 100 μL. The plates were incubated for 2 hours at room temperature and then filtered onto PEI coated GF/B filter plates, pre-soaked for 1 hour in Assay Buffer, using a 96-well plate Tomtec cell harvester. Five washes with 250 μL wash buffer (50 mM HEPES, 1 mM EDTA, 120 mM NaCl, pH 7.4) were performed at 4° C. to remove unbound radioactivity. The plates were dried then sealed from underneath using Packard plate sealers and MicroScint-O (50 μL) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^{125}$I]-Iodocyanopindolol binding) were determined using serial dilutions typically in the range 0.1 nM to 10 μM. Data was fitted to a four parameter logistic equation to determine the compound potency, which was expressed as pIC50 (negative log molar concentration inducing 50% inhibition of [$^{125}$I]-Iodocyanopindolol binding).

Dopamine D2

Membrane Preparation

Membranes containing recombinant human Dopamine Subtype D2s receptors were obtained from Perkin Elmer. These were diluted in Assay Buffer (50 mM HEPES, 1 mM EDTA, 120 mM NaCl, 0.1% gelatin, pH 7.4) to provide a final concentration of membranes that gave a clear window between maximum and minimum specific binding.

Experimental Method

Assays were performed in U-bottomed 96-well polypropylene plates. 30 μL [$^3$H]-spiperone (0.16 nM final concentration) and 30 μL of test compound (10× final concentration) were added to each test well. For each assay plate 8 replicates were obtained for [$^3$H]-spiperone binding in the presence of 30 μL vehicle (10% (v/v) DMSO in Assay Buffer; defining maximum binding) or 30 μL Haloperidol (10 μM final concentration; defining non-specific binding (NSB)). Membranes were then added to achieve a final volume of 300 μL. The plates were incubated for 2 hours at room temperature and then filtered onto PEI coated GF/B filter plates, pre-soaked for 1 hour in Assay Buffer, using a 96-well plate Tomtec cell harvester. Five washes with 250 μL wash buffer (50 mM HEPES, 1 mM EDTA, 120 mM NaCl, pH 7.4) were performed at 4° C. to remove unbound radioactivity. The plates were dried then sealed from underneath using Packard plate sealers and MicroScint-O (50 μL) was added to each well. The plates were sealed (TopSeal A) and filter-bound radioactivity was measured with a scintillation counter (Top-Count, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^3$H]-spiperone binding) were determined using serial dilutions typically in the range 0.1 nM to 10 μM. Data was fitted to a four parameter logistic equation to determine the compound potency, which was expressed as $pIC_{50}$ (negative log molar concentration inducing 50% inhibition of [$^3$H]-spiperone binding).

Onset Assay

Dunlin-Hartley guinea-pigs (between 200 g and 300 g on delivery) were supplied by a designated breeding establishment. The guinea-pigs were killed by cervical dislocation and the trachea removed. The adherent connective tissue was removed and each trachea cut into four rings. The tissue rings were then attached to an isometric transducer. The tissues were washed and a force of 1 g was applied to each ring. In all experiments a paired curve design was used. A priming dose of 1 μM methacholine was applied to the tissues. The tissues were then washed (three times, one minute between washes), the resting tension of 1 g was reapplied and the tissues were allowed to rest for 1 hour to equilibrate. Tissues were then contracted with 1 μM methacholine and once a steady response was obtained a cumulative concentration response curve to isoprenaline ($10^{-9}$ M-$10^{-5}$ M) was constructed. The tissues were then washed (three times, one minute between washes) and left to rest for an hour. At the end of the resting period the tissues were contracted with 1 μM methacholine and a $p[A]_{50}$ concentration of test compound added. Once the tissue had reached maximum relaxation, a $30 \times p[A]_{50}$ concentration of test compound was added. Once the tissue response had reached a plateau, 10 μM sotalol was added to the bath to confirm that the relaxation was $\beta_2$ mediated Data were collected using the ADInstruments chart4forwindows software, which measured the maximum tension generated at each concentration of agonist.

For each concentration of the isoprenaline cumulative concentration curve, the response was calculated as % relaxation of the methacholine-induced contraction. A curve was plotted of $\log_{10}$[agonist] (M) versus percentage inhibition of the methacholine-induced contraction. These data were then fitted to a non-linear regression curve fit. For each experiment, E/[A] curve data were fitted using a 4-parameter logistic function of the form:

$$E = \beta + \frac{(\beta - \alpha) \cdot [A]^m}{[A]^m + [A]_{50}^m}$$

E and [A] are the pharmacological effect (% relaxation) and concentration of the agonist respectively; $\alpha$, $\beta$, $[A]_{50}$ and m are the asymptote, baseline, location and slope parameters, respectively. The $p[A]_{50}$ and IA of each isoprenaline curve was determined from this fit, to determine if the tissue was viable for generating an onset time for the test compounds.

For each $p[A]_{50}$ concentration of the test compound, the response was calculated as % relaxation of the methacholine-induced contraction. The results were plotted % relaxation against time and the time taken to reach a 90% relaxation value was calculated and recorded.

The addition of a $30 \times p[A]_{50}$ concentration enabled determination of the maximum compound effect within the individual tissue. Hence, the % of the maximum compound effect at the $p[A]_{50}$ concentration was calculated and recorded.

Pharmacokinetics in the Rat

A dose solution of the test compound was prepared using a suitable dose vehicle. The concentration of the compound in the dose solution was assayed by diluting an aliquot to a nominal concentration of 50 μg·ml$^{-1}$ and calibrating against duplicate injections of a standard solution and a QC standard at this concentration. Compounds were administered intravenously as a bolus into a caudal vein to groups of three 250-350 g rats (approximately 1 ml·kg$^{-1}$). For the oral dose, a separate group of 2 or 3 animals were dosed by oral gavage (3 ml·kg$^{-1}$). Delivered doses were estimated by weight loss. Food was not usually withdrawn from animals prior to dosing, although this effect was investigated if necessary.

Blood samples (0.25 ml) were taken into 1 ml syringes from the caudal vein, transferred to EDTA tubes and plasma was prepared by centrifugation (5 min at 13000 rpm) soon after sample collection, before storage at −20° C. Typical sampling times were 2, 4, 8, 15, 30, 60, 120, 180, 240, 300 (min) or until the terminal t1/2 was accurately described.

The concentration of the analyte(s) were determined in plasma by quantitative mass spectrometry. Standard and quality control stock solutions were prepared at a concentration 1 mg/ml in methanol. A range of standard and QC stocks produced by serial dilution were added to control rat plasma (50 μl). The range of concentrations covered the range of levels of analyte present in the rat samples. Standards, QCs and samples underwent liquid extraction using 50 μl of organic solvent and 100 μl of organic solvent containing an internal standard, chosen to closely resemble the analyte. The samples were then mixed by repeated inversion, stored at −20° C. for at least 1 h, and centrifuged at 3500 rpm in a centrifuge for 20 minutes. Aliquots (120 μl) of each sample were transferred for analysis using LC-MSMS. Standard and quality control samples covering the range of concentrations found in the test samples were within 25% of the nominal concentration. Pharmacokinetic data analysis was achieved using WinNonlin. A standard non-compartmental analysis was used to estimate the parameters such as Tmax, Cmax, Lambda_z, t1/2_Lambda_z, AUCall, AUCINF (observed), Cl (observed), Vss (observed).

TABLE 1

| Compound of | $\beta_2$ pEC$_{50}$ | Intrinsic Activity | $\beta_1$ pEC$_{50}$ | $\alpha_{1D}$ pEC$_{50}$ |
|---|---|---|---|---|
| Example 1 | 9.3 | 0.8 | 7.9 | 7.2 |
| Example 3 | 9.5 | 0.9 | 8.0 | 6.8 |
| Example 10 | 9.5 | 1.0 | 6.7 | 6.5 |
| Example 13 | 8.7 | 1.0 | 6.8 | 6.3 |
| Example 15 | 9.1 | 0.8 | 7.8 | 7.4 |
| Example 22 | 9.7 | 1.0 | 6.1 | 7.6 |
| Example 29 | 9.1 | 0.8 | 8.1 | 7.4 |
| Example 36 | 9.2 | 0.8 | 7.3 | 6.7 |
| Example 40 | 8.6 | 0.8 | 7.4 | 7.0 |
| Example 45 | 9.4 | 1.0 | 7.2 | 7.6 |
| Example 51 | 9.0 | 1.1 | 5.9 | 6.0 |
| Example 53 | 9.2 | 0.9 | 6.6 | 6.4 |
| Example 61 | 9.2 | 0.9 | 7.1 | 6.5 |
| Example 64 | 9.1 | 0.8 | 6.3 | 6.4 |
| Example 71 | 9.1 | 0.9 | 6.4 | 7.5 |
| Example 72 | 9.0 | 0.9 | 7.0 | 6.4 |

The invention claimed is:
1. A compound of formula (I):

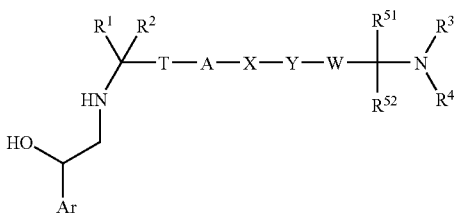

wherein: Ar is

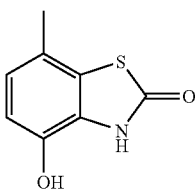

$R^1$ and $R^2$ are, independently, hydrogen or $C_{1-6}$ alkyl;
T is a bond, $CR^{33}R^{34}$, $CR^{35}R^{36}CR^{37}R^{38}$ or $CR^{39}R^{40}CR^{41}R^{42}CR^{43}R^{44}$;
W is a bond, $CR^{45}R^{46}$ or $CR^{47}R^{48}CR^{49}R^{50}$;
A is unsubstituted phenyl or phenyl substituted by one or more of the same or different: halogen, $CF_3$, $OCF_3$, $C_{1-6}$ alkyl, $C_{1-6}$ alkoxy or $S(O)_2(C_{1-4}$ alkyl);
X is a bond;
Y a bond, optionally substituted aryl or optionally substituted heteroaryl;
but A and Y not both a bond;
$R^3$ and $R^4$ are, independently, hydrogen, $C_{1-6}$ alkyl (optionally substituted by hydroxy, $C_{1-6}$ alkoxy, $NR^{63}R^{64}$, optionally substituted aryl, optionally substituted phenoxy or optionally substituted heteroaryl), heterocyclyl (optionally substituted by hydroxy, $C_{1-6}$ alkyl, $C_{1-6}$ alkoxy, $NR^{65}R^{66}$, optionally substituted aryl, optionally substituted phenoxy or optionally substituted heteroaryl) or $C_{3-6}$ cycloalkyl (optionally substituted by hydroxy, $C_{1-6}$ alkyl, $C_{1-6}$ alkoxy, $NR^{67}R^{68}$, optionally substituted aryl, optionally substituted phenoxy or optionally substituted heteroaryl);
or $R^3$ and $R^4$ join to form a 4- or 12-membered monocyclic or bicyclic ring optionally substituted by hydroxy, $NR^{69}R^{70}$, $C_{1-6}$ alkyl (optionally substituted by $NR^{55}R^{56}$), $C_{1-6}$ alkoxy (optionally substituted by $NR^{57}R^{58}$), optionally substituted phenyl or optionally substituted phenoxy; said ring being optionally fused to an optionally substituted aryl or optionally substituted heteroaryl group;
all the foregoing phenyl, aryl and heteroaryl groups are, independently, optionally substituted by halogen, $CF_3$, $OCF_3$, cyano, $CO_2H$, $OH$, nitro, $C_{1-6}$ alkyl (optionally substituted by $NR^{59}R^{60}$), $C_{3-6}$ cycloalkyl (optionally substituted by $NR^{71}R^{72}$), $C_{1-6}$ alkoxy (optionally substituted by $NR^{61}R^{62}$), $C(O)(C_{1-6}$ alkyl), $C(O)_2(C_{1-6}$ alkyl), $S(O)_rR^{25}$, $NR^{26}S(O)_2R^{27}$, $S(O)_2NR^{28}R^{29}$, $NHC(O)R^{30}$, $C(O)NR^{31}R^{32}$ or $NR^{53}R^{54}$;
r is 0, 1 or 2;
$R^{26}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, or $R^{72}$ are, independently, hydrogen or $C_{1-6}$ alkyl; and
$R^{25}$ and $R^{27}$ are, independently $C_{1-6}$ alkyl;
or a pharmaceutically acceptable salt thereof.

2. A compound of formula (I) as claimed in claim 1 wherein $R^1$ and $R^2$ are, independently, hydrogen or methyl.

3. A compound of formula (I) as claimed in claim 1 wherein T is $CH_2$ or $CH_2CH_2$.

4. A compound of formula (I) as claimed in claim 1 wherein Y is a bond, unsubstituted phenyl or phenyl substituted by one or more of the same or different: halogen, $CF_3$, $OCF_3$, $C_{1-6}$ alkyl, $C_{1-6}$ alkoxy or $S(O)_2(C_{1-4}$ alkyl).

5. A compound of formula (I) as claimed in claim 1 wherein $R^{51}$ and $R^{52}$ are, independently, hydrogen or methyl.

6. A compound of formula (I) as claimed in claim 1 wherein W is a bond.

7. A compound of formula (I) as claimed in claim 1 wherein $R^3$ is hydrogen.

8. A compound of formula (I) as claimed in claim 1 wherein $R^4$ is $C_{1-6}$ alkyl substituted by one or more of: $C_{1-6}$ alkoxy, optionally substituted phenyl or optionally substituted heteroaryl; or $R^4$ is $C_{3-6}$ cycloalkyl substituted by optionally substituted phenyl.

9. A compound of formula (I) as claimed in claim 1 wherein $R^3$ and $R^4$ join to form a 4- to 12-membered monocyclic or bicyclic ring optionally substituted by $C_{1-6}$ alkyl (optionally substituted by $NR^{55}R^{56}$) or $C_{1-6}$ alkoxy, said ring being optionally fused to an optionally substituted aryl or optionally substituted heteroaryl group; and $R^{55}$ and $R^{56}$ are, independently, hydrogen or $C_{1-6}$ alkyl.

10. A compound of formula (I) as claimed in claim 1 wherein the compound is:
7-{2-[2-(3-{[2-(2,6-Dichloro-phenyl)-ethylamino]-methyl}-phenyl)-ethylamino]-1R-hydroxy-ethyl}-4-hydroxy-3H-benzothiazol-2-one;
7-[2-(2-{3-[(2,2-Diphenyl-ethylamino)-methyl]-phenyl}-ethylamino)-1R-hydroxy-ethyl]-4-hydroxy-3H-benzothiazol-2-one;
7-[2-(2-{3-[(2-Chloro-benzylamino)-methyl]-phenyl}-ethylamino)-1R-hydroxy-ethyl]-4-hydroxy-3H-benzothiazol-2-one;
7-{2-[2-(3-{[2-(2-Fluoro-phenyl)-ethylamino]-methyl}-phenyl)-ethylamino]-1R-hydroxy-ethyl}-4-hydroxy-3H-benzothiazol-2-one;
4-Hydroxy-7-[1R-hydroxy-2-(2-{3-[(2-methoxy-1-methyl-ethylamino)-methyl]-phenyl}-ethylamino)-ethyl]-3H-benzothiazol-2-one;
4-Hydroxy-7-{1R-hydroxy-2-[2-(3-{[2-(7-methyl-1H-indol-3-yl)-ethylamino]-methyl}-phenyl)-ethylamino]-ethyl}-3H-benzothiazol-2-one;
7-{2-[2-(3-{[2-(2-Chloro-phenyl)-ethylamino]-methyl}-phenyl)-ethylamino]-1R-hydroxy-ethyl}-4-hydroxy-3H-benzothiazol-2-one;
7-{2-[2-(3-{[2-(2-Methoxyphenyl)-ethylamino]-methyl}-phenyl)-ethylamino]-1R-hydroxy-ethyl}-4-hydroxy-3H-benzothiazol-2-one;
4-Hydroxy-7-[1R-hydroxy-2-(2-{3-[(2R-phenylcycloprop-1S-ylamino)-methyl]-phenyl}-ethylamino)-ethyl]-3H-benzothiazol-2-one;
7-{2-[2-(3-{[2S-(4-Fluoro-phenyl)-cycloprop-1R-ylamino]-methyl}-phenyl)-ethylamino]-1R-hydroxy-ethyl}-4-hydroxy-3H-benzothiazol-2-one;
4-Hydroxy-7-[1R-hydroxy-2-(2-{3-[(2-pyridin-2-yl-ethylamino)-methyl]phenyl}-ethylamino)-ethyl]-3H-benzothiazol-2-one;

4-Hydroxy-7-[1R-hydroxy-2-(2-{3-[(2-methoxy-2-methyl-propylamino)methyl]-phenyl}ethylamino)ethyl]-3H-benzothiazol-2-one;

4-Hydroxy-7-[1R-hydroxy-2-(2-{3-[(2-methoxy-ethylamino)-methyl]-phenyl}-ethylamino)-ethyl]-3H-benzothiazol-2-one;

7-{2-[3-(3-{[2-(2,6-Dichloro-phenyl)-ethylamino]-methyl}-phenyl)-propylamino]-1R-hydroxy-ethyl}-4-hydroxy-3H-benzothiazol-2-one;

7-{2-[2-(3-{[2-(2,6-Dichloro-phenyl)-ethylamino]-methyl}-phenyl)-1-methyl-ethylamino]-1R-hydroxyethyl}-4-hydroxy-3H-benzothiazol-2-one;

4-Hydroxy-7-(1R-hydroxy-2-{2-[4-(2-phenylethyl)aminomethyl)phenyl]-ethylamino}ethyl)-3H-benzothiazol-2-one;

7-{2-[2-(4-{[2-(2,6-Dichloro-phenyl)-ethylamino]-methyl}-phenyl)-ethylamino]-1R-hydroxy-ethyl}-4-hydroxy-3H-benzothiazol-2-one;

7-{2-[2-(4-{[2-(2-Fluorophenyl)ethylamino]methyl}phenyl)ethylamino]-1R-hydroxyethyl}-4-hydroxy-3H-benzothiazol-2-one;

7-{2-[2-(4-{[2,2-diphenylethylamino]methyl}phenyl)ethylamino]-1R-hydroxyethyl}-4-hydroxy-3H-benzothiazol-2-one;

4-Hydroxy-7-{2-[2-(4-{[2-(2-methoxyphenyl)ethylamino]methyl}phenyl)ethylamino]-1R-hydroxyethyl}-3H-benzothiazol-2-one;

4-Hydroxy-7-{1R-hydroxy-2-[2-(4-{[2-(7-methyl-1H-indol-3-yl)-ethylamino]methyl}-phenyl)ethylamino]ethyl}-3H-benzothiazol-2-one;

4-Hydroxy-7-[1R-hydroxy-2-(2-{4-[(2-(2-pyridyl)ethylamino)methyl]phenyl}-ethylamino)ethyl]-3H-benzothiazol-2-one;

4-Hydroxy-7-[1R-hydroxy-2-(2-{4-[(2S-(4-fluorophenyl-1-cycloprop-1R-ylamino)methyl]phenyl}ethylamino)ethyl]-3H-benzothiazol-2-one;

4-Hydroxy-7-[1R-hydroxy-2-(2-{4-[(2S-phenyl-propylamino)-methyl]-phenyl}-ethylamino)-ethyl]-3H-benzothiazol-2-one;

7-{2-[2-(2-{[2-(2-Fluoro-phenyl)-ethylamino]-methyl}-phenyl)-ethylamino]-1R-hydroxy-ethyl}-4-hydroxy-3H-benzothiazol-2-one;

4-Hydroxy-7-[1-hydroxy-2-(2-{2'-[(3-isopropoxy-propylamino)-methyl]-biphenyl-4-yl}-ethylamino)-ethyl]-3H-benzothiazol-2-one;

4-hydroxy-7-[1R-hydroxy-2-({2-[2'-({[1R-phenylethyl]amino}methyl)biphenyl-4-yl]ethyl}amino)ethyl]-1,3-benzothiazol-2(3H)-one;

7-(2-{2-[3'-(1,3-Dihydro-iso-indol-2-ylmethyl)-biphenyl-4-yl]-ethylamino}-1R-hydroxy-ethyl)-4-hydroxy-3H-benzothiazol-2-one;

7-(2-{2-[3'-(Benzylamino-methyl)-biphenyl-3-yl]-ethylamino}-1R-hydroxy-ethyl)-4-hydroxy-3H-benzothiazol-2-one;

7-{2-[2-(3-{[2-(2-Fluoro-phenyl)-ethylamino]-methyl}-4-methoxy-phenyl)-ethylamino]-1R-hydroxy-ethyl}-4-hydroxy-3H-benzothiazol-2-one;

4-Hydroxy-7-[1R-hydroxy-2-(2-{3-[(3-phenyl-propylamino)-methyl]-phenyl}-ethylamino)-ethyl]-3H-benzothiazol-2-one;

4-Hydroxy-7-{1R-hydroxy-2-[2-(3-piperidin-1-ylmethyl-phenyl)-ethylamino]-ethyl}-3H-benzothiazol-2-one;

4-Hydroxy-7-(1R-hydroxy-2-{2-[3-(4-phenyl-piperidin-1-ylmethyl)-phenyl]-ethylamino}-ethyl)-3H-benzothiazol-2-one;

4-Hydroxy-7-[1R-hydroxy-2-(2-{3-[(methyl-phenethyl-amino)-methyl]-phenyl}-ethylamino)-ethyl]-3H-benzothiazol-2-one;

4-hydroxy-7-[(1R)-1-hydroxy-2-({2-[3-({[(1S)-2-methoxy-1-methylethyl]amino}methyl)phenyl]ethyl}amino)ethyl]-1,3-benzothiazol-2(3H)-one;

4-Hydroxy-7-[1R-hydroxy-2-({2-[3-({[2-methoxy]phenyl-1-methylethyl]amino}methyl)phenyl]ethyl}amino)ethyl]-1,3-benzothiazol-2(3H)-one;

4-Hydroxy-7-[1R-hydroxy-2-{2-[3-(isobutylaminomethyl)phenyl]-ethylamino}ethyl)]-3H-benzothiazol-2-one;

4-Hydroxy-7-[1R-hydroxy-2-(2-{3-[(3-iso-butoxypropylamino)methyl]phenyl}ethylamino)ethyl]-3H-benzothiazol-2-one;

4-Hydroxy-7-[1R-hydroxy-2-(2-{2'-[(2-pyridin-2-yl-ethylamino)-methyl]-biphenyl-4-yl}-ethylamino)-ethyl]-3H-benzothiazol-2-one;

4-Hydroxy-7-{1R-hydroxy-2-[2-(3-{[2-(1-oxy-pyridin-2-yl)-ethylamino]-methyl}-phenyl)-ethylamino]-ethyl}-3H-benzothiazol-2-one;

4-Hydroxy-7-[1R-hydroxy-2-(2-{3-[2-(2-methoxy-ethylamino)-ethyl]-phenyl}-ethylamino)-ethyl]-3H-benzothiazol-2-one;

4-Hydroxy-7-{1R-hydroxy-2-[2-(3-{2-[(pyridin-2-ylmethyl)-amino]ethyl}-phenyl)-ethylamino]-ethyl}-3H-benzothiazol-2-one;

7-{2-[2-(3-{2-[2-(2-Fluoro-phenyl)-ethylamino]-ethyl}-phenyl)-ethylamino]-1R-hydroxy-ethyl}-4-hydroxy-3H-benzothiazol-2-one;

7-(2-{2-[3-(2-Cyclohexylamino-ethyl)-phenyl]-ethylamino}-1R-hydroxy-ethyl)-4-hydroxy-3H-benzothiazol-2-one;

4-Hydroxy-7-[1R-hydroxy-2-(2-{3-[2-(2-methoxy-benzylamino)-ethyl]-phenyl}-ethylamino)-ethyl]-3H-benzothiazol-2-one;

4-Hydroxy-7-{1R-hydroxy-2-[2-(3-{2-[2-(2-methoxy-phenyl)-ethylamino]-ethyl}-phenyl)-ethylamino]-ethyl}-3H-benzothiazol-2-one;

7-(2-{2-[3-(2-Azepan-1-yl-ethyl)-phenyl]-ethylamino}-1R-hydroxy-ethyl)-4-hydroxy-3H-benzothiazol-2-one;

4-Hydroxy-7-[1R-hydroxy-2-(2-{3-[2-(1S-methoxymethyl-3-methyl-butylamino)-ethyl]-phenyl}-ethylamino)-ethyl]-3H-benzothiazol-2-one;

4-Hydroxy-7-[1R-hydroxy-2-(2-{3-[(1S-methoxymethyl-3-methyl-butylamino)-methyl]-phenyl}-ethylamino)-ethyl]-3H-benzothiazol-2-one;

4-Hydroxy-7-[1R-hydroxy-2-(2-{3-[(2-methoxy-benzylamino)-methyl]phenyl}-ethylamino)-ethyl]-3H-benzothiazol-2-one;

4-Hydroxy-7-{1R-hydroxy-2-[2-(3-pyrrolidin-1-ylmethyl-phenyl)-ethylamino]-ethyl}-3H-benzothiazol-2-one;

4-Hydroxy-7-{1R-hydroxy-2-(2-{4-piperidin-1-ylmethyl}phenyl)ethylamino)-ethyl}-3H-benzothiazol-2-one;

4-Hydroxy-7-{1R-hydroxy-2-[2-(4-isopropylaminomethyl)phenyl]ethylamino}-ethyl)-3H-benzothiazol-2-one;

4-Hydroxy-7-{1R-hydroxy-2-[2-(4-aminomethyl)phenyl]ethylamino}-ethyl)-3H-benzothiazol-2-one;

4-Hydroxy-7-{1R-hydroxy-2-[2-(4-{2-methoxy}ethylaminomethyl)phenyl]-ethylamino}-ethyl)-3H-benzothiazol-2-one;

4-Hydroxy-7-{1R-hydroxy-2-[2-(3-{2-hydroxyethylamino}methyl)phenyl]ethylamino}ethyl)-3H-benzothiazol-2-one;

4-Hydroxy-7-[1R-hydroxy-2-(2-{3-[(3-pyridin-2-yl-propylamino)-methyl]-phenyl}-ethylamino)-ethyl]-3H-benzothiazol-2-one;
4-Hydroxy-7-{1R-hydroxy-2-[2-(3-{[2-(2-hydroxy-phenyl)-ethylamino]-methyl}-phenyl)-ethylamino]-ethyl}-3H-benzothiazol-2-one;
4-Hydroxy-7-[1-hydroxy-2-(2-{3-[(2-hydroxy-benzylamino)-methyl]-phenyl}-ethylamino)-ethyl]-3H-benzothiazol-2-one;
7-[2-(2-{3-[(2-Fluoro-benzylamino)-methyl]-phenyl}-ethylamino)-1R-hydroxy-ethyl]-4-hydroxy-3H-benzothiazol-2-one;
4-Hydroxy-7-{1R-hydroxy-2-[2-(3-{[(pyridin-2-ylmethyl)-amino]-methyl}-phenyl)-ethylamino]-ethyl}-3H-benzothiazol-2-one;
4-Hydroxy-7-[1R-hydroxy-2-(2-{4-[(2-methoxy-benzylamino)-methyl]-phenyl}-ethylamino)-ethyl]-3H-benzothiazol-2-one;
4-Hydroxy-7-[1R-hydroxy-2-(2-{3-[(3-propoxy-propylamino)-methyl]-phenyl}-ethylamino)-ethyl]-3H-benzothiazol-2-one;
4-Hydroxy-7-[1R-hydroxy-2-(2-{3-[(3-isopropoxy-propylamino)-methyl]-phenyl}-ethylamino)-ethyl]-3H-benzothiazol-2-one;
4-Hydroxy-7-[1R-hydroxy-2-(2-{3-[(3-methoxy-benzylamino)-methyl]-phenyl}-ethylamino)-ethyl]-3H-benzothiazol-2-one;
7-[2-(2-{3-[(2-Ethoxy-benzylamino)-methyl]-phenyl}-ethylamino)-1R-hydroxy-ethyl]-4-hydroxy-3H-benzothiazol-2-one;
4-Hydroxy-7-[1-R-hydroxy-2-(2-{3-[(4-methoxy-benzylamino)-methyl]-phenyl}-ethylamino)-ethyl]-3H-benzothiazol-2-one;
4-Hydroxy-7-{1R-hydroxy-2-[2-(3-{[(2-methoxy-benzyl)-methyl-amino]-methyl}-phenyl)-ethylamino]-ethyl}-3H-benzothiazol-2-one;
4-Hydroxy-7-[1R-hydroxy-2-(2-{3-[(2-methoxy-benzylamino)-methyl]-phenyl}-ethylamino)-ethyl]-3H-benzothiazol-2-one;
4-Hydroxy-7-[1R-hydroxy-2-(2-{3-[(2-methoxy-benzylamino)-methyl]-phenyl}-ethylamino)-ethyl]-3H-benzothiazol-2-one;
7-{2-[2-(3-Azepan-1-ylmethyl-phenyl)-ethylamino]-1R-hydroxy-ethyl}-4-hydroxy-3H-benzothiazol-2-one;
4-Hydroxy-7-{1R-hydroxy-2-[2-(3-morpholin-4-ylmethyl-phenyl)-ethylamino]-ethyl}-3H-benzothiazol-2-one;
4-Hydroxy-7-{1R-hydroxy-2-[2-(3-piperidin-1-ylmethyl-phenyl)-ethylamino]-ethyl}-3H-benzothiazol-2-one;
4-Hydroxy-7-[1R-hydroxy-2-(2-{3-[(2-pyridin-2-yl-ethylamino)-methyl]-phenyl}-ethylamino)-ethyl]-3H-benzothiazol-2-one;
4-Hydroxy-7-[1R-hydroxy-2-(2-{3-[(1R-methoxymethyl-2-methyl-propylamino)-methyl]-phenyl}-ethylamino)-ethyl]-3H-benzothiazol-2-one;
4-Hydroxy-7-[1R-hydroxy-2-(2-{3-[(1R-methoxymethyl-2-methyl-propylamino)-methyl]-phenyl}-ethylamino)-ethyl]-3H-benzothiazol-2-one;
4-Hydroxy-7-[1R-hydroxy-2-(2-{3-[(1R-methoxymethyl-propylamino)-methyl]-phenyl}-ethylamino)-ethyl]-3H-benzothiazol-2-one;
4-Hydroxy-7-[1R-hydroxy-2-(2-{3-[(1S-methoxymethyl-propylamino)-methyl]-phenyl}-ethylamino)-ethyl]-3H-benzothiazol-2-one; or 4-Hydroxy-7-{1R-hydroxy-2-[2-(3-piperazin-1-ylmethyl-phenyl)-ethylamino]-ethyl}-3H-benzothiazol-2-one;

or a pharmaceutically acceptable salt thereof.

11. A process for preparing a compound of formula (I) as claimed in claim 1, the process comprising:

a) when $R^1$ is hydrogen and $R^3$ and $R^4$ are not hydrogen, reacting a compound of formula (II):

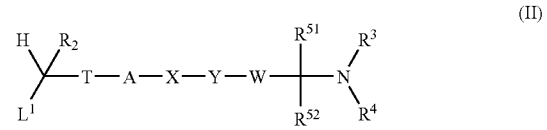

(II)

wherein $L^1$ is a leaving group and $R^2$, $R^3$, $R^4$, T, A, X, Y, W, $R^{51}$ and $R^{52}$ are as defined in claim 1, with a compound of formula (III), or a suitable salt thereof:

(III)

wherein Ar is as defined in claim 1 and $P^1$ is hydrogen or a protective group, in the presence of a base, followed by removal of the protective group;

b) when $R^1$ is hydrogen and $R^3$ or $R^4$ are not hydrogen, reacting a compound of formula (IV), or a suitable salt thereof:

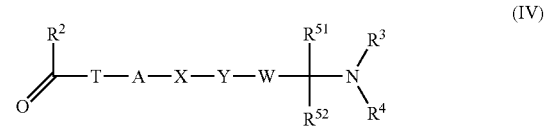

(IV)

wherein $R^2$, $R^3$, $R^4$, T, A, X, Y, W, $R^{51}$ and $R^{52}$ are as defined in claim 1, with a compound of formula (III), or a suitable salt thereof, in the presence of a suitable reducing agent;

c) when $R^1$ and $R^3$ are both hydrogen, reacting a compound of formula (V):

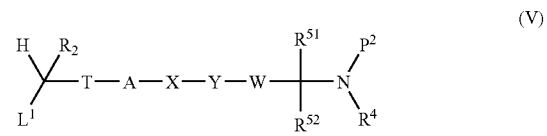

(V)

wherein $L^1$ is a leaving group, $P^2$ is a protective group and $R^2$, $R^4$, T, A, X, Y, W, $R^{51}$ and $R^{52}$ are as defined in claim 1, with a compound of formula (III), or a suitable salt thereof, in the presence of a base followed by removal of the protective group;

d) when $R^1$ and $R^3$ are both hydrogen, reacting a compound of formula (VI):

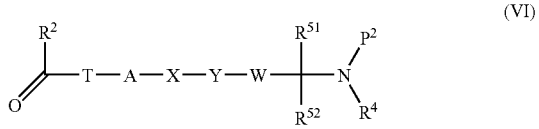

(VI)

wherein $R^2$, $R^4$, T, A, X, Y, W, $R^{51}$ and $R^{52}$ are as defined in claim 1, $P^2$ is a protective group with a compound of formula (III), or a suitable salt thereof, in the presence of a suitable reducing agent, followed by removal of the protective group;

e) when $R^3$ and $R^4$ are not hydrogen, reacting a compound of formula (VII), or a suitable salt thereof:

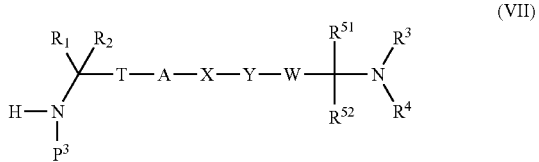

(VII)

wherein $R^1$, $R^2$, $R^3$, $R^4$, T, A, X, Y, W, $R^{51}$ and $R^{52}$ are as defined in claim 1, $P^3$ is hydrogen or an activating group with a compound of formula (VIII), or a suitable salt thereof:

(VIII)

wherein Ar is as defined in claim 1, $L^2$ is a leaving group and $P^1$ is as defined above, in the presence of a base, followed by removal of the protective groups;

f) when $R^3$ and $R^4$ are not hydrogen, reacting a compound of formula (VII), or a suitable salt thereof, with a compound of formula (IX), or a suitable salt thereof:

(IX)

wherein Ar is as defined in claim 1, in the presence of a base, followed by removal of the protective groups;

g) when $R^3$ and $R^4$ are not hydrogen, reacting a compound of formula (VII), or a suitable salt thereof, with a compound of formula (X), or a suitable salt thereof:

(X)

wherein Ar is as defined in claim 1 and $L^2$ is a leaving group, in the presence of a base, followed by reduction of the ketone, followed by removal of the protective groups;

h) when $R^3$ is hydrogen, reacting a compound of formula (XI):

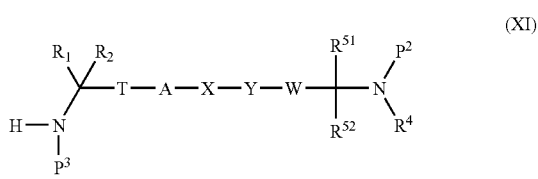

(XI)

wherein $R^1$, $R^2$, $R^4$, T, A, X, Y, W, $R^{51}$ and $R^{52}$ are as defined in claim 1 and $P^2$ is a protective group, with a compound of formula (VIII), (IX) or (X), or a suitable salt thereof, in the presence of a base, followed by removal of the protective groups;

i) when $R^{51}$ and $R^{52}$ are both hydrogen, reacting a compound of formula (XII):

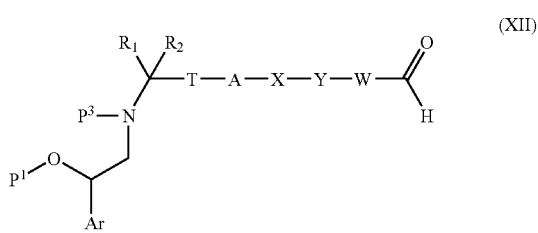

(XII)

wherein Ar, $R^1$, $R^2$, T, A, X, Y, and W are as defined in claim 1, $P^1$ is as defined above, and $P^3$ is a protective group, with a compound of formula (XIII), or a suitable salt thereof:

(XIII)

wherein $R^3$ and $R^4$ are as defined in claim 1, in the presence of a suitable reducing agent, followed by removal of the protective groups;

j) when $R^{51}$ and $R^{52}$ are both hydrogen, reacting a compound of formula (XIV):

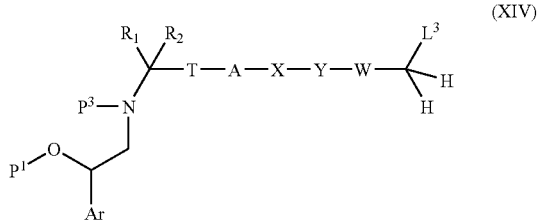

(XIV)

wherein Ar, $R^1$, $R^2$, T, A, X and W are as defined in claim 1, $P^1$ is as defined above, $P^3$ is a protective group and $L^3$ s a leaving group, with a compound of formula (XIII) or a suitable salt thereof, in the presence of a base, followed by removal of the protective groups;

k) when $R^1$ and $R^2$ are both hydrogen, and $R^3$ or $R^4$ are not hydrogen, reacting a compound of formula (XV), or a suitable salt thereof:

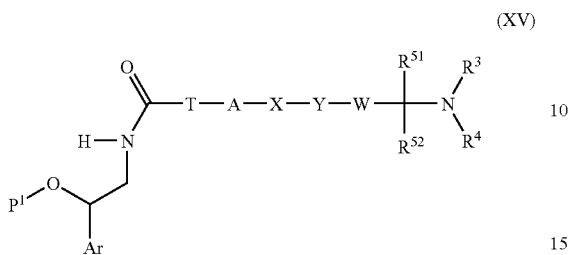

(XV)

wherein $R^3$, $R^4$, T, A, X, Y W, $R^{51}$ and $R^{52}$ are as defined in claim 1 and $P^1$ is as defined above, with a suitable reducing agent, followed by removal of the protective group;

l) when $R^1$ and $R^2$ are both hydrogen and $R^3$ is hydrogen, reacting a compound of formula (XVI):

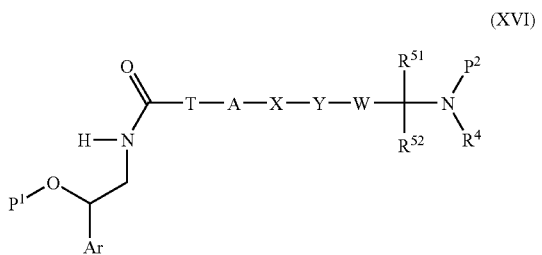

(XVI)

wherein $R^4$, T, A, X, Y, W, $R^{51}$ and $R^{52}$ are as defined in claim 1 and $P^2$ is as defined above, with a suitable reducing agent, followed by removal of the protective group;

and optionally after (a), (b), (c), (d), (e), (f), (g), (h), (i), (j), (k) or (l) carrying out one or more of the following:

converting the compound obtained to a further compound of the invention; and, or forming a pharmaceutically acceptable salt of the compound.

12. A pharmaceutical composition comprising a compound of formula (I) or a pharmaceutically acceptable salt thereof as claimed in claim 1 and a pharmaceutically acceptable adjuvant, diluent or carrier.

13. A combination comprising a compound of formula (I) as claimed in claim 1, or a pharmaceutically acceptable salt thereof, and one or more active agents selected from the list comprising:

a PDE4 inhibitor including an inhibitor of the isoform PDE4D;

a glucocorticoid receptor agonist;

a muscarinic receptor antagonist;

a modulator of chemokine receptor function; or, an inhibitor of p38 kinase function.

\* \* \* \* \*

UNITED STATES PATENT AND TRADEMARK OFFICE
CERTIFICATE OF CORRECTION

| | | |
|---|---|---|
| PATENT NO. | : 7,951,954 B2 | Page 1 of 1 |
| APPLICATION NO. | : 12/282634 | |
| DATED | : May 31, 2011 | |
| INVENTOR(S) | : Lilian Alcaraz, Andrew Lister and Garry Pairaudeau | |

It is certified that error appears in the above-identified patent and that said Letters Patent is hereby corrected as shown below:

Title page Item (54) title; and col. 1, line 1 (first line of the title),

"BEZOTHIAZOL" should read -- BENZOTHIAZOL --.

Title page Item (57), line 6 of the Abstract, "beta" should read -- beta2 --.

Col. 133, line 35, "Y a bond" should read -- Y is a bond --.

Col. 133, line 37, "A and Y not" should read -- A and Y are not --.

Col. 134, line 66 and col. 136, line 49, "methyl]phenyl" should read -- methyl]-phenyl --.

Col. 140, line 36, "Ware" should read -- W are --.

Col. 140, line 67, "$L^3$ s" should read -- $L^3$ is --.

Col. 141, line 18, "X Y W," should read -- X, Y, W, --.

Signed and Sealed this
Twenty-second Day of November, 2011

David J. Kappos
*Director of the United States Patent and Trademark Office*